(12) United States Patent
Shluzas

(10) Patent No.: US 8,366,747 B2
(45) Date of Patent: *Feb. 5, 2013

(54) APPARATUS FOR CONNECTING A LONGITUDINAL MEMBER TO A BONE PORTION

(75) Inventor: Alan E. Shluzas, West Roxbury, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 2140 days.

This patent is subject to a terminal disclaimer.

(21) Appl. No.: 10/969,293

(22) Filed: Oct. 20, 2004

(65) Prior Publication Data

US 2006/0084981 A1  Apr. 20, 2006

(51) Int. Cl.
 *A61B 17/70* (2006.01)
(52) U.S. Cl. ...................................... 606/264
(58) Field of Classification Search ............... 606/246, 606/250, 264–275, 278, 279, 30, 305, 307, 606/308, 328

See application file for complete search history.

(56) References Cited

U.S. PATENT DOCUMENTS

| | | |
|---|---|---|
| 4,805,602 A | 2/1989 | Puno et al. |
| 5,135,489 A | 8/1992 | Jepson et al. |
| 5,163,949 A | 11/1992 | Bonutti |
| 5,197,971 A | 3/1993 | Bonutti |
| 5,207,678 A | 5/1993 | Harms et al. |
| 5,295,994 A | 3/1994 | Bonutti |
| 5,345,927 A | 9/1994 | Bonutti |
| 5,360,431 A | 11/1994 | Puno et al. |
| 5,443,467 A | 8/1995 | Biedermann et al. |
| 5,454,365 A | 10/1995 | Bonutti |
| 5,466,237 A | 11/1995 | Byrd, III et al. |
| 5,474,555 A | 12/1995 | Puno et al. |
| 5,554,157 A | 9/1996 | Errico et al. |
| 5,601,590 A | 2/1997 | Bonutti et al. |
| 5,613,968 A | 3/1997 | Lin |
| 5,624,442 A | 4/1997 | Mellinger et al. |
| 5,639,074 A | 6/1997 | Greenhill et al. |
| 5,667,520 A | 9/1997 | Bonutti |
| 5,669,911 A | 9/1997 | Errico et al. |
| 5,672,176 A | 9/1997 | Biedermann et al. |
| 5,690,630 A | 11/1997 | Errico et al. |
| 5,725,588 A | 3/1998 | Errico et al. |

(Continued)

FOREIGN PATENT DOCUMENTS

| | | |
|---|---|---|
| EP | 1090595 | 12/2003 |
| WO | 03068083 | 8/2003 |

(Continued)

*Primary Examiner* — Eduardo C Robert
*Assistant Examiner* — David Comstock
(74) *Attorney, Agent, or Firm* — Seager Tufte & Wickhem LLC

(57) ABSTRACT

A device for provides access to a surgical location within a patient. The device has an elongate body that has a proximal portion, a distal portion, a first slot segment, and a second slot segment that is angled relative to said first slot segment. The elongate body defines a passage for accessing the surgical location with surgical instruments. The elongate body has a contracted configuration for insertion into the patient and an expanded configuration for providing access to the surgical location. The cross-sectional area of the passage at a first location of the elongate body is greater than the cross-sectional area of said passage at a second location of the elongate body. A movable tab is configured to extend into the second slot segment when the elongate body is in the expanded configuration to retain the elongate body in the expanded configuration.

29 Claims, 81 Drawing Sheets

U.S. PATENT DOCUMENTS

| | | | |
|---|---|---|---|
| 5,797,911 | A | 8/1998 | Sherman et al. |
| 5,817,094 | A | 10/1998 | Errico et al. |
| 5,879,350 | A | 3/1999 | Sherman et al. |
| 5,882,350 | A | 3/1999 | Ralph et al. |
| 5,885,286 | A | 3/1999 | Sherman et al. |
| 5,891,145 | A | 4/1999 | Morrison et al. |
| 5,961,499 | A | 10/1999 | Bonutti et al. |
| 6,022,350 | A | 2/2000 | Ganem |
| 6,030,389 | A | 2/2000 | Wagner et al. |
| 6,045,554 | A | 4/2000 | Grooms et al. |
| 6,053,917 | A | 4/2000 | Sherman et al. |
| 6,074,391 | A | 6/2000 | Metz-Stavenhagen et al. |
| 6,077,262 | A | 6/2000 | Schlapfer et al. |
| 6,090,111 | A | 7/2000 | Nichols |
| 6,113,601 | A | 9/2000 | Tatar |
| 6,139,550 | A | 10/2000 | Michelson |
| 6,171,299 | B1 | 1/2001 | Bonutti |
| 6,251,112 | B1 | 6/2001 | Jackson |
| 6,258,090 | B1 | 7/2001 | Jackson |
| 6,261,287 | B1 | 7/2001 | Metz-Stavenhagen |
| 6,280,442 | B1 | 8/2001 | Barker et al. |
| 6,287,311 | B1 | 9/2001 | Sherman et al. |
| 6,302,888 | B1 | 10/2001 | Mellinger et al. |
| 6,338,730 | B1 | 1/2002 | Bonutti et al. |
| 6,358,266 | B1 | 3/2002 | Bonutti |
| RE37,665 | E | 4/2002 | Ralph et al. |
| 6,371,957 | B1 | 4/2002 | Amrein et al. |
| 6,379,356 | B1 | 4/2002 | Jackson |
| 6,440,137 | B1 | 8/2002 | Horvath et al. |
| 6,443,953 | B1 | 9/2002 | Perra et al. |
| 6,454,768 | B1 | 9/2002 | Jackson |
| 6,485,491 | B1 | 11/2002 | Farris et al. |
| 6,488,681 | B2 | 12/2002 | Martin et al. |
| 6,511,099 | B2 | 1/2003 | Bartholoma et al. |
| 6,537,276 | B2 | 3/2003 | Metz-Stavenhagen |
| 6,540,748 | B2 | 4/2003 | Lombardo |
| 6,547,725 | B1 | 4/2003 | Paolitto et al. |
| 6,554,834 | B1 | 4/2003 | Crozet et al. |
| 6,565,565 | B1 | 5/2003 | Yuan et al. |
| 6,582,436 | B2 | 6/2003 | Schlapfer et al. |
| 6,585,740 | B2 | 7/2003 | Schlapfer et al. |
| 6,623,486 | B1 | 9/2003 | Weaver et al. |
| 6,837,889 | B2 | 1/2005 | Shluzas |
| 6,858,030 | B2 | 2/2005 | Martin et al. |
| 6,905,500 | B2 | 6/2005 | Jeon et al. |
| 7,018,378 | B2 | 3/2006 | Biedermann et al. |
| RE39,089 | E | 5/2006 | Ralph et al. |
| 7,066,937 | B2 | 6/2006 | Shluzas |
| 7,128,743 | B2 | 10/2006 | Metz-Stavenhagen |
| 7,144,396 | B2 | 12/2006 | Shluzas |
| 7,179,225 | B2 | 2/2007 | Shluzas et al. |
| 2001/0001119 | A1 | 5/2001 | Lombardo |
| 2002/0091386 | A1 | 7/2002 | Martin et al. |
| 2002/0133154 | A1 | 9/2002 | Saint Martin |
| 2002/0138076 | A1 | 9/2002 | Biedermann et al. |
| 2003/0004512 | A1 | 1/2003 | Farris et al. |
| 2003/0014068 | A1 | 1/2003 | Bonutti et al. |
| 2004/0102781 | A1 | 5/2004 | Jeon |
| 2005/0107789 | A1 | 5/2005 | Sweeney |
| 2005/0192580 | A1 | 9/2005 | Dalton |
| 2005/0245942 | A1 | 11/2005 | DiPoto |
| 2005/0251192 | A1 | 11/2005 | Shluzas et al. |
| 2005/0273131 | A1 | 12/2005 | Shluzas et al. |
| 2006/0069404 | A1 | 3/2006 | Shluzas et al. |
| 2006/0084891 | A1 | 4/2006 | Barthe et al. |
| 2006/0271057 | A1 | 11/2006 | Shluzas et al. |
| 2007/0021750 | A1 | 1/2007 | Shluzas et al. |

FOREIGN PATENT DOCUMENTS

| | | |
|---|---|---|
| WO | 2004000145 | 12/2003 |
| WO | 2004022108 | 3/2004 |
| WO | 2004103188 | 12/2004 |
| WO | 2005018466 | 3/2005 |
| WO | 2005041863 | 5/2005 |
| WO | 2005046492 | 5/2005 |
| WO | 2005096968 | 10/2005 |
| WO | 2006045089 | 4/2006 |

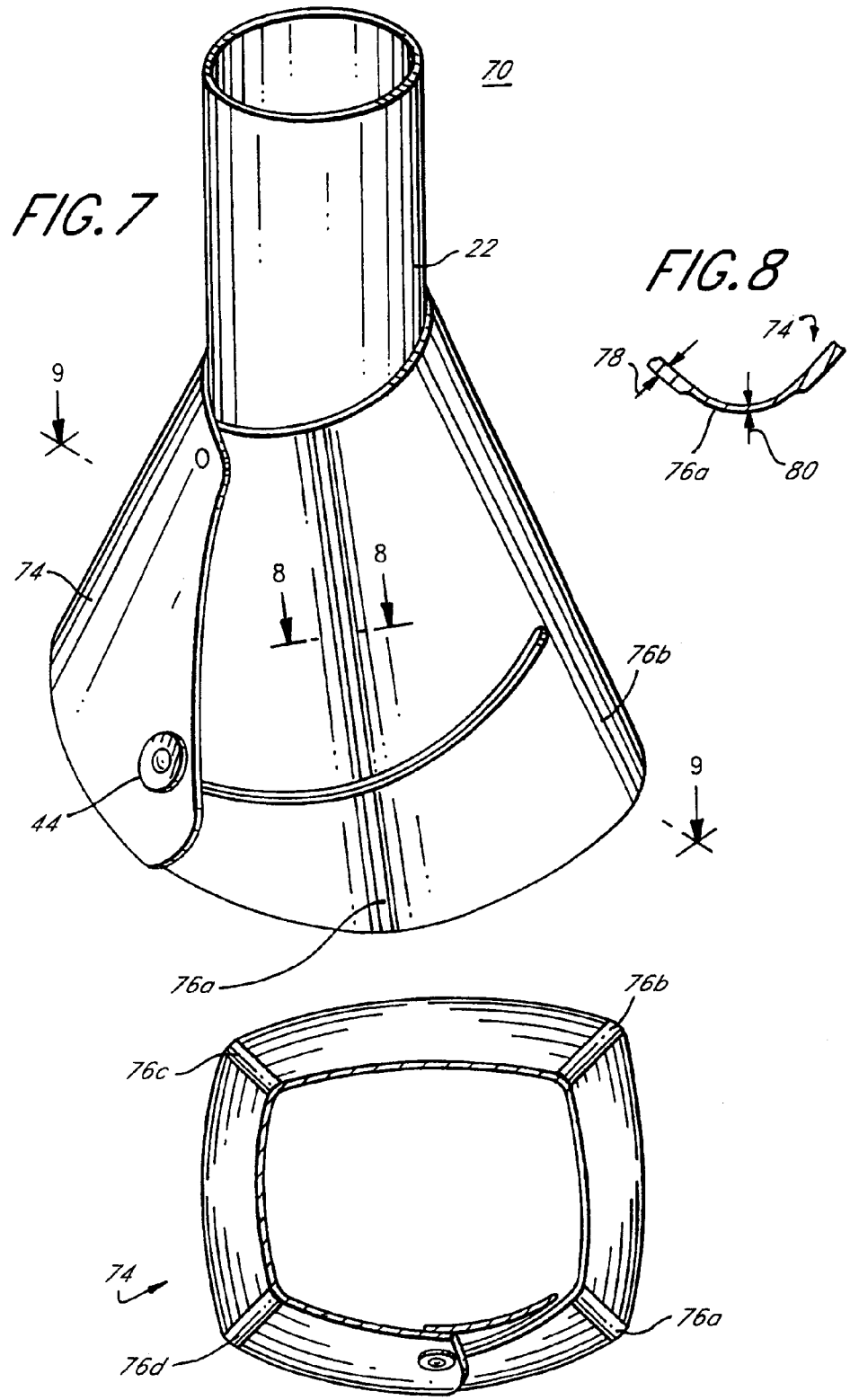

FIG. 15
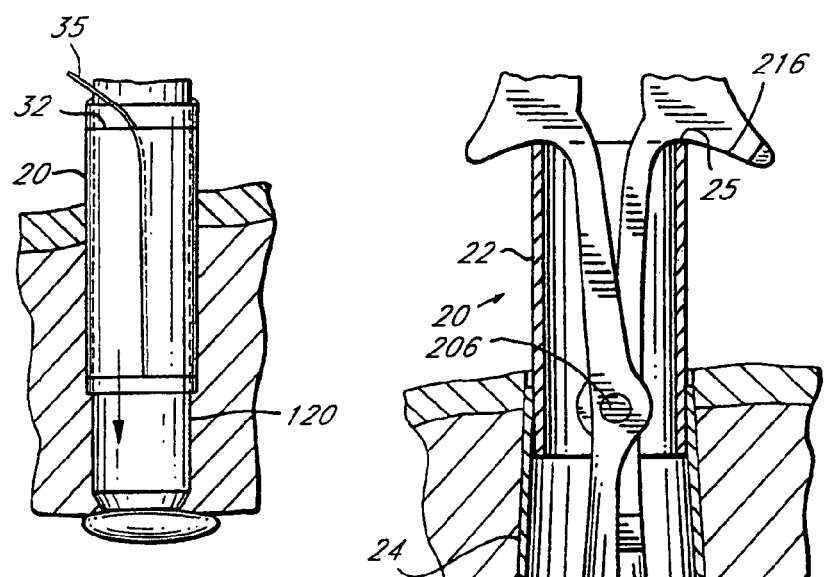
FIG. 18
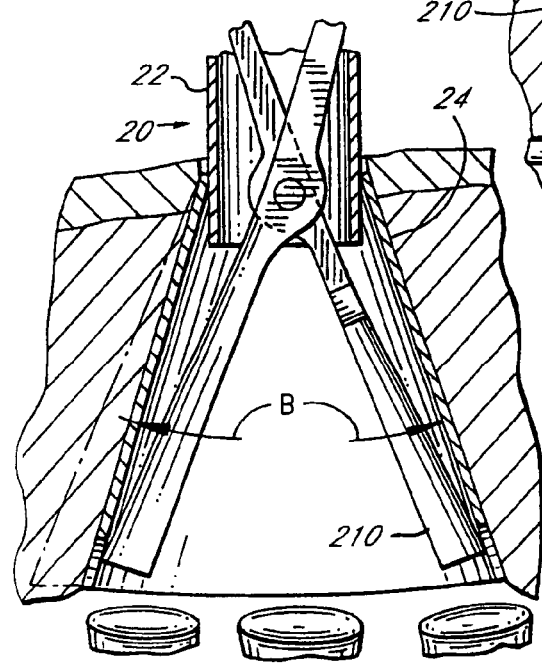
FIG. 19

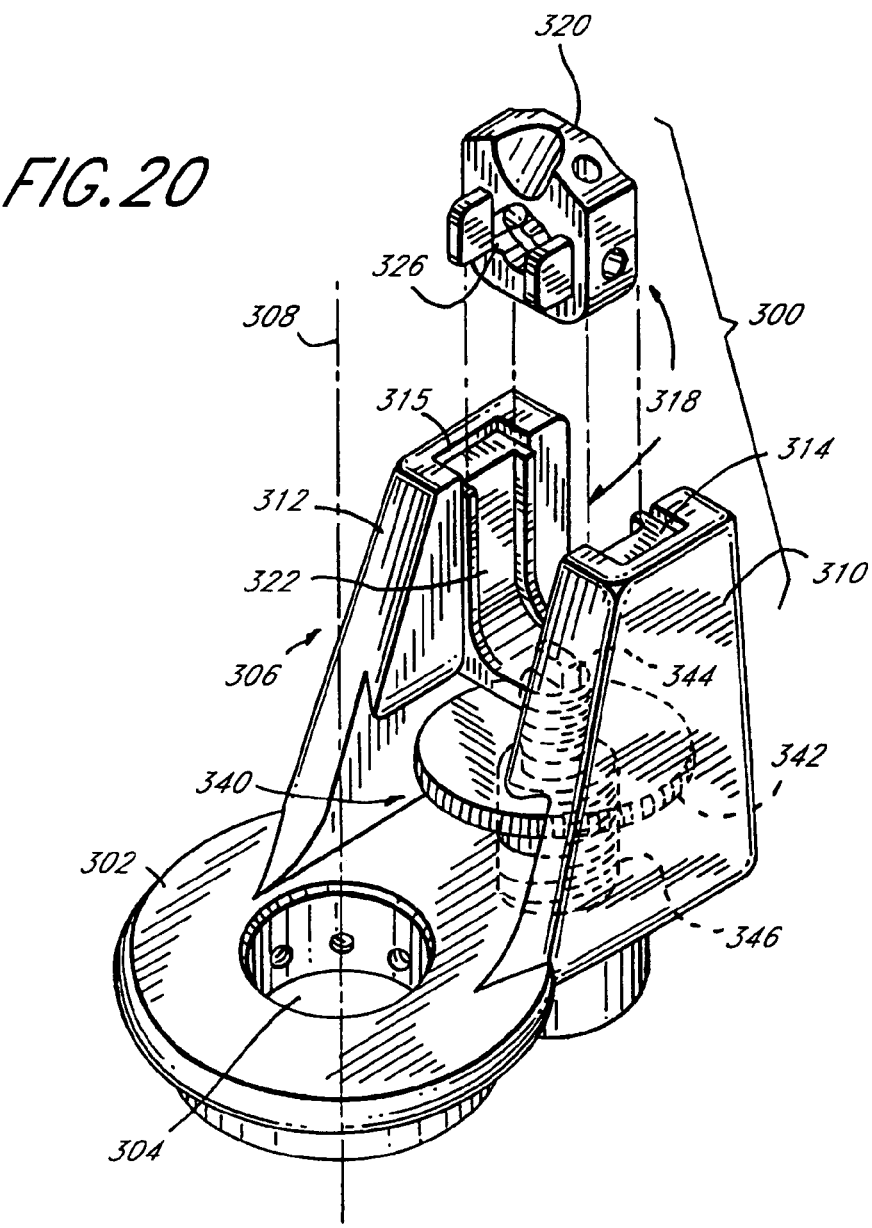

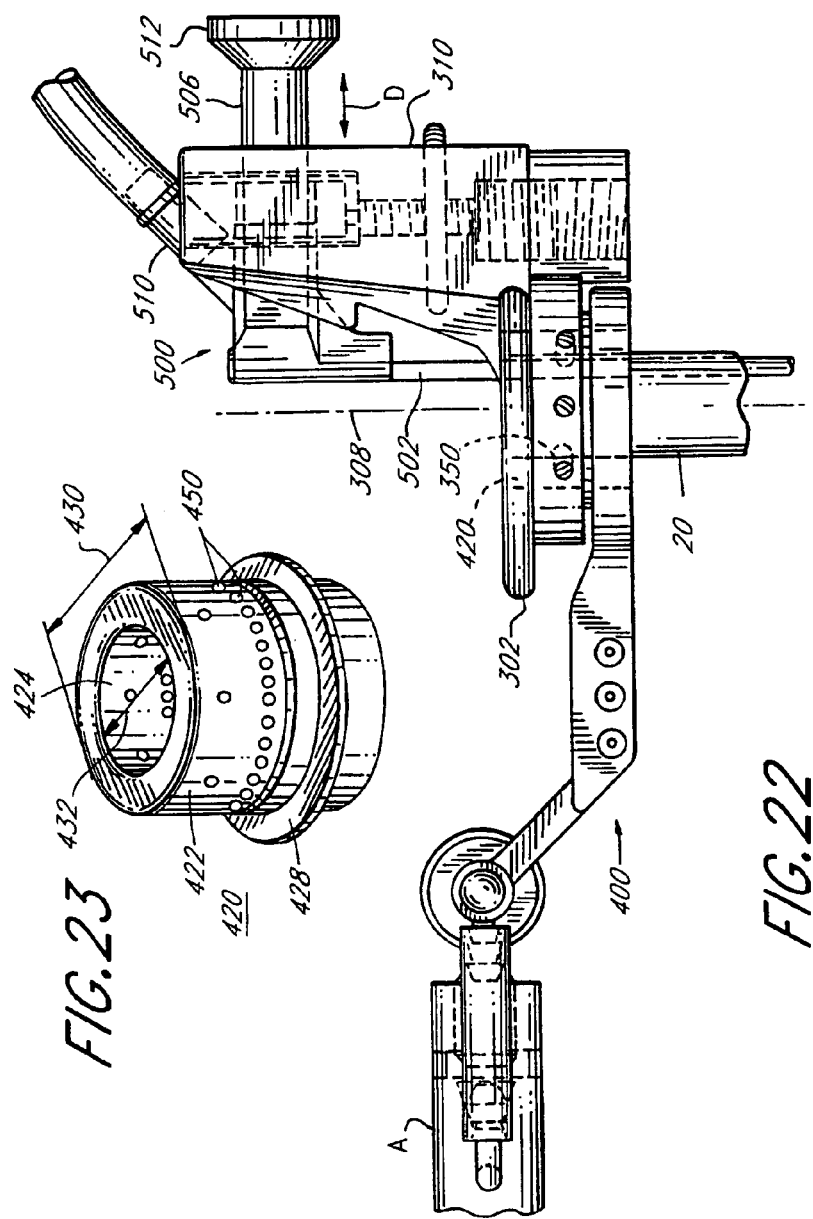

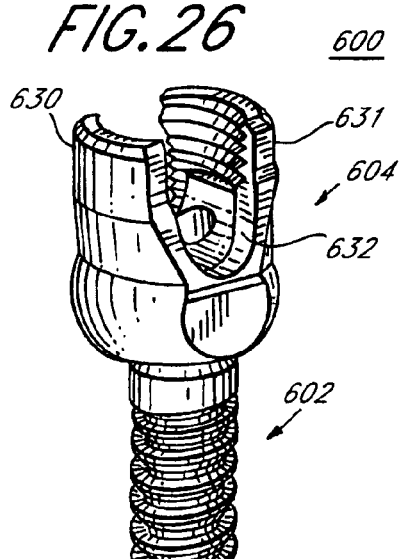
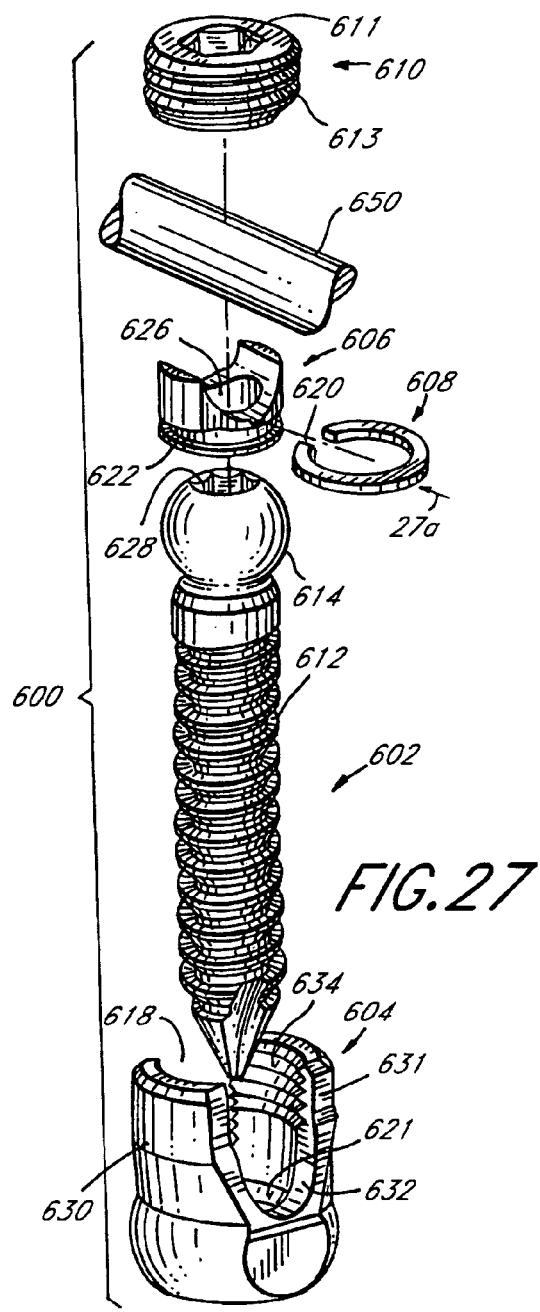

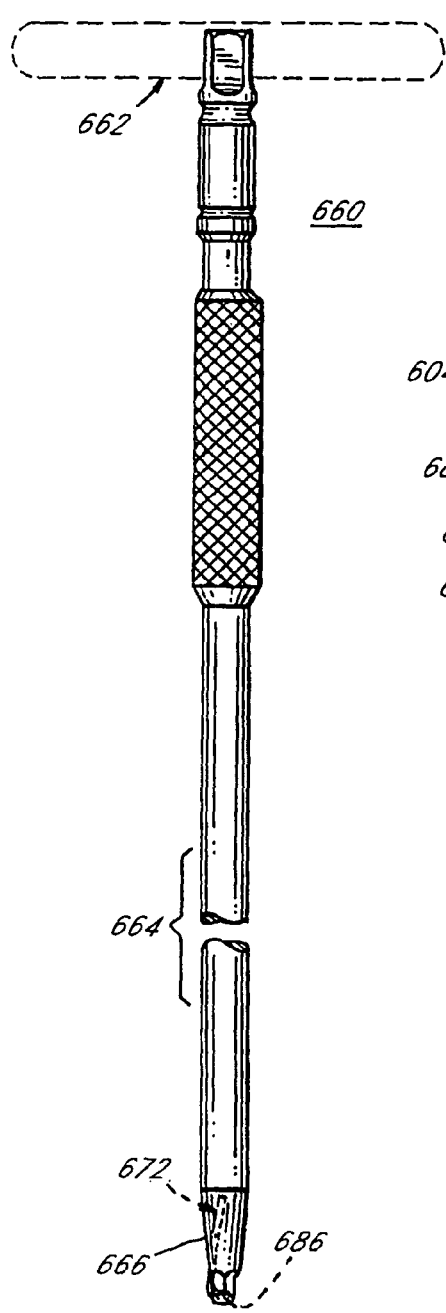
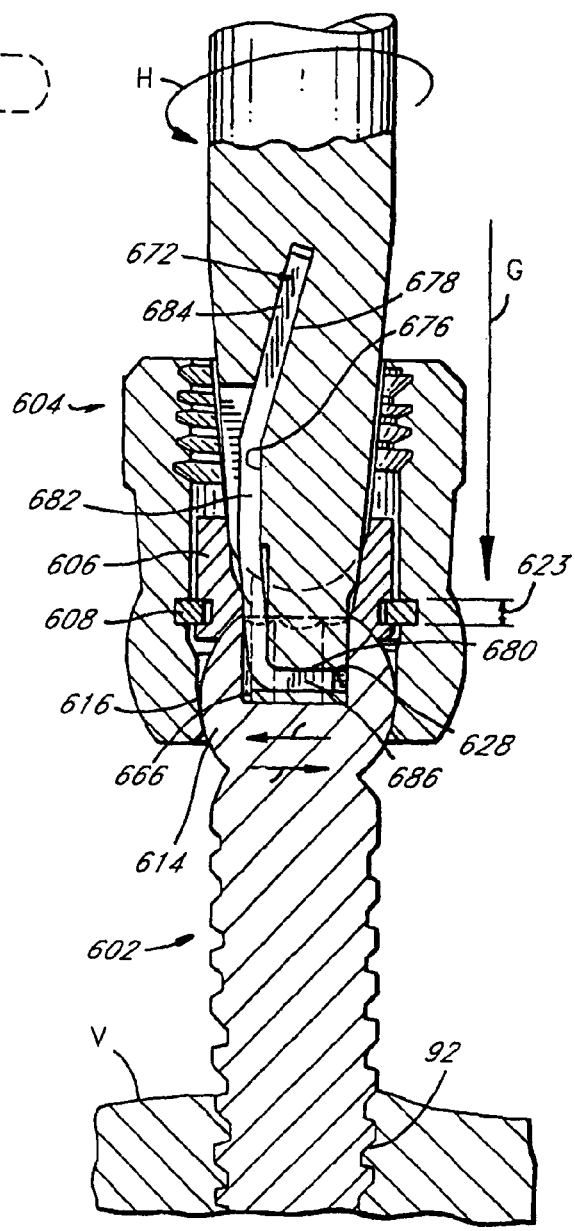

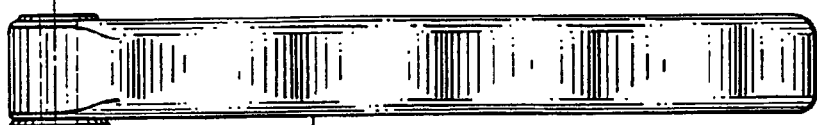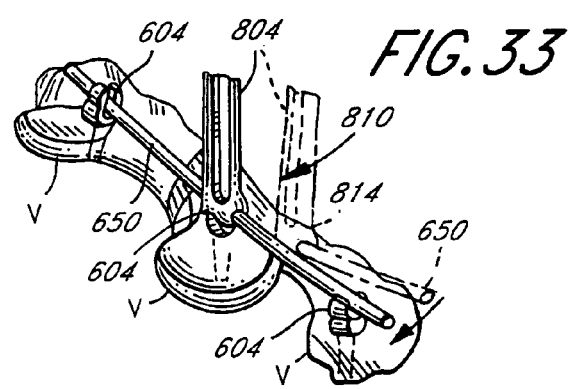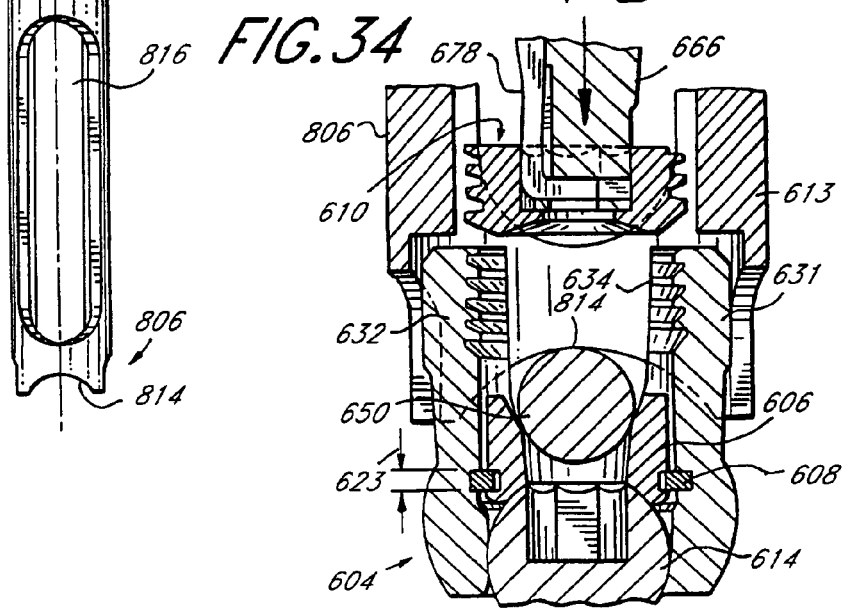

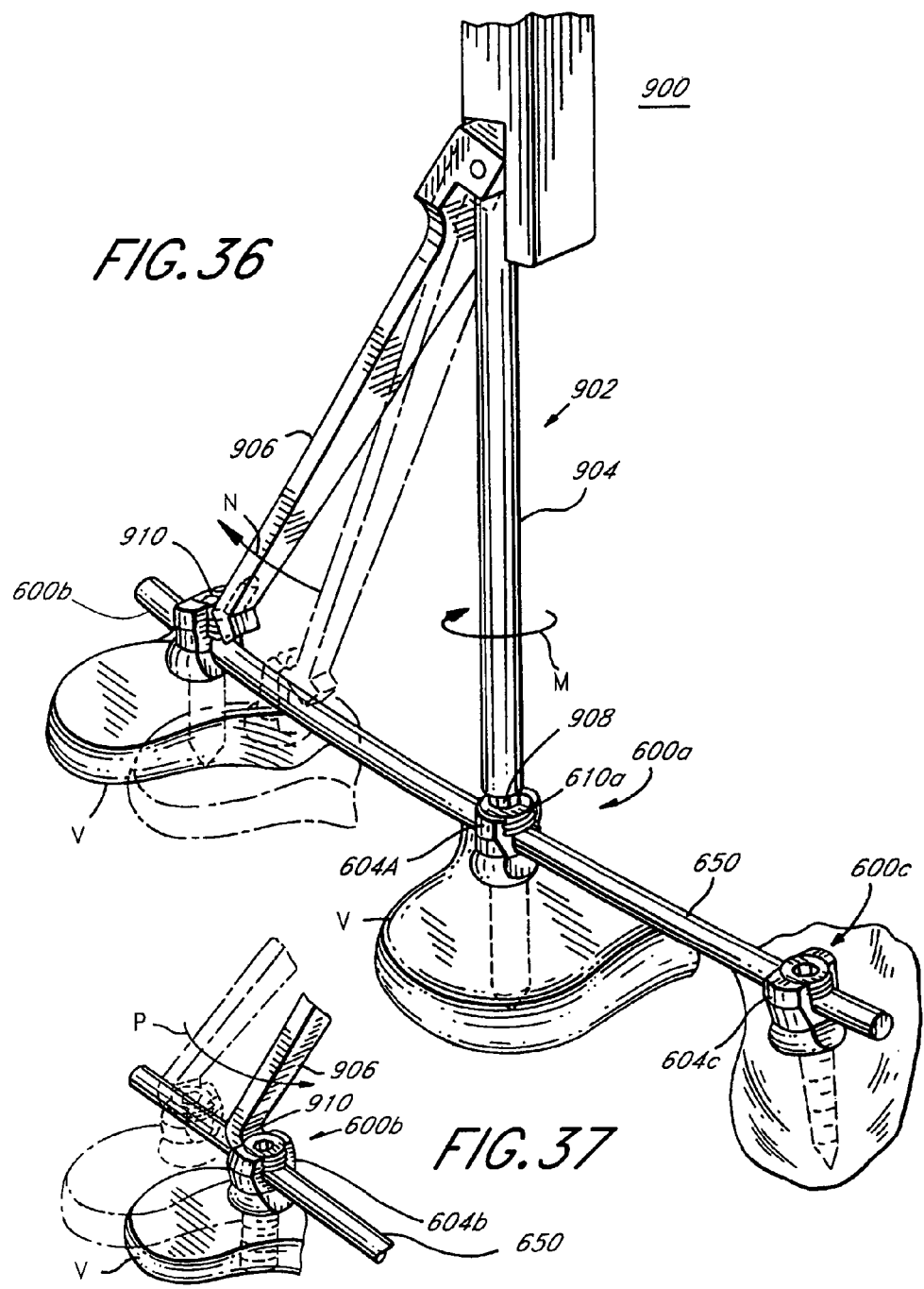

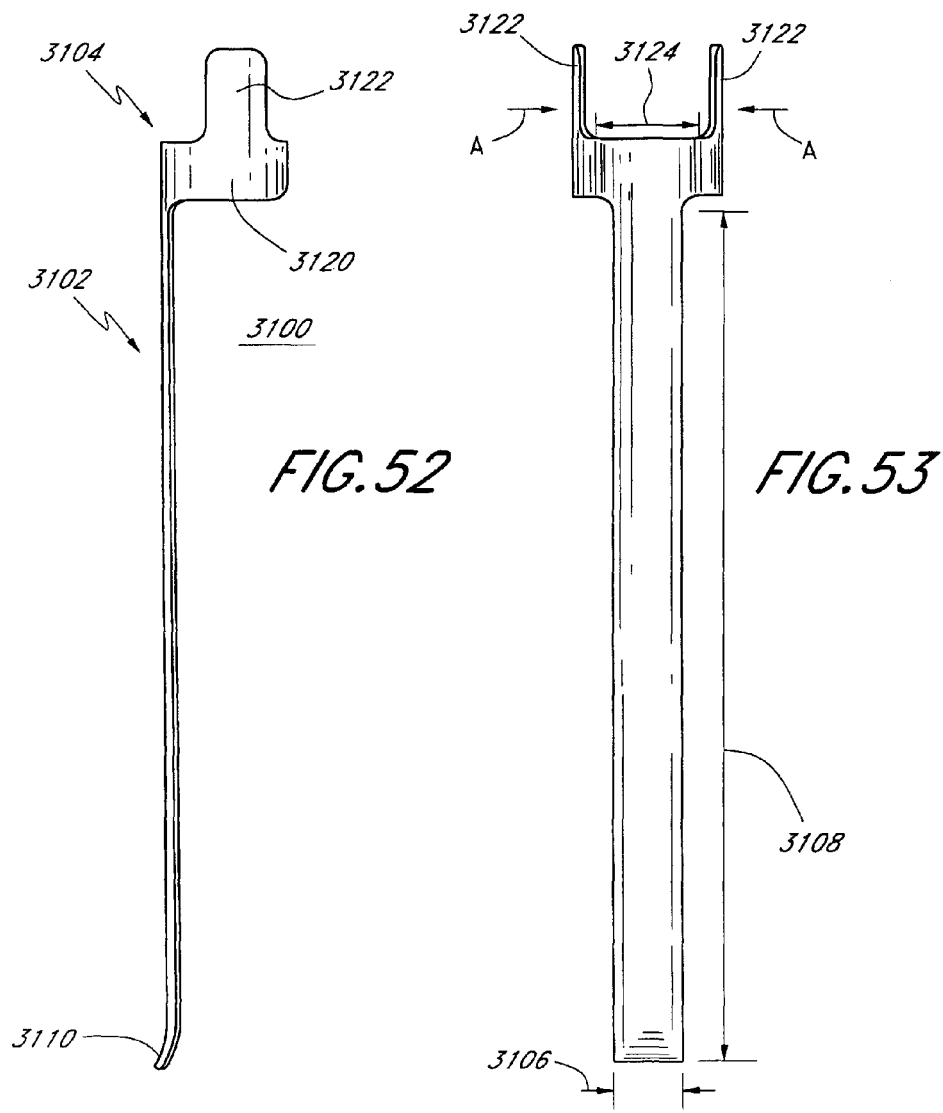

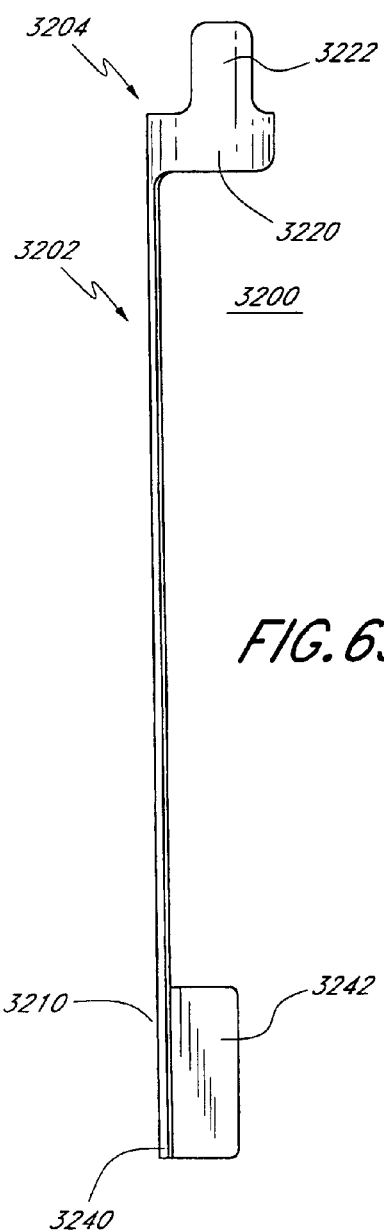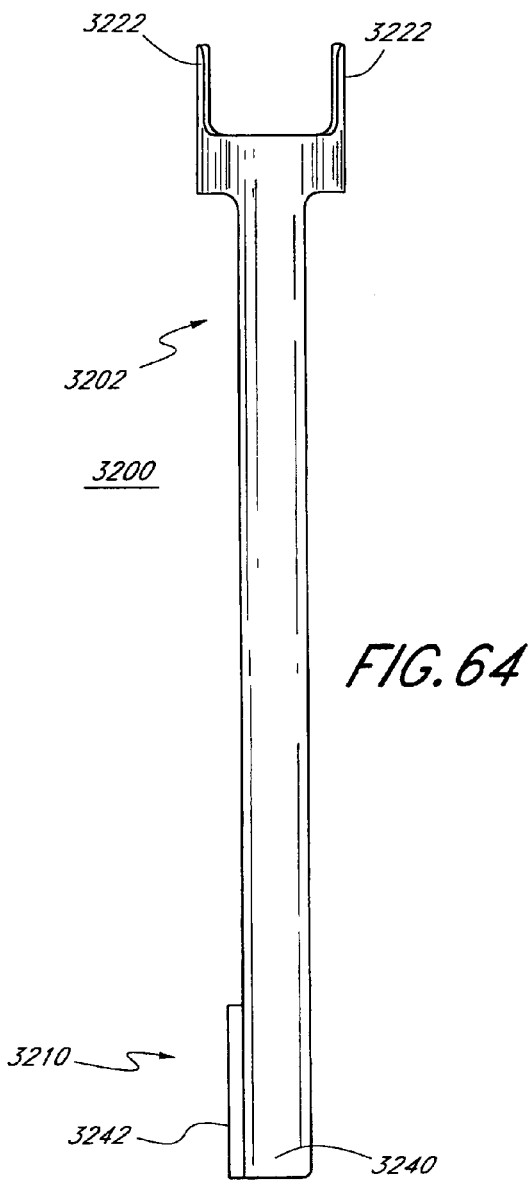

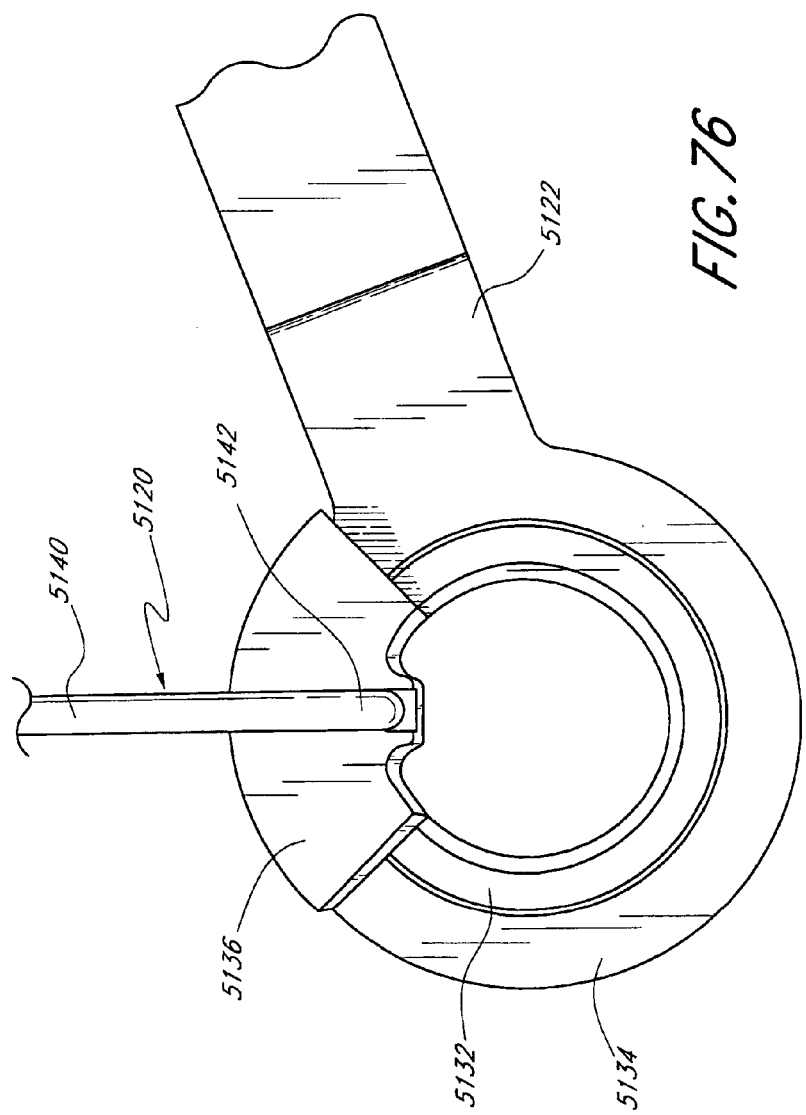

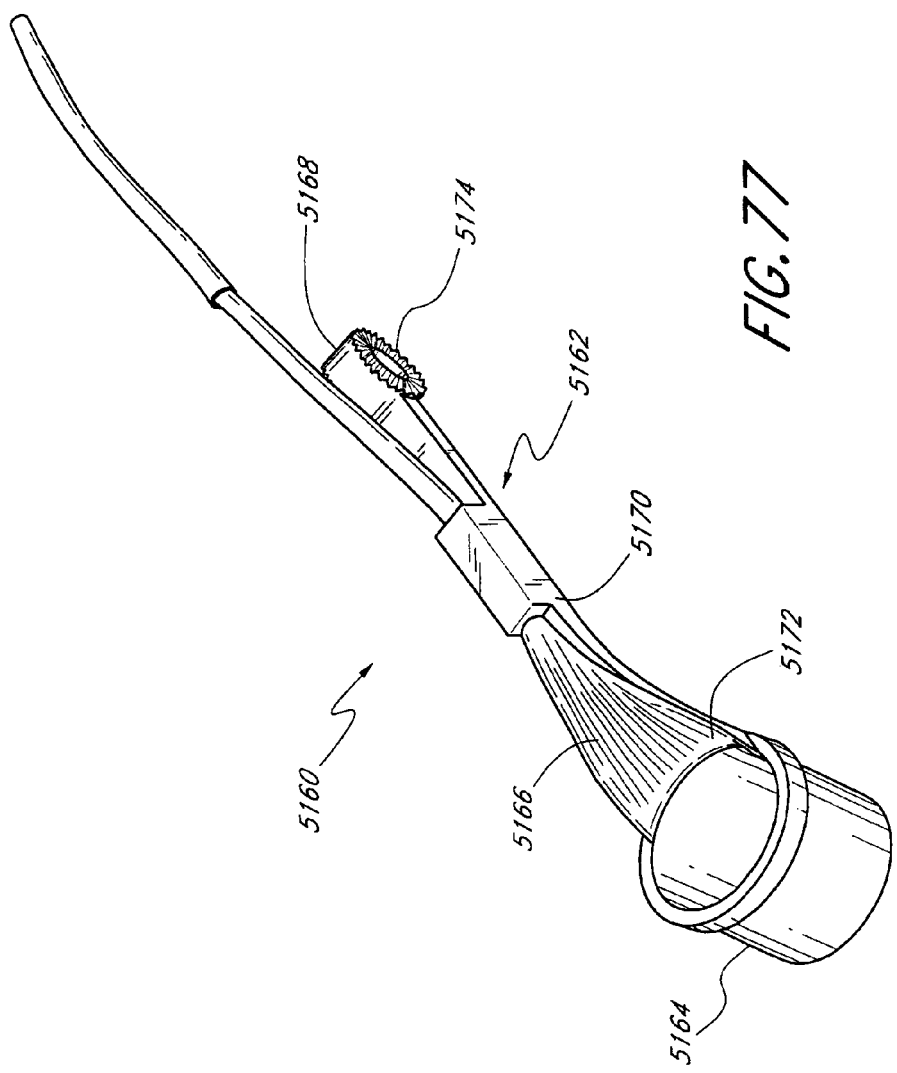

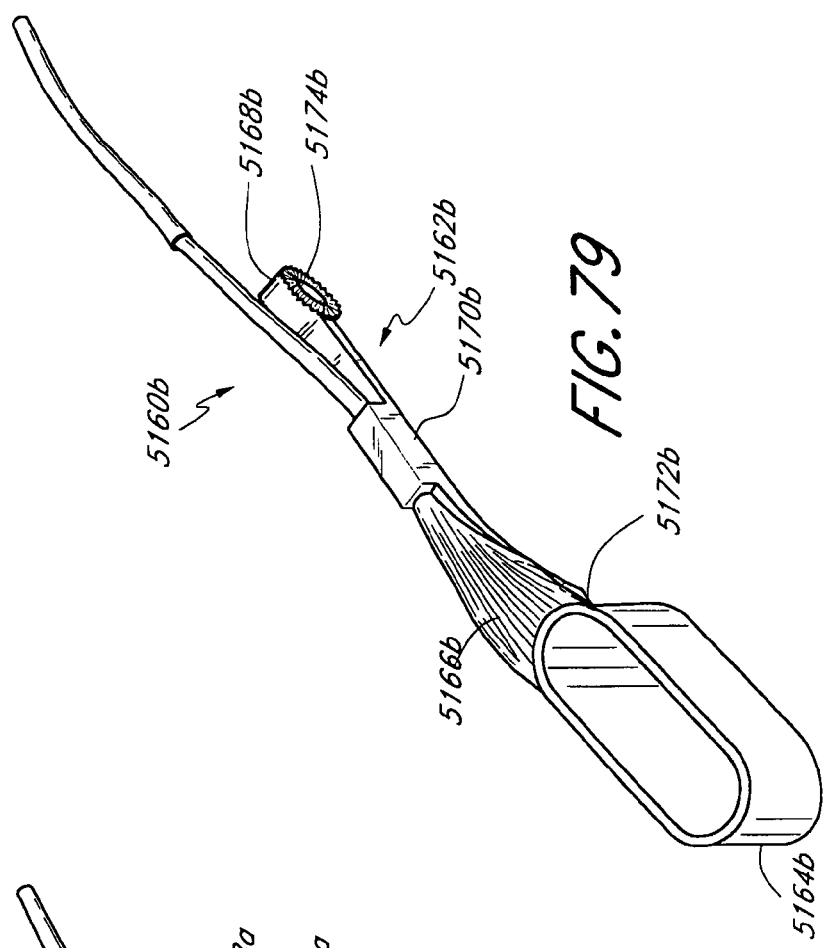
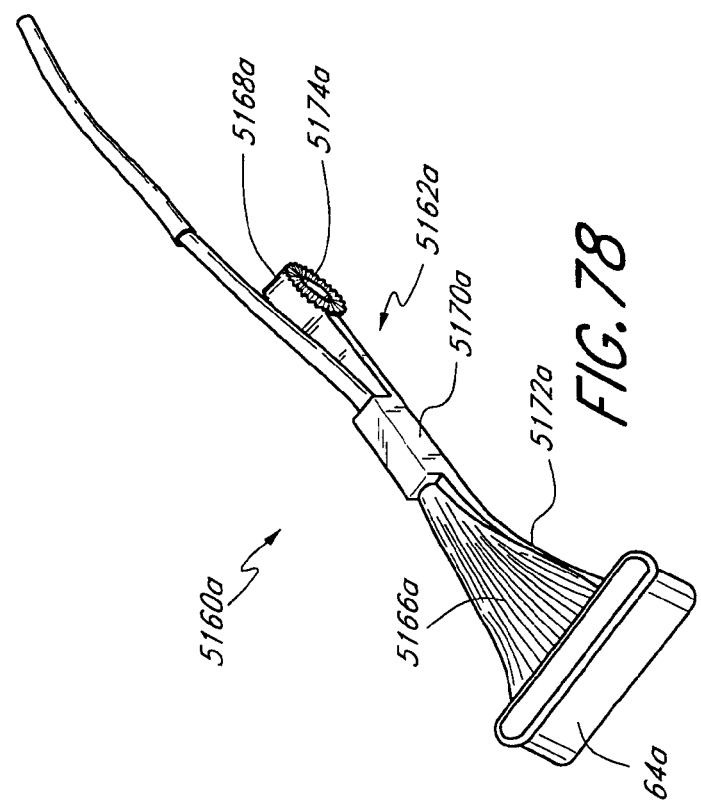

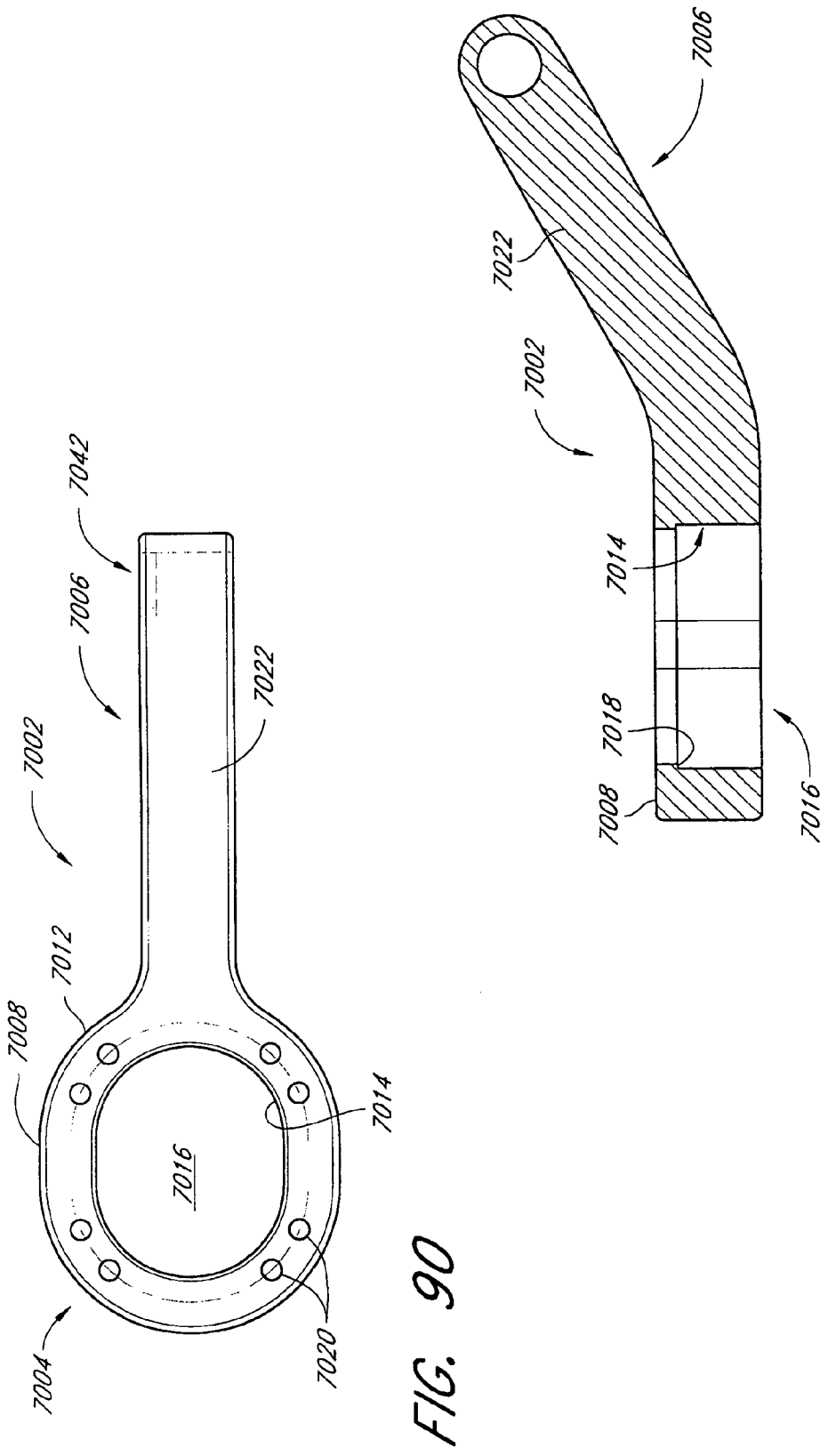

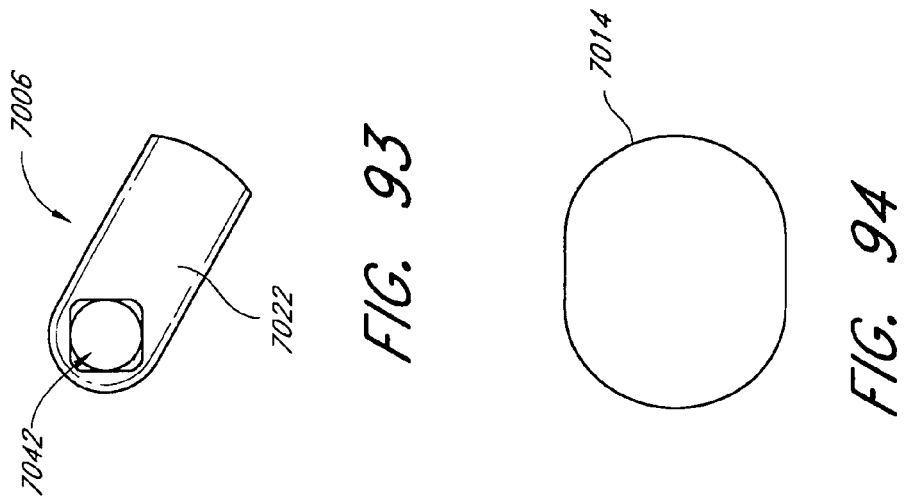
FIG. 93
FIG. 94
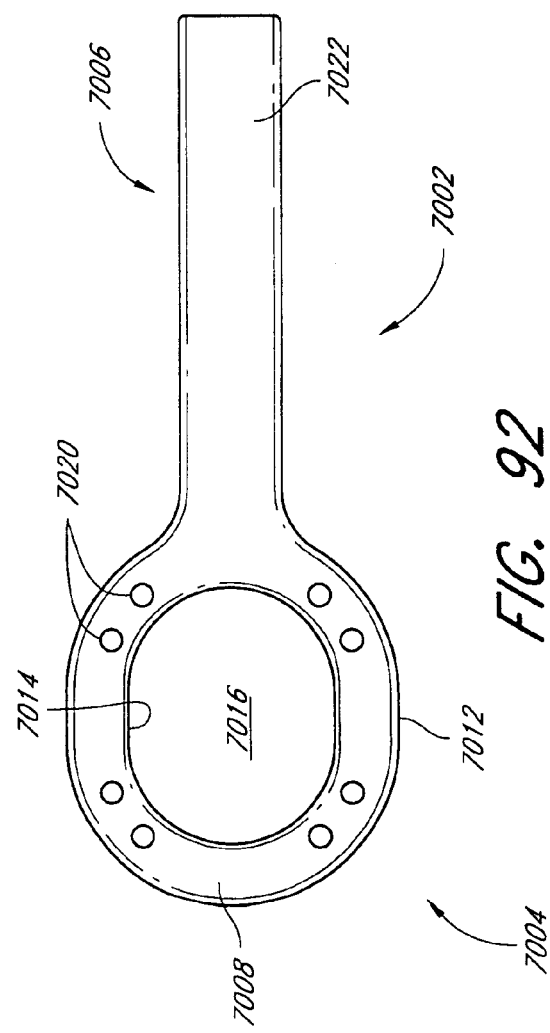
FIG. 92

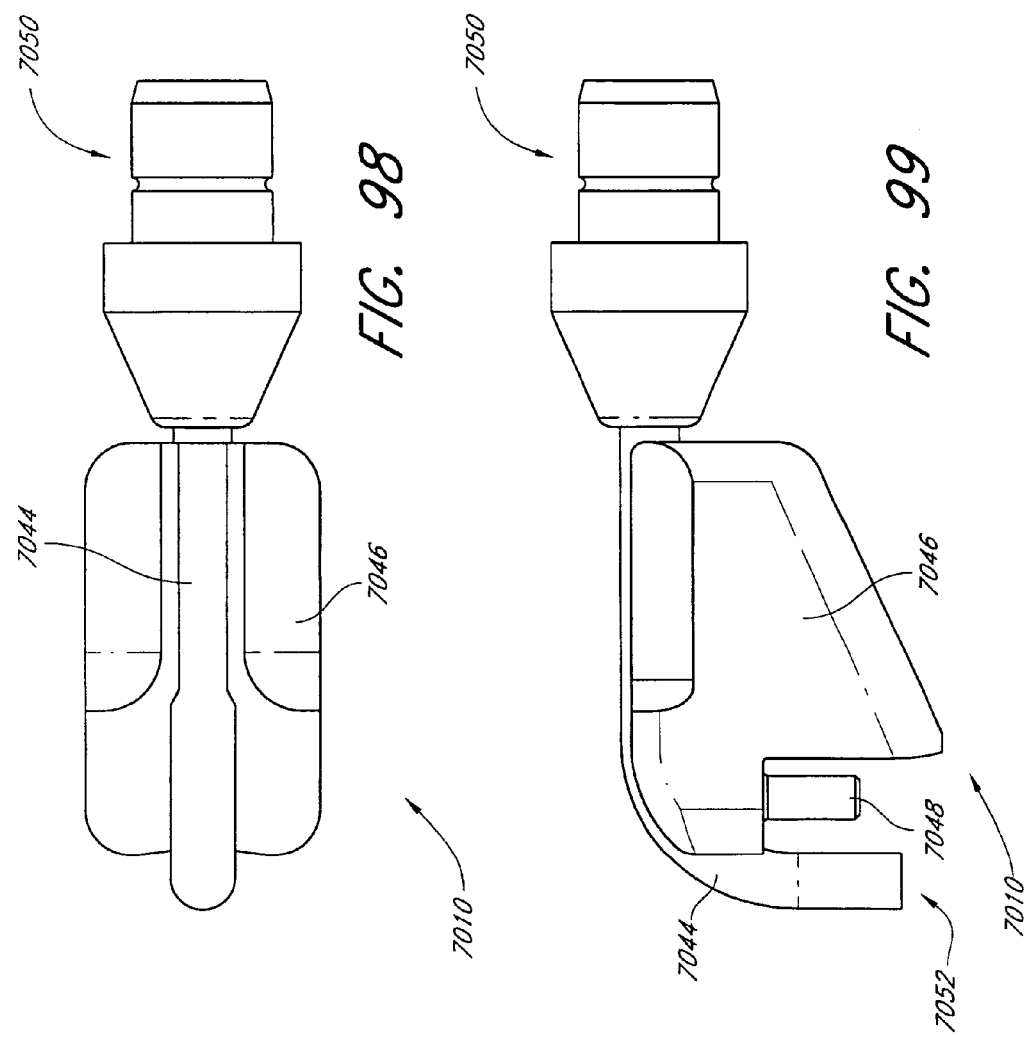

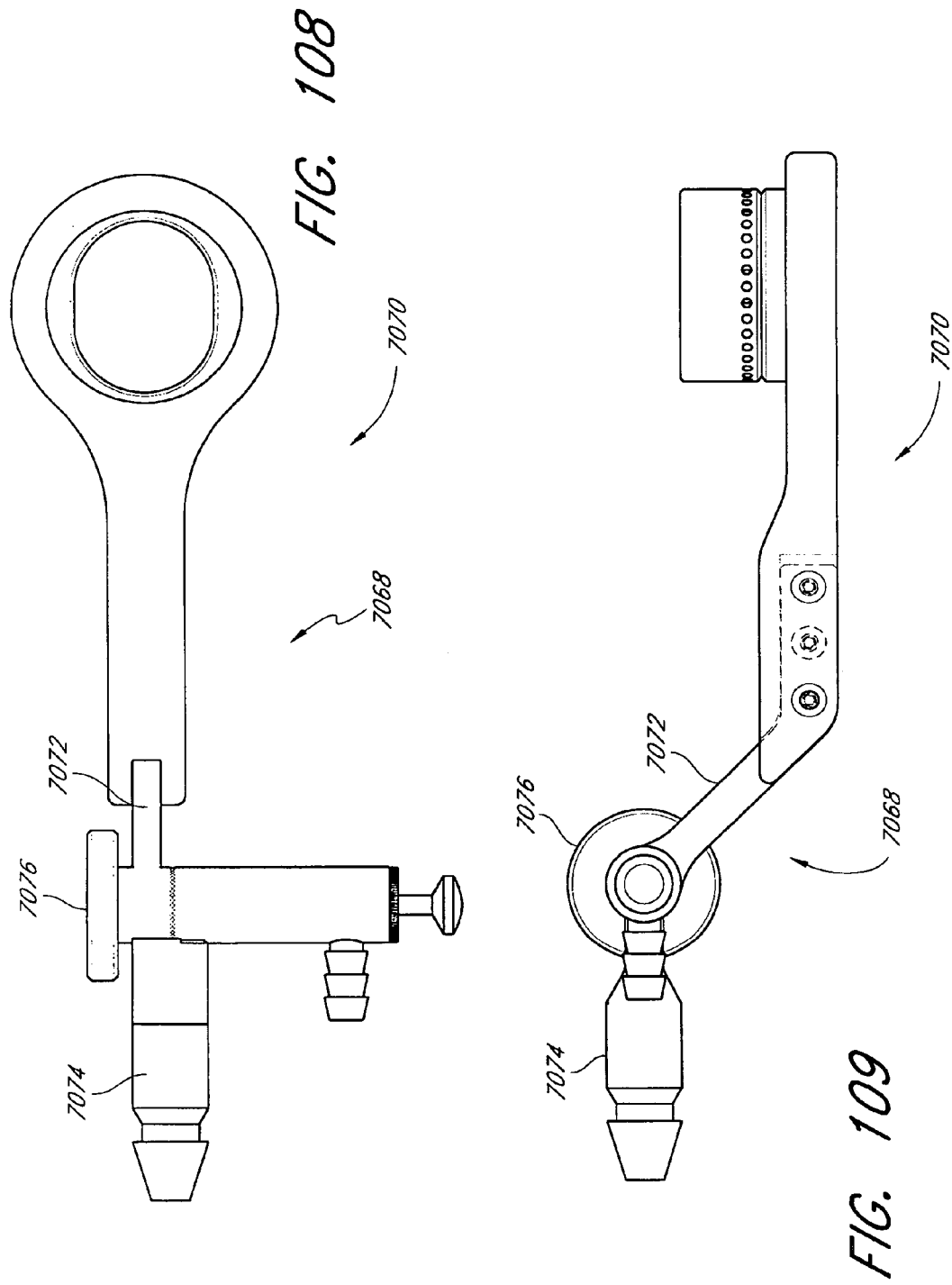

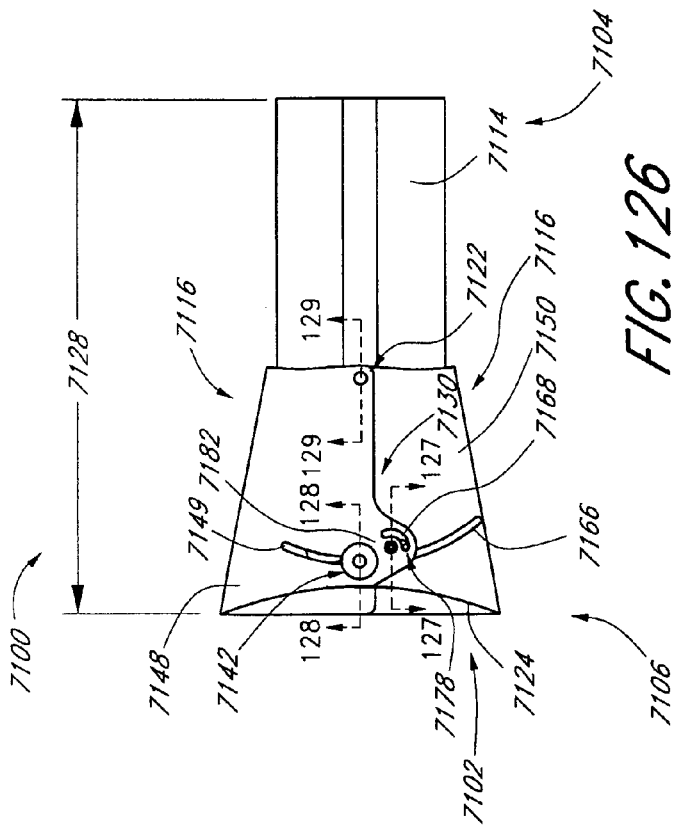
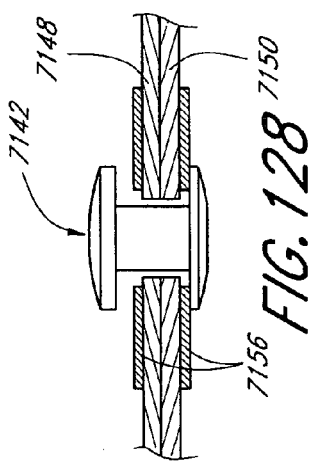
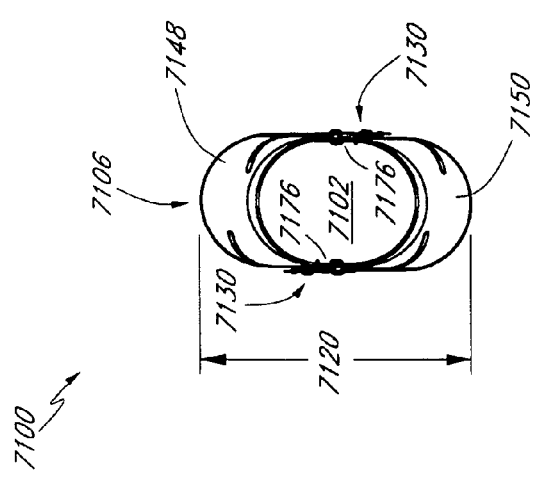
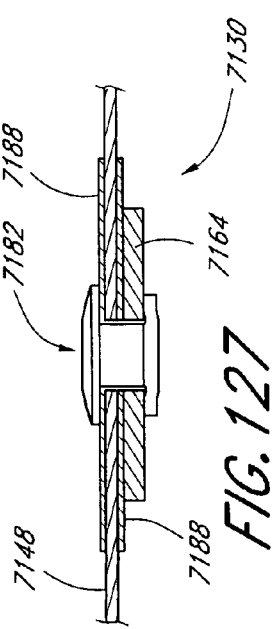
FIG. 126
FIG. 128
FIG. 125
FIG. 127

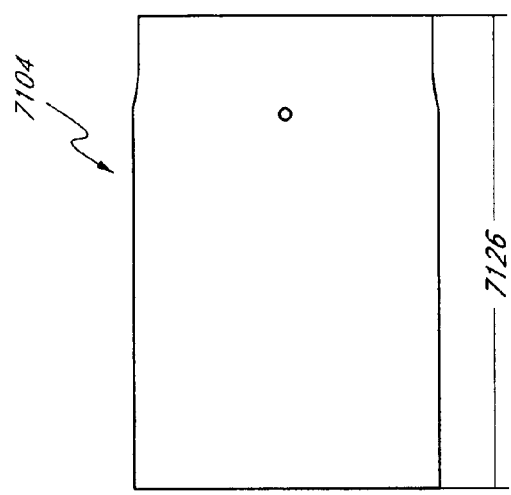
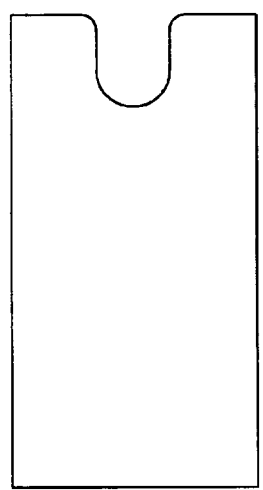
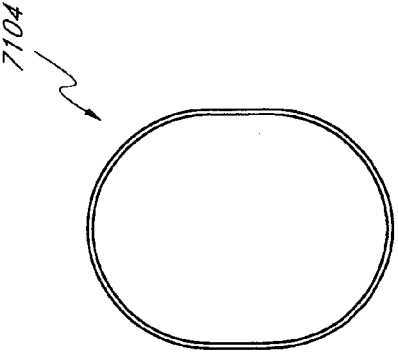

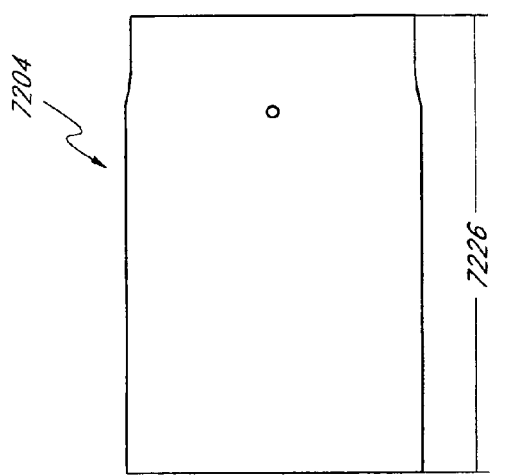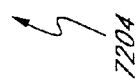

APPARATUS FOR CONNECTING A LONGITUDINAL MEMBER TO A BONE PORTION

BACKGROUND OF THE INVENTION

1. Field of the Invention

This application relates to surgical systems and assemblies that include an access device for minimally invasive surgery, and in particular relates to systems and devices that provide access to a surgical location, e.g. adjacent a spine, for one or more instruments to perform a procedure at the surgical location. More particularly, this application relates to an apparatus which can be used to retain bone portions, such as vertebrae of a spinal column, in a desired spatial relationship.

2. Description of the Related Art

An apparatus for retaining vertebrae of a spinal column in a desired spatial relationship includes a longitudinal member extendable along the spinal column. A fastener engageable with a vertebra of the spinal column connects the longitudinal member to the vertebra. A housing has a first passage through which the longitudinal member extends and a second passage with a longitudinal axis extending transverse to the first passage. The fastener extends through an opening in the housing into the second passage. The longitudinal axis of the fastener is positionable in any one of a plurality of angular positions relative to the longitudinal axis of the second passage.

A spacer received in the housing is engageable with the fastener and the longitudinal member. A clamping member threadably engages the housing to clamp the longitudinal member, the spacer, and the housing to the fastener to prevent movement of the fastener relative to the housing.

SUMMARY OF THE INVENTION

In one embodiment, polyaxial screws and apparatus comprising such screws which may be used to retain bone portions in a desired spatial relationship are provided. The apparatus includes a longitudinal member connectable with a bone portion. A fastener having a longitudinal axis is engageable with the bone portion to connect the longitudinal member to the bone portion. A housing has a first passage configured to receive the longitudinal member. The housing has a second passage with a longitudinal axis extending transverse to the first passage. The fastener extends through an opening in the housing into the second passage and is movable relative to the housing. The longitudinal axis of the fastener is positionable in any one of a plurality of angular positions relative to the longitudinal axis of the second passage.

A spacer received in the second passage of the housing is engageable with the fastener and the longitudinal member. A spring member engageable with the spacer applies a force to prevent relative movement between the fastener and the housing when the longitudinal member is disengaged from the spacer and the spacer engages the fastener. The fastener and the housing are manually movable relative to each other against the force when the longitudinal member is disengaged from the spacer and the member applies the force. The spring member is an arched ring-shaped member with diametrically opposite sides bent toward each other when the spring member is disengaged from the housing and the spacer. A clamping mechanism clamps the longitudinal member, the spacer and the housing to the fastener to prevent movement of the fastener relative to the housing.

In accordance with another embodiment, the apparatus includes a longitudinal member connectable with a bone portion. A fastener engageable with the bone portion has a longitudinal axis and connects the longitudinal member to the bone portion. A housing has a first passage through which the longitudinal member extends. The housing has a second passage with a longitudinal axis extending transverse to the first passage. The fastener extends through an opening in the housing into the second passage and is movable relative to the housing. The longitudinal axis of the fastener is positionable in any one of a plurality of angular positions relative to the longitudinal axis of the second passage. A spacer received in the second passage of the housing is engageable with the fastener and the longitudinal member. The spacer includes an axially extending portion extending from a surface engaging the fastener. The axially extending portion is spaced from the fastener. A clamping mechanism clamps the longitudinal member, the spacer, and the housing to the fastener to prevent movement of the fastener relative to the housing.

In accordance with another embodiment, an apparatus includes a longitudinal member connectable with a bone portion. A fastener engageable with the bone portion has a longitudinal axis and connects the longitudinal member to the bone portion. A housing has a first passage through which the longitudinal member extends. The housing has a radially outwardly extending surface. The radially extending surface defines a circumferentially extending groove. The housing includes a thread extending axially from an upper surface of the housing to the groove. A clamping mechanism threadably engageable with the thread on the housing clamps the longitudinal member to the housing to prevent movement of the rod relative to the housing.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 7 is a perspective view of another embodiment of an access device in an enlarged configuration.

FIG. 8 is an enlarged sectional view of the access device of FIG. 7 taken along lines 8-8 of FIG. 7.

FIG. 9 is a sectional view of the access device of FIG. 7 taken along lines 9-9 of FIG. 7.

FIG. 15 is a sectional view illustrating one embodiment of a stage of one embodiment of a method for treating the spine of a patient.

FIG. 18 is a sectional view of the expander apparatus of FIGS. 16-17 inserted into the access device of FIG. 2, which has been inserted into a patient.

FIG. 19 is a sectional view of the expander apparatus of FIGS. 16-17 inserted into the access device of FIG. 2 and expanded to the expanded configuration to retract tissue.

FIG. 20 is an exploded perspective view of one embodiment of an endoscope mount platform.

FIG. 22 is a side view of the endoscope mount platform of FIG. 20 illustrated with one embodiment of an indexing arm and one embodiment of an endoscope.

FIG. 23 is a perspective view of one embodiment of an indexing collar of the endoscope mount platform FIG. 20.

FIG. 26 is a perspective view of one embodiment of a fastener.

FIG. 27 is an exploded perspective view of the fastener of FIG. 26.

FIG. 27(a) is an enlarged side view of one embodiment of a biasing member illustrated in FIG. 27 taken from the perspective of the arrow 27a.

FIG. 28 is a perspective view of one embodiment of a surgical instrument.

FIG. 29 is an enlarged sectional view of the fastener of FIGS. 26-27 coupled with the surgical instrument of FIG. 28, illustrating one embodiment of a stage of one embodiment of a method for treating the spine of a patient.

FIG. 32 is a side view of one embodiment of another surgical instrument.

FIG. 33 is a perspective view similar to FIG. 31 illustrating the apparatuses of FIGS. 26 and 32, in one embodiment of a stage of one embodiment of a method for treating the spine of a patient.

FIG. 34 is an enlarged sectional view of the apparatus of FIGS. 26 and 32, illustrating one embodiment of a stage of one embodiment of a method for treating the spine of a patient.

FIG. 36 is an enlarged view in partial section illustrating one embodiment of a stage of one embodiment of a method for treating the spine of a patient.

FIG. 37 is a partial view of illustrating one embodiment of a stage of one embodiment of a method for treating the spine of a patient.

FIG. 52 is a side view of an apparatus according to another embodiment.

FIG. 53 is a front view of the apparatus of FIG. 52.

FIG. 63 is a side view, similar to FIG. 52, of another apparatus.

FIG. 64 is a front view, similar to FIG. 55, of the embodiment of FIG. 63.

FIG. 76 is a top view of the surgical system of FIG. 74.

FIG. 77 is a perspective view of one embodiment of a lighting element.

FIG. 78 is a perspective view of another embodiment of a lighting element.

FIG. 79 is a perspective view of another embodiment of a lighting element.

FIG. 90 is a top view of the light post mount or visualization mount of FIG. 89.

FIG. 91 is a side cross section view of the light post mount or visualization mount of FIG. 89.

FIG. 92 is a bottom view of the light post mount or visualization mount of FIG. 89.

FIG. 93 is a side view of a support portion of the light post mount or visualization mount of FIG. 89.

FIG. 94 is a schematic view of the cross section of a passage of the light post mount or visualization mount of FIG. 89.

FIG. 98 is a top view of a light post or visualization element, according to one embodiment.

FIG. 99 is a side view of the light post or visualization element of FIG. 98.

FIG. 108 is a top view of an indexing collar assembly, having an indexing collar, according to one embodiment.

FIG. 109 is a side view of the indexing collar assembly of FIG. 108.

FIG. 116 is a bottom view of the indexing collar of FIG. 108.

FIG. 117 illustrates a portion of the indexing collar of FIG. 108.

FIG. 118 is a bottom perspective view of the indexing collar of FIG. 108.

FIG. 119 is a top perspective view of the indexing collar of FIG. 108.

FIG. 120 is a side view of an oval or oblong shaped dilator, according to one embodiment.

FIG. 121 is an end view of the dilator of FIG. 120.

FIG. 122 is another side view of the dilator of FIG. 120.

FIG. 123 is a side view of an access device assembly in a low profile configuration, according to one embodiment.

FIG. 124 is a front view of the access device assembly of FIG. 123.

FIG. 125 is a top view of the access device assembly of FIG. 123 in an expanded configuration.

FIG. 126 is a front view of the access device assembly of FIG. 123 in an expanded configuration.

FIG. 127 is a cross section view of a lock coupling location of the access device assembly of FIG. 123, taken along section plane 127-127.

Figure 123:
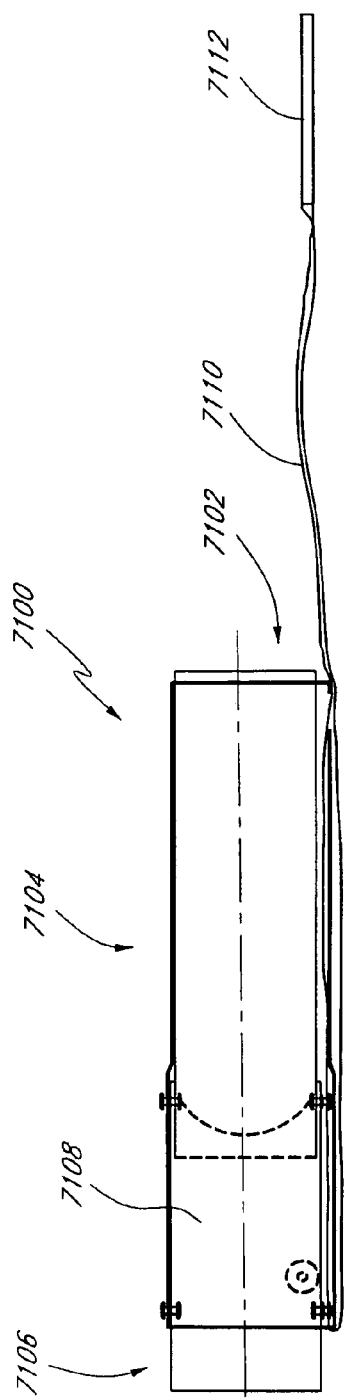

FIG. 128 is a cross section view of a skirt coupling location of the access device assembly of FIG. 123, taken along section plane 128-128.

Figure 129:
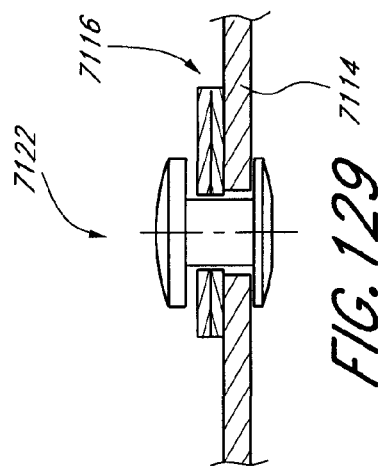

FIG. 129 is a cross section view of a proximal portion coupling location of the access device assembly of FIG. 123, taken along section plane 129-129.

FIG. 130 is a top view of a proximal portion of the access device of FIG. 123.

FIG. 131 is a front view of the proximal portion of the access device of FIG. 123.

FIG. 132 is a side view of the proximal portion of the access device of FIG. 123.

Figure 133:
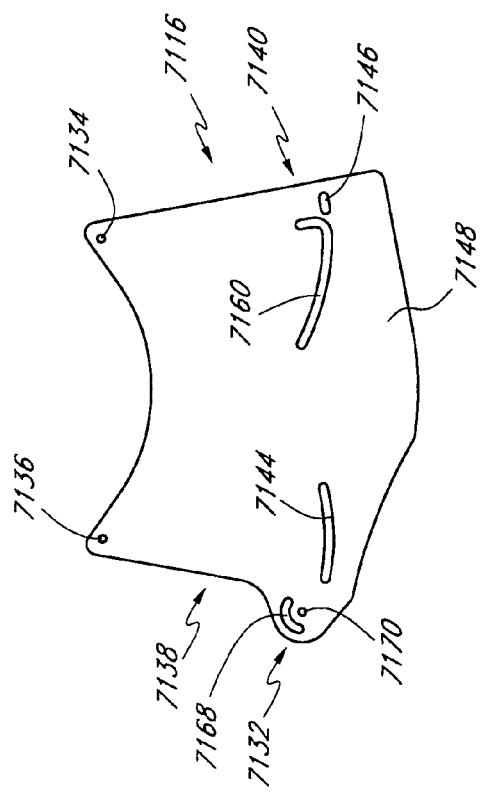

FIG. 133 illustrates a first locking skirt portion of a distal portion of the access device of FIG. 123.

Figure 134:
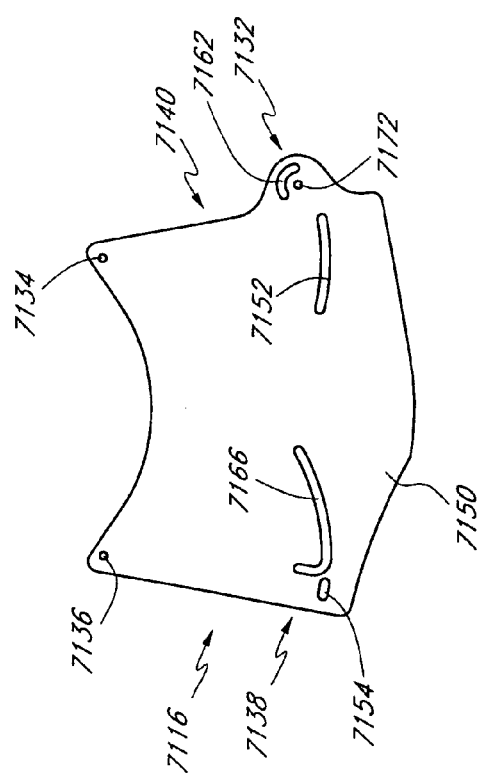

FIG. 134 illustrates a second locking skirt portion of the distal portion of the access device of FIG. 123.

Figure 135:
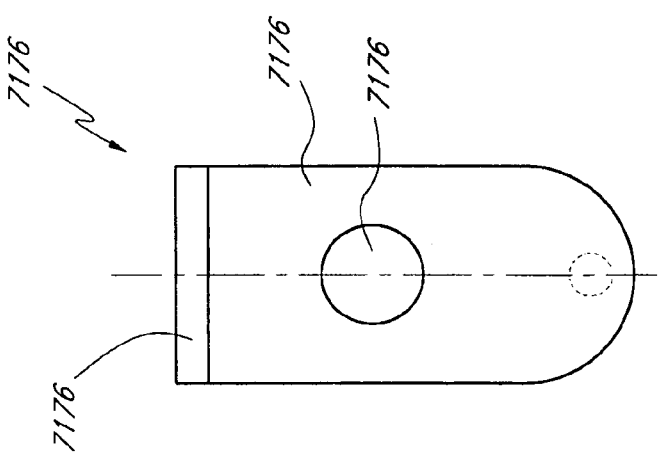

FIG. 135 is a side view of a locking element of the access device of FIG. 123.

Figure 136:
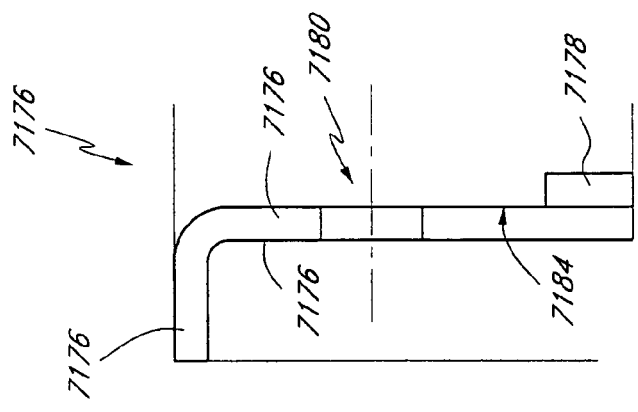

FIG. 136 is a side view of a locking element of the access device of FIG. 123.

Figure 137:
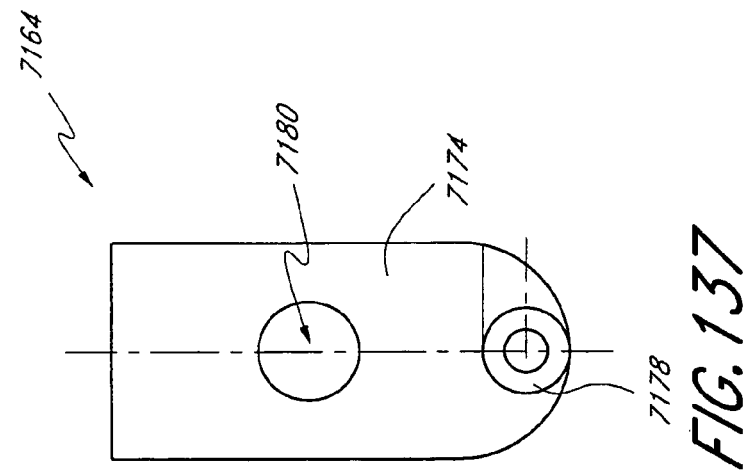

FIG. 137 is a side view of a locking element of the access device of FIG. 123.

Figure 138:
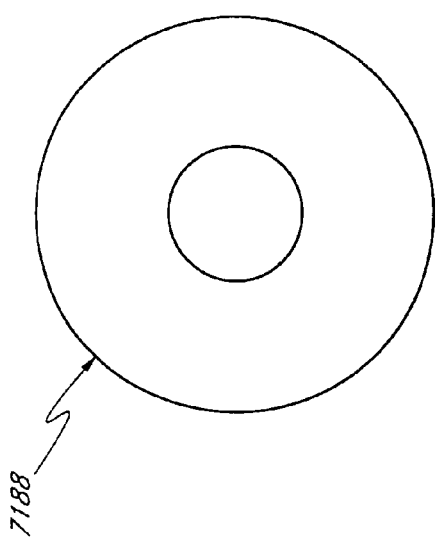

FIG. 138 illustrates a friction washer of the access device of FIG. 123.

Figure 139:
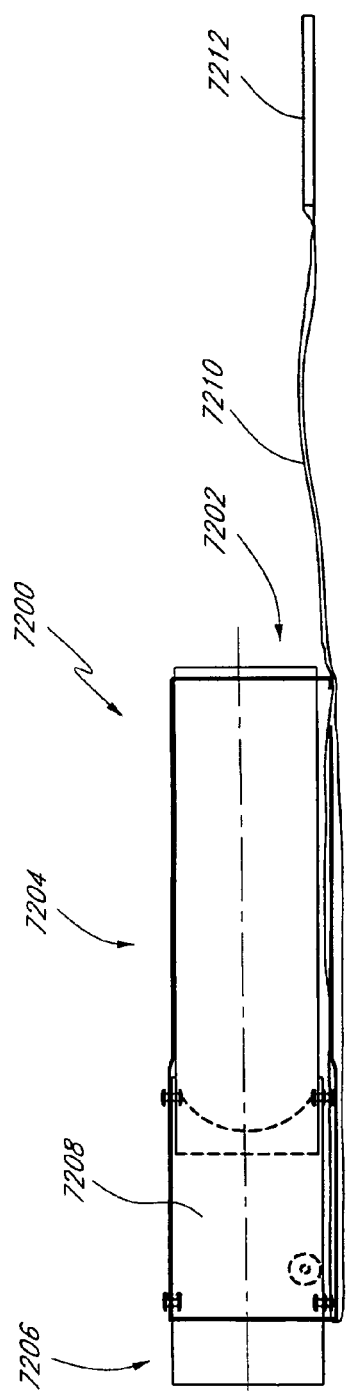

FIG. 139 is a side view of an access device assembly in a low profile configuration, according to another embodiment.

Figure 140:
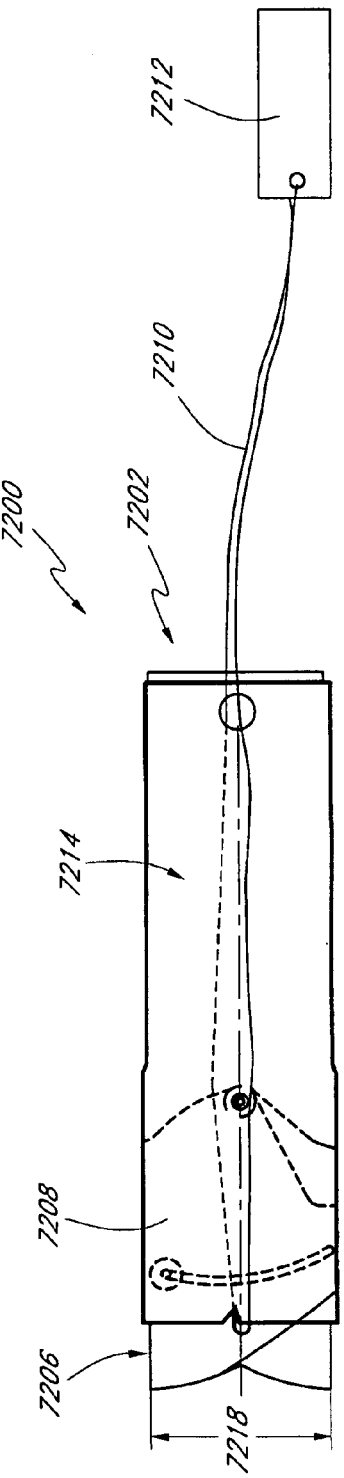

FIG. 140 is a front view of the access device assembly of FIG. 139.

Figure 141:
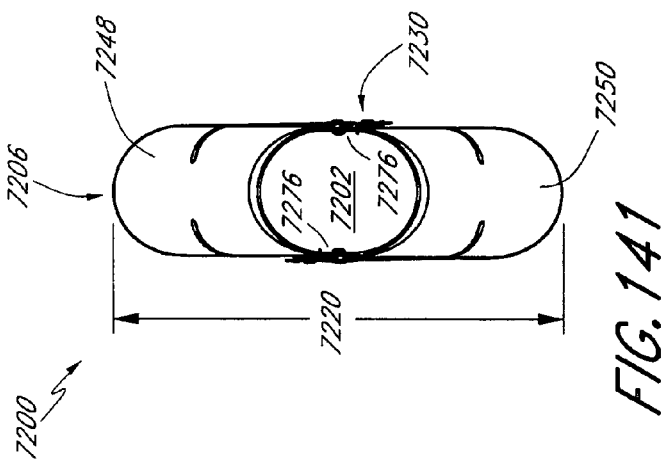

FIG. 141 is a top view of the access device assembly of FIG. 139 in an expanded configuration.

Figure 142:
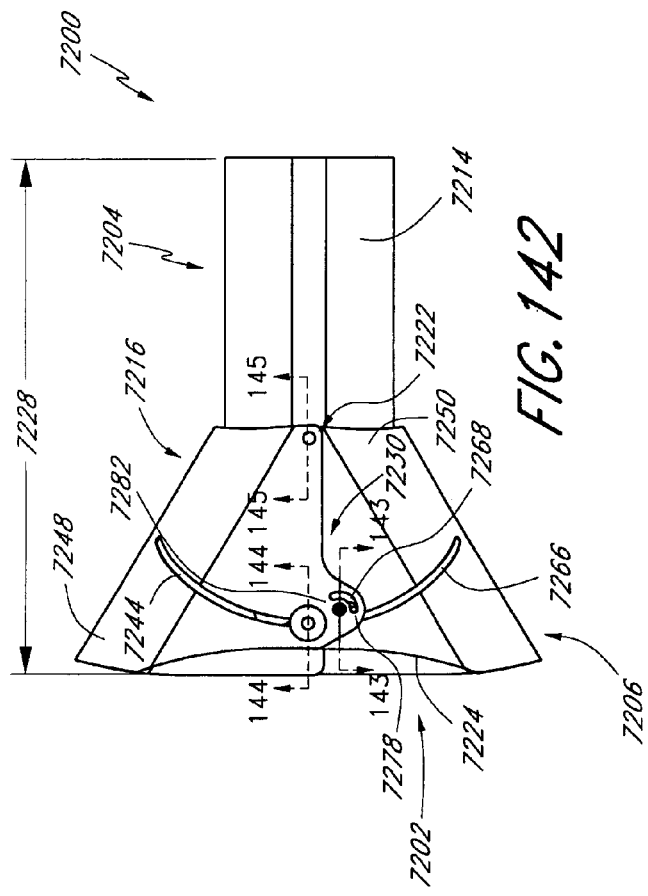

FIG. 142 is a front view of the access device assembly of FIG. 139 in an expanded configuration.

Figure 143:
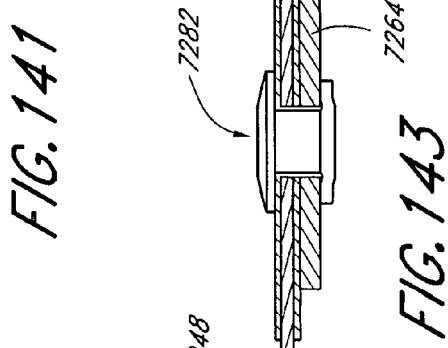

FIG. 143 is a cross section view of a lock coupling location of the access device assembly of FIG. 139, taken along section plane 143-143.

Figure 144:
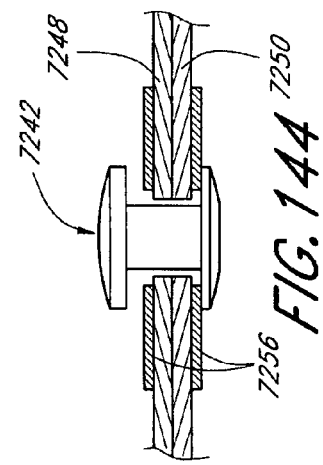

FIG. 144 is a cross section view of a skirt coupling location of the access device assembly of FIG. 139, taken along section plane 144-144.

Figure 145:
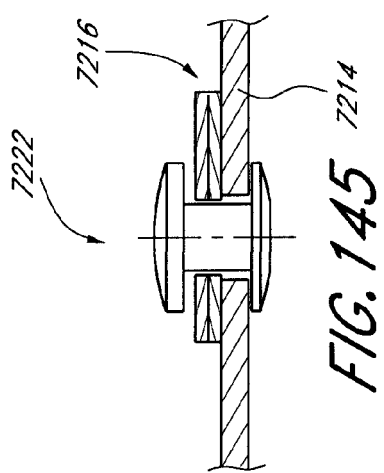

FIG. 145 is a cross section view of a proximal portion coupling location of the access device assembly of FIG. 139, taken along section plane 145-145.

FIG. 146 is a top view of a proximal portion of the access device of FIG. 139.

FIG. 147 is a front view of the proximal portion of the access device of FIG. 139.

FIG. 148 is a side view of the proximal portion of the access device of FIG. 139.

Figure 149:
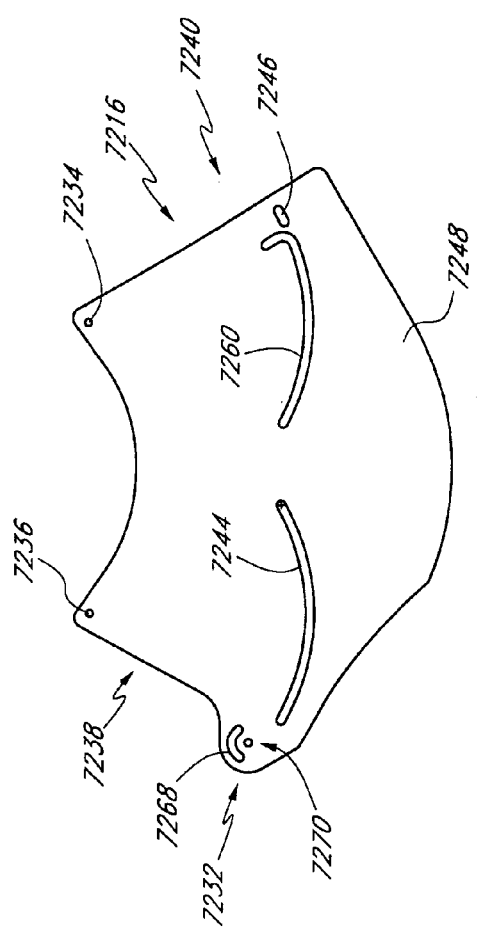

FIG. 149 illustrates a first locking skirt portion of a distal portion of the access device of FIG. 139.

Figure 150:
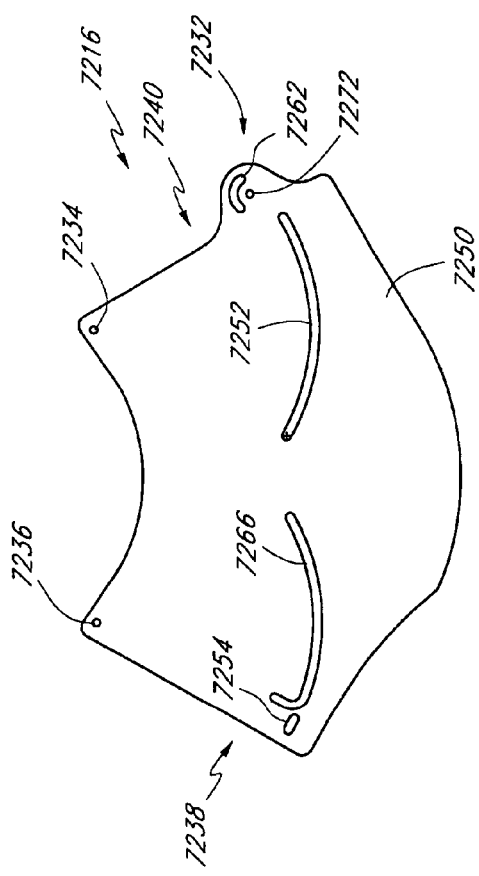

FIG. 150 illustrates a second locking skirt portion of the distal portion of the access device of FIG. 139.

Figure 151:
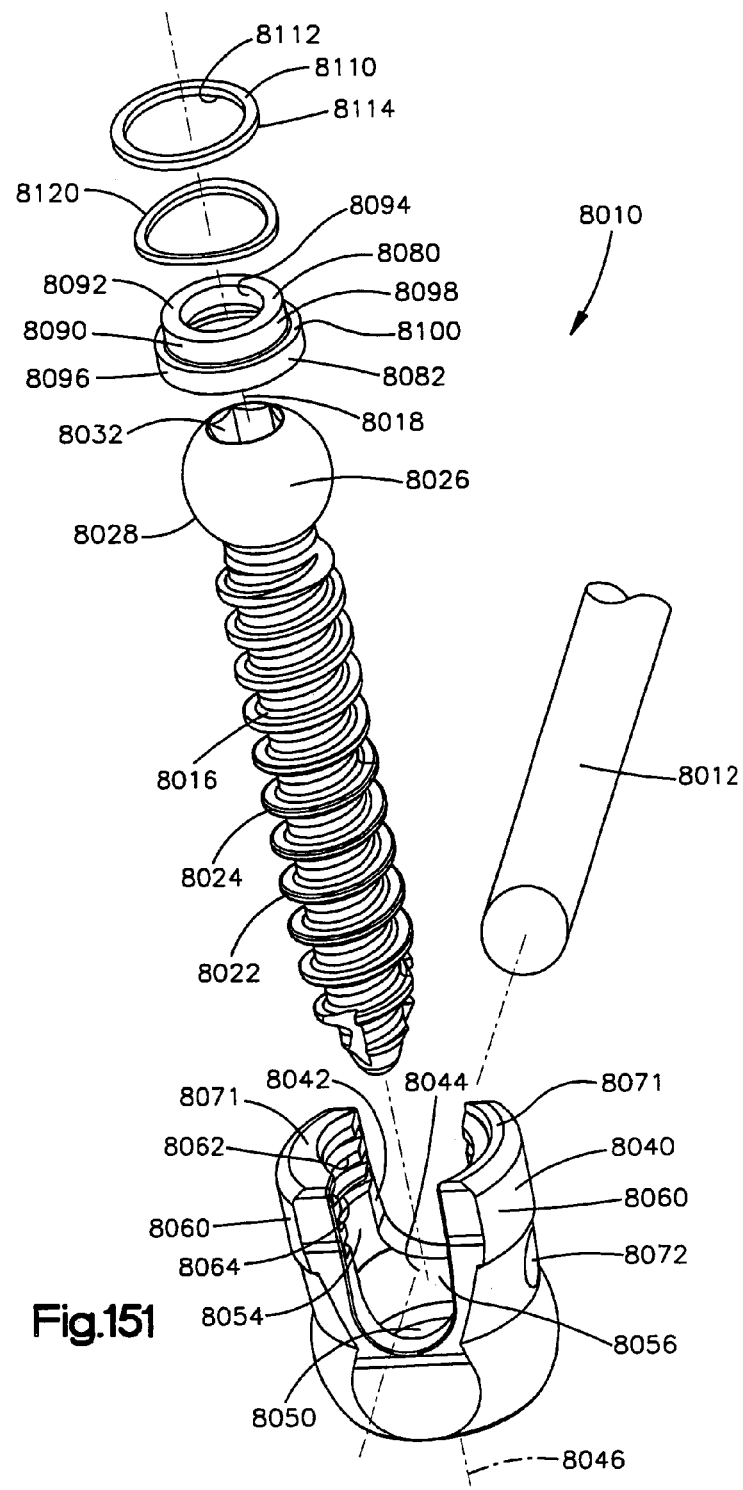

FIG. 151 is an exploded view of a portion of an apparatus constructed in accordance with one embodiment.

Figure 152:
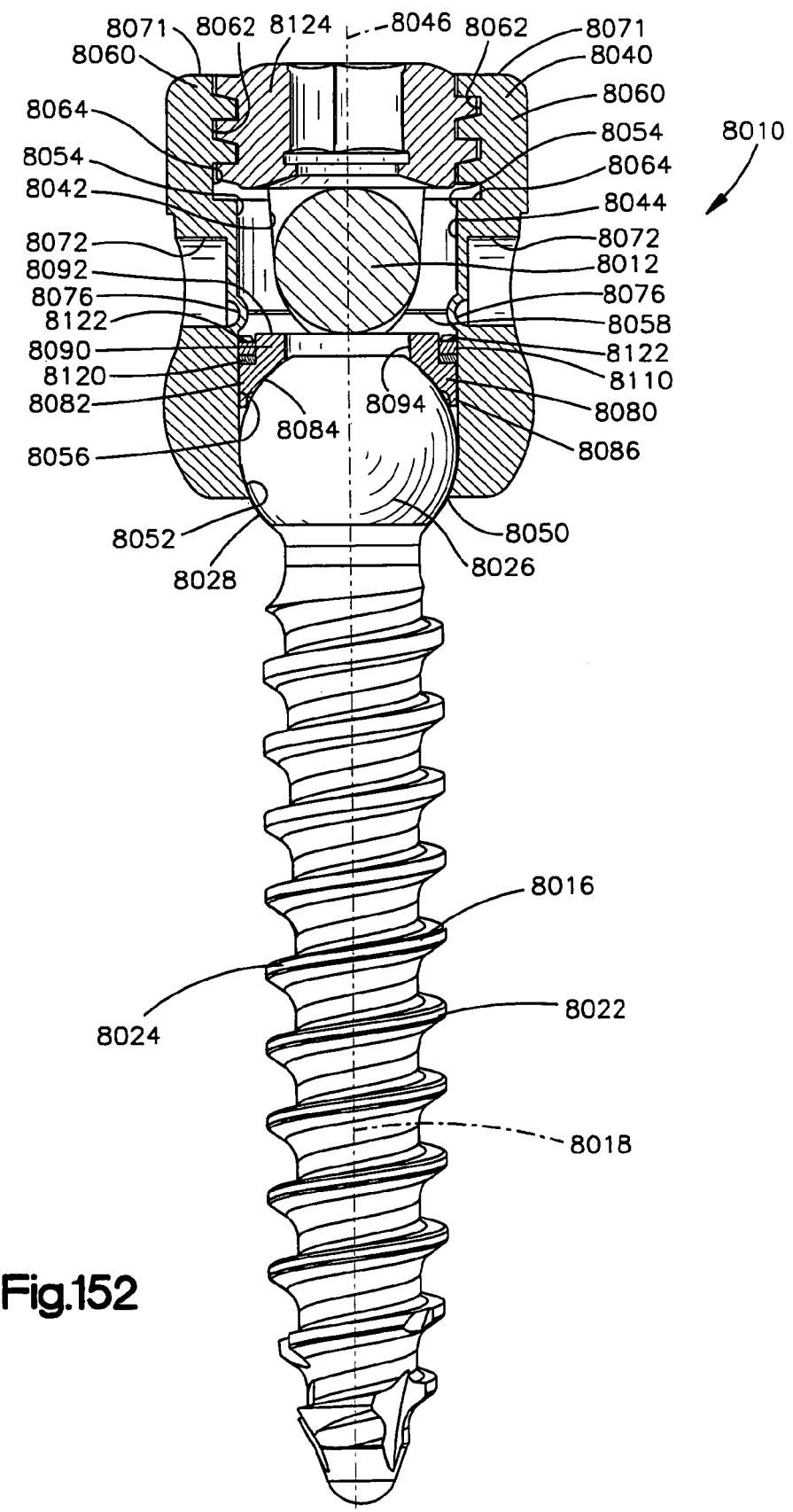

FIG. 152 is a sectional view of the apparatus of FIG. 151.

Figure 153:
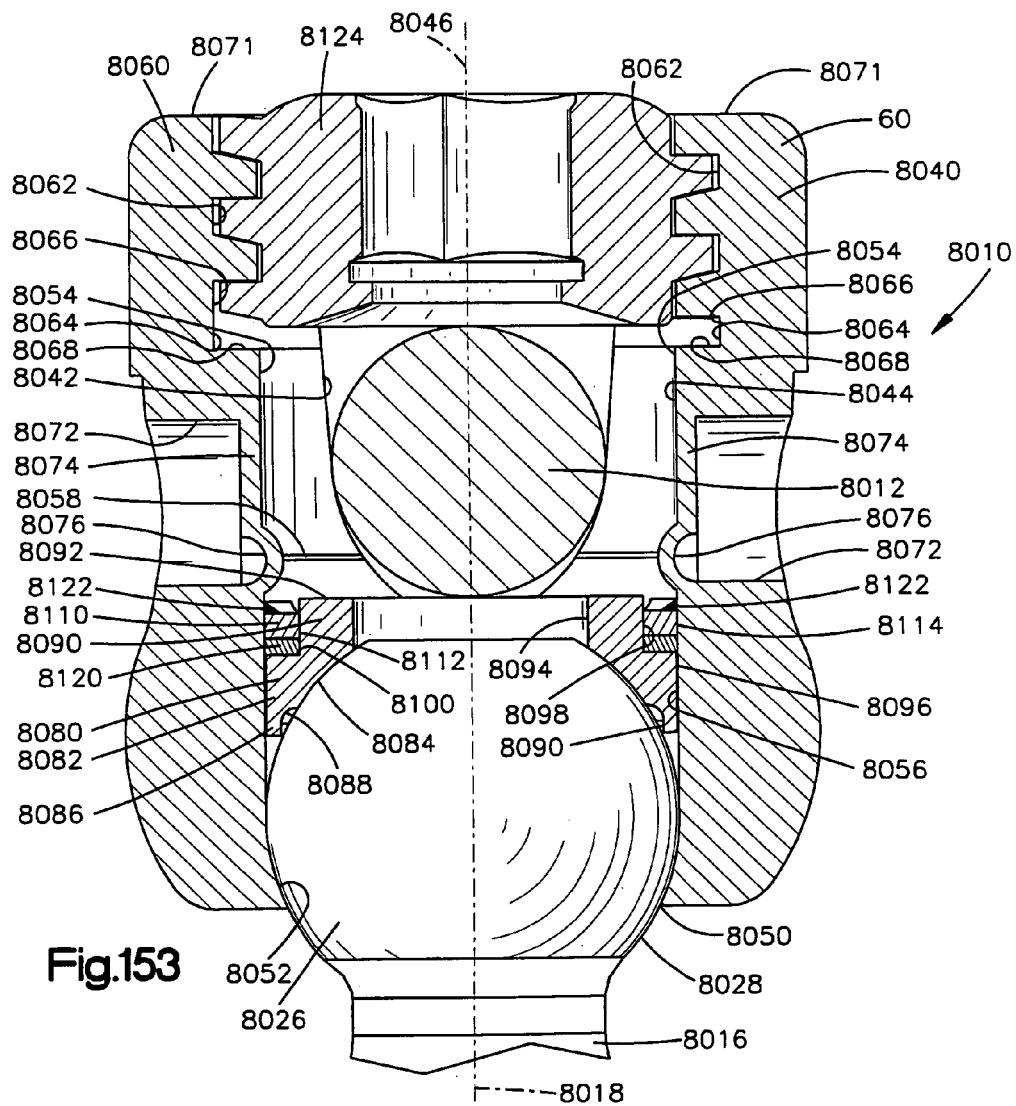

FIG. 153 is an enlarged sectional view of a portion of the apparatus of FIG. 151.

Figure 154:
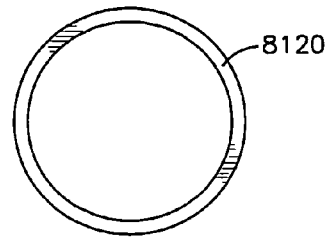

FIG. 154 is a plan view of a spring member of the apparatus of FIG. 151.

Figure 155:

FIG. 155 is a side view of the spring member of FIG. 154.

DETAILED DESCRIPTION OF THE PREFERRED EMBODIMENTS

As should be understood in view of the following detailed description, this application is primarily directed to, though not necessarily limited to, apparatuses and methods for treating the spine of a patient through an access device. More particularly, the systems described below provide access to surgical locations at or near the spine and provide a variety of tools useful in performing treatment of the spine. Also, the systems described herein enable a surgeon to perform a wide variety of methods as described herein. Some of the methods disclosed and enabled by the systems disclosed herein use an apparatus for retaining bone portions, such as vertebrae of a spinal column, in a desired spatial relationship. Apparatuses for retaining bone portions are described in more detail below in connection with FIGS. 26-37 and FIGS. 151-155.

I. Systems for Performing Procedures at a Surgical Location

Various embodiments of apparatuses and procedures described herein will be discussed in terms of minimally invasive procedures and apparatuses, e.g., of endoscopic apparatuses and procedures. However, many aspects of the present invention may find use in conventional, open, and mini-open procedures. As used herein, the term "proximal," as is traditional, refers to the end portion of the apparatus that is closest to the operator, while the term "distal" refers to the end portion that is farthest from the operator.

Figure 1:
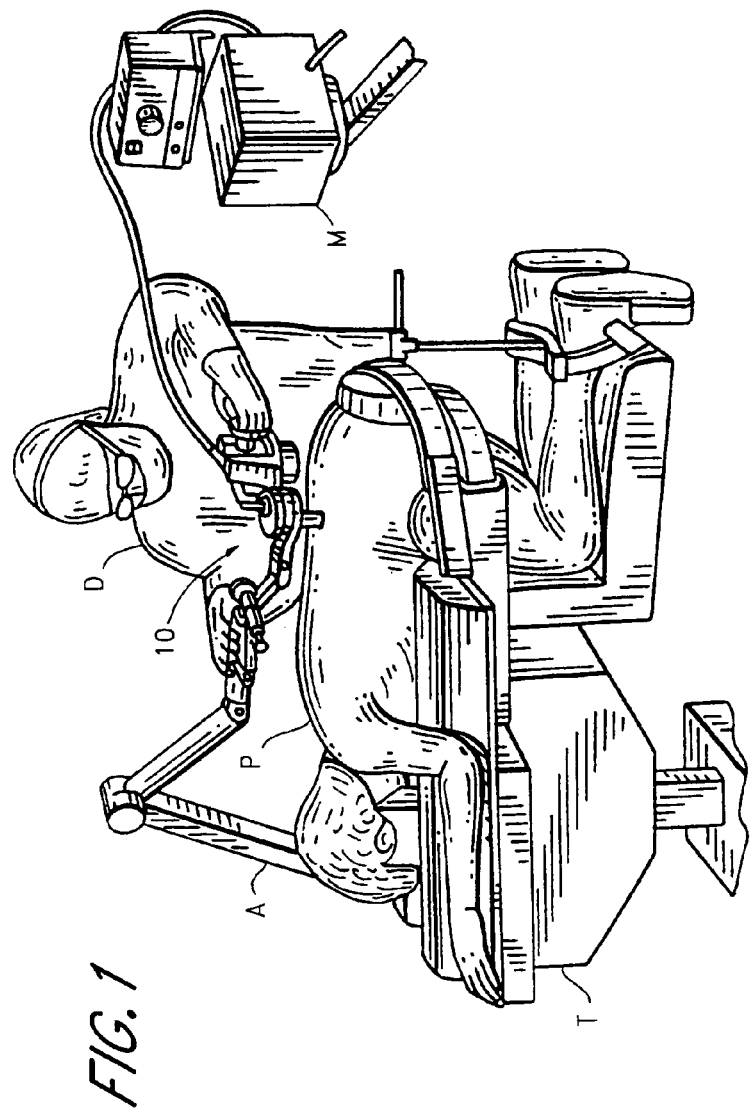
FIG. 1 is a perspective view of one embodiment of a surgical system and one embodiment of a method for treating the spine of a patient.
Figure 2:
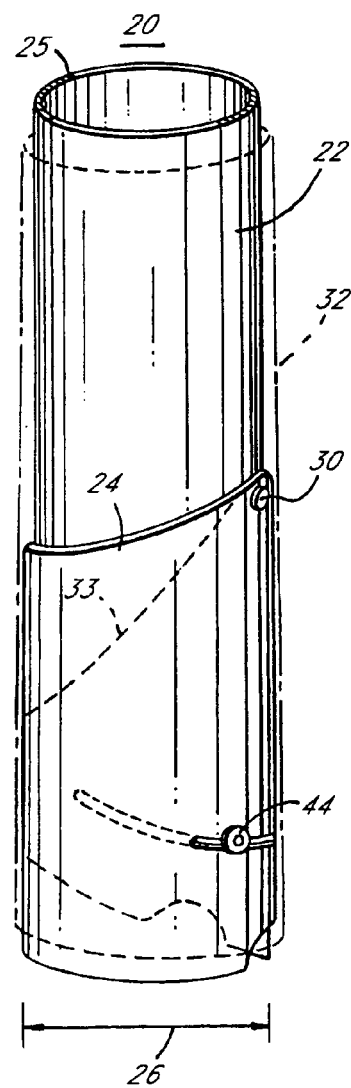
FIG. 2 is a perspective view of one embodiment of an access device in a reduced profile configuration.

FIG. 1 shows one embodiment of a surgical system 10 that can be used to perform a variety of methods or procedures. In one embodiment, as discussed more fully below, the patient P is placed in the prone position on operating table T, taking care that the abdomen is not compressed and physiological lordosis is preserved. The physician D is able to access the surgical site and perform the surgical procedure with the components of the system 10, which will be described in greater detail herein. The system 10 may be supported, in part, by a mechanical support arm A, such as the type generally disclosed in U.S. Pat. No. 4,863,133, which is hereby incorporated by reference herein in its entirety. One mechanical arm of this type is manufactured by Leonard Medical, Inc., 1464 Holcomb Road, Huntington Valley, Pa., 19006.

Visualization of the surgical site may be achieved in any suitable manner, e.g., by use of a viewing element, such as an endoscope, a camera, loupes, a microscope, direct visualization, or any other suitable viewing element, or a combination of the foregoing. In one embodiment, the viewing element provides a video signal representing images, such as images of the surgical site, to a monitor M. The viewing element may be an endoscope and camera that captures images to be displayed on the monitor M whereby the physician D is able to view the surgical site as the procedure is being performed. The endoscope and camera will be described in greater detail herein.

The systems are described herein in connection with minimally invasive postero-lateral spinal surgery. One such procedure is a two level postero-lateral fixation and fusion of the spine involving the L4, L5, and S1 vertebrae. In the drawings, the vertebrae will generally be denoted by reference letter V. The usefulness of the apparatuses and procedures is neither restricted to the postero-lateral approach nor to the L4, L5, and S1 vertebrae. The apparatuses and procedures may be used in other anatomical approaches and with other vertebra (e) within the cervical, thoracic, and lumbar regions of the spine. The procedures may be directed toward surgery involving one or more vertebral levels. Some embodiments are useful for anterior and/or lateral procedures. Moreover, it is believed that embodiments of the invention are also particularly useful where any body structures must be accessed beneath the skin and muscle tissue of the patient, and/or where it is desirable to provide sufficient space and visibility in order to manipulate surgical instruments and treat the underlying body structures. For example, certain features or instrumentation described herein are particularly useful for minimally invasive procedures, e.g., arthroscopic procedures. As discussed more fully below, one embodiment of an apparatus described herein provides an access device that has an expandable distal portion. In addition to providing greater access to a surgical site than would be provided with device having a constant cross-section, the expandable distal portion prevents or substantially prevents the access device, or instruments extended therethrough to the surgical site, from dislodging or popping out of the operative site.

In one embodiment, the system 10 includes an access device that provides an internal passage for surgical instruments to be inserted through the skin and muscle tissue of the patient P to the surgical site. The term "access device" is used in its ordinary sense to mean a device that can provide access and is a broad term and it includes structures having an elongated dimension and defining a passage, e.g., a cannula or a conduit. The access device is configured to be inserted through the skin of the patient to provide access during a surgical procedure to a surgical location within a patient, e.g., a spinal location. The term "surgical location" is used in its ordinary sense (i.e. a location where a surgical procedure is performed) and is a broad term and it includes locations subject to or affected by a surgery. The term "spinal location" is used in its ordinary sense (i.e. a location at or near a spine) and is a broad term and it includes locations adjacent to or associated with a spine that may be sites for surgical spinal procedures. The access device also can retract tissue to provide greater access to the surgical location.

The access device preferably has a wall portion defining a reduced profile configuration for initial percutaneous insertion into the patient. This wall portion may have any suitable arrangement. In one embodiment, discussed in more detail below, the wall portion has a generally tubular configuration that may be passed over a dilator that has been inserted into the patient to atraumatically enlarge an opening sufficiently large to receive the access device therein.

The wall portion of the access device preferably can be subsequently expanded to an enlarged configuration, by moving against the surrounding muscle tissue to at least partially define an enlarged surgical space in which the surgical procedures will be performed. In a sense, it acts as its own dilator. The access device may also be thought of as a retractor, and may be referred to herein as such. Both the distal and proximal portion may be expanded, as discussed further below. However, the distal portion preferably expands to a greater extent than the proximal portion, because the surgical procedures are to be performed at the surgical site, which is adjacent the distal portion when the access device is inserted into the patient.

While in the reduced profile configuration, the access device preferably defines a first unexpanded configuration. Thereafter, the access device can enlarge the surgical space defined thereby by engaging the tissue surrounding the access device and displacing the tissue outwardly as the access device expands. The access device preferably is sufficiently rigid to displace such tissue during the expansion thereof. The access device may be resiliently biased to expand from the reduced profile configuration to the enlarged configuration. In addition, the access device may also be manually expanded by an expander device with or without one or more surgical instruments inserted therein, as will be described below. The surgical site preferably is at least partially defined by the expanded access device itself. During expansion, the access device can move from a first overlapping configuration to a second overlapping configuration.

In some embodiments, the proximal and distal portions are separate components that may be coupled together in a suitable fashion. For example, the distal end portion of the access device may be configured for relative movement with respect to the proximal end portion in order to allow the physician to position the distal end portion at a desired location. This relative movement also provides the advantage that the proximal portion of the access device nearest the physician D may remain substantially stable during such distal movement. In one embodiment, the distal portion is a separate component that is pivotally or movably coupled with the proximal portion. In another embodiment, the distal portion is flexible or resilient in order to permit such relative movement.

A. Systems and Devices for Establishing Access

1. Access Devices

One embodiment of an access device is illustrated in FIGS. 2-6 and designated by reference number 20. In one embodiment, the access device 20 includes a proximal wall portion 22 that has a tubular configuration, and a distal wall portion that has an expandable skirt portion 24. The skirt portion 24 preferably is enlargeable from a reduced profile configuration having an initial dimension 26 (illustrated in FIG. 2) and corresponding cross-sectional area, to an enlarged configuration having a second dimension 28 (illustrated in FIG. 4) and corresponding cross-sectional area. In one embodiment, the skirt portion 24 is coupled with the proximal wall portion 22 with a rivet 30, pin, or similar connecting device to permit movement of the skirt portion 24 relative to the proximal wall portion 22.

Figure 3:
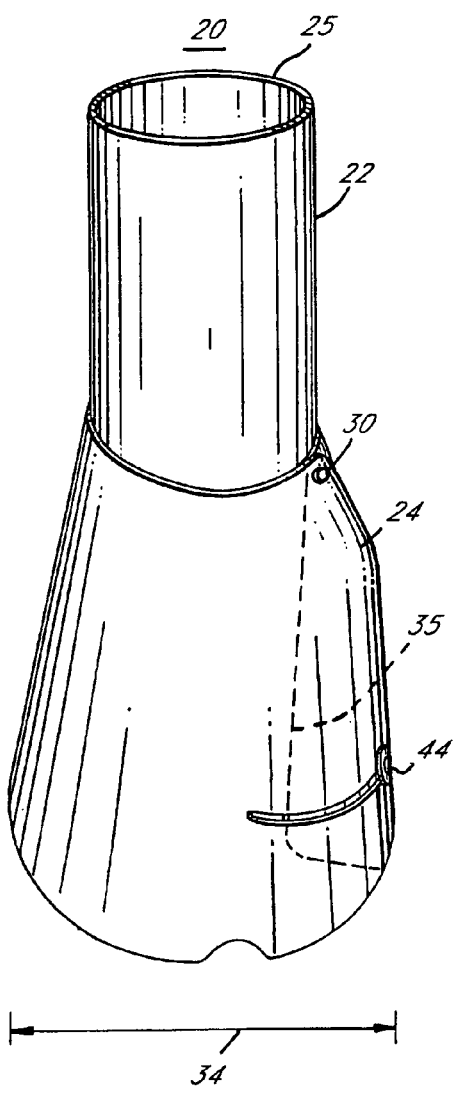
FIG. 3 is a perspective view of the access device of FIG. 2 in a first enlarged configuration.
Figure 4:
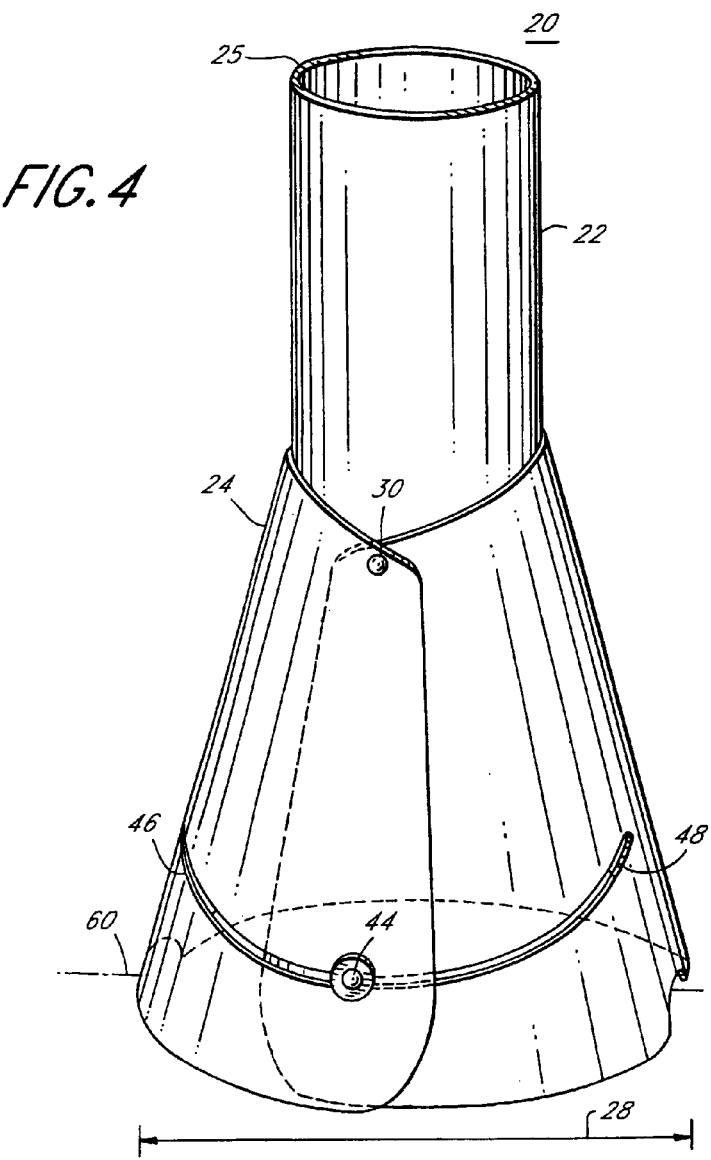
FIG. 4 is a perspective view of the access device of FIG. 2 in a second enlarged configuration.
Figure 6:
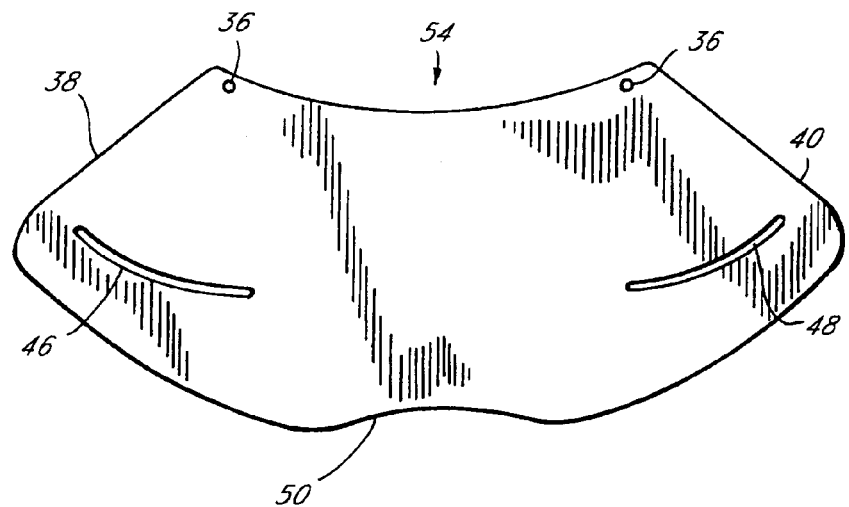
FIG. 6 is a view of another embodiment of a skirt portion of an access device.

In the illustrated embodiment, the skirt portion 24 is manufactured from a resilient material, such as stainless steel. The skirt portion 24 preferably is manufactured so that it normally assumes an expanded configuration as illustrated in FIG. 4. With reference to FIG. 3, the skirt portion 24 may assume an intermediate dimension 34 and corresponding cross-sectional area, which is greater than the initial dimension 26 of the reduced profile configuration of FIG. 2, and smaller than the dimension 28 of the enlarged configuration of FIG. 4. The skirt portion 24 may assume the intermediate configuration of FIG. 3 when deployed in the patient in response to the force of the tissue acting on the skirt portion 24. The intermediate dimension 34 can depend upon several factors, such as the rigidity of the skirt portion 24, the surrounding tissue, and whether such surrounding tissue has relaxed or tightened during the course of the procedure. An outer sleeve 32 (illustrated in dashed line in FIG. 2) may be provided. Preferably, the outer sleeve surrounds the access device 20 and maintains the skirt portion 24 in the reduced profile configuration prior to insertion into the patient. The outer sleeve 32 may be made of plastic. Where provided, the outer sleeve 32 preferably is configured to be easily deployed. For example, a release device may be provided that releases or removes the outer sleeve 32 upon being operated by the user. In one embodiment, a braided polyester suture is embedded within the sleeve 32, aligned substantially along the longitudinal axis thereof. In use, when the suture is withdrawn, the outer sleeve 32 is torn, allowing the access device 20 to resiliently expand from the reduced profile configuration of FIG. 2 to the expanded configurations of FIGS. 3-4. While in the reduced profile configuration of FIG. 2, the skirt portion 24 defines a first overlapping configuration 33, as illustrated by the dashed line. As the skirt portion 24 resiliently expands, the skirt portion 24 assumes the expanded configuration, as illustrated in FIGS. 3-4.

The skirt portion 24 preferably is sufficiently rigid that it is capable of displacing the tissue surrounding the skirt portion 24 as it expands. Depending upon the resistance exerted by surrounding tissue, the skirt portion 24 preferably is sufficiently rigid to provide some resistance against the tissue to remain in the configurations of FIGS. 3-4. Moreover, the expanded configuration of the skirt portion 24 is at least partially supported by the body tissue of the patient. The rigidity of the skirt portion 24 and the greater expansion at the distal portion preferably creates a stable configuration that is at least temporarily stationary in the patient. This arrangement preferably frees the physician from the need to actively support the access device 20, e.g., prior to adding an endoscope mount platform 300 and a support arm 400 (see FIGS. 21-22).

Figure 5:
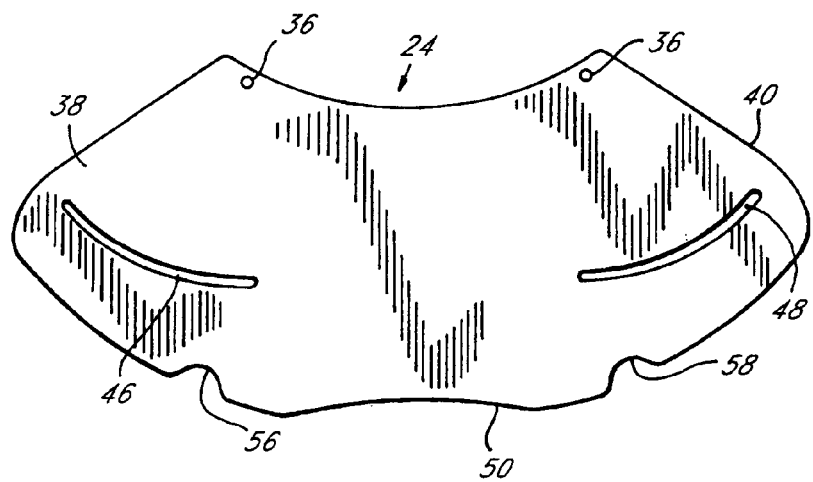
FIG. 5 is a view of one embodiment of a skirt portion of an access device.

One embodiment of the skirt portion 24 of the access device 20 is illustrated in an initial flattened configuration in FIG. 5. The skirt portion 24 may be manufactured from a sheet of stainless steel having a thickness of about 0.007 inches (0.178 mm). In various embodiments, the dimension 28 of the skirt portion 24 is about equal to or greater than 50 mm, is about equal to or greater than 60 mm, is about equal to or greater than 70 mm, is about equal to or greater than 80 mm, or is any other suitable size, when the skirt portion 24 is in the enlarged configuration. In one embodiment, the dimension 28 is about 63 mm, when the skirt portion 24 is in the enlarged configuration. The unrestricted shape of the skirt portion 24 is a circular shape in one embodiment and is an oblong shape in another embodiment. In another embodiment, the skirt portion 24 has an oval shape, wherein the dimension 28 defines a longer dimension of the skirt portion 24 and would be about 85 mm. In another embodiment, the skirt portion 24 has an oval shape and the dimension 28 defines a longer dimension of the skirt portion 24 of about 63 mm. An increased thickness, e.g., about 0.010 inches (0.254 mm), may be used in connection with skirt portions having a larger diameter, such as about 65 mm. Other materials, such as nitinol or plastics having similar properties, may also be useful.

As discussed above, the skirt portion 24 preferably is coupled with the proximal wall portion 22 with a pivotal connection, such as rivet 30. A pair of rivet holes 36 can be provided in the skirt portion 24 to receive the rivet 30. The skirt portion 24 also has two free ends 38 and 40 in one embodiment that are secured by a slidable connection, such as a second rivet 44 (not shown in FIG. 5, illustrated in FIGS. 2-4). A pair of complementary slots 46 and 48 preferably are defined in the skirt portion 24 adjacent the free ends 38 and 40. The rivet 44 is permitted to move freely within the slots 46 and 48. This slot and rivet configuration allows the skirt portion 24 to move between the reduced profile configuration of FIG. 2 and the enlarged or expanded configurations of FIGS. 3-4. The use of a pair of slots 46 and 48 reduces the risk of the "button-holing" of the rivet 44, e.g., a situation in which the opening of the slot becomes distorted and enlarged such that the rivet may slide out of the slot, and cause failure of the device. The likelihood of such occurrence is reduced in skirt portion 24 because each of the slots 46 and 48 in the double slot configuration has a relatively shorter length than a single slot configuration. Being shorter, the slots 46, 48 are less likely to be distorted to the extent that a rivet may slide out of position. In addition, the configuration of rivet 44 and slots 46 and 48 permits a smoother operation of enlarging and reducing the skirt portion 24, and allows the skirt portion 24 to expand to span three or more vertebrae, e.g., L4, L5, and S1. This arrangement enables multi-level procedures, such as multilevel fixation procedures alone or in combination with a variety of other procedures, as discussed below. Other embodiments include a single slot rather than the slots 46, 48, or more than two slots.

An additional feature of the skirt portion 24 is the provision of a shallow concave profile 50 defined along the distal edge of the skirt portion 24, which allows for improved placement of the skirt portion 24 with respect to the body structures and the surgical instruments defined herein. In one embodiment, a pair of small scalloped or notched portions 56 and 58 are provided, as illustrated in FIG. 5. When the skirt portion 24 is assembled, the notched portions 56 and 58 are generally across from each other. When the skirt portion 24 is applied to a patient, the notched portions 56, 58 are oriented in the ceph-caudal direction (indicated by a dashed line 60 in FIG. 4). In this arrangement, instruments and implants, such as an elongated member 650 used in a fixation procedure (described in detail below), may extend beyond the area enclosed by the skirt portion 24 without moving or raising the skirt portion 24, e.g., by allowing the elongated member 650 (or other implant or instrument) to pass under the skirt portion 24. The notched portions 56, 58 also enable the elongated member 650 (or other implant or instrument) to extend beyond the portion of the surgical space defined within the outline of the distal end of the skirt portion 24. The notched portions 56, 58 are optional, as illustrated in connection with another embodiment of an access device 54, illustrated in FIG. 6, and may be eliminated if, for example, the physician deems the notches to be unnecessary for the procedures to be performed. For example, in some fixation procedures such extended access is not needed, as discussed more fully below. As illustrated in FIG. 4, the skirt portion 24 may be expanded to a substantially conical configuration having a substantially circular or elliptical profile.

Furthermore, it is contemplated that the skirt portion 24 of the access device 20 can include a stop that retains the skirt portion in an expanded configuration, as shown in U.S. patent application Ser. No. 10/361,887, filed Feb. 10, 2003, now U.S. Application Patent Publication No. US2003/153927A1, which is hereby incorporated by reference in its entirety herein.

In another embodiment, features may be provided on the skirt portion 24 which facilitate the bending of the skirt portion at several locations to provide a pre-formed enlarged configuration. For example, another embodiment of an access device 70, illustrated in FIGS. 7-9, provides a skirt portion 74 that has four sections 76a, 76b, 76c, 76d having a reduced thickness. For a skirt portion 74 having a thickness 78 of about 0.007 inches (0.178 mm), reduced thickness sections 76a, 76b, 76c, 76d may have a thickness 80 of about 0.002-0.004 inches (0.102 mm) (FIG. 8). The reduced thickness sections 76a, 76b, 76c, 76d may have a width 82 of about 1-5 mm. The thickness 78 of the skirt portion 74 may be reduced by milling or grinding, as is known in the art. When the skirt portion 74 is opened, it moves toward a substantially rectangular configuration, as shown in FIG. 9, subject to the resisting forces of the body tissue. In another embodiment (not shown), a skirt portion may be provided with two reduced thickness sections (rather than the four reduced thickness sections of skirt 74) which would produce an oblong, substantially "football"-shaped access area.

Figure 10:
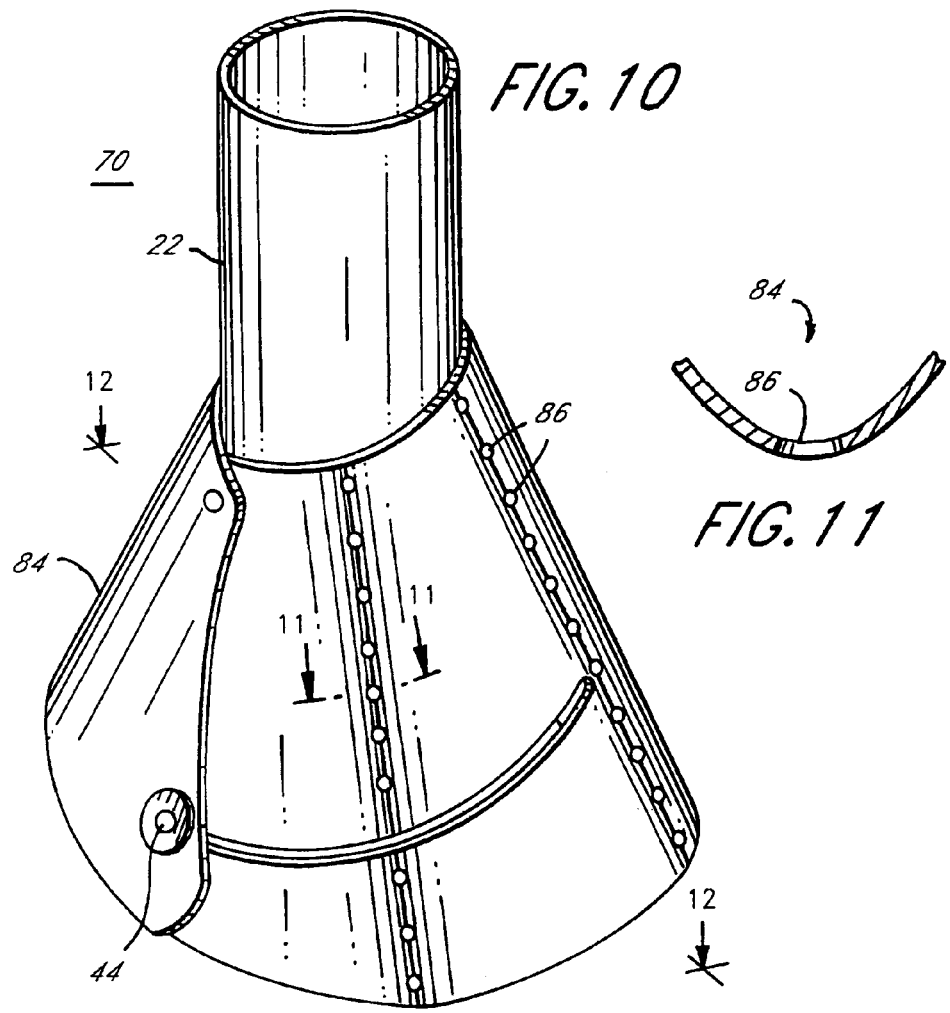
FIG. 10 is a perspective view of another embodiment of an access device in an enlarged configuration.
Figure 11:
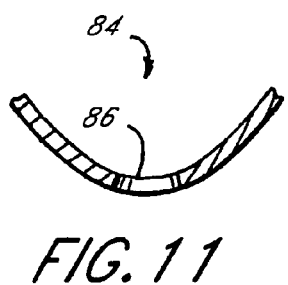
FIG. 11 is an enlarged sectional view of the access device of FIG. 10 taken along lines 11-11 of FIG. 10.
Figure 12:
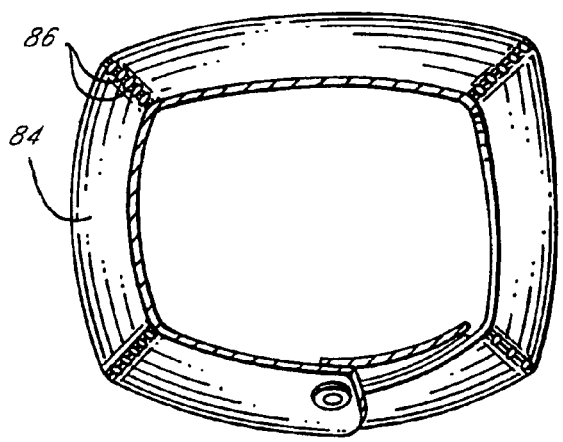
FIG. 12 is a sectional view of the access device of FIG. 10 taken along lines 12-12 of FIG. 10.

FIGS. 10-12 show another embodiment of an access device 80. The access device 80 has a skirt portion 84 with a plurality of perforations 86. The perforations 86 advantageously increase the flexibility at selected locations. The size and number of perforations 86 may vary depending upon the desired flexibility and durability. In another embodiment, the skirt portion 84 may be scored or otherwise provided with a groove or rib in order to facilitate the bending of the skirt portion at the desired location.

Figure 13:
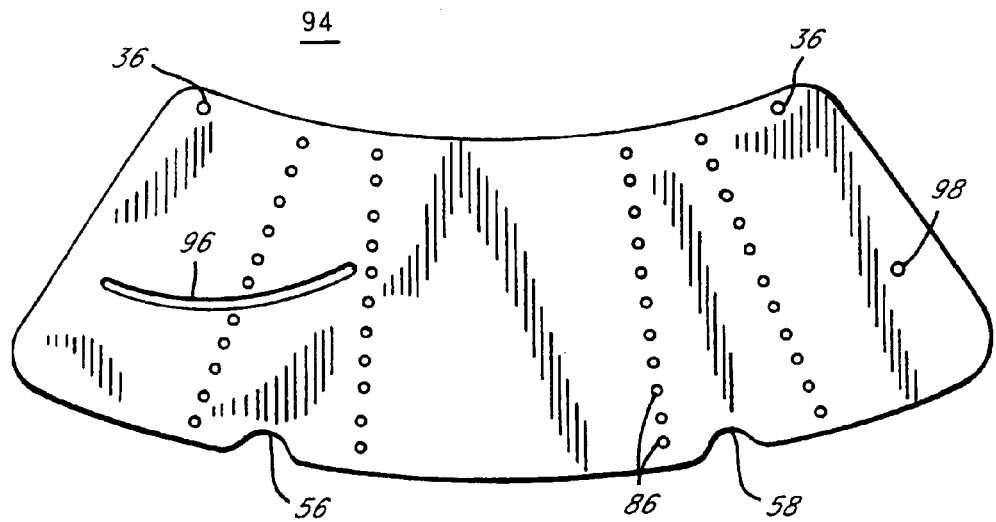
FIG. 13 is a view of a portion of another embodiment of the access device.
Figure 14:
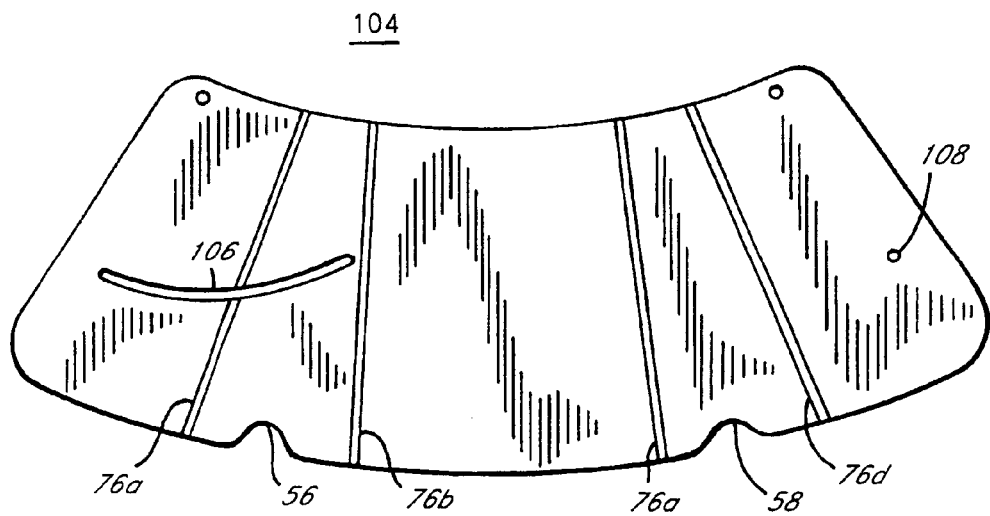
FIG. 14 is a view of a portion of another embodiment of the access device.

FIG. 13 illustrates another embodiment of an access device that has a skirt portion 94 having one slot 96 and an aperture 98. A rivet (not shown) is stationary with respect to the aperture 98 and slides within the slot 96. FIG. 14 illustrates another embodiment of an access device that has a skirt portion 104 that includes an aperture 108. The apertures 108 receives a rivet (not shown) that slides within elongated slot 106.

Another embodiment of an access device comprises an elongate body defining a passage and having a proximal end and a distal end. The elongate body has a proximal portion and a distal portion. The proximal portion has an oblong or generally oval shaped cross section in one embodiment. The term "oblong" is used in its ordinary sense (i.e., having an elongated form) and is a broad term and it includes a structure having a dimension, especially one of two perpendicular dimensions, such as, for example, width or length, that is greater than another and includes shapes such as rectangles, ovals, ellipses, triangles, diamonds, trapezoids, parabolas, and other elongated shapes having straight or curved sides. The term "oval" is used in its ordinary sense (i.e., egg like or elliptical) and is a broad term and includes oblong shapes having curved portions.

The proximal portion comprises an oblong, generally oval shaped cross section over the elongated portion. It will be apparent to those of skill in the art that the cross section can be of any suitable oblong shape. The proximal portion can be any desired size. The proximal portion can have a cross-sectional area that varies from one end of the proximal portion to another end. For example, the cross-sectional area of the proximal portion can increase or decrease along the length of the proximal portion. Alternatively, the proximal portion can have a constant cross section over its length. Preferably, the proximal portion is sized to provide sufficient space for inserting multiple surgical instruments through the elongate body to the surgical location. The distal portion preferably is expandable and may comprise first and second overlapping skirt members. The degree of expansion of the distal portion is determined by an amount of overlap between the first skirt member and the second skirt member in one embodiment.

The elongate body of the access device has a first location distal of a second location. The elongate body preferably is capable of having a configuration when inserted within the patient wherein the cross-sectional area of the passage at the first location is greater than the cross-sectional area of the passage at the second location. The passage preferably is capable of having an oblong shaped cross section between the second location and the proximal end. In some embodiments the passage preferably is capable of having a generally elliptical cross section between the second location and the proximal end. Additionally, the passage preferably is capable of having a non-circular cross section between the second location and the proximal end. Additionally, in some embodiments, the cross section of the passage can be symmetrical about a first axis and a second axis, the first axis being generally normal to the second axis. Other embodiments having an oblong cross-section are discussed below in connection with FIGS. 67-73B.

Further details and features pertaining to access devices and systems are described in U.S. Pat. No. 6,652,553, application Ser. No. 10/361,887, filed Feb. 10, 2003, application Ser. No. 10/280,489, filed Oct. 25, 2002, and application Ser. No. 10/678,744 filed Oct. 2, 2003, which are incorporated by reference in their entireties herein.

2. Dilators and Expander Devices

According to one embodiment of a procedure, an early stage involves determining a point in the skin of the patient at which to insert the access device 20. The access point preferably corresponds to a posterior-lateral aspect of the spine. Manual palpation and Anterior-Posterior (AP) fluoroscopy may be used to determine preferred or optimal locations for forming an incision in the skin of the patient. In one application, the access device 20 preferably is placed midway (in the cephcaudal direction) between the L4 through S1 vertebrae, centrally about 4-7 cm from the midline of the spine.

After the above-described location is determined, an incision is made at the location. A guide wire (not shown) is introduced under fluoroscopic guidance through the skin, fascia, and muscle to the approximate surgical site. A series of dilators is used to sequentially expand the incision to the desired width, about 23 mm in one procedure, preferably minimizing damage to the structure of surrounding tissue and muscles. A first dilator can be placed over the guide wire to expand the opening. The guide wire may then be removed. A second dilator, slightly larger than the first dilator, is placed over the first dilator to expand the opening further. Once the second dilator is in place, the first dilator may be removed. This process of (1) introducing a next-larger-sized dilator coaxially over the previous dilator and (2) optionally removing the previous dilator(s) when the next-larger-sized dilator is in place continues until an opening of the desired size is created in the skin, muscle, and subcutaneous tissue. According to one application, the desired opening size is about 23 mm. (Other dimensions of the opening, e.g., about 20 mm, about 27 mm, about 30 mm, etc., are also useful with this apparatus in connection with spinal surgery, and still other dimensions are contemplated.)

FIG. 15 shows that following placement of a dilator 120, which is the largest dilator in the above-described dilation process, the access device 20 is introduced in its reduced profile configuration and positioned over the dilator 120. The dilator 120 is subsequently removed from the patient, and the access device 20 remains in position.

Once positioned in the patient, the access device 20 may be enlarged to provide a passage for the insertion of various surgical instruments and to provide an enlarged space for performing the procedures described herein. As described above, the access device may achieve the enlargement in several ways. In one embodiment, a distal portion of the access device may be enlarged, and a proximal portion may maintain a constant diameter. The relative lengths of the proximal portion 22 and the skirt portion 24 may be adjusted to vary the overall expansion of the access device 20. Alternatively, such expansion may extend along the entire length of the access device 20. In one application, the access device 20 may be expanded by removing a suture 35 and tearing the outer sleeve 32 surrounding the access device 20, and subsequently allowing the skirt portion 24 to resiliently expand towards its fully expanded configuration as (illustrated in FIG. 4) to create an enlarged surgical space from the L4 to the S1 vertebrae. The resisting force exerted on the skirt portion 24 may result in the skirt portion 24 assuming the intermediate configuration illustrated in FIG. 3. Under many circumstances, the space created by the skirt portion 24 in the intermediate configuration is a sufficiently large working space to perform the procedure described herein. Once the skirt portion 24 has expanded, the rigidity and resilient characteristics of the skirt portion 24 preferably allow the access device 20 to resist closing to the reduced profile configuration of FIG. 2 and to at least temporarily resist being expelled from the incision. These characteristics create a stable configuration for the access device 20 to remain in position in the body, supported by the surrounding tissue. It is understood that additional support may be needed, especially if an endoscope is added.

According to one embodiment of a procedure, the access device 20 may be further enlarged at the skirt portion 24 using an expander apparatus to create a surgical access space. An expander apparatus useful for enlarging the access device has a reduced profile configuration and an enlarged configuration. The expander apparatus is inserted into the access device in the reduced profile configuration, and subsequently expanded to the enlarged configuration. The expansion of the expander apparatus also causes the access device to be expanded to the enlarged configuration. In some embodiments, the expander apparatus may increase the diameter of the access device along substantially its entire length in a generally conical configuration. In other embodiments, the expander apparatus expands only a distal portion of the access device, allowing a proximal portion to maintain a relatively constant diameter.

In addition to expanding the access device, in some embodiments the expander apparatus may also be used to position the distal portion of the access device at the desired location for the surgical procedure. The expander can engage an interior wall of the access device to move the access device to the desired location. For embodiments in which the distal portion of the access device is relatively movable with respect to the proximal portion, the expander apparatus is useful to position the distal portion without substantially disturbing the proximal portion.

Figure 17:
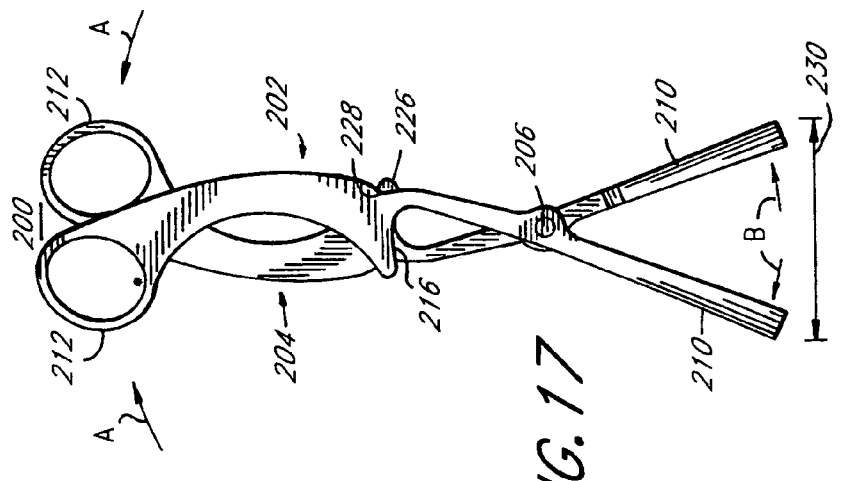
FIG. 17 is a side view of the expander apparatus of FIG. 16 in an expanded configuration.
Figure 16:
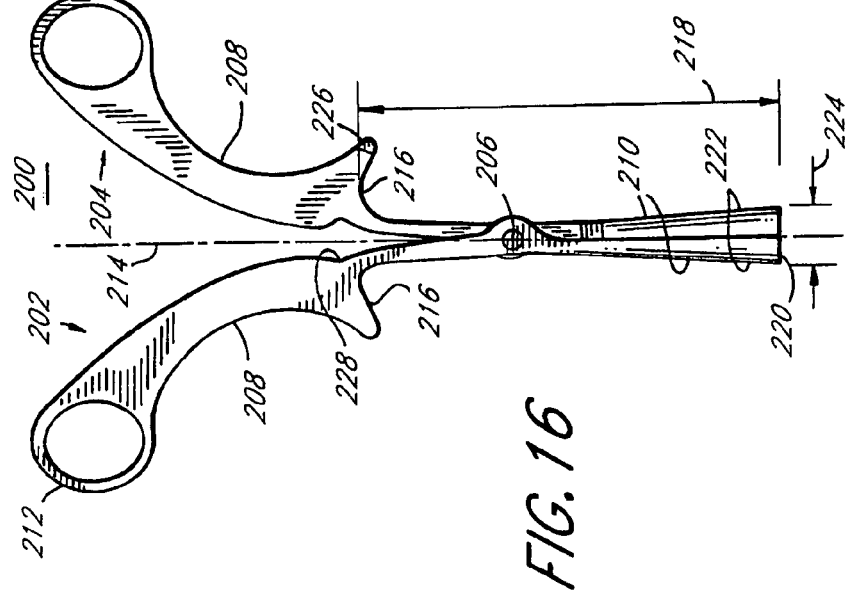
FIG. 16 is a side view of one embodiment of an expander apparatus in a reduced profile configuration.

In some procedures, an expander apparatus is used to further expand the skirt portion 24 towards the enlarged configuration (illustrated in FIG. 4). The expander apparatus is inserted into the access device, and typically has two or more members that are movable to engage the interior wall of the skirt portion 24 and apply a force sufficient to further expand the skirt portion 24. FIGS. 16 and 17 show one embodiment of an expander apparatus 200 that has a first component 202 and a second component 204. The first component 202 and the second component 204 of the expander apparatus 200 are arranged in a tongs-like configuration and are pivotable about a pin 206. The first and second components 202 and 204 can be constructed of steel having a thickness of about 9.7 mm. Each of the first and second components 202 and 204 has a proximal handle portion 208 and a distal expander portion 210. Each proximal handle portion 208 has a finger grip 212 that may extend transversely from an axis, e.g., a longitudinal axis 214, of the apparatus 200. The proximal handle portion 208 may further include a stop element, such as flange 216, that extends transversely from the longitudinal axis 214. The flange 216 preferably is dimensioned to engage the proximal end 25 of the access device 20 when the apparatus 200 is inserted a predetermined depth. This arrangement provides a visual and tactile indication of the proper depth for inserting the expander apparatus 200. In one embodiment, a dimension 218 from the flange 216 to the distal tip 220 is about 106 mm. The dimension 218 is determined by the length of the access device 20, which in turn is a function of the depth of the body structures beneath the skin surface at which the surgical procedure is to be performed. The distal portions 210 are each provided with an outer surface 222 for engaging the inside wall of the skirt portion 24. The outer surface 222 is a frustoconical surface in one embodiment. The expander apparatus 200 has an unexpanded distal width 224 at the distal tip 220 that is about 18.5 mm in one embodiment.

In use, the finger grips 212 are approximated towards one another, as indicated by arrows A in FIG. 17, which causes the distal portions 210 to move to the enlarged configuration, as indicated by arrows B. The components 202 and 204 are also provided with a cooperating tab 226 and shoulder portion 228 which are configured for mutual engagement when the distal portions 210 are in the expanded configuration. In the illustrated embodiment, the expander apparatus 200 has an expanded distal width 230 that extends between the distal portions 210. The expanded distal width 230 can be about 65 mm or less, about as large as 83 mm or less, or any other suitable width. The tab 226 and shoulder portion 228 together limit the expansion of the expander apparatus 200 to prevent expansion of the skirt portion 24 of the access device 20 beyond its designed dimension, and to minimize trauma to the underlying tissue. Further features related to the expander apparatus are described in U.S. Pat. No. 6,652,553, issued Nov. 25, 2003, which is incorporated by reference in its entirety herein.

When the access device 20 is inserted into the patient and the outer sleeve 32 is removed, the skirt portion 24 expands to a point where the outward resilient expansion of the skirt portion 24 is balanced by the force of the surrounding tissue. The surgical space defined by the access device 20 may be sufficient to perform any of a number of surgical procedures or combination of surgical procedures described herein. However, if it is desired to expand the access device 20 further, the expander apparatus 200, or a similar device, may be inserted into the access device 20 in the reduced profile configuration until the shoulder portions 216 are in approximation with the proximal end 25 of the skirt portion 24 of the access device 20, as shown in FIG. 18.

FIG. 18 shows the expander apparatus 200 inserted in the access device 20 in the reduced profiled configuration. Expansion of the expander apparatus 200 is achieved by approximating the handle portions 212 (not shown in FIG. 18), which causes the distal portions 210 of the expander apparatus 200 to move to a spaced apart configuration. As the distal portions 210 move apart and contact the inner wall of the skirt portion 24, the rivet 44 is allowed to slide within the slots 46 and 48 of the skirt portion 24, thus permitting the skirt portion 24 to expand. When the distal portions 210 reach the maximum expansion of the skirt portion 24 (illustrated by a dashed line in FIG. 19), the tab 226 and shoulder portion 228 of the expander apparatus 200 come into engagement to prevent further expansion of the tongs-like portions (as illustrated in FIG. 17). Alternatively, the access device 20 may be expanded with another device that can selectively have a reduced profile configuration and an expanded configuration, e.g., a balloon or similar device.

An optional step in the procedure is to adjust the location of the distal portion of the access device 20 relative to the body structures to be operated on. For example, the expander apparatus 200 may also be used to engage the inner wall of the skirt portion 24 of the access device 20 in order to move the skirt portion 24 of the access device 20 to the desired location. For an embodiment in which the skirt portion 24 of the access device 20 is relatively movable relative to the proximal portion, e.g. by use of the rivet 30, the expander apparatus 200 is useful to position the skirt portion 24 without substantially disturbing the proximal portion 22 or the tissues closer to the skin surface of the patient. As will be described below, the ability to move the distal end portion, e.g., the skirt portion 24, without disturbing the proximal portion is especially beneficial when an additional apparatus is coupled with the proximal portion of the access device, as described below.

B. Systems and Devices for Stabilization and Visualization

Some procedures can be conducted through the access device 20 without any additional peripheral components being connected thereto. In other procedures it may be beneficial to provide at least one of a support device and a viewing element. As discussed more fully below, support devices can be advantageously employed to provide support to peripheral equipment and to surgical tools of various types. Various embodiments of support devices and viewing elements are discussed herein below.

1. Support Devices

One type of support device that can be coupled with the access device 20 is a device that supports a viewing element. In one embodiment, an endoscope mount platform 300 and indexing arm 400 support an endoscope 500 on the proximal end 25 of the access device 20 for remotely viewing the surgical procedure, as illustrated in FIGS. 20-23. The endoscope mount platform 300 may also provide several other functions during the surgical procedure. The endoscope mount platform 300 preferably includes a base 302 that extends laterally from a central opening 304 in a generally ring-shaped configuration. In one application, the physician views the procedure primarily by observing a monitor, when inserting surgical instruments into the central opening 304. The base 302 advantageously enables the physician by providing a visual indicator (in that it may be observable in the physician's peripheral vision) as well as tactile feedback as instruments are lowered towards the central opening 304 and into the access device 20.

The endoscope mount platform 300 preferably has a guide portion 306 at a location off-set from the central opening 304 that extends substantially parallel to a longitudinal axis 308. The base 302 can be molded as one piece with the guide portion 306. The base 302 and guide portion 306 may be constructed with a suitable polymer, such as, for example, polyetheretherketone (PEEK).

The guide portion 306 includes a first upright member 310 that extends upward from the base 302 and a second upright member 312 that extends upward from the base 302. In one embodiment, the upright members 310, 312 each have a respective vertical groove 314 and 315 that can slidably receive an endoscopic mount assembly 318.

Figure 25:
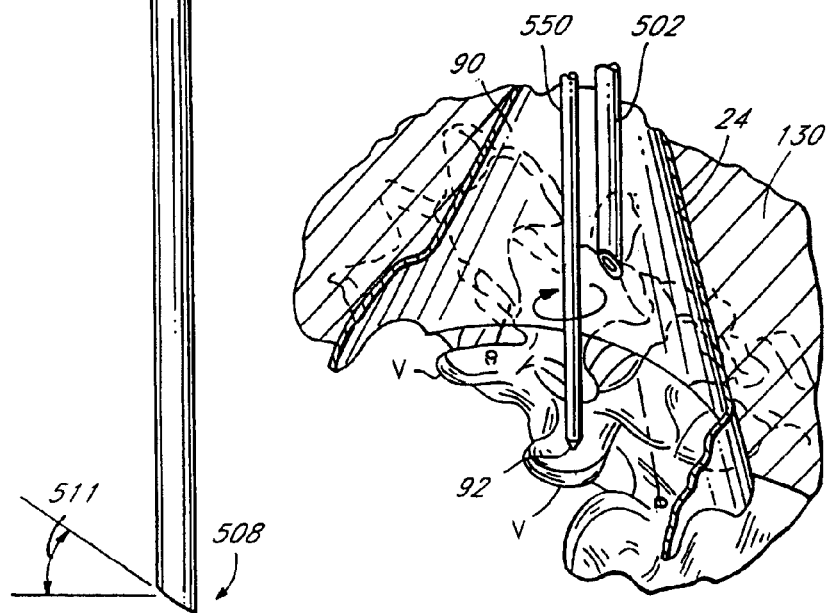
FIG. 25 is a partial sectional view of one embodiment of a stage of one embodiment of a method for treating the spine of a patient.

The endoscope 500 (not shown in FIG. 20) can be movably mounted to the endoscope mount platform 300 with the endoscope mount assembly 318 in one embodiment. The endoscope mount assembly 318 includes an endoscope mount 320 and a saddle unit 322. The saddle unit 322 is slidably mounted within the grooves 314 and 315 in the upright members 310 and 312. The endoscope mount 320 receives the endoscope 500 through a bore 326 which passes through the endoscope mount 320. Part of the endoscope 500 may extend through the access device 20 substantially parallel to longitudinal axis 308 into the patient's body 130, as shown in FIG. 25.

The endoscope mount 320 is removably positioned in a recess 328 defined in the substantially "U"-shaped saddle unit 322. In one embodiment, the saddle unit 322 is selectively movable in a direction parallel to the longitudinal axis 308 in order to position the endoscope 500 at the desired height within the access device 20. The movement of the endoscope 500 by way of the saddle unit 322 also advantageously enables the physician to increase visualization of a particular portion of the surgical space defined by the access device, e.g., by way of a zoom feature, as required for a given procedure or a step of a procedure.

In one embodiment, an elevation adjustment mechanism 340, which may be a screw mechanism, is positioned on the base 302 between the upright members 310 and 312. The elevation adjustment mechanism 340 can be used to selectively move a viewing element, e.g., the endoscope 500 by way of the saddle unit 322. In one embodiment, the elevation adjustment mechanism 340 comprises a thumb wheel 342 and a spindle 344. The thumb wheel 343 is rotatably mounted in a bore in the base 302. The thumb wheel 342 has an external thread 346 received in a cooperating thread in the base 302. The spindle 344 is mounted for movement substantially parallel to the central axis 308. The spindle 344 preferably has a first end received in a rectangular opening in the saddle unit 322, which inhibits rotational movement of the spindle 344. The second end of the spindle 344 has an external thread that cooperates with an internal thread formed in a bore within the thumb wheel 342. Rotation of the thumb wheel 342 relative to the spindle 344 causes relative axial movement of the spindle unit 344 along with the saddle unit 322. Further details and features related to endoscope mount platforms are described in U.S. Pat. Nos. 6,361,488, issued Mar. 26, 2002; 6,530,880, issued Mar. 11, 2003, and U.S. patent application Ser. No. 09/940,402, filed Aug. 27, 2001, published as Publication No. 2003/0040656 on Feb. 27, 2003, which are incorporated by reference in their entireties herein.

Figure 21:
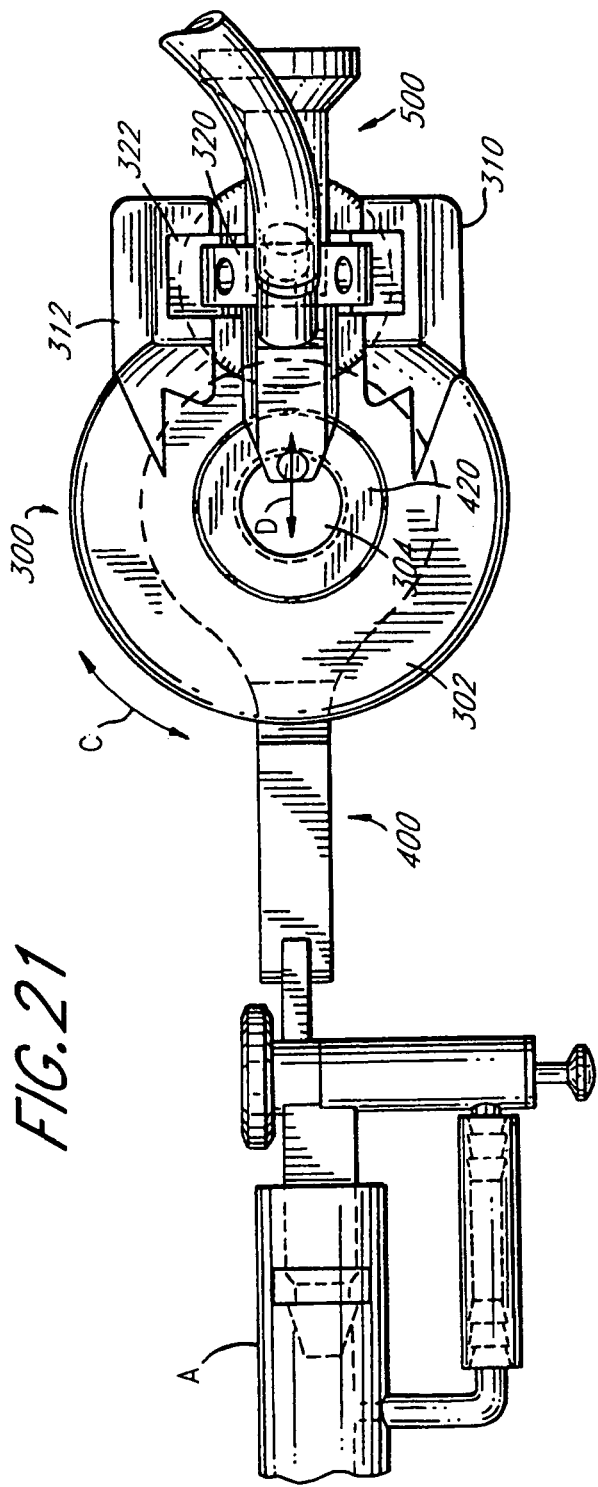
FIG. 21 is a top view of the endoscope mount platform of FIG. 20 coupled with one embodiment of an indexing arm and one embodiment of an endoscope.

FIGS. 21-23 show that the endoscope mount platform 300 is mountable to the support arm 400 in one embodiment. The support arm 400, in turn, preferably is mountable to a mechanical support, such as mechanical support arm A, discussed above in connection with FIG. 1. The support arm 400 preferably rests on, or is otherwise coupled with, the proximal end 25 of the access device 20. In one embodiment, the support arm 400 is coupled with an indexing collar 420, which is configured to be received in the central opening 304 of the base 302 of endoscope mount platform 300. The indexing collar 420 is substantially toroidal in section and has an outer peripheral wall surface 422, an inner wall surface 424, and a wall thickness 426 that is the distance between the wall surfaces 422, 424. The indexing collar 420 further includes a flange 428, which supports the indexing collar 420 on the support arm 400.

In one embodiment, a plurality of collars 420 may be provided to make the surgical system 10 modular in that different access devices 20 may be used with a single endoscope mount platform 300. For example, access devices 20 of different dimensions may be supported by providing indexing collars 420 to accommodate each access device size while using a single endoscope mount platform 300. The central opening 304 of the endoscope mount platform 300 can have a constant dimension, e.g., a diameter of about 32.6 mm. An appropriate indexing collar 420 is selected, e.g., one that is appropriately sized to support a selected access device 20. Thus, the outer wall 422 and the outer diameter 430 are unchanged between different indexing collars 420, although the inner wall 424 and the inner diameter 432 vary to accommodate differently sized access devices 20.

The indexing collar 420 can be positioned at or rested on the proximal portion of the access device 20 to allow angular movement of the endoscope mount platform 300 with respect thereto about the longitudinal axis 308 (as indicated by an arrow C in FIG. 21). The outer wall 422 of the index collar 420 includes a plurality of hemispherical recesses 450 that can receive one or more ball plungers 350 on the endoscope mount platform 300 (indicated in dashed line). This arrangement permits the endoscope mount platform 300, along with the endoscope 500, to be fixed in a plurality of discrete angular positions. Further details and features related to support arms and indexing collars are described in U.S. Pat. No. 6,361,488, issued Mar. 26, 2002, U.S. Pat. No. 6,530,880 issued Mar. 11, 2003, and application Ser. No. 09/940,402 filed Aug. 27, 2001, published as Publication No. 2003/0040656 on Feb. 27, 2003, which are incorporated by reference in their entireties herein.

2. Viewing Elements

As discussed above, a variety of viewing elements and visualization techniques are embodied in variations of the surgical system 10. One viewing element that is provided in one embodiment is an endoscope.

Figure 24:
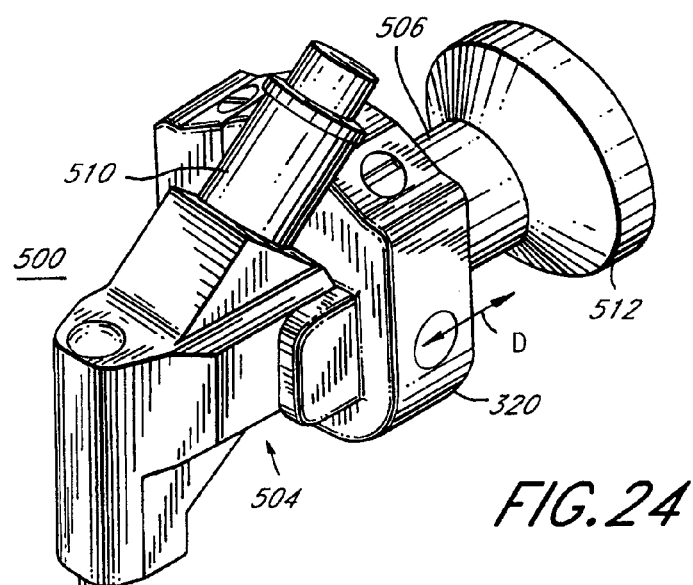
FIG. 24 is a perspective view of one embodiment of an endoscope.

FIG. 24 shows one embodiment of the endoscope 500 that has an elongated configuration that extends into the access device 20 in order to enable viewing of the surgical site. In particular, the endoscope 500 has an elongated rod portion 502 and a body portion 504. The rod portion 502 extends generally perpendicularly from the body portion 504. In one embodiment, the rod portion 502 of endoscope 500 has a diameter of about 4 mm and a length of about 106 mm. Body portion 504 may define a tubular portion 506 configured to be slidably received in the bore 326 of endoscope mount 320 as indicated by an arrow D. The slidable mounting of the endoscope 500 on the endoscope mount platform 300 permits the endoscope 500 to adjust to access device configurations that have different diameters. Additional mobility of the endoscope 500 in viewing the surgical site may be provided by rotating the endoscope mount platform 300 about the central axis 308 (as indicated by arrow C in FIG. 21).

The rod portion 502 supports an optical portion (not shown) at a distal end 508 thereof. In one embodiment, the rod portion 502 defines a field of view of about 105 degrees and a direction of view 511 of about 25-30 degrees. An eyepiece 512 preferably is positioned at an end portion of the body portion 504. A suitable camera (not shown) preferably is attached to the endoscope 500 adjacent the eyepiece 512 with a standard coupler unit. A light post 510 can supply illumination to the surgical site at the distal end portion 508. A preferred camera for use in the system and procedures described herein is a three chip unit that provides greater resolution to the viewed image than a single chip device.

C. Apparatuses and Methods for Performing Spinal Procedures

The surgical assembly 10 described above can be deployed to perform a wide variety of surgical procedures on the spine. In many cases, the procedures are facilitated by inserting the access device and configuring it to provide greater access to a surgical location, as discussed above and by coupling the support arm 400 and the endoscope mount platform 300 with the proximal portion, e.g., on the proximal end 25, of the access device 20 (FIGS. 1 and 22). As discussed above, visualization of the surgical location is enhanced by mounting a viewing element, such as the endoscope 500, on the endoscope mount platform 300. Having established increased access to and visualization of the surgical location, a number of procedures may be effectively performed.

Generally, the procedures involve inserting one or more surgical instruments into the access device 20 to manipulate or act on the body structures that are located at least partially within the operative space defined by the expanded portion of the access device 20. FIG. 25 shows that in one method, the skirt portion 24 of access device 20 at least partially defines a surgical site or operative space 90 in which the surgical procedures described herein may be performed. Depending upon the overlap of the skirt portion, the skirt portion may define a surface which is continuous about the perimeter or which is discontinuous, having one or more gaps where the material of the skirt portion does not overlap.

One procedure performable through the access device 20, described in greater detail below, is a two-level spinal fusion and fixation. Surgical instruments inserted into the access device may be used for debridement and decortication. In particular, the soft tissue, such as fat and muscle, covering the vertebrae may be removed in order to allow the physician to visually identify the various "landmarks," or vertebral structures, which enable the physician to determine the location for attaching a fastener or an apparatus to vertebrae or to perform other procedures, as will be described herein. Any suitable fastener or apparatus may be attached to the vertebrae, including a fastener 600, and an apparatus 8010, discussed below, and additional fasteners and apparatuses incorporated by reference herein. Enabling visual identification of the vertebral structures enables the physician to perform the procedure while viewing the surgical area through the endoscope, microscope, loupes, or other viewing element, or in a conventional, open manner.

Tissue debridement and decortication of bone are completed using one or more of a debrider blade, a bipolar sheath, a high speed burr, and any other conventional manual instrument. The debrider blades are used to excise, remove and aspirate the soft tissue. The bipolar sheath is used to achieve hemostasis through spot and bulk tissue coagulation. Additional features of debrider blades and bipolar sheaths are described in U.S. Pat. No. 6,193,715, assigned to Medical Scientific, Inc., which is incorporated by reference in its entirety herein. The high speed burr and conventional manual instruments are also used to continue to expose the structure of the vertebrae.

1. Fixation Systems and Devices

Having increased visualization of the pertinent anatomical structure, various procedures may be carried out on the structures. In one procedure, one or more fasteners are attached to adjacent vertebrae V. As discussed in more detail below, the fasteners can be used to provide temporary or permanent fixation and to provide dynamic stabilization of the vertebrae V. These procedures may combined with other procedures, such as procedures employing other types of implant, e.g., procedures employing fusion devices, prosthetic disc components, or other suitable implants. In some procedures, fasteners are attached to the vertebrae before or after fusion devices are inserted between the vertebrae V. Fusion systems and devices are discussed further below.

In one application, the desired location and orientation of the fastener is determined before the fastener is applied to the vertebra. The desired location and orientation of the fastener may be determined in any suitable manner. For example, the pedicle entry point of the L5 vertebrae may be located by identifying visual landmarks alone or in combination with lateral and A/P fluoroscopy, as is known in the art. With continued reference to FIG. 25, an entry point 92 into the vertebra V is prepared. In procedure, the entry point 92 may be prepared with an awl 550. The entry point 92 corresponds to the pedicle in one procedure. The entry point 92 may be prepared in any suitable manner, e.g., employing a bone probe, a tap, and a sounder to create and verify the integrity of the prepared vertebra. The sounder, as is known in the art, determines whether the hole that is made is surrounded by bone on all sides, and can be used to confirm that there has been no perforation of the pedicle wall.

After the hole in the pedicle beneath the entry point 92 is prepared, a fastener may be advanced into the hole. Prior to advancing the fastener, or at any other point during the procedure, it may be desirable to adjust the location of the distal portion of the access device 20. The distal portion of the access device 20 may be adjusted by inserting the expander apparatus 200 into the access device 20, expanding the distal portions 210, and contacting the inner wall of the skirt portion 24 to move the skirt portion 24 to the desired location. This step may be performed while the endoscope 500 is positioned within the access device 20, and without substantially disturbing the location of the proximal portion of the access device 20 to which the endoscope mount platform 300 may be attached.

FIGS. 26-27 illustrate one embodiment of a fastener 600 that is particularly applicable in procedures involving fixation. Other apparatuses that may be applicable in such procedures and in other procedure are described in connection with FIGS. 151-155 and are incorporated by reference herein below. The fastener 600 preferably includes a screw portion 602, a housing 604, a spacer member 606, a biasing member 608, and a clamping member, such as a cap screw 610. The screw portion 602 has a distal threaded portion 612 and a proximal, substantially spherical joint portion 614. The threaded portion 612 is inserted into the hole that extends away from the entry point 92 into the vertebrae, as will be described below. The substantially spherical joint portion 614 is received in a substantially annular, partly spherical recess 616 in the housing 604 in a ball and socket joint relationship (see also FIG. 29).

As illustrated in FIG. 27, the fastener 600 is assembled by inserting the screw portion 602 into a bore in a passage 618 in the housing 604 until the joint portion 614 engages the annular recess 616. The screw portion 602 is retained in the housing 604 by the spacer member 606 and by the biasing member 608. The biasing member 608 provides a biasing force to drive the spacer member 606 into frictional engagement with the joint portion 614 of the screw member 602 and the annular recess 616 of the housing 604. The biasing provided by the biasing member 602 frictionally maintains the relative positions of the housing 604 with respect to the screw portion 602. The biasing member 608 preferably is selected such that biasing force prevents unrestricted movement of the housing 604 relative to the screw portion 602. However, in some embodiments the biasing force is insufficient to resist the application of force by a physician to move the housing 604 relative to the screw portion 602. In other words, this biasing force is strong enough maintain the housing 604 stationary relative to the screw portion 602, but this force may be overcome by the physician to reorient the housing 604 with respect to the screw member 602, as will be described below.

In the illustrated embodiment, the biasing member 608 is a resilient ring having a gap 620, which permits the biasing member 608 to radially contract and expand. FIG. 27(*a*) illustrates that the biasing member 608 may have an arched shape, when viewed end-on. The arched shape of the spring member 608 provides the biasing force, as will be described below. The spacer member 606 and the biasing member 608 are inserted into the housing 604 by radially compressing the biasing member into an annular groove 622 in the spacer member 606. The spacer member 606 and the biasing member 608 are slid into the passage 618 until the distal surface of the spacer member 606 engages the joint portion 614 of the screw portion 602, and the biasing member 608 expands radially into the annular groove 622 in the housing 604. The annular groove 622 in the housing 604 has a dimension 623 that is smaller than the uncompressed height of the arched shape of the biasing member 608. When the biasing member 608 is inserted in the annular groove 620, the biasing member 608 is flattened against its normal bias, thereby exerting the biasing force to the spacer member 606. It is understood that similar biasing members, such as coiled springs, belleville washers, or the like may be used to supply the biasing force described herein.

The spacer member 606 is provided with a longitudinal bore 626, which provides access to a hexagonal recess 628 in the proximal end of the joint portion 614 of the screw member 602. The proximal portion of the housing 604 includes a pair of upright members 630 and 631 that are separated by substantially "U"-shaped grooves 632. A recess for receiving elongated member 650 is defined by the pair of grooves 632 between upright members 630 and 631. Elongated member 650 preferably is configured to be placed distally into the housing 604 in an orientation substantially transverse to the longitudinal axis of the housing 604, as will be described below. The inner walls of the upright members 630 and 631 are provided with threads 634 for attachment of the cap screw 610 by threads 613 therein.

Additional features of the fastener 600 are also described in U.S. patent application Ser. No. 10/075,668, filed Feb. 13, 2002, published as U.S. Application Publication No. 2003/0153911A1 on Aug. 14, 2003, and application Ser. No. 10/087,489, filed Mar. 1, 2002, published as U.S. Application Publication No. 2003/0167058A1 on Sep. 4, 2003, which are incorporated by reference in their entireties herein.

According to one application, the fastener 600 is inserted into the access device 20 and guided to the prepared hole at the entry point 92 in the vertebrae. The fastener 600 preferably is simultaneously supported and advanced into the hole so that the fastener 600 is secured in the in the hole beneath the entry point 92. In the illustrated embodiment the fastener 600 is supported and attached to the bone by an endoscopic screwdriver apparatus 660, illustrated in FIGS. 28-29. The screwdriver 660 includes a proximal handle portion 662 (illustrated in dashed line), an elongated body portion 664, and a distal tool portion 666.

The distal tool portion 666, as illustrated in greater detail in FIG. 29 includes a substantially hexagonal outer periphery that is received in the substantially hexagonal recess 628 in the joint portion 614 of the screw member 602. A spring member at the distal tool portion 666 releasably engages the hexagonal recess 628 of the screw member 602 to support the fastener 600 during insertion and tightening. In the illustrated embodiment, a spring member 672 is configured to engage the side wall of the recess 628. More particularly, a channel or a groove is provided in the tip portion 666 for receiving the spring member 672. The channel or groove includes a medial longitudinal notch portion 676, a proximal, angled channel portion 678, and a distal substantially transverse channel portion 680. The spring member 672 is preferably manufactured from stainless steel and has a medial portion 682, proximal portion 684, and a transverse distal portion 686. The medial portion 682 is partially received in the longitudinal notch portion 676. The proximal portion 684 preferably is angled with respect to the medial portion 682 and is fixedly received in the angled channel portion 678. The transverse distal portion 686 preferably is slidably received in the transverse channel 680. The medial portion 682 of the spring member 672 is partially exposed from the distal tip portion 666 and normally is biased in a transverse outward direction with respect to the longitudinal axis (indicated by arrow E), in order to supply bearing force against the wall of the recess 628. Alternatively, the distal tip portion of the screwdriver may be magnetized in order to hold the screw portion 602. Similarly, the distal tip portion may include a ball bearing or similar member which is normally biased in a radially outward direction to engage the interior wall of the recess 628 to secure the fastener 600 to the screwdriver distal tip 666. Other means may be provided for temporarily but securely coupling the fastener 600 with the screwdriver distal tip 666.

The insertion of the fastener 600 into the prepared hole that extends into the vertebrae from the entry point 92 may be achieved by insertion of screwdriver 660 into access device 20 (indicated by arrow G). This procedure may be visualized by the use of the endoscope 500 in conjunction with fluoroscopy, or by way of any other suitable viewing element. The screw portion 602 is threadedly advanced by the endoscopic screwdriver 660 into the prepared hole that extends beneath the entry point 92 (indicated by arrow H). The endoscopic screwdriver 660 is subsequently separated from the fastener 600, by applying a force in the proximal direction, and thereby releasing the distal tip portion 666 from the hexagonal recess 628 (e.g., causing the transverse distal portion 686 of the spring member 672 to slide within the transverse recess 680 against the bias, indicated by arrow F), and removing the screwdriver 660 from the access device 20. An alternative method may use a guidewire, which is fixed in the hole beneath the entry point 92, and a cannulated screw which has an internal lumen and is guided over the guidewire into the hole beneath the entry point 92. Where a guidewire system is used, the screwdriver also would be cannulated so that the screwdriver would fit over the guidewire.

For a two-level fixation, it may be necessary to prepare several holes and attach several fasteners 600. Preferably, the access device 20 is sized to provide simultaneous access to all vertebrae in which the surgical procedure is being performed. In some cases, however, additional enlargement or repositioning of the distal portion of the access device 20 may be helpful in providing sufficient access to the outer vertebrae, e.g., the L4 and S1 vertebrae. In the illustrated embodiment, the expander apparatus 200 may be repeatedly inserted into the access device 20 and expanded in order to further open or to position the skirt portion 24. In one procedure, additional fasteners are inserted in the L4 and S1 vertebrae in a similar fashion as the fastener 600 inserted into the L5 vertebra as described above. (When discussed individually or collectively, a fastener and/or its individual components will be referred to by the reference number, e.g., fastener 600, housing 604, and all fasteners 600. However, when several fasteners and/or their components are discussed in relation to one another, an alphabetic subscript will be used, e.g., fastener 600a is moved towards fastener 600b.)

In one application, after the fasteners 600 are advanced into the vertebrae, the housing portions 604 of the fasteners 600 are substantially aligned such that their upright portions 630 and 631 face upward, and the notches 632 are substantially aligned to receive the elongated member 650 therein. The frictional mounting of the housing 604 to the screw member 602, described above, allows the housing 604 to be temporarily positioned until a subsequent tightening step is performed, described below.

Positioning of the housing portions 604 may be performed by the use of an elongated surgical instrument capable of contacting and moving the housing portion to the desired orientation. One such instrument for positioning the housings 604 is a grasper apparatus 700, illustrated in FIG. 30. The grasper apparatus 700 includes a proximal handle portion 702, an elongated body portion 704, and distal nose portion 706. The distal nose portion 706 includes a pair of grasping jaws 708a and 708b, which are pivotable about pin 710 by actuation of the proximal handle portion 702. The grasping jaws 708a and 708b are illustrated in the closed position in FIG. 30. Pivoting the movable handle 714 towards stationary handle 712 causes longitudinal movement of actuator 716, which in turn pivots the jaw 708b towards an open position (illustrated in dashed line). The biasing members 718 and 720 are provided to return the handles 712 and 714 to the open position and bias the jaws 708a and 708b to the closed position.

In one application, the elongated member 650 is inserted into the access device 20. In one application, the elongated member 650 is manufactured from a biocompatible material and is sufficiently strong to maintain the position of the vertebrae, or other body structures, coupled by the elongate member 650 with little or no relative motion therebetween. In one embodiment, the elongated members 650 are manufactured from Titanium 6/4 or titanium alloy. The elongated member 650 also may be manufactured from stainless steel or any other suitable material. The transverse shape, width (e.g., radii), and lengths of the elongated members 650 are selected by the physician to provide the best fit for the positioning of the screw heads. Such selection may be performed by placing the elongated member 650 on the skin of the patient overlying the location of the fasteners and viewed fluoroscopically. For example, a 70 mm preformed rod having a 3.5" bend radius may be selected for the spinal fixation.

Figure 30:
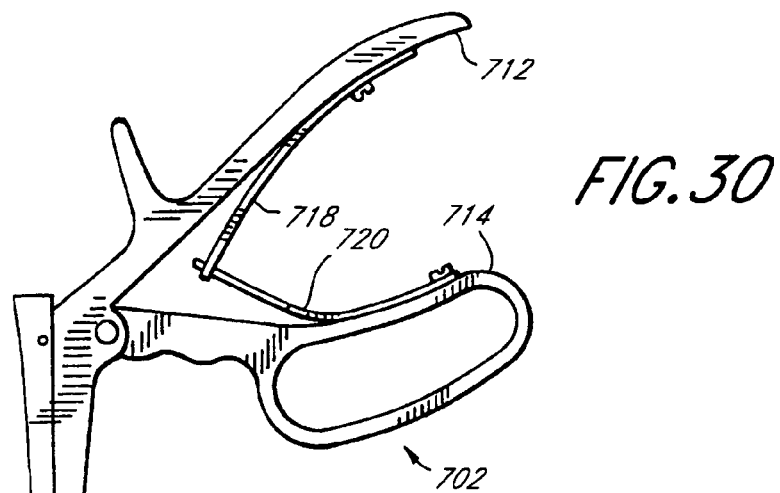
FIG. 30 is side view of one embodiment of another surgical instrument.

In one application, the elongated member 650 is fixed to each of the fasteners 600, and more particularly, to the housings 604 of each fastener 600. The grasper apparatus 700, described above, is also particularly useful for inserting the elongated member 650 into the access device 20 and positioning it with respect to each housing 604. As illustrated in FIG. 30, the jaws 708a and 708b of the grasper apparatus 700 each has shaped (e.g., curved) contact portions 722a and 722b for contacting and holding the outer surface of the elongated member 650.

Figure 31:
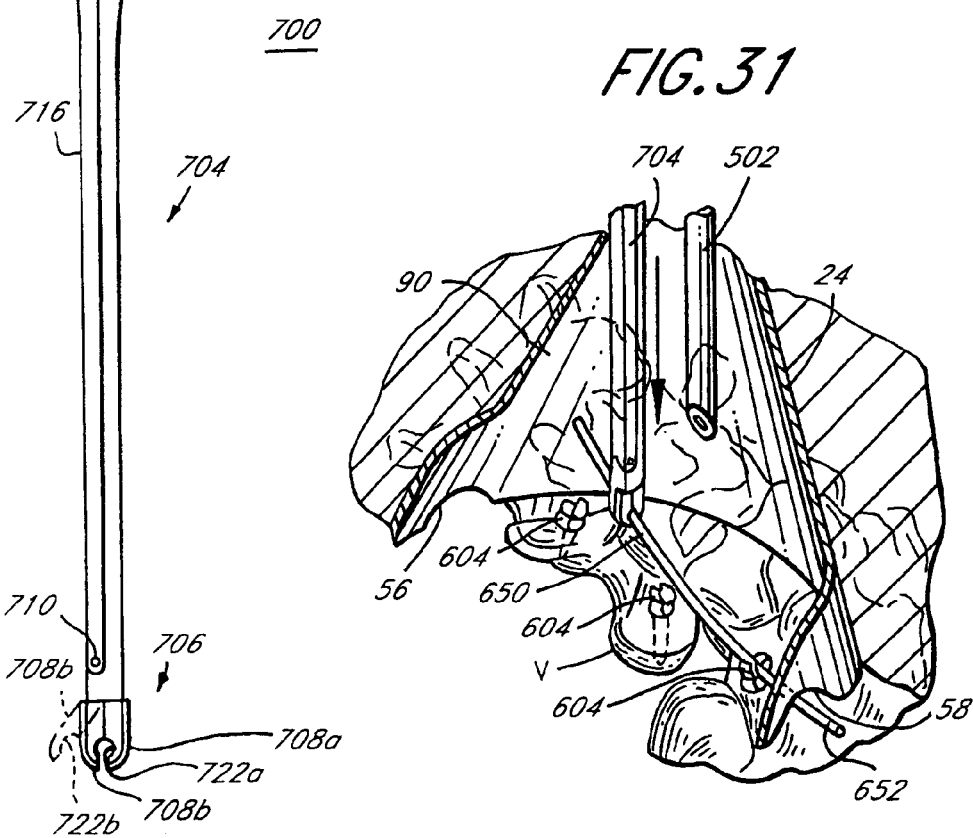
FIG. 31 is a partial sectional view of one embodiment of a stage of one embodiment of a method for treating the spine of a patient.

As illustrated in FIG. 31, the grasper apparatus 700 may be used to insert the elongated member 650 into the operative space 90 defined at least partially by the skirt portion 24 of the access device 20. In some embodiments, the cut-out portions 56 and 58 provided in the skirt portion 24 assist in the process of installing the elongated member 650 with respect to the housings 604. The cut-out portions 56 and 58 allow an end portion 652 of the elongated member 650 to extend beyond the operative space without raising or repositioning the skirt portion 24. The elongated member 650 is positioned within the recesses in each housing 604 defined by grooves 632 disposed between upright members 630 and 631. The elongated member 650 is positioned in an orientation substantially transverse to the longitudinal axis of each housing 604.

Further positioning of the elongated member 650 may be performed by guide apparatus 800, illustrated in FIG. 32. Guide apparatus 800 is useful in cooperation with an endoscopic screwdriver, such as endoscopic screwdriver 660 (illustrated in FIG. 28), in order to position the elongated member 650, and to introduce and tighten the cap screw 610, described above and illustrated in FIG. 27. Tightening of the cap screw 610 with respect to the housing 604 fixes the orientation of the housing 604 with respect to the screw portion 602 and fixes the position of the elongated member 650 with respect to the housings 604.

In the illustrated embodiment, the guide apparatus 800 has a proximal handle portion 802, an elongated body portion 804, and a distal tool portion 806. The elongated body portion 804 defines a central bore 808 (illustrated in dashed line) along its longitudinal axis 810. The central bore 808 is sized and configured to receive the endoscopic screwdriver 660 and cap screw 610 therethrough. In the exemplary embodiment, the diameter of the central bore 808 of the elongated body portion 804 is about 0.384-0.388 inches (9.75-9.86 mm) in diameter, and the external diameter of the endoscopic screwdriver 660 (FIG. 28) is about 0.25 inches (6.35 mm). The proximal handle portion 802 extends transverse to the longitudinal axis 810, which allows the physician to adjust the guide apparatus 800 without interfering with the operation of the screwdriver 660.

The distal portion 806 of the apparatus includes several shaped cut out portions 814 which assist in positioning the elongated member 650. As illustrated in FIG. 33, the cut out portions 814 are sized and configured to engage the surface of elongated member 650 and move the elongated member 650 from an initial location (illustrated in dashed line) to a desired location. In the illustrated embodiment, the cut out portions 814 are semicircular, to match the round elongated member 650. However, other shaped cut out portions may be provided to match other shaped elongated members.

As illustrated in FIG. 34, the guide apparatus 800 is used in cooperation with the endoscopic screwdriver 660 to attach the cap screw 610. The distal end of the body portion 804 includes a pair of elongated openings 816. The openings 816 provide a window to enable the physician to endoscopically view the cap screw 610 retained at the distal tip 666 of the endoscopic screw driver 660. Fewer or more than two openings can be provided and the openings 816 need not be elongated.

The guide apparatus 800 and the endoscopic screwdriver 660 cooperate as follows in one application. The guide apparatus 800 is configured to be positioned in a surrounding configuration with the screwdriver 600. In the illustrated embodiment, the body portion 804 is configured for coaxial placement about the screwdriver 660 in order to distribute the contact force of the guide apparatus 800 on the elongated member 650. The distal portion 806 of the guide apparatus 800 may bear down on the elongated member 650 to seat the elongated member 650 in the notches 632 in the housing 604. The "distributed" force of the guide apparatus 800 may contact the elongated member 650 on at least one or more locations. In addition, the diameter of central bore 808 is selected to be marginally larger than the exterior diameter of cap screw 610, such that the cap screw 610 may freely slide down the central bore 808, while maintaining the orientation shown in FIG. 34. This configuration allows the physician to have effective control of the placement of the cap screw 610 into the housing 604. The cap screw 610 is releasably attached to the endoscopic screwdriver 660 by means of spring member 672 engaged to the interior wall of hexagonal recess 611 as it is inserted within the bore 808 of the body portion 804 of guide apparatus 800. The cap screw 610 is attached to the housing 604 by engaging the threads 615 of the cap screw 610 with the threads 634 of the housing.

Figure 35:
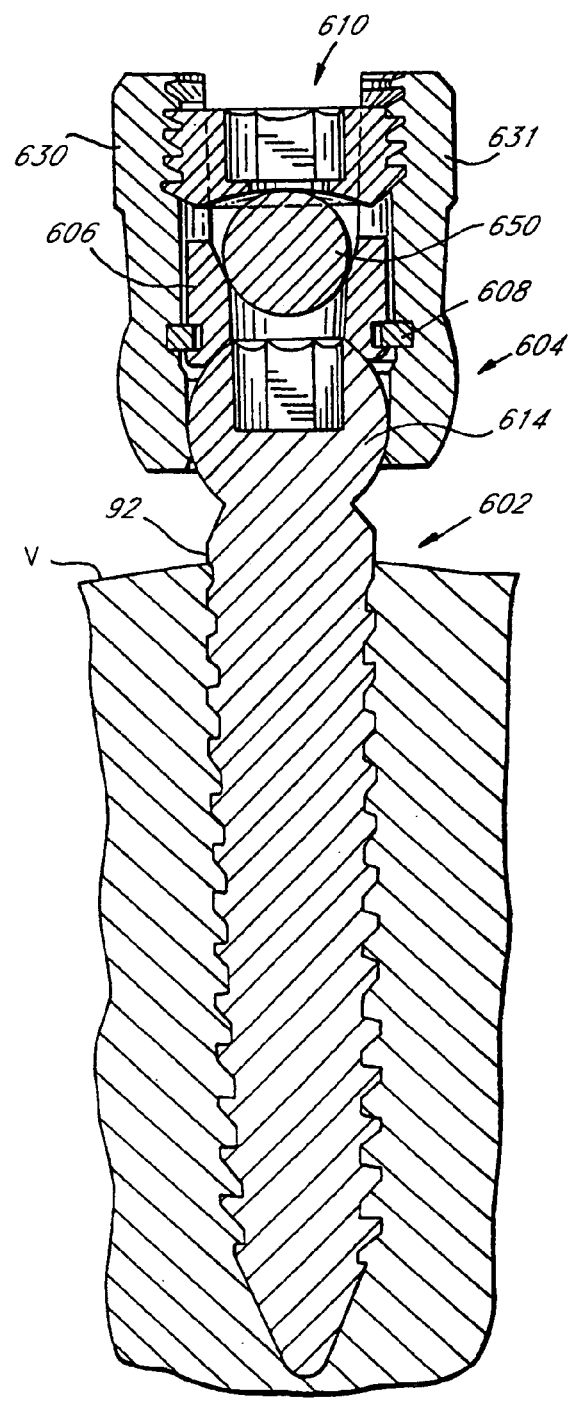
FIG. 35 is an enlarged sectional similar to FIG. 34, illustrating one embodiment of a stage of one embodiment of a method for treating the spine of a patient.

As illustrated in FIG. 35, tightening of the cap screw 610 fixes the assembly of the housing 604 with respect to the elongated member 650. In particular, the distal surface of the cap screw 610 provides a distal force against the elongated member 650, which in turn drives the spacer member 606 against the joint portion 614 of the screw portion 602, which is fixed with respect to the housing 604.

If locations of the vertebrae are considered acceptable by the physician, then the fixation procedure is substantially complete once the cap screws 610 have been attached to the respective housings 604, and tightened to provide a fixed structure as between the elongated member 650 and the various fasteners 600. However, if compression or distraction of the vertebrae with respect to one another is required additional apparatus would be used to shift the vertebrae prior to final tightening all of the cap screws 610.

In the illustrated embodiment, this step is performed with a surgical instrument, such as a compressor-distractor instrument 900, illustrated in FIG. 36, which is useful to relatively position bone structures in the cephcaudal direction and to fix their position with respect to one another. Thus, the compressor-distractor instrument 900 has the capability to engage two fasteners 600 and to space them apart while simultaneously tightening one of the fasteners to fix the spacing between the two vertebrae, or other bone structures. Moreover, the compressor-distractor instrument 900 may also be used to move two fasteners 600, and the vertebrae attached thereto into closer approximation and fix the spacing therebetween.

The distal tool portion 902 of one embodiment of the compressor-distractor instrument 900 is illustrated in FIG. 36. The distal tool portion 902 includes a driver portion 904 and a spacing member 906. The driver portion 904 has a distal end portion 908 with a plurality of wrenching flats configured to engage the recess 611 in the proximal face of the cap screw 610, and to apply torque to the cap screw. The driver portion 904 is rotatable about the longitudinal axis (indicated by arrow M) to rotate the cap screw 610 relative to the fastener 600. Accordingly, the driver portion 904 can be rotated to loosen the cap screw 610 on the fastener 600 and permit movement of the elongated member 650 connected with the vertebra relative to the fastener 600 connected with the vertebra. The cap screw 610 can also be rotated in order to tighten the cap screw 610 and clamp the elongated member 650 to the fastener 600.

The distal tool portion 902 may also include a spacing member, such as spacing member 906, which engages an adjacent fastener 600b while driver member 904 is engaged with the housing 604a to move the fastener 600b with respect to the fastener 600a. In the exemplary embodiment, spacing member 906 comprises a jaw portion that is pivotably mounted to move between a first position adjacent the driver portion and a second position spaced from the driver portion, as shown in FIG. 36. The distal tip 910 of the spacing member 906 is movable relative to the driver portion 904 in a direction extending transverse to the longitudinal axis. (Further details and features related to compressor-distractor apparatuses are described in U.S. application Ser. No. 10/178,875, filed Jun. 24, 2002, entitled "SURGICAL INSTRUMENT FOR MOVING VERTEBRAE," published as U.S. Patent Application Publication No. 2003/0236529A1 on Dec. 25, 2003, which is incorporated by reference in its entirety herein. Also, further details and features related to other apparatuses for manipulating implants and bone segments (e.g., vertebrae) to which implants are coupled are described in U.S. Pat. No. 6,648,888, issued Nov. 18, 2003, entitled "SURGICAL INSTRUMENT FOR MOVING VERTEBRAE.")

As illustrated in FIG. 36, the spacer member 906 can be opened with respect to the driver portion 904 to space the vertebrae farther apart (as indicated by arrow N). The distal portion 910 of the spacer member 906 engages the housing 604b of fastener 600b and moves fastener 600b further apart from fastener 600a to distract the vertebrae. Where the vertebrae are to be moved closer together, e.g. compressed, the spacer member 906 is closed with respect to the driver portion 904 (arrow P), as illustrated in FIG. 37. The distal portion 910 of the spacer member 906 engages the housing 604b of the fastener 600b and moves the fastener 600b towards the fastener 600a. When the spacing of the vertebrae is acceptable to the physician, the cap screw 610a is tightened by the driver member 904, thereby fixing the relationship of the housing 604a with respect to the elongated member 650, and thereby fixing the position of the vertebrae, or other bone structures, with respect to one another. In one application, once the elongated member 650 is fixed with respect to the fasteners 600, the fixation portion of the procedure is substantially complete.

2. Fusion Systems and Devices

Although fixation may provide sufficient stabilization, in some cases it is also desirable to provide additional stabilization. For example, where one or more discs has degraded to the point that it needs to be replaced, it may be desirable to position an implant, e.g., a fusion device, a prosthetic disc, a disc nucleus, etc., in the intervertebral space formerly occupied by the disc.

Figure 48:
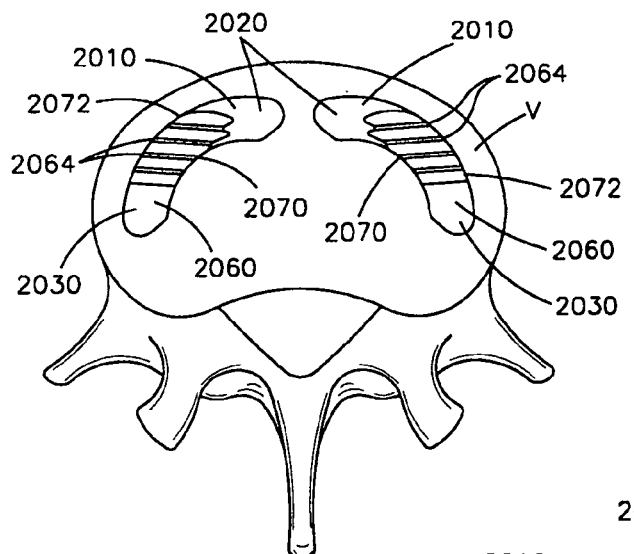
FIG. 48 is a view showing a pair of the spinal implants of FIG. 38 in first relative positions between adjacent vertebrae.
Figure 49:
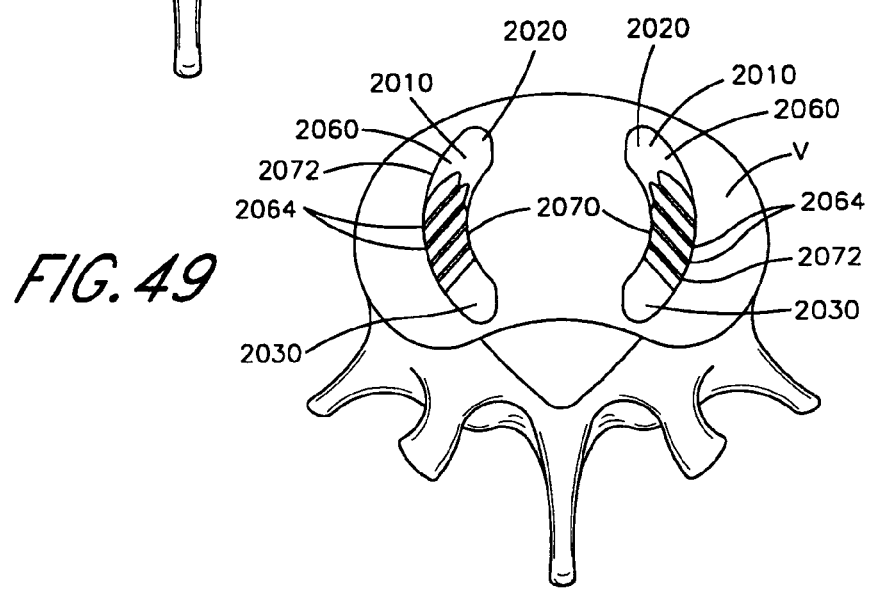
FIG. 49 is a view showing a pair of the spinal implants of FIG. 38 in second relative positions between adjacent vertebrae.

In one application, a fusion device is inserted between adjacent vertebrae V. Portions of the fusion procedure can be performed before, during, or after portions of the fixation procedure. FIGS. 38-42 illustrate one embodiment of a fusion device, referred to herein as a spinal implant 2010, that is inserted between adjacent vertebrae. The spinal implant 2010 preferably is placed between adjacent vertebrae to provide sufficient support to allow fusion of the adjacent vertebrae, as shown in FIGS. 48-49. The spinal implants 2010 are preferably made from an allograft material, though other materials could also be used, including autograft, xenograft, or some non-biologic biocompatible material, such as titanium or stainless steel. Also, where non-biologic materials are used, the implant 2010 may be configured as a cage or other suitable configuration.

Figure 41:
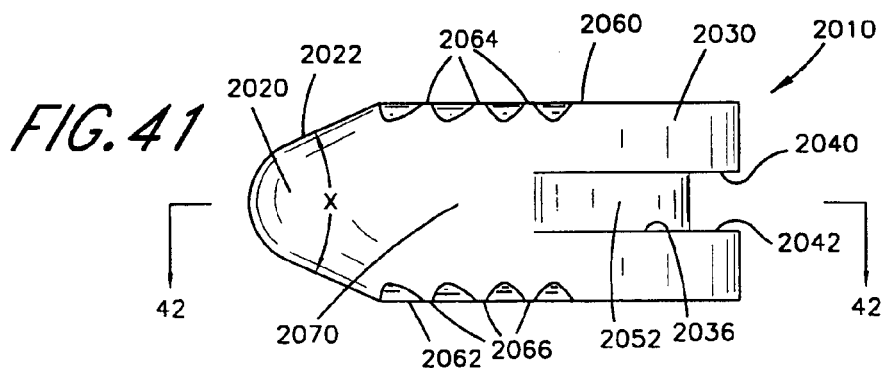
FIG. 41 is a side view of the spinal implant of FIG. 38 showing the first side surface.
Figure 42:
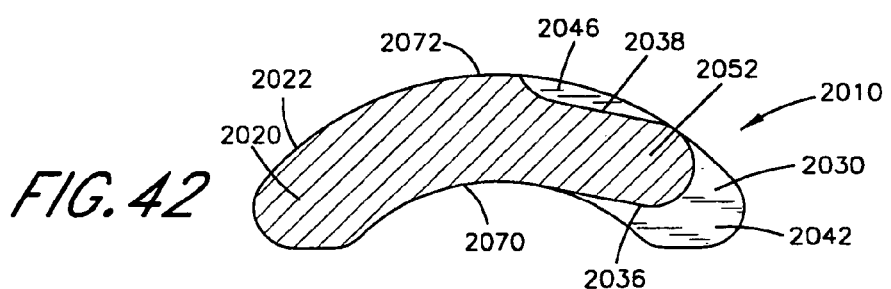
FIG. 42 is a cross-sectional view of the spinal implant taken along the line 42-42 in FIG. 41.

The spinal implant 2010 (FIGS. 38-42) has a first end 2020 for insertion between adjacent vertebrae V. The first end 2020 has a tapered surface 2022 to facilitate insertion of the implant between adjacent vertebrae V. The surface 2022 defines an angle X of approximately 45° as shown in FIG. 41.

Figure 51:
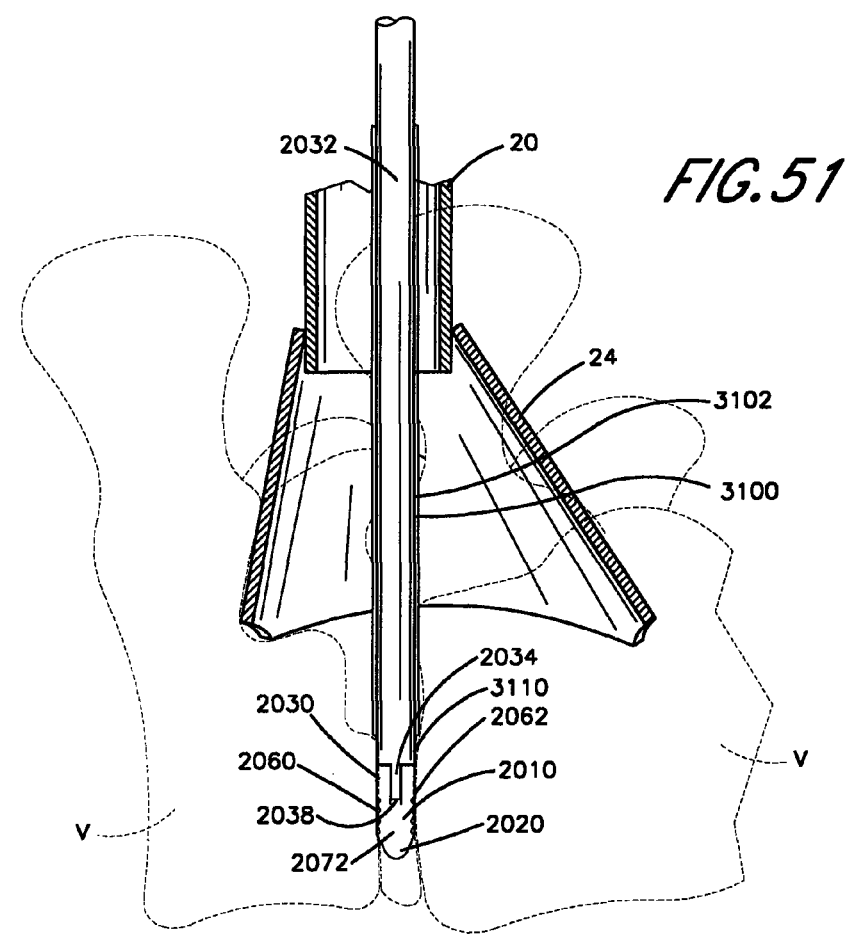
FIG. 51 is a view showing a spinal implant being inserted between the adjacent vertebrae according to another embodiment.
Figure 54:
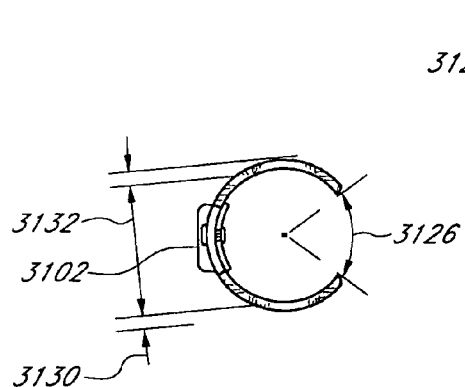
FIG. 54 is a top view of the apparatus of FIG. 52.
Figure 56:
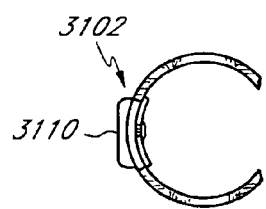
FIG. 56 is a bottom view of the apparatus of FIG. 52.
Figure 55:
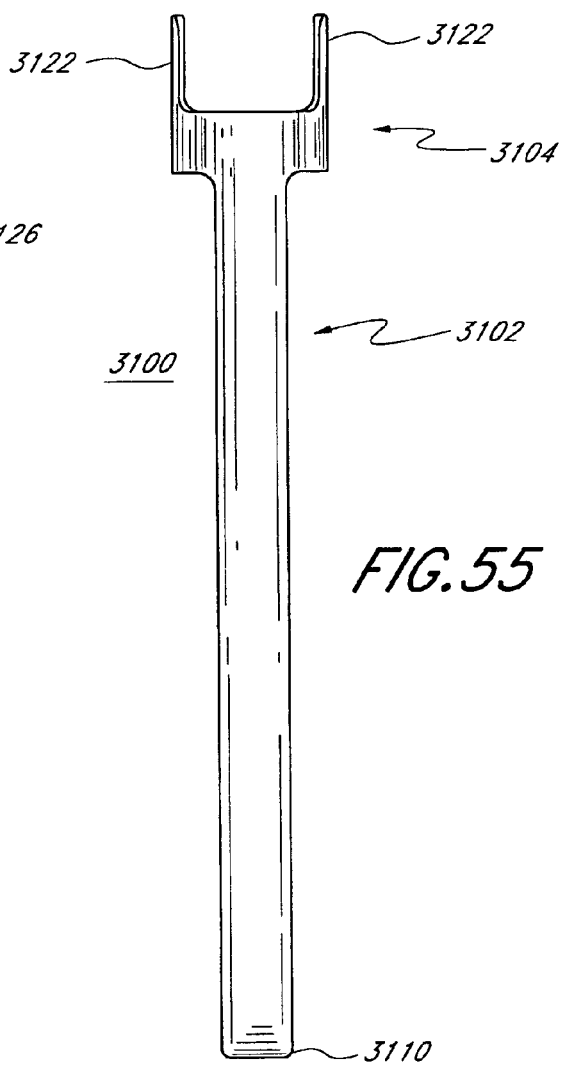
FIG. 55 is a back view of the apparatus of FIG. 52.

The spinal implant 2010 (FIGS. 38-39) has a second end 2030 that is engageable with a tool 2032 (FIG. 51) for inserting the implant between the adjacent vertebrae V. The tool 2032 has a pair of projections 2034, one of which is shown in FIG. 51, that extend into recesses 2036 and 2038 in the end 2030 of the implant 2010. The recesses 2036 and 2038 (FIGS. 38-39) extend from the second end 2030 toward the first end 2020. The recess 2036 (FIG. 41) is defined by an upper surface 2040 and a lower surface 2042 extending generally parallel to the upper surface 2040. The recess 2038 (FIG. 39) has a lower surface 2046 and an upper surface 2048. The upper surface 2048 extends generally parallel to the lower surface 2046.

The recesses 2036 and 2038 define a gripping portion 2052. The projections 2034 on the tool 2032 extend into the recesses 2036 and 2038 and grip the gripping portion 2052. The projections 2034 engage the upper and lower surfaces 2040 and 2042 of the recess 2036 and the upper and lower surfaces 2046 and 2048 of the recess 2038. Accordingly, the tool 2032 can grip the implant 2010 for inserting the implant between the adjacent vertebrae V.

Figures 38, 39:
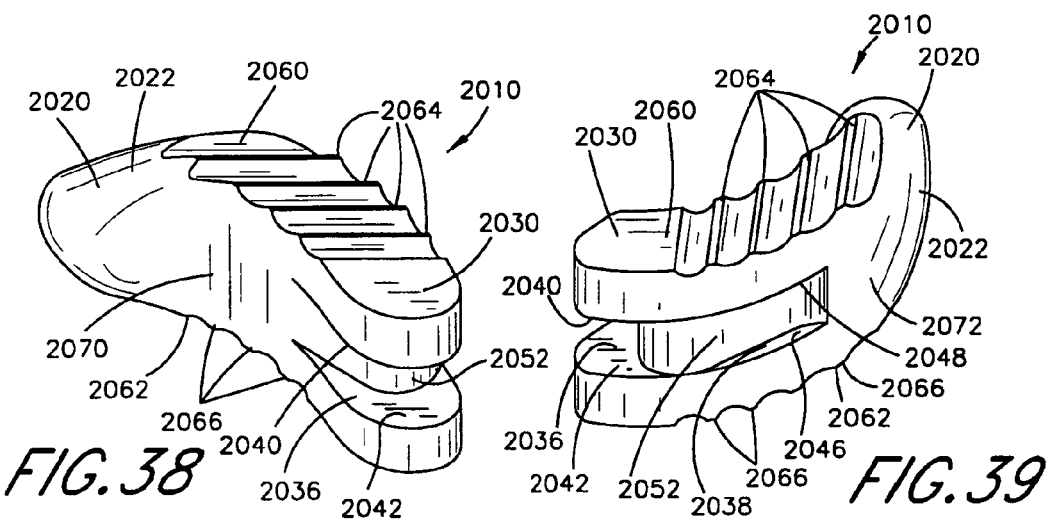
FIG. 38 is a perspective view of a spinal implant or fusion device constructed according to another embodiment showing a first side surface of the spinal implant.
FIG. 39 is a perspective view of the spinal implant of FIG. 38 showing a second side surface of the spinal implant.
Figure 40:
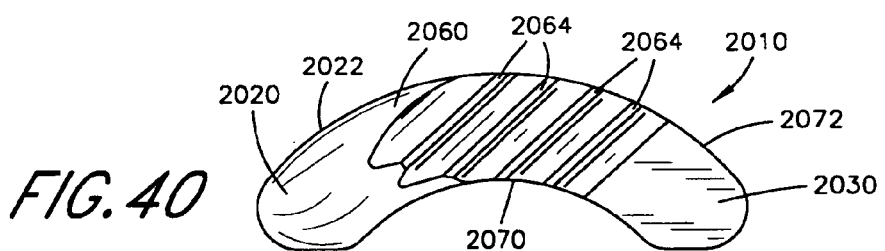
FIG. 40 is a plan view of the spinal implant of FIG. 38 showing an upper surface of the spinal implant.

As viewed in FIGS. 38-41, the implant 2010 has an upper surface 2060 for engaging the upper vertebra V. The implant 2010 has a lower surface 2062, as viewed in FIGS. 38-41, for engaging the lower vertebra V. The upper and lower surfaces 2060 and 2062 extend from the first end 2020 to the second end 2030 of the implant 2010 and parallel to the upper and lower surfaces 2040, 2042, 2046, and 2048 of the recesses 2036 and 2038. The upper surface 2060 has teeth 2064 for engaging the upper vertebra V. The lower surface 2062 has teeth 2066 for engaging the lower vertebra V. Although FIGS. 38-39 show four teeth 2064 and four teeth 2066, it is contemplated that any number of teeth could be used.

A first side surface 2070 and a second side surface 2072 extend between the upper and lower surfaces 2060 and 2062. The first side surface 2070 extends along a first arc from the first end 2022 of the implant 2010 to the second end 2030. The second side surface 2072 extends along a second arc from the first end 2022 to the second end 2030. The first and second side surfaces 2070 and 2072 are concentric and define portions of concentric circles. The teeth 2064 and 2066 extend parallel to each other and extend between the side surfaces 2070 and 2072 and along secant lines of the concentric circles defined by the side surfaces.

The implant 2010 preferably is formed by harvesting allograft material from a femur, as known in the art. The femur is axially cut to form cylindrical pieces of allograft material. The cylindrical pieces are then cut in half to form semi-cylindrical pieces of allograft material. The semi-cylindrical pieces of allograft material are machined into the spinal implants 2010.

A pair of spinal implants 2010 may be placed bilaterally between the adjacent vertebrae V. The access device 20 is positioned in the patient's body adjacent the vertebrae V. The skirt portion 24 of the access device 20 preferably is in a radially expanded condition to provide a working space adjacent the vertebrae V as described above. Disc material between the vertebrae V can be removed using instruments such as kerrisons, rongeurs, or curettes. A microdebrider may also be utilized to remove the disc material. An osteotome, curettes, and scrapers can be used to prepare end plates of the vertebrae V for fusion. Preferably, an annulus of the disc is left between the vertebrae V.

Distracters can be used to sequentially distract the disc space until the desired distance between the vertebrae V is achieved. The fusion device or implant 2010 is placed between the vertebrae V using the tool 2032. The first end 2020 of the implant 2010 is inserted first between the vertebrae V. The implant 2010 is pushed between the vertebrae V until the end 2030 of the implant is between the vertebrae. A second spinal implant 2010 is inserted on the ipsilateral side using the same procedure.

A shield apparatus 3100 with an elongated portion 3102 may be used to facilitate insertion of the implants 2010 between the vertebrae V. A distal portion 3110 of the apparatus 3100 may be placed in an annulotomy. The implant 2010 is inserted with the side surface 2170 facing the elongated portion 3102 so that the apparatus 3100 can act as a "shoe horn" to facilitate or guide insertion of the implants 2010 between the vertebrae.

The implants 2010 may be inserted between the vertebrae V with the first ends 2020 located adjacent each other and the second ends 2030 spaced apart from each other, as shown in FIG. 48. The implants 2010 may also be inserted between the vertebrae V with the first ends 2020 of the implants 2010 spaced apart approximately the same distance that the second ends 2030 are spaced apart. It is contemplated that the implants 2010 may be inserted in any desired position between the vertebrae V. It is also contemplated that in some embodiments only one implant 2010 may be inserted between the vertebrae V. Furthermore, it is contemplated that the implants 2010 may be inserted between vertebrae using an open procedure.

Figure 50:
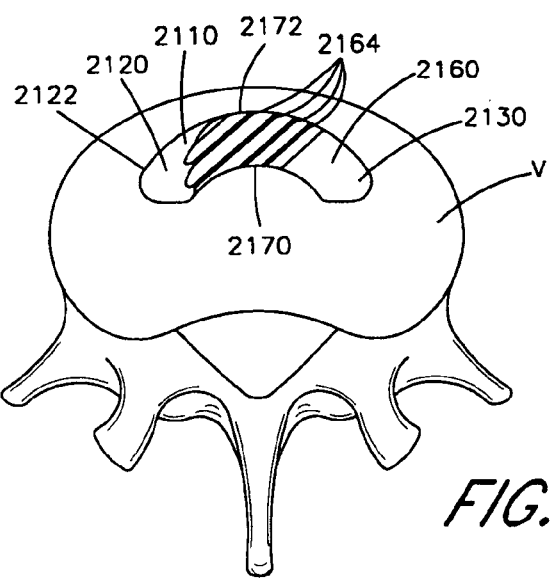
FIG. 50 is a view showing the spinal implant of FIG. 43 between adjacent vertebrae.

Another embodiment of a fusion device or spinal implant 2110 is illustrated in FIGS. 43-47. The spinal implant 2110 is substantially similar to the embodiment disclosed in FIGS. 38-42. The implant 2110 is placed between the adjacent vertebrae V to provide sufficient support to allow fusion of the adjacent vertebrae, as shown in FIG. 50. The spinal implant 2110 is preferably made from an allograft material, though the materials described above in connection with the spinal implant 2010 may also be used. Also, as with the implant 2010, the implant 2110 may be formed as a cage or other suitable configuration.

Figure 65:
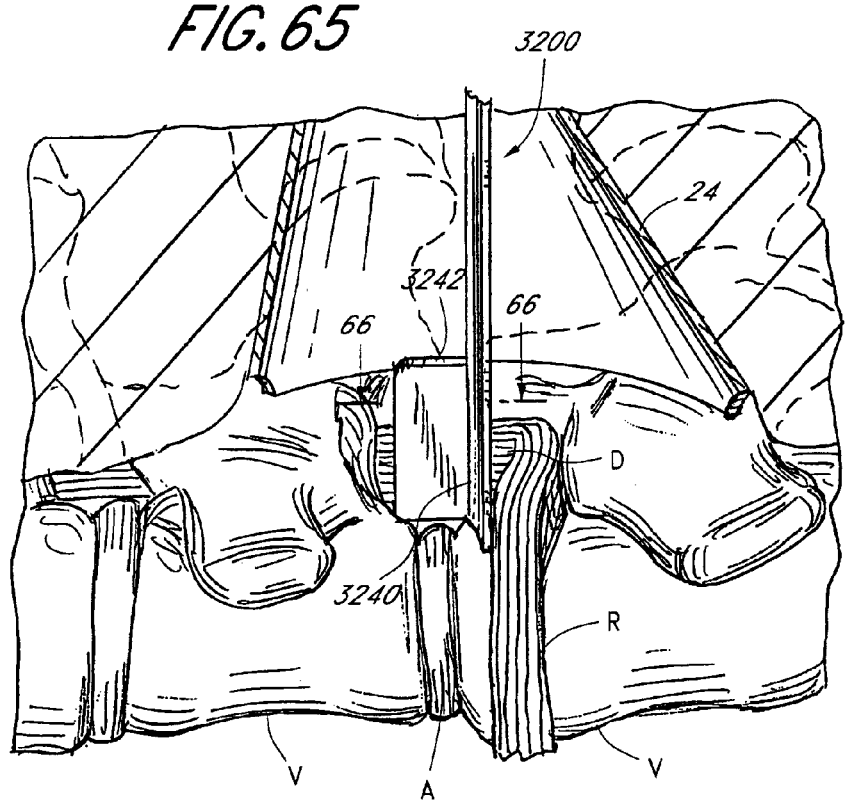
FIG. 65 is a sectional view, similar to FIG. 57, of the apparatus of FIG. 63, used in conjunction with additional structure in a patient.

The spinal implant 2110 (FIGS. 43-47) has a first end 2120 for insertion between the adjacent vertebrae V. The first end 2120 has a tapered surface 2122 to facilitate insertion of the implant between the adjacent vertebrae V. The surface 2122 defines an angle Y of approximately 45° as shown in FIG. 65.

The spinal implant 2110 (FIGS. 43-44) has a second end 2130 that is engageable with the projections 2034 on the tool 2032 for inserting the implant between the adjacent vertebrae V. The projections 2034 extend into recesses 2136 and 2138 in the end 2130 of the implant 2110. The recesses 2136 and 2138 extend from the second end 2130 toward the first end 2120. The recess 2136 (FIGS. 43 and 46) is defined by an upper surface 2140 and a lower surface 2142 extending generally parallel to the upper surface 2140. The recess 2138 (FIG. 44) has a lower surface 2146 and an upper surface 2148 extending generally parallel to the lower surface 2146.

The recesses 2136 and 2138 define a gripping portion 2152. The projections 2034 on the tool 2032 extend into the recesses 2136 and 2138 and grip the gripping portion 2152. The projections 2034 engage the upper and lower surfaces 2140 and 2142 of the recess 2136 and the upper and lower surfaces 2146 and 2148 of the recess 2138. Accordingly, the tool 2032 can grip the implant 2110 for inserting the implant between the adjacent vertebrae V.

Figures 43, 44:
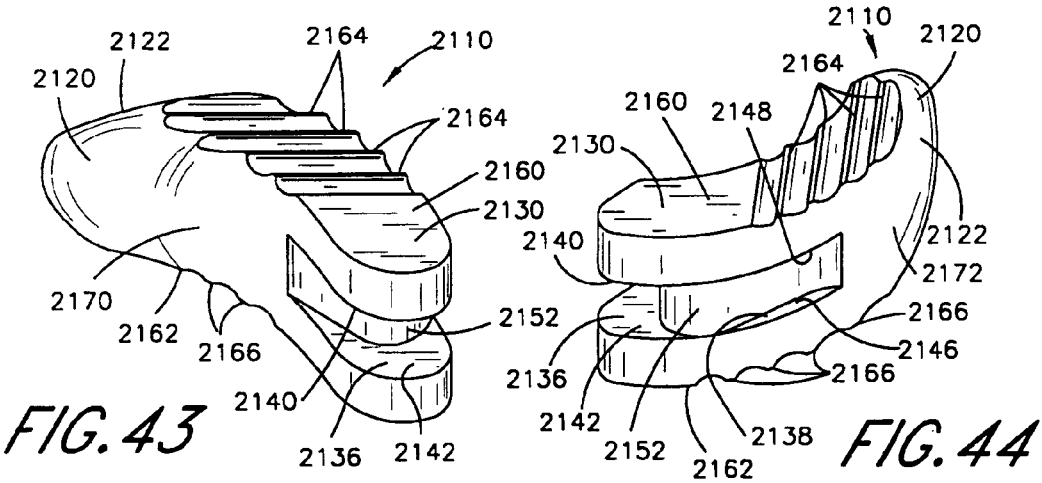
FIG. 43 is a perspective view of another embodiment of a spinal implant constructed according to another embodiment showing a first side surface of the spinal implant.
FIG. 44 is a perspective view of the spinal implant of FIG. 43 showing a second side surface of the spinal implant.
Figure 45:
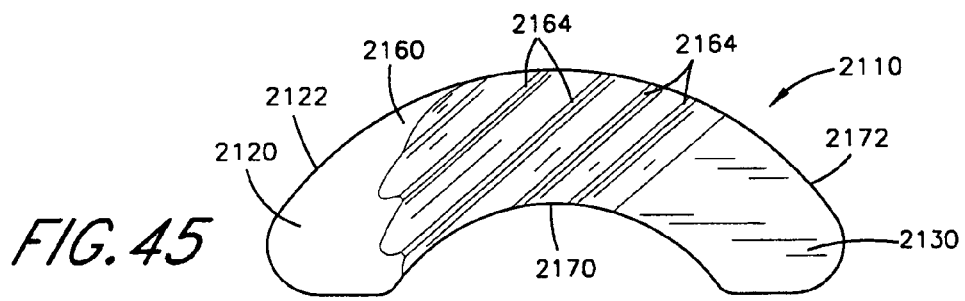
FIG. 45 is a plan view of the spinal implant of FIG. 43 showing an upper surface of the spinal implant.
Figure 46:
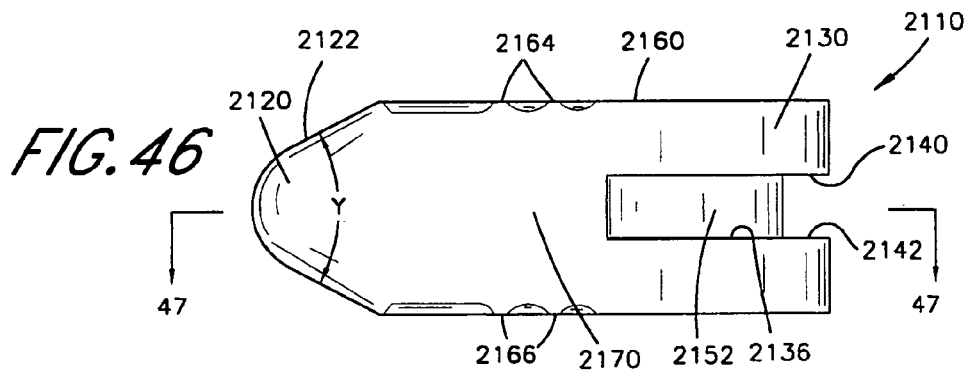
FIG. 46 is a side view of the spinal implant of FIG. 43 showing the first side surface.
Figure 47:
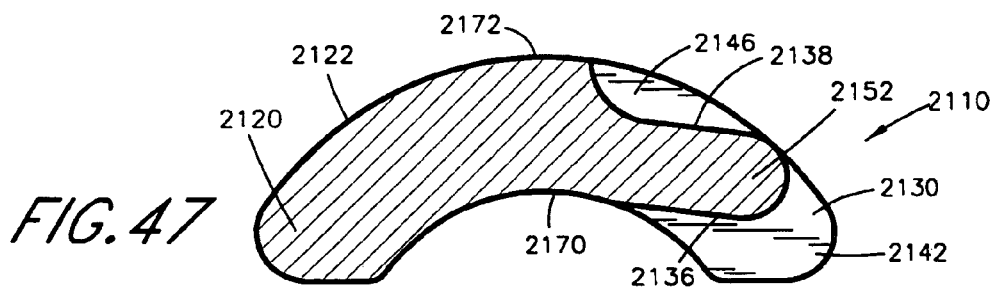
FIG. 47 is a cross-sectional view of the spinal implant taken along the line 47-47 in FIG. 46.

As viewed in FIGS. 43-46, the implant 2110 has an upper surface 2160 for engaging the upper vertebra V. The implant 2110 has a lower surface 2162, as viewed in FIGS. 43-46, for engaging the lower vertebra V. The upper and lower surfaces 2160 and 2162 extend from the first end 2120 to the second end 2130 of the implant 2110 and parallel to the upper and lower surfaces 2140, 2142, 2146, and 2148 of the recesses 2136 and 2138. The upper surface 2160 has teeth 2164 for engaging the upper vertebra V. The lower surface 2162 has teeth 2166 for engaging the lower vertebra V. Although FIG. 44 shows four teeth 2164 and four teeth 2166, it is contemplated that any number of teeth could be used.

A first side surface 2170 and a second side surface 2172 extend between the upper and lower surfaces 2160 and 2162. The first side surface 2170 extends along a first arc from the first end 2122 of the implant 2110 to the second end 2130. The second side surface 2172 extends along a second arc from the first end 2120 to the second end 2130. The first and second side surfaces 2170 and 2172 are concentric and define portions of concentric circles. The teeth 2164 and 2166 extend parallel to each other and between the side surfaces 2170 and 2172 along secant lines of the concentric circles defined by the side surfaces.

The implant 2110 preferably is formed by harvesting allograft material from a femur, as is known in the art. The femur is axially cut to form cylindrical pieces of allograft material. The cylindrical pieces are then cut in half to form semi-cylindrical pieces of allograft material. The semi-cylindrical pieces of allograft material are machined into the spinal implants 2110.

A spinal implant 2110 is placed unilaterally between the adjacent vertebrae V. The access device 20 is positioned in the patient's body adjacent the vertebrae V. The skirt portion 24 of the access device 20 preferably is in a radially expanded condition to provide a working space adjacent the vertebrae V as described above. Disc material between the vertebrae V can be removed using instruments such as kerrisons, rongeurs, or curettes. A microdebrider may also be utilized to remove the disc material. An osteotome, curettes, and scrapers can be used to prepare end plates of the vertebrae V for fusion. Preferably, an annulus of the disc is left between the vertebrae V.

Distracters are used to sequentially distract the disc space until the desired distance between the vertebrae V is achieved. The implant 2110 is placed between the vertebrae V using the tool 2032. It is contemplated that the apparatus 3100 could be used also. The first end 2120 of the implant 2110 is inserted first between the vertebrae V. The implant 2110 is pushed between the vertebrae V until the end 2130 of the implant is between the vertebrae. It is contemplated that the implant 2110 may be inserted in any desired position between the vertebrae V. It is also contemplated that in some embodiments more than one implant 2110 may be inserted between the vertebrae.

The apparatus or shield 3100 for use in placing the fusion devices or spinal implants between the vertebrae is illustrated in FIGS. 52-56. The apparatus 3100 preferably includes an elongated body portion 3102, which protects the nerve root or dura, and a mounting portion 3104, which allows for the surgeon to releasably mount the apparatus 3100 to the access device 20. Consequently, the surgeon is able to perform the surgical procedures without requiring the surgeon or an assistant to continue to support the apparatus 3100 throughout the procedure, and without reducing the field of view.

The apparatus 3100 may be manufactured from a biocompatible material such as, for example, stainless steel. In the illustrated embodiment, apparatus 3100 is manufactured from stainless steel having a thickness of about 0.02 inches (0.508 mm) to about 0.036 inches (0.914 mm). The elongated body portion 3102 has dimensions that correspond to the depth in the body in which the procedure is being performed, and to the size of the body structure that is to be shielded by elongated body portion 3102. In the exemplary embodiment, the elongated body portion 3102 has a width 3106 of about 0.346 inches (8.79 mm) and a length of about 5.06 inches (128.5 mm) (FIG. 53), although other dimensions would be appropriate for spinal surgical procedures performed at different locations, or for surgical procedures involving different body structures. The distal tip portion 3110 of the apparatus 3100 may have a slightly curved "bell mouth" configuration which allows for atraumatic contact with a body structure, such as a nerve. It is contemplated that the elongated body portion may have any desired shape.

The mounting portion 3104 preferably allows the apparatus 3100 to be secured to a support structure in any number of ways. In the exemplary embodiment, mounting portion 3104 may include a ring portion. With reference to FIGS. 52-56, ring portion 3120 has a substantially ring-shaped configuration with an opening 3124, which defines an angle 3126 of about 90 degrees of the total circumference of the ring portion 3120. As will be described in greater detail below, the angle 3126 is a nominal value, because the ring portion 3104 is resilient, which permits the opening 3124 to change size during the mounting process.

In the illustrated embodiment, the mounting portion 3104 has a substantially cylindrical configuration in order to be mounted within the interior lumen of the access device 20, as will be described below. The ring portion 3104 has an exterior dimension 3130 of about 0.79 inches (20.1 mm), and an interior dimension 3132 of about 0.76 inches (19.3 mm). It is understood that the dimensions of the ring portion 3104 can be different, such as, for example, where the access device 20 has a different interior dimension. Moreover, the cylindrical shape of the ring portion 3104 can change, such as, for example, where the apparatus 3100 is used with a support member having a differently shaped internal lumen.

Finger grip portions 3122 preferably extend from the mounting portion 3104 and allow the surgeon to apply an inwardly directed force (as indicated by arrows A) to the ring portion 3120. The resilient characteristics of the ring portion 3120 allow the material to deflect thereby reducing the exterior dimension 3130 and reducing the spacing 3124. Releasing the finger grip portions 3122 allows the ring portion to move towards its undeflected condition, thereby engaging the interior wall of the access device 20.

The elongated body portion 3102 and the mounting portion 3104 may be manufactured from a single component, such as a sheet of stainless steel, and the mounting portion 3104 may be subsequently formed into a substantially cylindrical shape. In another embodiment, the mounting portion 3104 may be manufactured as a separate component and coupled with the elongated body portion, by techniques such as, for example, welding and/or securement by fasteners, such as rivets.

The access device 20 serves as a stable mounting structure for apparatus 3100. In particular, mounting portion 3104 is releasably mounted to the interior wall of proximal wall portion 22 of access device 20. Elongated body portion 3102 extends distally into the operative site to protect the desired body structure, such as the nerve, as will be described below.

Figures 58, 59:
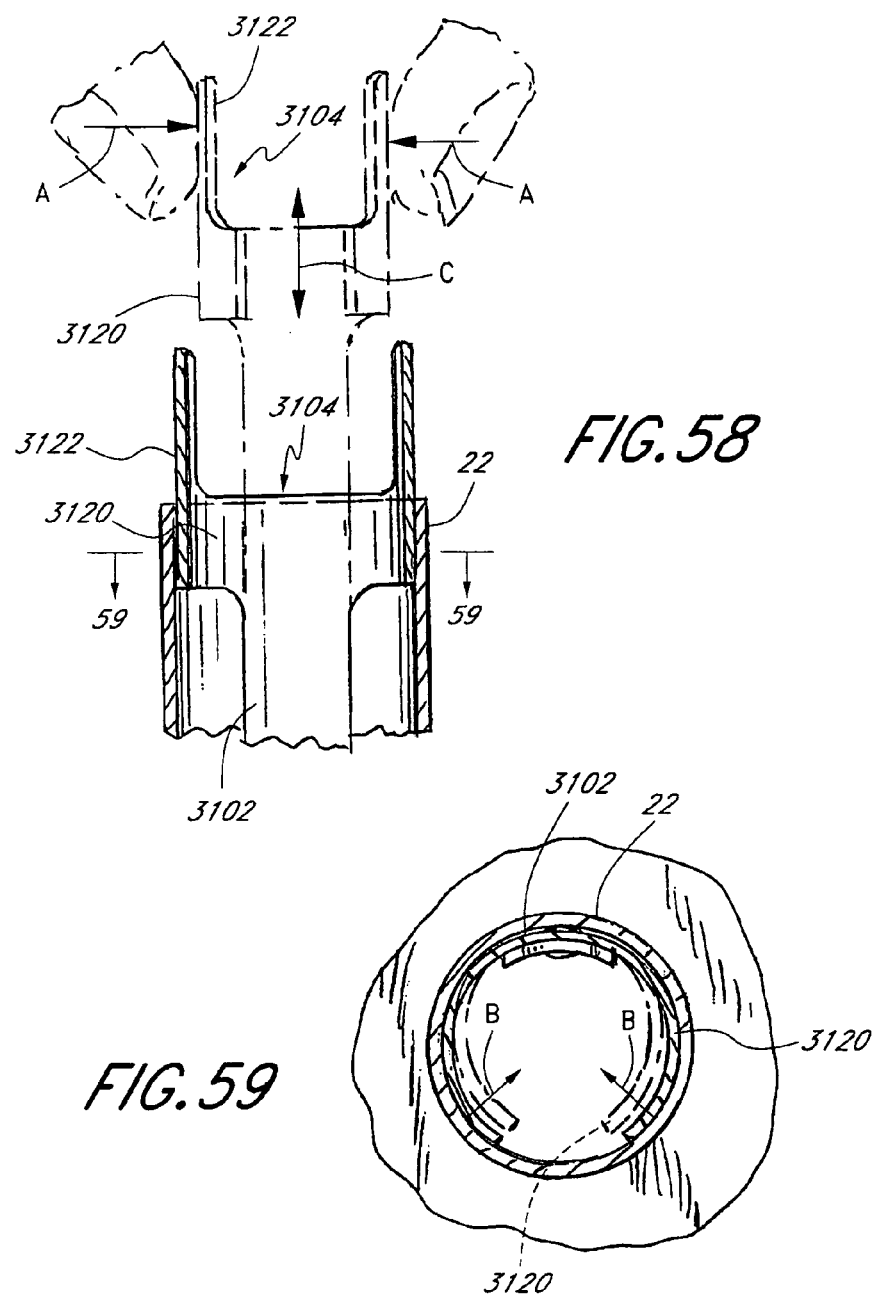
FIG. 58 is a longitudinal sectional view of the apparatus of FIG. 57 taken from line 58-58 of FIG. 57.
FIG. 59 is a transverse sectional view of the apparatus of FIG. 58 taken from line 59-59 of FIG. 58.

To install the apparatus 3100 within the interior passage of the proximal wall portion 22, the surgeon may apply an inwardly directed force on the ring portion 3120, thereby causing the ring portion to resiliently deform, as illustrated by dashed line and arrows B in FIG. 59. The surgeon subsequently inserts the apparatus 3100 into the interior lumen of the proximal wall portion 22 (as indicated by arrow C) to the position of ring portion 3104 illustrated in solid line in FIG. 58. When the surgeon releases the finger grip portions 3122, the ring portion 3120 resiliently moves towards its undeflected configuration, thereby engaging the interior lumen of the proximal wall portion 22. Advantages of some embodiments include that the mounting portion 3104 is easily removed and/or moved with respect to the access device 20 without disturbing the position of the access device 20 or any other instrumentation.

Figure 57:
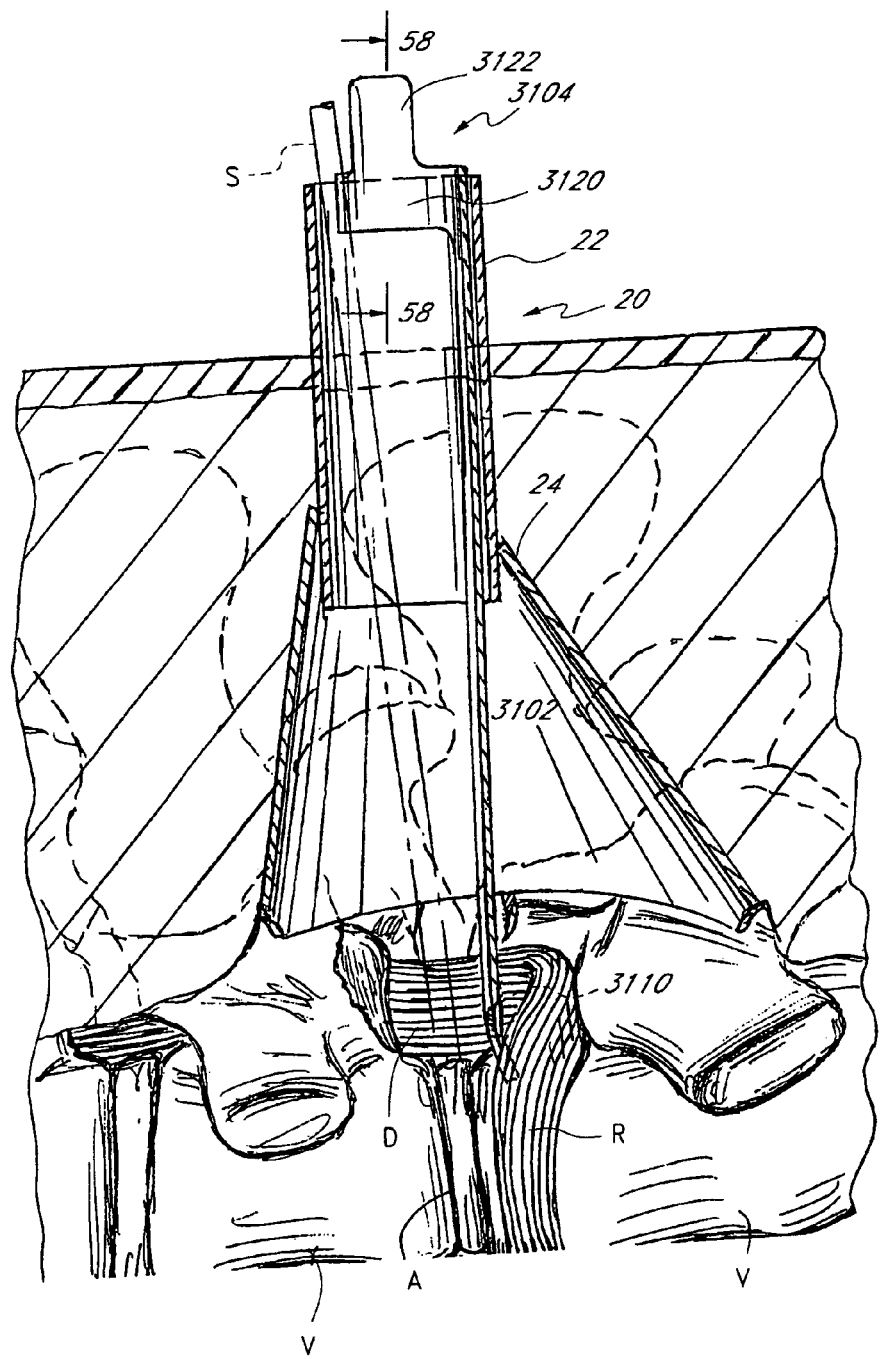
FIG. 57 is a sectional view of the apparatus of FIG. 52, used in conjunction with additional structure in a patient.

As illustrated in FIG. 57, the configuration of the mounting portion 3104 and the elongated body portion 3102 allow the elongated body portion to occupy a small space along the periphery of the proximal wall portion 3122. This allows the apparatus to protect the desired body structure without blocking access for the insertion of other surgical instrumentation, and without blocking visibility by the surgeon during the procedure.

The mounting portion 3104 is one exemplary configuration for mounting the apparatus 3100 to the support structure. It is contemplated that the apparatus 3100 may be mounted within the access device 20 in any suitable manner.

When in position, the distal end portion 3110 covers the exiting nerve root R, while exposing the disc annulus A (See FIG. 57). As discussed above, the debridement and decortication of tissue covering the vertebrae, as well as a facetectomy and/or laminectomy if indicated, are preferably performed prior to the insertion of apparatus 3100 into the surgical space. Accordingly, in some embodiments, there is no need to displace or retract tissue, and apparatus 3100 merely covers the nerve root and does not substantially displace the nerve root or any other body tissue. It is understood that the term "cover" as used herein refers to apparatus 3100 being adjacent to the body structure, or in contact with the body structure without applying significant tension or displacement force to the body structure.

Additional surgical instrumentation S may be inserted into the access device to perform procedures on the surrounding tissue. For example, an annulotomy may be performed using a long handled knife and kerrisons. A discectomy may be completed by using curettes and rongeurs. Removal of osteophytes which may have accumulated between the vertebrae may be performed using osteotomes and chisels.

Figure 60:
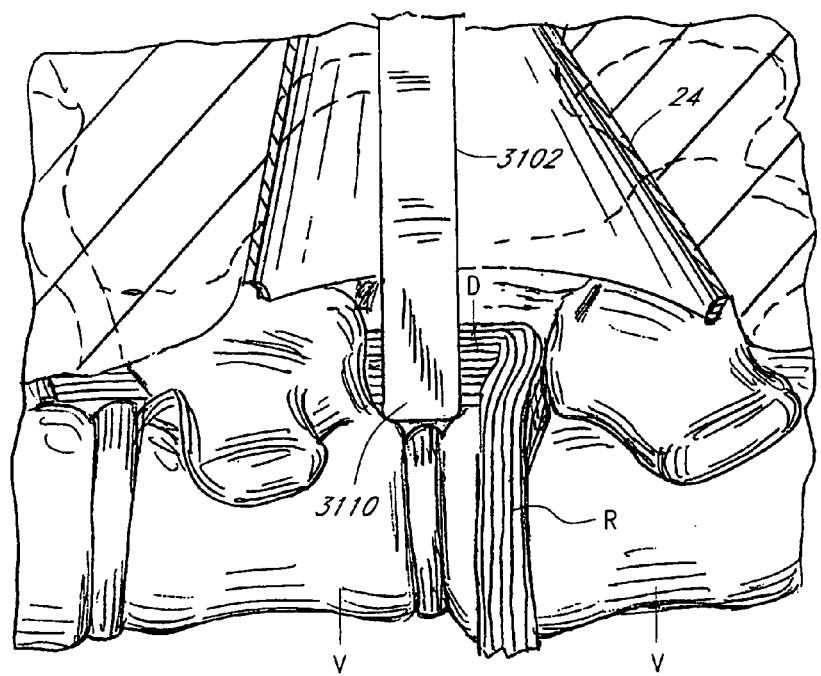
FIG. 60 is a sectional view, similar to FIG. 57, illustrating an alternative position of the apparatus of FIG. 52.

As illustrated in FIG. 60, the elongated body portion 3102 preferably is rotated to protect the spinal cord, or dura D, during the above procedures. The surgeon may change the position of the apparatus 3100 by approximating the finger grips 3122 to release the ring portion from engagement with the inner wall of the proximal wall portion 20, and then re-position the apparatus 3100 without disturbing the access device 20 (as shown in FIG. 58).

Figure 61:
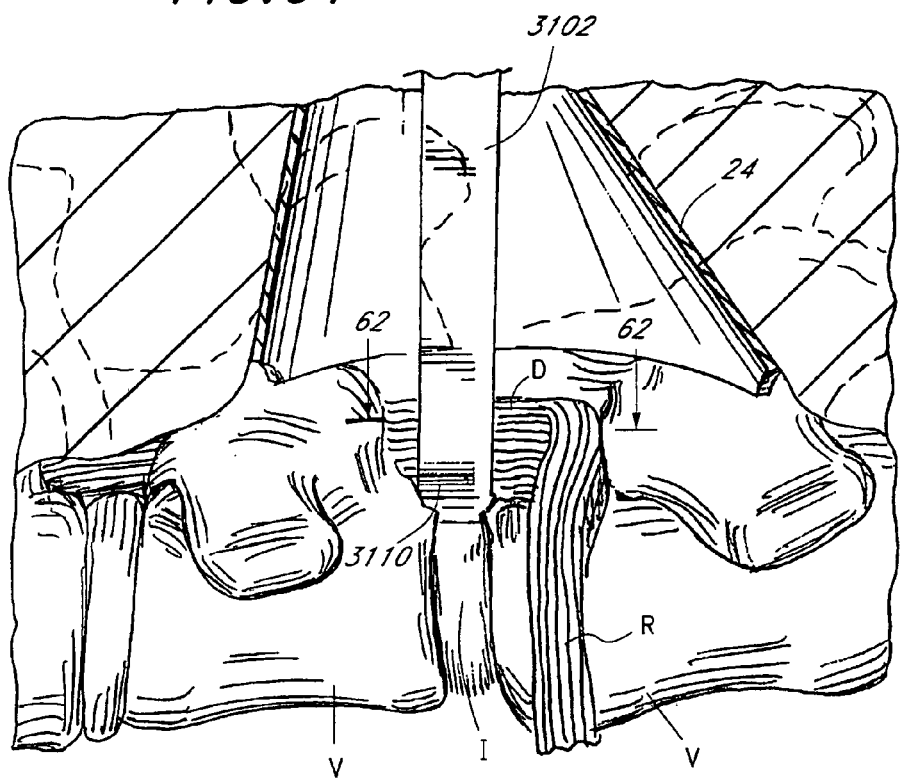
FIG. 61 is a sectional view, similar to FIG. 57, illustrating another alternative position of the apparatus of FIG. 52.
Figure 62:
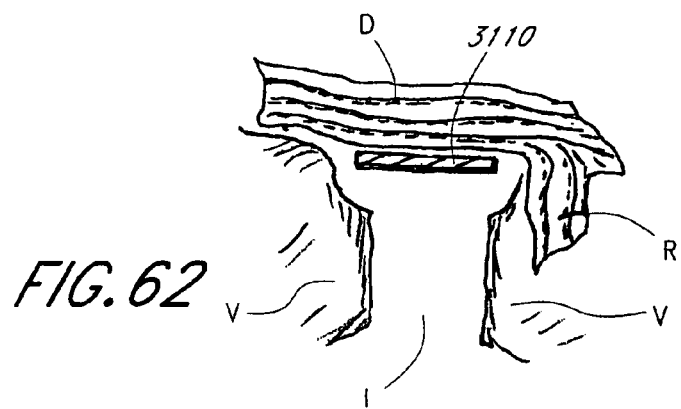
FIG. 62 is a transverse sectional view of the apparatus of FIG. 61, taken along lines 62-62 of FIG. 61.

During certain surgical procedures, it may be useful to introduce crushed bone fragments or the fusion devices 2010 or 2110 to promote bone fusion. As illustrated in FIGS. 61-62, apparatus 3100 is useful to direct the implants into the space I between adjacent vertebrae V. As shown in the figures, the distal portion 3110 of the elongated body portion 3102 is partially inserted into the space I. The distal end portion 3110, is positioned between adjacent vertebrae V, and creates a partially enclosed space for receiving the implants or other material therein.

Another embodiment of the apparatus or shield is illustrated in FIGS. 63-64, and designated apparatus 3200. Apparatus 3200 is substantially identical to apparatus 3100, described above, with the following differences noted herein. In particular, distal end portion 3210 includes a pair of surfaces 3240 and 3242. Surface 3240 is an extension of elongated shield portion 3202, and surface 3242 extends at an angle with respect to surface 3240. In the exemplary embodiment, surfaces 3240 and 3242 defined an angle of about 90 degrees between them. Alternatively another angle between surfaces 3240 and 3242 may be defined as indicated by the body structures to be protected.

Figure 66:
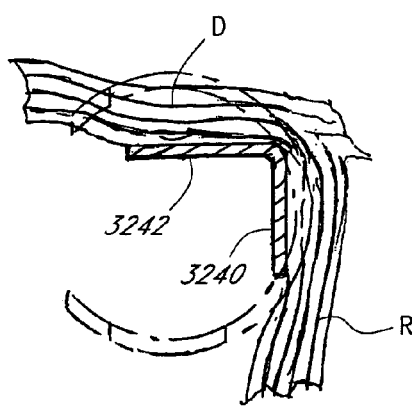
FIG. 66 is a transverse sectional view of the apparatus of FIG. 63, taken along lines 66-66 of FIG. 65.

Distal end portion 3210 allows the apparatus to provide simultaneous shielding of both the dura D and the nerve root R. In FIGS. 65-66, surface 3242 shields the dura D, and surface 3240 shields the nerve root R. It is understood that surfaces 3240 and 3242 may be interchanged with respect to which tissue they protect during the surgical procedure.

According to the exemplary embodiment, once the fusion and fixation portions of the procedure have been performed, the procedure is substantially complete. The surgical instrumentation, such as the endoscope 500 can be withdrawn from the surgical site. The access device 20 is also withdrawn from the site. The muscle and fascia typically close as the access device 20 is withdrawn through the dilated tissues in the reduced profile configuration. The fascia and skin incisions are closed in the typical manner, with sutures, etc. The procedure described above may be repeated for the other lateral side of the same vertebrae, if indicated.

II. Surgical Procedures that may be Performed with the Systems Described Herein

As discussed above, the systems disclosed herein provide access to a surgical location at or near the spine of a patient to enable procedures on the spine. These procedures can be applied to one or more vertebral levels, as discussed above. Additional procedures and combinations of procedures that may be performed using the systems described herein are discussed below. In various forms, these procedures involve an anterior lumbar interbody fusion, a minimally invasive lumbar interbody fusion, and other procedures particularly enabled by the access devices and systems described above.

A. Procedures Involving Anterior Lumbar Interbody Fusion

The access devices and systems described herein are amenable to a variety of procedures that may be combined with an anterior lumbar interbody fusion (referred to herein as an "ALIF").

In one embodiment of a first method, three adjacent vertebrae, such as the L4, the L5, and the S1 vertebrae of the spine, are treated by first performing an ALIF procedure. Such a procedure may be performed in a convention manner. The ALIF involves exposing a portion of the spine, in particular the vertebrae and discs located in the interbody spaces, i.e., the spaces between adjacent vertebrae. Any suitable technique for exposing the interbody spaces may be employed, e.g., an open, mini-open, or minimally invasive procedure. In one embodiment, the interbody spaces between the L4, L5, and S1 vertebrae are exposed to the surgeon. Once exposed, the surgeon may prepare the interbody space, if needed, in any suitable manner. For example, some or all of the disc may be removed from the interbody space and the height of the interbody space may be increased or decreased. The interbody space between the L4 and the L5 vertebrae may be exposed separately from the interbody space between the L5 and S1 vertebrae or they may be generally simultaneously exposed and prepared.

After the interbody space has been exposed and prepared, a suitable fusion procedure may be performed. For example, in one example fusion procedure, one or more fusion devices may be placed in the interbody space. Any suitable fusion device may be used, e.g., a fusion cage, a femoral ring, or another suitable implant. Various embodiments of implants and techniques and tools for the insertion of implants are described in U.S. application Ser. No. 10/280,489, filed Oct. 25, 2002, which has been published as Publication No. 2003/0073998 on Apr. 17, 2003, which is hereby incorporated by reference herein in its entirety. In one variation, one or more fusion cages may be placed in an interbody space, e.g., between the L4 and L5 vertebrae, between the L5 and S1 vertebrae, or between the L4 and L5 vertebrae and between the L5 and S1 vertebrae. In another variation, one or more femoral rings may be substituted for one or more of the fusion cages and placed between the L4 and L5 vertebrae and/or between the L5 and S1 vertebrae. In another variation, one or more fusion devices are combined with a bone growth substance, e.g., bone chips, to enhance bone growth in the interbody space(s).

After anterior placement of the fusion device, an access device is inserted into the patient to provide access to a spinal location, as described above. A variety of anatomical approaches may be used to provide access to a spinal location using the access device 20. The access device preferably is inserted generally posteriorly. As used herein the phrase "generally posteriorly" is used in its ordinary sense and is a broad term that refers to a variety of surgical approaches to the spine that may be provided from the posterior side, i.e., the back, of the patient, and includes, but is not limited to, posterior, postero-lateral, and transforaminal approaches. Any of the access devices described or incorporated herein, such as the access device 20, could be used.

The distal end of the access device may be placed at the desired surgical location, e.g., adjacent the spine of the patient with a central region of the access device over a first vertebrae. In one procedure, the distal end of the access device is inserted until it contacts at least a portion of at least one of the vertebrae being treated or at least a portion of the spine. In another procedure, the distal end of the access device is inserted until it contacts a portion of the spine and then is withdrawn a small amount to provide a selected gap between the spine and the access device. In other procedures, the access device may be inserted a selected amount, but not far enough to contact the vertebrae being treated, the portion of the vertebrae being treated, or the spine.

The access device may be configured, as described above, to provide increased access to the surgical location. The access device can have a first configuration for insertion to the surgical location over the first vertebra and a second configuration wherein increased access is provided to the adjacent vertebrae. The first configuration may provide a first cross-sectional area at a distal portion thereof. The second configuration may provide a second cross-sectional area at the distal portion thereof. The second cross-sectional area preferably is enlarged compared to the first cross-sectional area. In some embodiments, the access device may be expanded from the first configuration to the second configuration to provide access to the adjacent vertebrae above and below the first vertebra.

When it is desired to treat the L4, L5, and S1 vertebrae, the access device may be inserted over the L5 vertebrae and then expanded to provide increased access to the L4 and S1 vertebrae. In one embodiment, the access device can be expanded to an oblong shaped configuration wherein the access device provides a first dimension of about 63 mm, and a second dimension perpendicular to the first dimension of about 24 mm. In another embodiment, the access device can be expanded to provide a first dimension of about 63 mm, and a second dimension perpendicular to the first dimension of about 27 mm. These dimensions provide a surgical space that is large enough to provide access to at least three adjacent vertebrae without exposing excessive amounts of adjacent tissue that is not required to be exposed for the procedures being performed. Other dimensions and configurations are possible that would provide the needed access for procedures involving three adjacent vertebrae.

When the access device is in the second configuration, fixation of the three vertebrae may be performed. As discussed above, fixation is a procedure that involves providing a generally rigid connection between at least two vertebrae. Any of the fixation procedures discussed above could be used in this method, as could other fixation procedures. One fixation procedure that could be used is discussed above in connection with FIG. 36 wherein the fasteners 600a, 600b, and 600c are advanced through the access device 20 to three adjacent vertebrae and are attached to the vertebrae. The three fasteners 600a, 600b, and 600c are interconnected by the elongated member 650. The three fasteners 600a, 600b, and 600c and the elongate member 650 comprise a first fixation assembly. A second fixation assembly may be applied to the patient on the opposite side of the spine, i.e., about the same location on the opposite side of the medial line of the spine. Other fixation procedures could be applied, e.g., including two fasteners that coupled with the L4 and the S1 vertebrae and an elongate member interconnecting these vertebrae.

One variation of the first method provides one level of fixation on the anterior side of the patient, e.g., when the fusion device is placed in the interbody space. For example, fixation of the L5 and S1 vertebrae could be provided on the anterior side of the spine, in addition to the other procedures set forth above (e.g., a two level postero-lateral fixation). Also, fixation of the L4 and L5 vertebrae could be provided on the anterior side of the spine, in addition to the other procedures set forth above (e.g., a two level postero-lateral fixation).

In a second method, substantially the same steps as set forth above in connection with the first method would be performed. In addition, after the access device is inserted, a decompression procedure is performed through the access device. A decompression procedure is one where unwanted bone is removed from one or more vertebrae. Unwanted bone can include stenotic bone growth, which can cause impingement on the existing nerve roots or spinal cord. Decompression procedures that may be performed include laminectomy, which is the removal of a portion of a lamina(e), and facetectomy, which is the removal of a portion of one or more facets. In one variation of this method, decompression includes both a facetectomy and a laminectomy. Any suitable tool may be used to perform decompression. One tool that is particularly useful is a kerrison.

In a third method, substantially the same steps as set forth above in connection with the first method would be performed. That is, an ALIF procedure is performed in combination with a fixation procedure. In addition, a fusion procedure may be performed through the access device which may have been placed generally posteriorly, e.g., postero-laterally, tranforaminally or posteriorly, whereby bone growth is promoted between the vertebrae and the fixation assembly, including at least one of the fasteners 600a, 600b, 600c and/or the elongate element 650. This procedure is also referred to herein as an "external fusion" procedure.

One example of an external fusion procedure that may be performed involves placement of a substance through the access device intended to encourage bone growth in and around the fixation assembly. Thus, fusion may be enhanced by placing a bone growth substance adjacent any of the fasteners 600a, 600b, 600c and/or the elongate member 650. The bone growth substance may take any suitable form, e.g., small bone chips taken from the patient (e.g., autograft), from another donor source (e.g., allograft or xenograft), and orthobiologics.

After the bone growth substance is applied to the fixation assembly, the access device is removed. Absent the retracting force provided by the access device, the patient's tissue generally collapses onto the bone growth substance. The tissue will thereby maintain the position of the bone growth substance adjacent to the fixation assembly. The presence of the bone growth substance can cause bone to bridge across from the vertebra(e) to one or more components of the fixation assembly.

In a fourth method, substantially the same steps as set forth above in connection with the second method would be performed. That is, an ALIF procedure is performed anteriorly, and a decompression procedure and a fixation procedure are performed through the access device which may be placed generally posteriorly, e.g., postero-laterally, tranforaminally, or posteriorly. In addition, bone growth substance is placed in and around a fixation assembly through the access device, as discussed above in connection with the third method. The bone growth substance encourages bone to bridge across from the vertebrae to the fixation assembly.

In a fifth method, an ALIF procedure is performed, as discussed above in connection with the second method. After one or more fusion devices is placed in the interbody space, access is provided by way of the access device, as discussed above, from any suitable anatomical approach, e.g., a generally posterior approach. Preferably, a postero-lateral approach is provided. After access has been provided, a bone growth substance, such as those discussed above in connection with the third method, is delivered through the access device. The bone growth substance is placed adjacent an interbody space, e.g., the space between the L4 and the L5 vertebrae and/or between the L5 and the S1 vertebrae. The bone growth substance encourages fusion of the adjacent vertebrae, e.g., L4 to L5 and/or L5 to S1, by stimulating or enhancing the growth of bone between adjacent vertebrae, as discussed above.

In a sixth method, substantially the same steps described in connection with the first method are performed, except that the fixation procedure is optional. In one variation of the sixth method, the fixation procedure is not performed. However, after the access device is inserted, a bone growth substance is placed in and around one or more interbody spaces through the access device. Where the sixth method involves a two level procedure, the bone growth substance can be placed adjacent the interbody space between the L4 and the L5 vertebra and/or between the L5 and the S1 vertebra. Thus, bone growth may occur in the interbody space and adjacent the interbody space between the vertebrae.

The foregoing discussion illustrates that an ALIF procedure can be combined with a variety of procedures that can be performed through an access device disclosed herein. In addition, though not expressly set forth herein, any combination of the procedures discussed above, and any other suitable known procedure, may also be combined and performed through the access devices described herein, as should be understood by one skilled in the art.

B. Spine Procedures Providing Minimally Invasive Lumbar Interbody Fusion

Another category of procedures that may be performed with the access devices and systems described above involves a minimally invasive lumbar interbody fusion (referred to herein as a "MILIF"). MILIF procedures are particularly advantageous because they permit the surgeon to perform a wide variety of therapeutic procedures without requiring fusion by way of an anterior approach, as is required in an ALIF. This provides a first advantage of allowing the surgeon to perform all procedures from the same side of the patient and also possibly from the same approach. Also, the access devices and systems disclosed herein provide the further advantage of enabling two level procedures, and many other related procedures, to be performed by way of a single percutaneous access. These and other advantages are explained more fully below.

In a first MILIF method, a two level postero-lateral fixation of the spine involving three adjacent vertebrae, such as the L4, L5, and S1 vertebrae, is provided. Analogous one level procedures and two level procedures involving any other three vertebrae also may be provided. In addition, the access devices and systems described herein could be used or modified to accommodate other multi-level procedures, such as a three level procedure. The surgeon inserts an access device such as described herein to a surgical location near the spine. As discussed above, the access devices are capable of a wide variety of anatomical approaches. In this procedure, a postero-lateral approach is preferred. Once the access device is inserted to a location adjacent the spine, as discussed above, it may be configured, e.g., expanded, as discussed above, to a configuration wherein sufficient access is provided to the surgical location.

Any suitable fusion process may then be performed. For example, an implant may be advanced through the access device into the interbody space in order to maintain disc height and allow bone growth therein, e.g., as in a fusion procedure. In order to ease insertion of the implant, it may be beneficial to prepare the interbody space. Interbody space preparation may involve removal of tissue or adjusting the height of the interbody space through the access device, such as in a distraction procedure. Once the interbody space is prepared, a suitable implant may be advanced through the access device into the interbody space, taking care to protect surrounding tissues. Various embodiments of implants and techniques and tools for their insertion are described in U.S. application Ser. No. 10/280,489, incorporated by reference herein. In general, the implant preferably is an allograft strut that is configured to maintain disc height and allow bone growth in the interbody space.

In addition to providing a suitable fusion, the first method provides fixation of the vertebrae. The fixation procedure may take any suitable form, e.g., any of the fixation procedures similar to those disclosed above. In particular, when the access device is in the expanded or enlarged configuration, fixation of the three adjacent vertebrae may be performed. One fixation procedure that could be used is discussed above in connection with FIG. 36 wherein the fasteners 600a, 600b, and 600c are advanced through the access device 20 to three adjacent vertebrae and are attached to the vertebrae. The three fasteners 600a, 600b, and 600c are interconnected by way of the elongated member 650. As discussed above, a second fixation assembly may be applied to the patient on the opposite side of the spine, e.g., about the same location on the opposite side of the medial line of the spine.

In a second MILIF method, substantially the same procedures set forth above in connection with the first MILIF method are performed. In addition, a suitable decompression procedure may be performed, as needed. As discussed above, decompression involves removal of unwanted bone by way of a suitable decompression technique that may be performed through the access device. In one embodiment, decompression is performed through the access device after the access device has been expanded. As discussed above, suitable decompression techniques include a laminectomy, a facetectomy, or any other similar procedure. Decompression for the L4, the L5, and/or the S1 vertebrae may be needed and can be performed through the access devices described herein without requiring the access device to be moved from one position to another.

In a third MILIF method, substantially the same procedures set forth above in connection with the first MILIF method are performed. In addition, a further fusion procedure, e.g., a fusion procedure external to the interbody space, is provided. The external fusion procedure is performed adjacent to the interbody space wherein bone growth may be promoted in the proximity of the fixation assembly, e.g., above the postero-lateral boney elements of the spine, such as the facet joints and the transverse processes. In one embodiment, when the fixation assembly comprising the fasteners 600a, 600b, 600c and/or the elongate element 650 has been applied to three adjacent vertebrae, a substance is applied through the access device to one or more components of the fixation assembly to maintain or enhance the formation and/or growth of bone in the proximity of the fixation assembly. For example, a bone growth substance may be placed adjacent any of the fasteners 600a, 600b, 600c and/or the elongate member 650. Bone growth substance may take any suitable form, e.g., small bone chips taken from the patient (e.g., autograft), from another donor source (e.g., allograft or xenograft), and orthobiologics.

After the bone growth substance is applied to the fixation assembly, the access device is removed. Absent the retracting force provided by the access device, the patient's tissue generally collapses onto the bone growth substance. The tissue will thereby maintain the position of the bone growth substance adjacent to the fixation assembly. The presence of the bone growth substance advantageously causes bone to grow between the vertebrae and the fixation assembly to form a bridge therebetween.

A fourth MILIF method involves substantially the same procedures performed in connection with the third MILIF method. In particular, one or more implants are positioned in the interbody spaces through an access device, a fixation procedure is performed through the access device, and a further fusion procedure is performed wherein bone growth substance is positioned adjacent the interbody space through the access device. In addition, a decompression procedure is performed through the access device that may include a facetectomy and/or a laminectomy.

A fifth MILIF method involves substantially the same procedures performed in connection with the first MILIF method, except that the fixation is optional. In one embodiment, the fixation is not performed. In addition, a further fusion procedure is performed through the access device wherein bone growth substance is positioned adjacent the interbody space, as discussed above.

A sixth MILIF method is substantially the same as the fifth MILIF method, except that a further fusion procedure is performed through the access device. In particular, an implant is positioned in the interbody space through an access device, a decompression procedure is performed through the access device, and a further fusion procedure is performed whereby bone growth substance is placed adjacent the interbody space through the access device. As discussed above, the decompression procedure may include a facetectomy, a laminectomy, and any other suitable procedure. As with any of the methods described herein, the procedures that make up the sixth MILIF method may be performed in any suitable order. Preferably the decompression procedure is performed before the external fusion procedure.

The foregoing discussion illustrates that a MILIF procedure can include a variety of procedures that can be performed through an access device described herein. In addition, though not expressly set forth herein, any combination of the procedures discussed above, and any other suitable known procedures, may also be combined, as should be understood by one skilled in the art.

C. Other Multi-Level Procedures

While the foregoing procedures have involved interbody fusion, the access devices and systems described herein can be employed in a variety of single level and multi-level procedures (e.g., more than two levels) that do not involve an interbody fusion. For example, a discectomy can be performed through the access devices described herein without implanting an interbody fusion device thereafter, e.g., to remove a hemeation. In another embodiment, a discectomy can be performed in more than one interbody space without inserting an interbody fusion device into each interbody space, e.g., to remove multiple herneations. In another embodiment, a single or multi-level decompression procedure can be performed to remove unwanted bone growth.

It will be understood that the foregoing is only illustrative of the principles of the invention, and that various modifications, alterations, and combinations can be made by those skilled in the art without departing from the scope and spirit of the invention. Some additional features and embodiments are described below.

Figure 67:
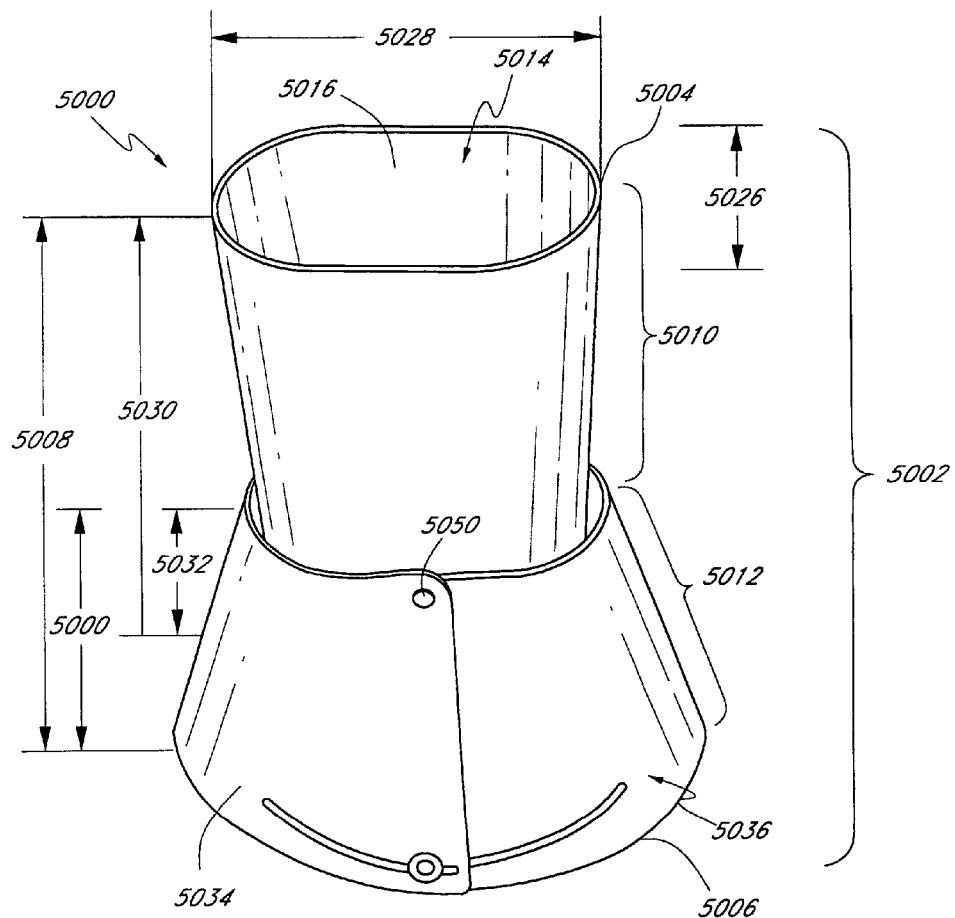
FIG. 67 is a perspective view of an access device according to another embodiment.
Figure 68:
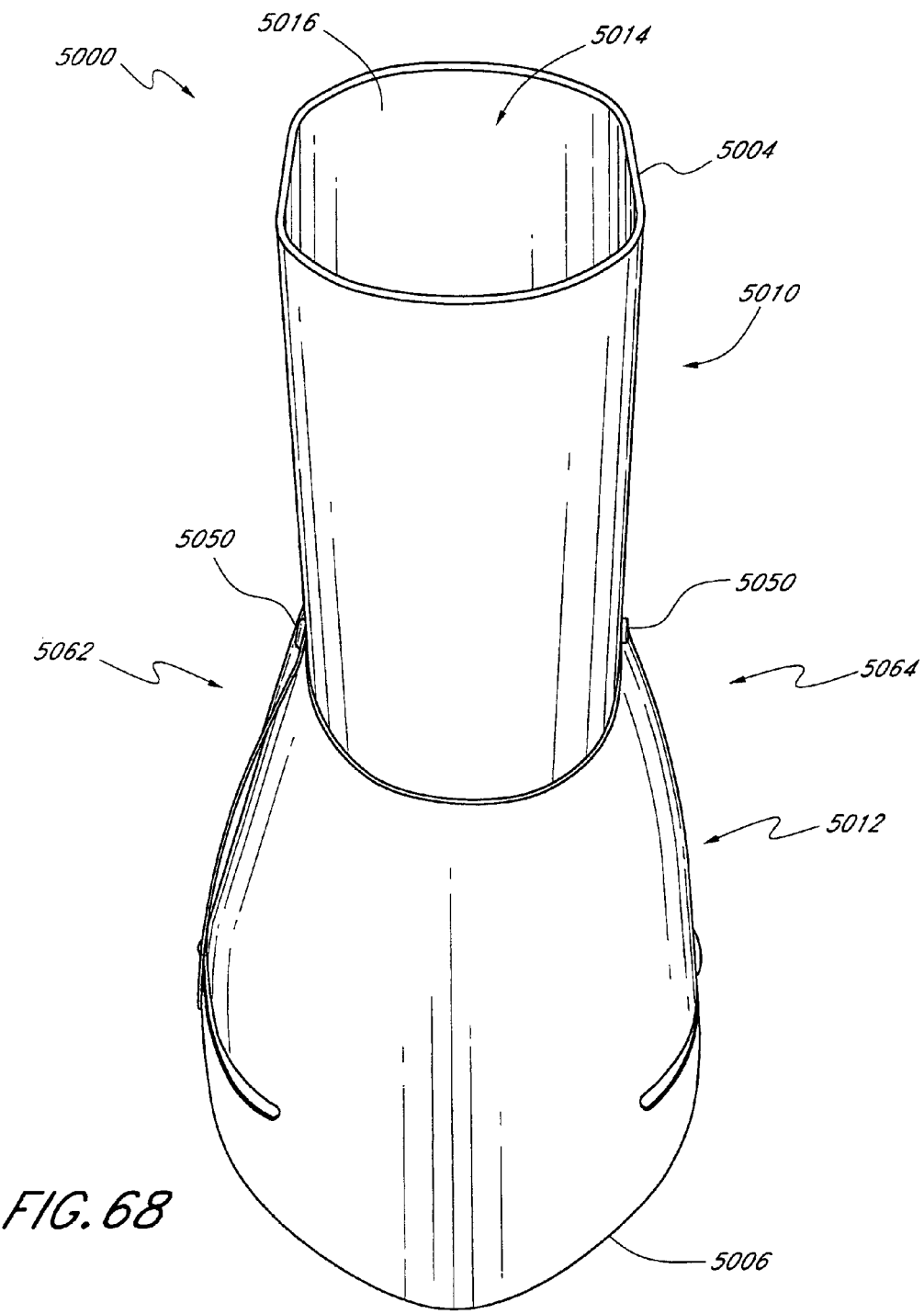
FIG. 68 is a side perspective view of the access device of FIG. 67.

III. Additional Features and Embodiments of Systems and Methods for Performing Surgical Procedures FIGS. 67-75 illustrate various embodiments of another access device designated by reference number 5000. The term "access device" is used in its ordinary sense to mean a device that can provide access and is a broad term and it includes structures having an elongated dimension and defining a passage, e.g., a cannula or a conduit. With reference to FIGS. 67 and 68, the access device 5000 is configured to be inserted through the skin of the patient to provide access during a surgical procedure to a surgical location within a patient, e.g., a spinal location. The term "surgical location" is used in its ordinary sense (i.e. a location where a surgical procedure is performed) and is a broad term and it includes locations subject to or affected by a surgery. The term "spinal location" is used in its ordinary sense (i.e. a location at or near a spine) and is a broad term and it includes locations adjacent to or associated with a spine that may be sites for surgical spinal procedures. The access device 5000 also can retract tissue to provide greater access to the surgical location.

The access device 5000 has an elongate body 5002 that has a proximal end 5004 and a distal end 5006. With reference to FIGS. 67 and 68, the elongate body 5002 has a length 5008 between the proximal end 5004 and the distal end 5006. The length 5008 is selected such that when the access device 5000 is applied to a patient during a surgical procedure, the distal end 5006 can be positioned inside the patient adjacent the spinal location. When so applied, the proximal end 5004 is preferably outside the patient at a suitable height, as discussed more fully below.

In one embodiment, the elongate body 5002 comprises a proximal portion 5010 and a distal portion 5012. The proximal portion 5010 has an oblong or generally oval shaped cross section in one embodiment. The term "oblong" is used in its ordinary sense (i.e., having an elongated form) and is a broad term and it includes a structure having a dimension, especially one of two perpendicular dimensions, such as, for example, width or length, that is greater than another and includes shapes such as rectangles, ovals, ellipses, triangles, diamonds, trapezoids, parabolas, and other elongated shapes having straight or curved sides. The term "oval" is used in its ordinary sense (i.e., egg like or elliptical) and is a broad term and includes oblong shapes having curved portions.

The distal portion 5012 is expandable in one embodiment. At least one passage 5014 extends through the elongate body 5002 between the proximal end 5004 and the distal end 5006, e.g., through the proximal and distal portions 5010, 5012. The passage 5014 is defined by a smooth metal inner surface 5016 that extends substantially entirely around the perimeter of the passage 5014 between the proximal and distal ends 5004, 5006 in one embodiment. The inner surfaces 5016 can take other forms, e.g., employing other materials, different but generally constant smoothness, and/or varying degrees of smoothness.

Figure 71:
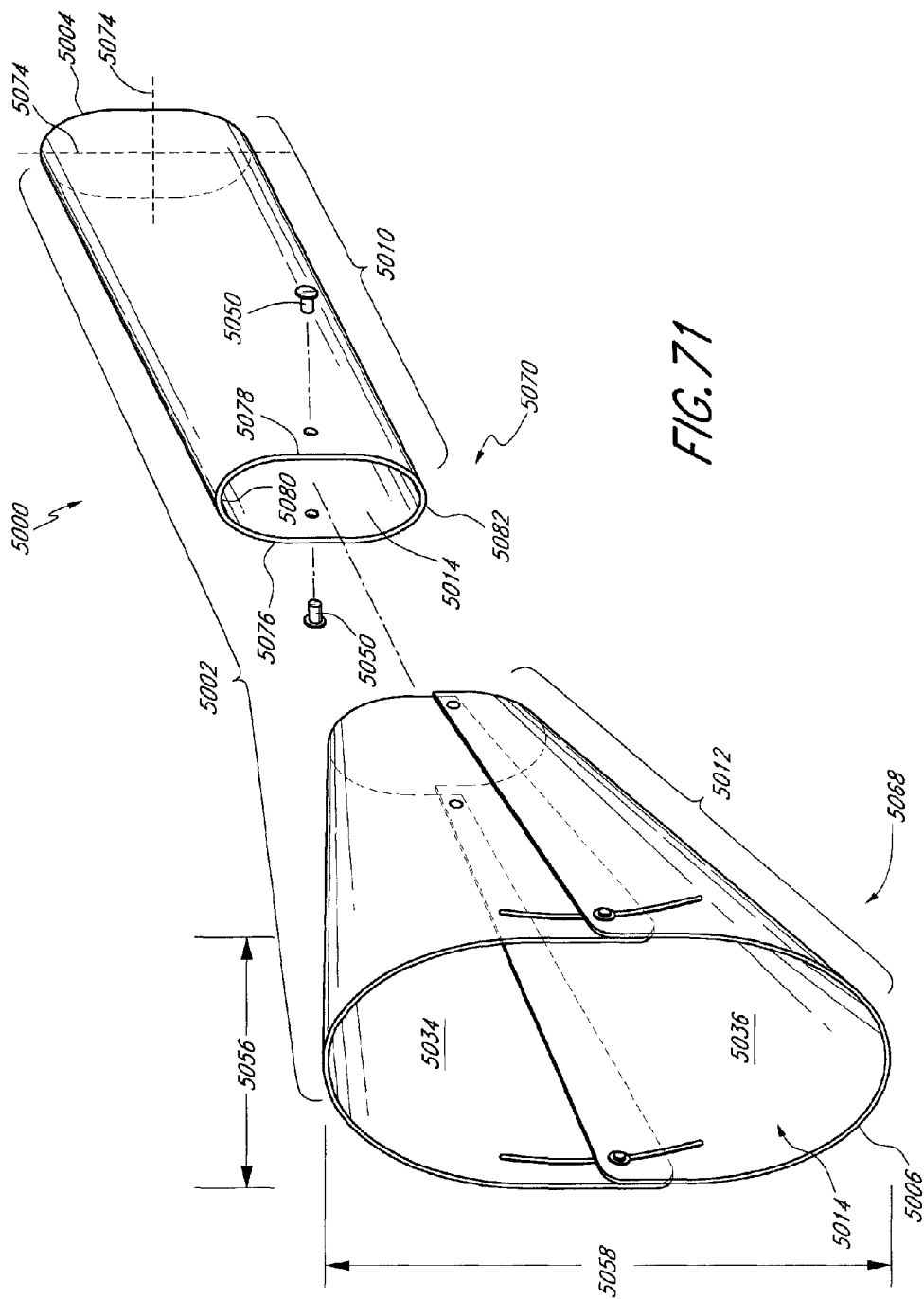
FIG. 71 is an exploded perspective view of the access device of FIG. 67 in an expanded configuration with some portions shown in hidden line.
Figure 72:
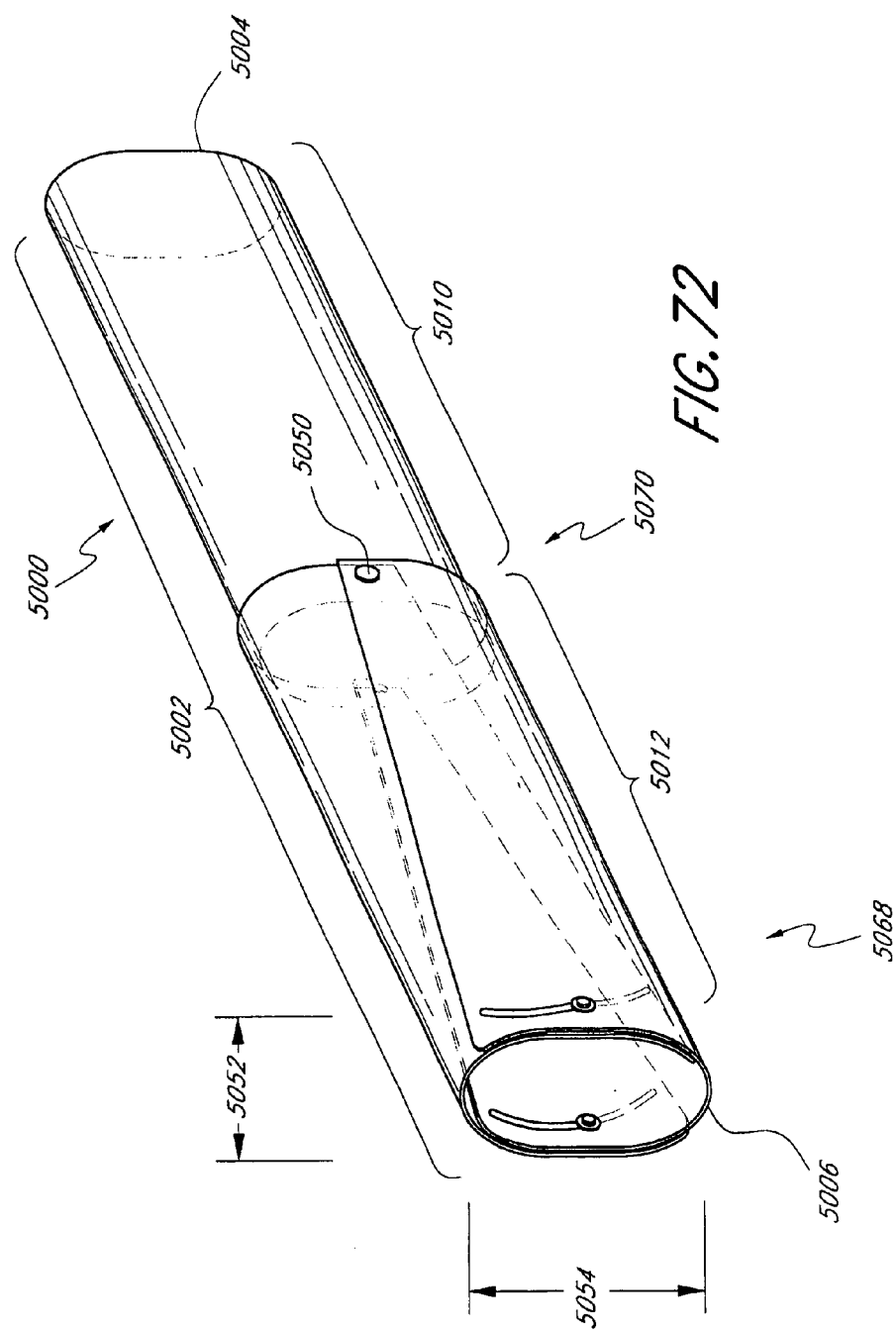
FIG. 72 is a perspective view of the access device of FIG. 67 in a contracted configuration with some portions shown in hidden line.

In one embodiment, the elongate body 5002 is expandable from a first configuration, shown in FIG. 72, to a second configuration, shown in FIG. 71. In one embodiment, the elongate body 5002 is movable from the first configuration to the second configuration when inserted within the patient, as discussed above. In the first configuration, the access device 5000 is configured, e.g., sized, for insertion into the patient. As discussed more fully below, in one embodiment, the passage 5014 has a relatively small transverse cross-sectional area at the distal end 5006 of the first configuration of the access device 5000. For example, the passage 5014 can have a cross-sectional area about equal to the cross-sectional area of the proximal end 5004, or less.

In the second configuration, the cross-sectional area of the passage 5014 at the distal end 5006 is greater than the cross-sectional area of the passage 5014 at the proximal end 5004 in one embodiment. The second configuration is particularly well suited for performing surgical procedures in the vicinity of a spinal location. Other configurations and arrangements of the access device 5000 are discussed herein below.

As shown in FIGS. 67 and 68, in one embodiment, the proximal portion 5010 and the distal portion 5012 are discrete, i.e., separate members. In other embodiments, the proximal and distal portions 5010, 5012 are a unitary member. In the illustrated embodiment, the proximal portion 5010 comprises an oblong, generally oval shaped cross section over the elongated portion. It will be apparent to those of skill in the art that the cross section can be of any suitable oblong shape. The proximal portion 5010 can be any desired size. The proximal portion 5010 can have a cross-sectional area that varies from one end of the proximal portion 5010 to another end. For example, the cross-sectional area of the proximal portion 5010 can increase or decrease along the length of the proximal portion 5010. Preferably, the proximal portion 5010 is sized to provide sufficient space for inserting multiple surgical instruments through the elongate body 5002 to the surgical location. In one embodiment, the cross-sectional area of the proximal portion 5010 can have a generally elliptical shape. In some embodiments, the generally elliptical shape can include generally straight side portions.

Figure 70:
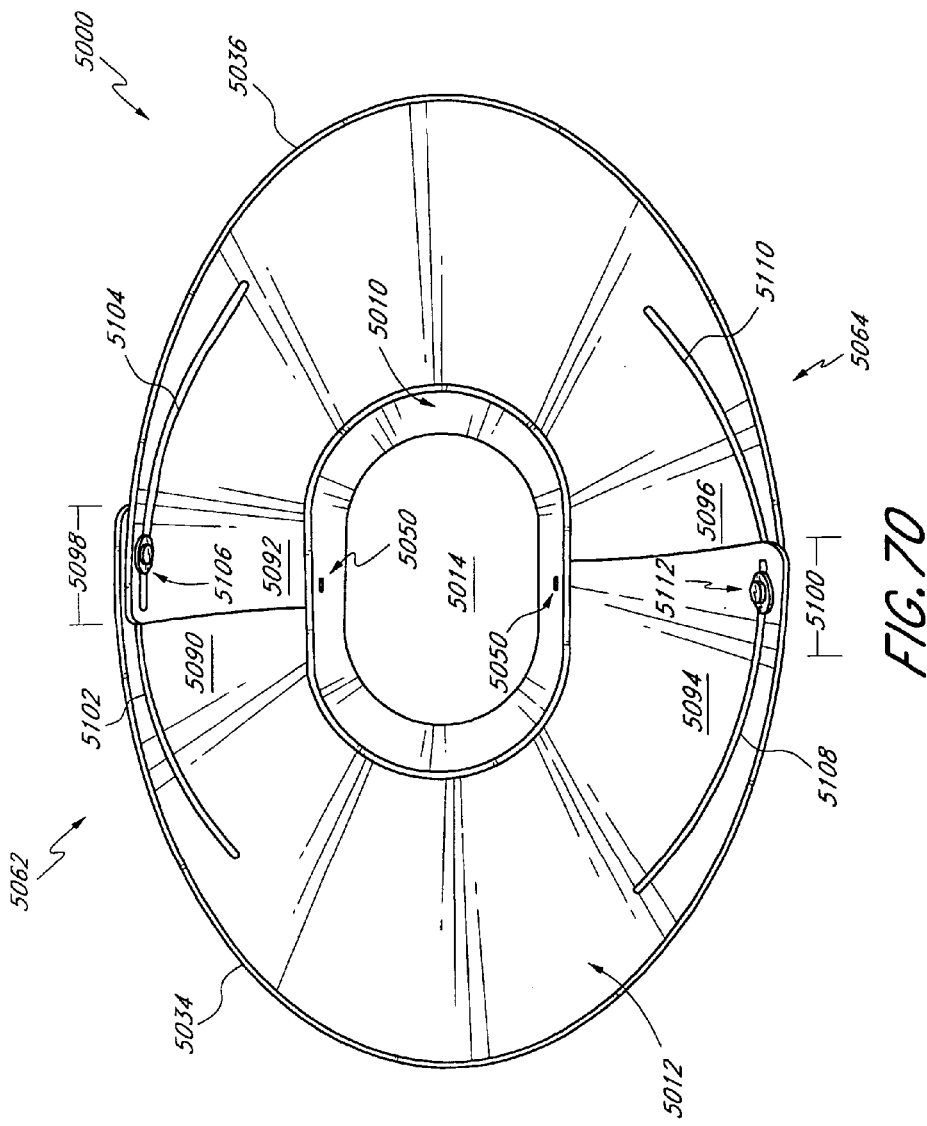
FIG. 70 is an end view of the access device of FIG. 67.

As shown in FIG. 67, the generally oval shaped cross section of the proximal portion 5010 in one embodiment has a first dimension 5026 of about 24 mm and a second dimension 5028 of about 35 mm. The first and second dimensions 5026, 5028 could range from at least about 10 mm up to about 70 mm or more. The proximal portion 5010 in one embodiment has a third dimension 5030 of about 50 mm, but the third dimension 5030 could range from about 10 mm up to about 180 mm or more. In one embodiment, the proximal portion 5010 extends distally at least partially into the distal portion 5012 of the device 5000, as shown in FIG. 70. In FIG. 67, the proximal portion 5010 extends a distance 5032 of about 10 mm into the distal portion 5012. The proximal portion 5010 can extend a distance 5032 of between about 5 mm and about 20 mm into the distal portion 5012 in some embodiments. The exposed portion of the proximal portion 5010 (e.g., the portion thereof that extends proximally of the distal portion 5012) can be of any suitable height. Additionally, the distance 5032 that the proximal portion 5010 extends into the distal portion 5012 can be increased or decreased, as desired.

As shown in FIGS. 67 and 68, the proximal portion 5010 is coupled with the distal portion 5012, e.g., with one or more couplers 5050. The proximal and distal portions 5010, 5012 are coupled on a first lateral side 5062 and on a second lateral side 5064 with the couplers 5050 in one embodiment. When applied to a patient in a posterolateral procedure, either of the first or second lateral sides 5062, 5064 can be a medial side of the access device 5000, i.e., can be the side nearest to the patient's spine. The couplers 5050 can be any suitable coupling devices, such as, for example, rivet attachments. In one embodiment, the couplers 5050 are located on a central transverse plane of the access device 5000.

Figure 69:
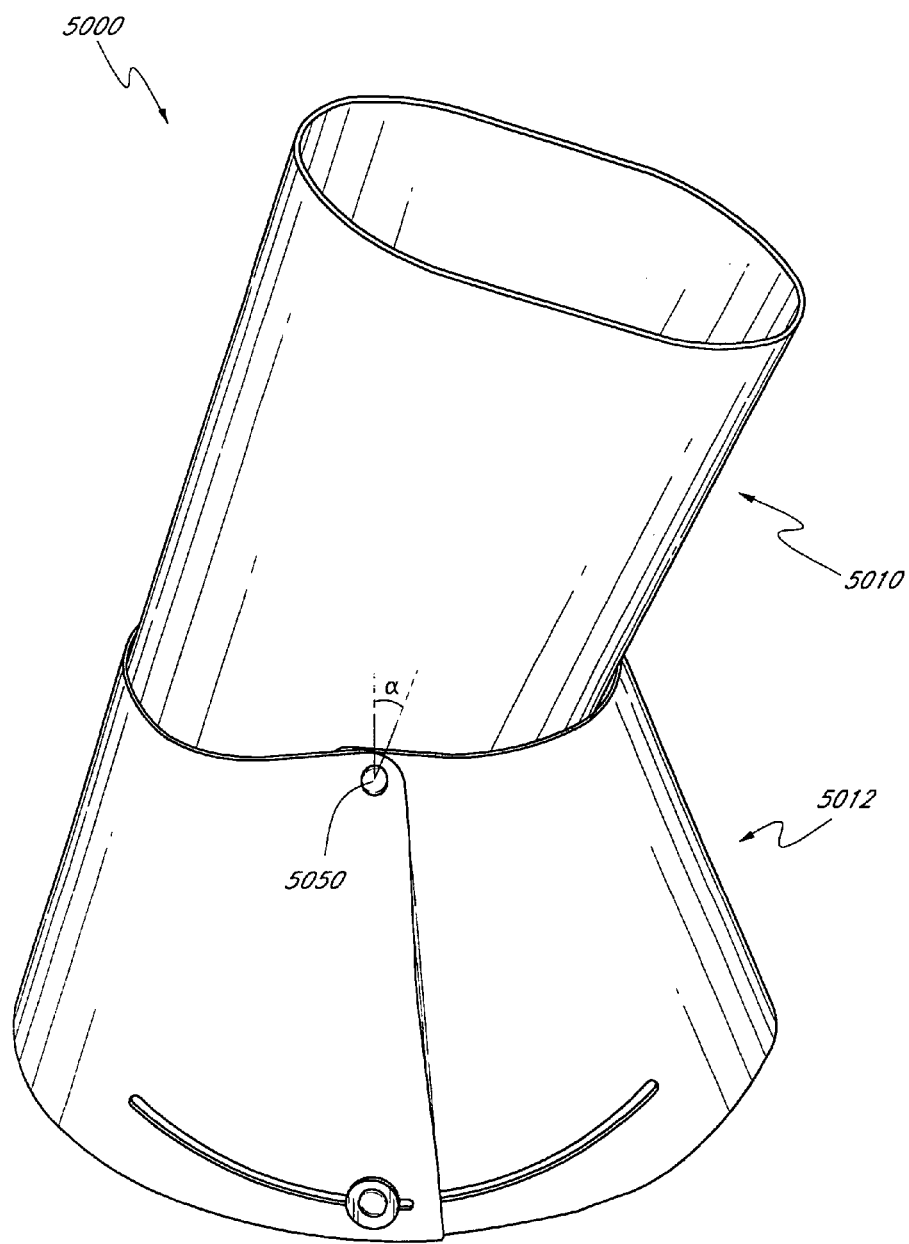
FIG. 69 is a perspective view of the access device of FIG. 67 in a pivoted configuration.

The couplers 5050 preferably allow for at least one of rotation and pivotal movement of the proximal portion 5010 relative the distal portion 5012. A portion of the range of rotation and pivotal movement of the proximal portion 5010 relative the distal portion 5012 can be seen by comparing the position of the proximal portion 5010 in FIG. 67 to the position thereof in FIG. 69. In FIG. 69, the proximal portion 5010 is seen at an angle $\alpha$ of about 20 degrees with respect to a transverse plane extending vertically through the couplers. One skilled in the art will appreciate that rotating or pivoting the proximal portion 5010 to the angle $\alpha$ permits enhanced visualization of and access to a different portion of the spinal location accessible through the access device 5000 than would be visualized and accessible at a different angle. Depending on the size of the distal portion 5012, the angle $\alpha$ can be greater than, or less than, 20 degrees. Preferably, the angle $\alpha$ is between about 10 and about 40 degrees.

The pivotable proximal portion 5010 allows for better access to the surgical location and increased control of surgical instruments. Additionally, the generally oval shape of the proximal portion 5010 has increased the cross-sectional area available for a variety of procedures, some of which may require or benefit from more proximal end exposure. Embodiments having a generally oval shape can also be employed advantageously in procedures such as the lateral or posterolateral placement of artificial disks, as well as other developing procedures.

As discussed above, the distal portion 5012 is expandable in one embodiment. As shown in FIG. 70, the degree of expansion of the distal portion 5012 is determined by an amount of overlap between a first skirt member 5034 and a second skirt member 5036 in one embodiment. In particular, the first skirt member 5034 has a first overlapping portion 5090 on the first lateral side 5062 and the second skirt member 5036 has a second overlapping portion 5092 on the first lateral side 5062. The first skirt member 5034 has a third overlapping portion 5094 on the second lateral side 5064 and the second skirt member 5036 has a fourth overlapping portion 5096 on the second lateral side 5064. The first and second overlapping portions 5090, 5092 overlap to define a first overlap area 5098. The third and fourth overlapping portions 5094, 5096 overlap to define a second overlap area 5100. The extents of the first and second overlap areas 5098, 5100 preferably are reduced when the distal portion 5012 is in the second configuration. The extents of the first and second overlap areas 5098, 5100 preferably are increased when the distal portion 5012 is in the first configuration.

The distal portion 5012 preferably is manufactured from a rigid material, such as stainless steel. The distal portion 5012 of the access device 5000 can be manufactured from a sheet of stainless steel having a thickness of between about 0.003-0.010 inches (0.076-0.254 mm). In some embodiments, the thickness is about 0.007 inches (0.178 mm). Nitinol, plastics, and other suitable materials can also be used.

In some embodiments, the distal portion 5012 can be manufactured so that it normally assumes an expanded configuration. Additionally, the distal portion 5012 can assume an intermediate configuration and corresponding cross-sectional area, which has greater dimensions than the first configuration, and smaller dimensions than the second configuration. Alternatively, an expander apparatus, similar to those previously discussed herein, can be used to expand the distal portion 5012 a suitable amount.

The skirt members 5034, 5036 preferably are slidably coupled together. In one embodiment, the first and second skirt members 5034, 5036 are slidably coupled with each other with at least one guide member disposed in at least one slot defined in each of the skirt members 5034, 5036. In particular, a first slot 5102 is formed in the first overlapping portion 5090 of the first skirt member 5034 and a second slot 5104 is formed in the second overlapping portion 5092 of the second skirt member 5036 on the first lateral side 5062 of the access device 5000. A guide member 5106 extends through the first and second slots 5102, 5104 and is translatable therein. Similarly, a third slot 5108 is formed in the third overlapping portion 5094 of the first skirt member 5034 and a fourth slot 5110 is formed in the fourth overlapping portion 5096 of the second skirt member 5036 on the second lateral side 5064 of the access device 5000. A guide member 5112 extends through the third and fourth slots 5108, 5110 and is translatable therein.

Any suitable mechanism for slidably coupling the skirt members 5034, 5036 can be used. In the illustrated embodiment, two floating rivets are used as guide members 5106, 5112. In another embodiment, one or more of the slots 5102, 5104, 5108, 5110 can include a locking or ratcheting mechanism (not shown). Locking mechanism is used in its ordinary sense (i.e. a mechanism to maintain relative positions of members) and is a broad term and it includes structures having detent arrangements, notches, and grooves. Some additional examples of locking mechanisms are disclosed in U.S. patent application Ser. No. 10/361,887, filed Feb. 10, 2003, entitled "Structure for Receiving Surgical Instruments," published as application publication No. US2003/0153927 on Aug. 14, 2003, which is hereby incorporated by reference herein in its entirety.

With reference to FIGS. 67-72, as discussed above, the skirt members 5034, 5036 preferably pivot about couplers 5050 joining the proximal portion 5010 with the distal portion 5012. The distal portion 5012 preferably pivots on an axis perpendicular to the longitudinal axis of the access device 5000. This arrangement is particularly useful for providing surgical access to anatomical features generally located and oriented along the Cephalad-Caudal direction.

As discussed above, the access device 5000 can be expanded from the first configuration to the second configuration by way of the movement of the first skirt member 5034 relative to the second skirt member 5036. In the illustrated embodiment, the distal portion 5012 is generally oval shaped both in the first configuration, when the device 5000 is generally contracted, and in the second configuration, when the device 5000 is generally expanded. However, the distal portion 5012 may be configured to transition from a generally circular cross-section distal end (or other convenient shape) in the first configuration to a generally oval cross-section distal end in the second configuration.

As best seen in FIG. 72, the distal portion 5012 preferably has a first dimension 5052 in the first configuration of approximately 24 mm and a second dimension 5054 of approximately 35 mm. As best seen in FIG. 71, the distal portion 5012 preferably has a first dimension 5056 of approximately 45 mm and a second dimension 5058 of approximately 70 mm in the second configuration. Accordingly, in one embodiment in the expanded configuration the distal portion 5012 opens distally to approximately 45 mm by 70 mm. The distal portion 5012 can be arranged to open more or less, as needed or desired. For example, the distal portion 5012 can take on an oval shape wherein the second dimension 5058 is longer than 70 mm, e.g., about 85 mm or more. Alternatively, the distal portion 5012 can have a shape wherein the second dimension 5058 is shorter than 70 mm, e.g., about 45 mm or less. Similarly, in some embodiments the first dimension 5052 can be longer or shorter than 45 mm, e.g., about 35 mm or about 55 mm. As shown in FIG. 67, the distal portion 5012 has a height 5060 that is approximately 45 mm. However, one skilled in the art should recognize that the height 5060 of the distal portion 5012 can be any suitable height. The height 5060 preferably is within the range of about 20 mm to about 150 mm. Access devices having relatively shorter skirt heights 5060 may be advantageous for use with patients having relatively less muscle tissue near the surgical location and generally require smaller incisions. Access devices having relatively longer skirt height 5060 may be advantageous for use with patients having relatively more muscle tissue near the surgical location, and may provide greater access.

The distal portion 5012 preferably is sufficiently rigid that it is capable of displacing surrounding tissue as the distal portion 5012 expands. Depending upon the resistance exerted by the surrounding tissue, the distal portion 5012 is sufficiently rigid to provide some resistance against the tissue to remain in the second, expanded configuration. Moreover, the second configuration is at least partially supported by the body tissue of the patient. The displaced tissue tends to provide pressure distally on the distal portion 5012 to at least partially support the access device 5000 in the second configuration. The rigidity of the distal portion 5012 and the greater expansion at the distal end 5006 creates a stable configuration that is at least temporarily stationary in the patient, which at least temporarily frees the physician from the need to actively support the elongate body 5002.

Another advantageous aspect of the access device 5000 is illustrated with reference to FIGS. 71 and 72. In particular, the elongate body 5002 has a first location 5068 and a second location 5070. The first location 5068 is distal of the second location 5070. The elongate body 5002 is capable of having a configuration when inserted within the patient wherein the cross-sectional area of the passage 5014 at the first location 5068 is greater than the cross-sectional area of the passage 5014 at the second location 5070. The passage 5014 is capable of having an oblong shaped cross section between the second location 5070 and the proximal end 5004.

In some embodiments the passage 5014 preferably is capable of having a generally elliptical cross section between the second location 5070 and the proximal end 5004. Additionally, the passage 5014 preferably is capable of having a non-circular cross section between the second location 5070 and the proximal end 5004. Additionally, in some embodiments, the cross section of the passage 5014 can be symmetrical about a first axis 5072 and a second axis 5074, the first axis 5072 being generally normal to the second axis 5074.

As shown in FIG. 71, the configuration of the elongate body 5002 between the first location 5068 and the second location 5070 is generally conical, when the elongate body 5002 is expanded within the patient. The term "conical" is used in its ordinary sense (i.e. a surface formed by line segments joining every point of the boundary of a closed base to a common vertex) and is a broad term and it includes structures having a generally oblong, or oval, cross section, as well as structures having a surface that extends only partially toward a vertex. In some embodiments, the first location 5068 can be near a distal end 5006 of the elongate body 5002, and the second location 5070 can be near a proximal end 5004 of the elongate body 5002.

In the illustrated embodiment, the elongate body 5002 has an oblong shaped cross section near its proximal end 5004 at least when the elongate body 5002 is in the second configuration. In some embodiments, the elongate body 5002 has an oblong shaped cross section along substantially the entire length between the proximal end 5004 and the second location 5070.

Additionally, in some embodiments the passage 5014 can have a generally oval shaped cross section between the second location 5070 and the proximal end 5004. The elongate body preferably has a generally oval shaped cross section at its proximal end 5004 at least when the elongate body 5002 is in the second configuration. The elongate body 5002 can have a generally oval shaped cross section along substantially the entire length between the proximal end 5004 and the second location 5070. The passage 5014 can also have a cross section between the second location 5070 and the proximal end 5004 where the cross section is defined by first and second generally parallel opposing side portions 5076, 5078 and first and second generally arcuate opposing side portions 5080, 5082.

Figure 73:
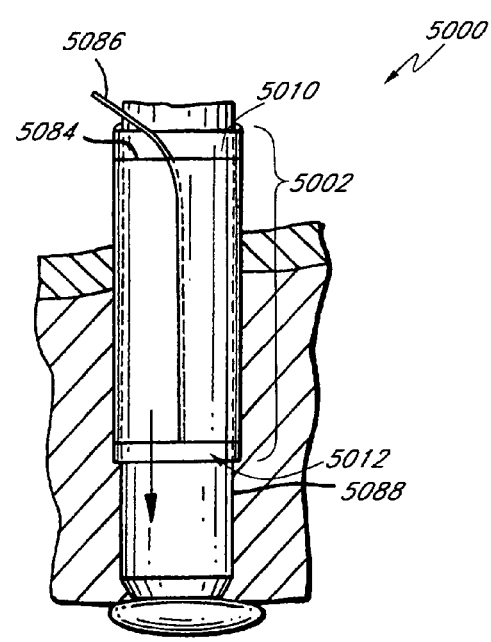
FIG. 73 is a partial sectional view of the access device of FIG. 67 in an early stage of a procedure.

In some embodiments, it is useful to provide a structure to maintain the access device 5000 in an un-expanded state until expansion of the device is desired. As shown in FIG. 73, in one embodiment an outer sleeve 5084, e.g., a plastic sleeve, is provided which surrounds the access device 5000 and maintains the distal portion 5012 in the first configuration. The outer sleeve 5084 can be produced to function as previously described herein with reference to other embodiments. For example, the outer sleeve 5084 can have a braided polyester suture 5086 embedded within it, aligned substantially along the longitudinal axis thereof, such that when the suture 5086 is withdrawn, the sleeve 5084 is torn, which allows the access device 5000 to expand, either resiliently or mechanically, from the first configuration to the second configuration.

In a method for accessing a surgical location within a patient an access device, such as the access device 5000, is provided. As stated above, the elongate body 5002 is capable of having a first configuration sized for insertion into the patient. The elongate body 5002 is capable of having a second configuration when expanded within the patient. In the second configuration, the cross-sectional area of the passage 5014 at a first location 5068 is greater than the cross-sectional area of the passage 5014 at a second location 5070. The first location 5068 is distal to the second location 5070. The passage 5014 is capable of having an oblong shaped cross section between the second location 5070 and the proximal end 5004. The method comprises inserting the access device 5000, in the first configuration, into the patient to the surgical location and expanding the device to the second configuration.

The access device 5000 is inserted to a spinal location in some methods. As shown in FIG. 73, an oblong shaped dilator 5088 preferably is inserted into the patient prior to insertion of the access device 5000. In some applications, the access device 5000 may be inserted laterally to the spinal location. In other applications, the device 5000 is inserted posterolaterally to the spinal location. In some applications, the device 5000 is inserted anteriorly to the spinal location. The device 5000 preferably can be expanded in a cephalad-caudal direction at a spinal location.

With reference to FIG. 73, an early stage in one method involves determining an access point in the skin of the patient to insert the access device 5000. An incision is made at the determined location. In some cases, the incision is approximately 1" to 2" long. A guide wire (not shown) is introduced under fluoroscopic guidance through the incision and past the skin, fascia, and muscle to the approximate surgical site. A series of oblong, or generally oval shaped, dilators is used to sequentially expand the incision to the desired widths, about 24 mm by 35 mm for the illustrated embodiment, without damaging the structure of surrounding tissue and muscles. In one technique, a first oblong dilator is placed over the guide wire, which expands the opening. The guide wire is then subsequently removed. A second oblong dilator that is slightly larger than the first dilator is placed over the first dilator, which expands the opening further. Once the second dilator is in place, the first dilator is subsequently removed. This process of (1) introducing a next-larger-sized dilator coaxially over the previous dilator and (2) subsequently removing the previous dilator when the next-larger-sized dilator is in place continues until an opening of the desired size is created in the skin, muscle, and subcutaneous tissue. For the illustrated embodiment, these dimensions are about 24 mm by about 35 mm. (Other dimensions for the openings that are useful with some embodiments in connection with spinal surgery range from about 20 mm to about 50 mm, and still other dimensions are contemplated.) In other techniques, a series of dilators having circular (or other shaped) cross-sections are used to partially dilate the opening. Then, a final dilator having a circular inner diameter and an oblong or generally oval shaped outer perimeter can be used to further dilate the opening.

As illustrated in FIG. 73, following placement of the largest oblong, or generally oval shaped dilator 5088, the access device 5000, in the first configuration, is introduced and positioned in a surrounding relationship over the dilator 5088. The dilator 5088 is subsequently removed from the patient, and the access device 5000 is allowed to remain in position.

Once the access device 5000 is positioned in the patient, it can be enlarged to provide a passage 5014 for the insertion of various surgical instrumentation and an enlarged space for performing the procedures described herein. As described above, the elongate body 5002 can accommodate the enlargement in several ways. In the illustrated embodiment, the distal portion 5012 of the device 5000 can be enlarged, and the proximal portion 5010 can maintain an oblong shape. The relative lengths of the proximal portion 5010 and the distal portion 5012 can be adjusted to vary the overall expansion of the access device 5000. Alternatively, in some embodiments expansion can extend along the entire length of the elongate body 5002.

In the illustrated embodiment, the access device 5000 can be expanded by removing the suture 5086 and tearing the sleeve 5084 surrounding the access device 5000, and subsequently expanding the distal portion 5012 mechanically, or allowing the distal portion 5012 to resiliently expand towards the expanded configuration, to create an enlarged surgical space. In some embodiments, the enlarged surgical space extends from the L4 to the S1 vertebrae.

The access device 5000 can be enlarged at its distal portion 5012 using an expander apparatus to create a surgical access space. An expander apparatus useful for enlarging the elongate body 5002 has a reduced profile configuration and an enlarged configuration. Additionally, the expander apparatus can have an oblong, or generally oval shape. The expander apparatus is inserted into the elongate body 5002 in the reduced profile configuration, and subsequently expanded to the enlarged configuration. The expansion of the expander apparatus also causes the elongate body 5002 to be expanded to the enlarged configuration. In some embodiments, the expander apparatus can increase the cross-sectional area of the elongate body 5002 along substantially its entire length. In other embodiments, the expander apparatus expands only a distal portion 5012 of the elongate body 5002, allowing a proximal portion 5010 to maintain a constant oblong, or generally oval shape. Other expander apparatus are disclosed in U.S. patent application Ser. No. 10/665,754, entitled "Surgical Tool for Use in Expanding a Cannula", filed on Sep. 19, 2003.

In addition to expanding the elongate member 5002, the expander apparatus can also be used to position the distal portion 5012 of the elongate member 5002 at the desired location for the surgical procedure in a manner similar to that described previously with reference to another embodiment.

Once the distal portion 5012 has expanded, the rigidity and resilient characteristics of the distal portion 5012 allow the elongate body 5002 to resist closing to the first configuration and to at least temporarily resist being expelled from the incision. These characteristics create a stable configuration for the elongate body 5002 to remain in position in the body, supported by the surrounding tissue.

The access device 5000, like the other access devices described herein, has a wide variety of applications wherein the passage 5014 provides access to one or more surgical instruments for performing a surgical procedure. In one application, the passage 5014 provides access to perform a two level posterolateral fixation of the spine involving the L4, L5 and S1 vertebrae. The access devices 5000 can be used to deliver a wide variety of fixation elements, including rigid, semi-rigid, or dynamic fixation elements. The access devices are not limited to the posterolateral approach nor to the L4, L5 and S1 vertebrae. The access devices may be applied in other anatomical approaches and with other vertebrae within the cervical, thoracic and lumbar spine. The access devices can be applied in procedures involving one or more vertebral levels and in anterior and lateral procedures. Further procedures in which the access devices described herein can be applied include procedures involving orthobiologics, bone morphogenetic proteins, and blood concentrators. The access devices can also be used with procedures involving prosthetics, such as disc nucleus replacement, facet joint replacement, or total disc replacement. The access devices can also be applied in procedures involving vertebroplasty, where a crushed vertebra is brought back to its normal height.

The access devices described herein also can be used in connection with interbody fusion, and fusion of the facets and transverse processes. Some of the fusion procedures that can be performed via the access devices described herein employ allograft struts, bone filling material (e.g., autograft, allograft or synthetic bone filling material), and cages and/or spacers. The cages and the spacers can be made of metal, a polymeric material, a composite material, or any other suitable material. The struts, cages, and spacers are used in the interbody space while the bone filling material can be used both interbody and posterolaterally. Any of the foregoing or other fusion procedures can be used in combination with the orthobiologics and can be performed via the access devices described herein.

Some examples of uses of the access devices described in other procedures and processes, as well as further modifications and assemblies, are disclosed in U.S. patent application Ser. No. 10/845,389, filed May 13, 2004, entitled "Access Device For Minimally Invasive Surgery," and in U.S. patent application Ser. No. 10/658,736, filed Sep. 9, 2003 which are hereby incorporated by reference herein in their entireties.

Figure 74:
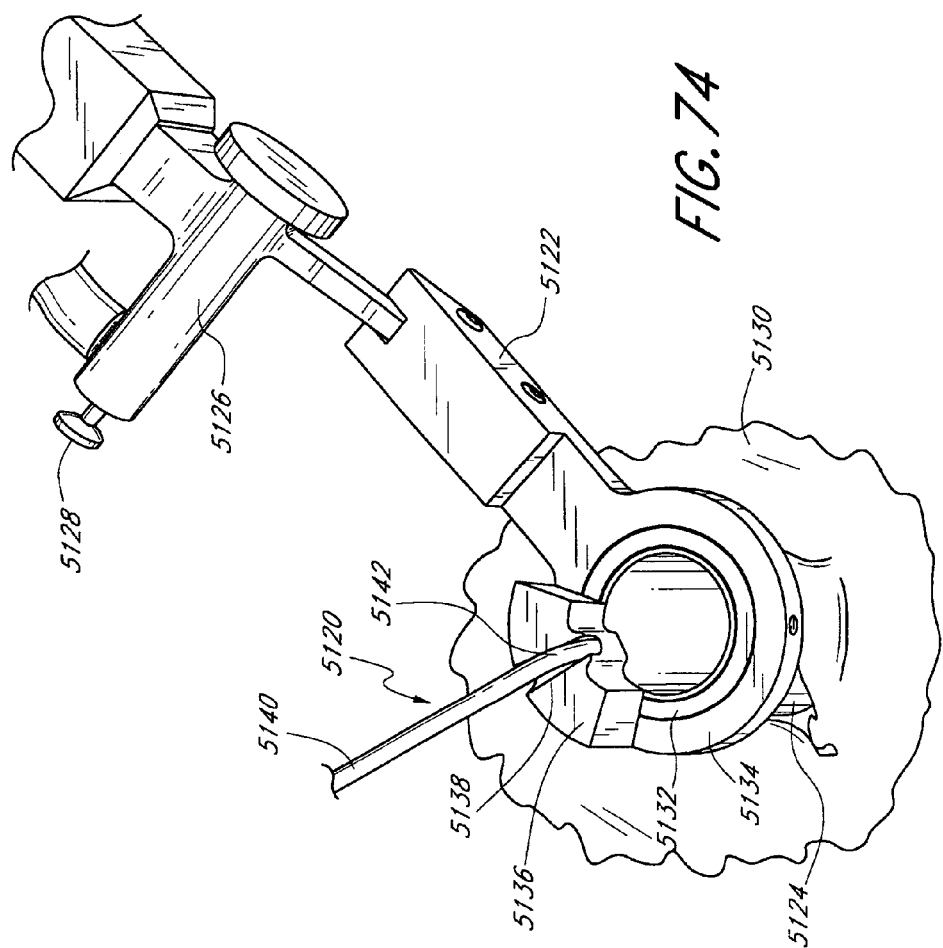
FIG. 74 is a perspective view of a portion of one embodiment of a surgical system that includes an access device, a support arm, and a lighting element shown applied to a patient.
Figure 75:
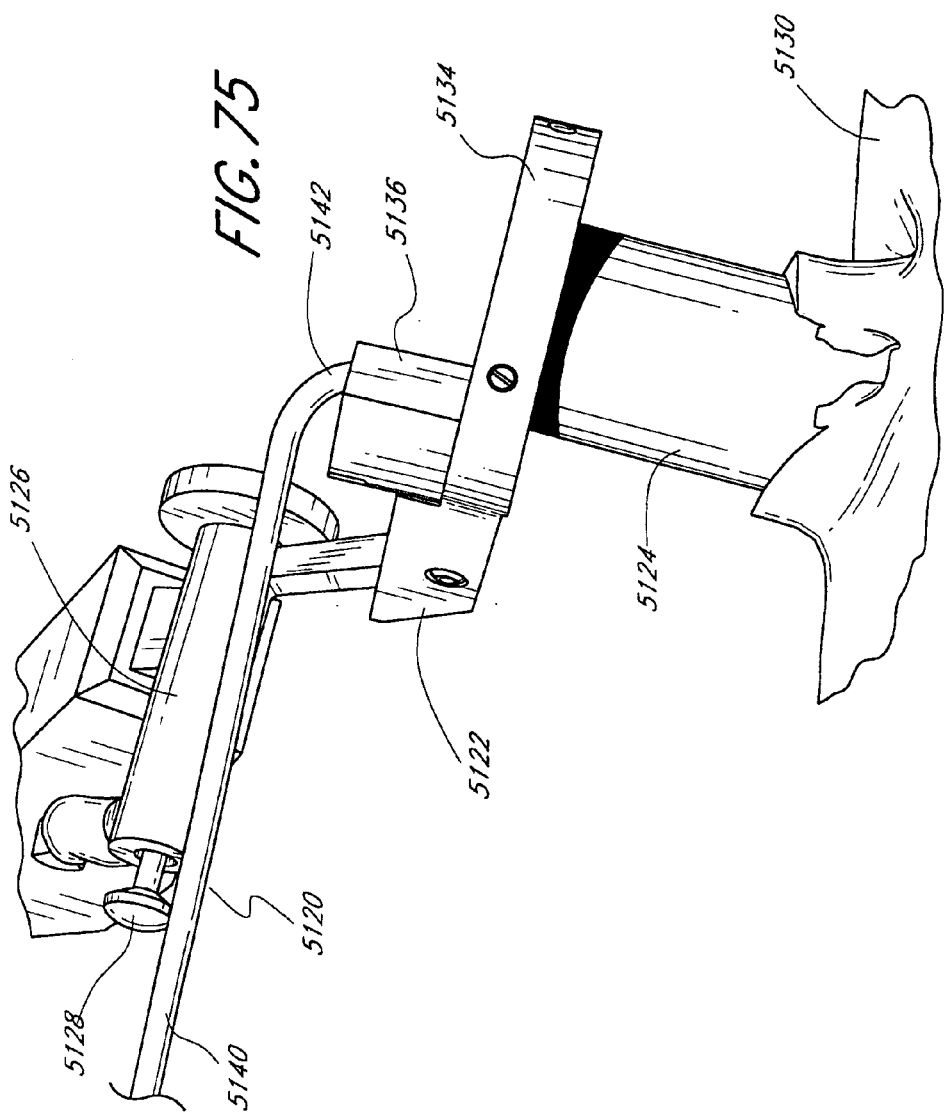
FIG. 75 is a perspective side view of the surgical system of FIG. 74 shown applied to a patient.

FIGS. 74-79 illustrate embodiments having lighting elements. FIGS. 74-76 illustrate one embodiment of a lighting element 5120 coupled with a support arm 5122 compatible with an access device 5124 having a proximal portion with a generally circular cross section. In other embodiments, support arms can be configured to be coupled with access devices having proximal portions with generally oblong or oval cross sections.

The support arm 5122 preferably is coupled with the access device 5124 to provide support for the access device 5124 during a procedure. As shown in FIGS. 74 and 75, the support arm 5122 comprises a pneumatic element 5126 for maintaining the support arm 5122 in a desired position. Depressing a button 5128 coupled with a valve of the pneumatic element 5126 releases pressure and allows the support arm 5122 and access device 5124 to be moved relative the patient 5130. Releasing the button 5128 of the pneumatic element 5126 increases pressure and maintains the access device 5124 and support arm 5122 in the desired position. The support arm 5122, as shown, is configured for use with a mechanical arm using suction, or a vacuum to maintain the access device in a desired location. One of skill in the art will recognize that various other support arms and mechanical arms can be used. For example, commercially available mechanical arms having clamping mechanisms can be used as well as suction or pressure based arms.

As shown in FIGS. 74-76, the support arm 5122 can comprise an inner ring portion 5132 and an outer ring portion 5134 for surrounding the access device 5124 at its proximal end. In the illustrated embodiment, the inner and outer ring portions 5132, 5134 are fixed relative each other. In other embodiments the inner and outer ring portions 5132, 5134 can move relative each other. The support arm 5122 preferably comprises a lighting element support portion 5136. In the illustrated embodiment, the lighting element support portion 5136 extends above upper surfaces of the inner and outer ring portions 5132, 5134. The lighting element support portion 5136 can extend from the inner ring portion 5132, the outer ring portion 5134, or both. The lighting element support portion 5136 can have a notch or groove 5138 for receiving and supporting the lighting element 5120. Additionally, the lighting element support portion 5136 can have one or more prongs extending at least partially over the lighting element 5120 to hold it in place.

In the illustrated embodiment, the lighting element 5120 has an elongated proximal portion 5140 and a curved distal portion 5142. The proximal portion 5140 of the lighting element 5120 preferably is coupled with a light source (not shown). The curved distal portion of the lighting element 5120 in one embodiment extends only a short distance into the access device and is configured to direct light from the light source down into the access device 5124. In another embodiment, the lighting element 5120 can be provided such that it does not extend into the access device. In such an embodiment, the right portions 5132 and 5134 only partially surround the proximal end of the access device 5124. Providing a lighting element 5120 for use with the access device 5124 preferably allows a user to see down into the access device 5124 to view a surgical location. Accordingly, use of a lighting element 5120 can, in some cases, enable the user to perform a procedure, in whole or in part, without the use of an endoscope. In one embodiment, the lighting element 5120 enables a surgeon to perform the procedure with the use of microscopes or loupes.

FIGS. 74-79 illustrate other embodiments of lighting elements. As shown in FIG. 77, a lighting element 5160 comprises a support member 5162, an access device insert 5164, and fiber optic elements 5166. The support member 5162 has a proximal end 5168, a central portion 5170, and a distal end 5172. The proximal end 5168 preferably has a coupling portion 5174 for coupling the support member 5162 to a support arm or other support system (not shown). The central portion 5170 preferably is coupled with the fiber optic elements 5166 to provide support there to. The distal end 5172 preferably is coupled with the access device insert 5164.

In the illustrated embodiment, the access device insert 5164 is configured to be inserted in an access device having a proximal portion with a generally circular cross section. The access device insert 5164 is coupled with the fiber optic elements 5166. The fiber optic elements 5166 extend down into the access device insert 5164 so that the ends of the fiber optic elements 5166 can direct light down inside an access device along side portions there of.

FIGS. 78 and 79 illustrate other embodiments of lighting elements similar to the embodiment described with reference to FIG. 77. Components of the lighting elements shown in FIGS. 108 and 109 that were described with reference to FIG. 77 are given the same reference numerals that were used in FIG. 77, except that an "a" is added in FIG. 78 and a "b" is added in FIG. 79. As shown in FIGS. 78 and 79, access device inserts 5164a, 5164b are configured to be inserted into access devices having proximal portions with generally oblong, or oval, cross sections. As shown in FIG. 78, the access device insert 5164a has a generally oblong or oval shaped cross section. The access device insert 5164a is coupled with the fiber optic elements 5166a along a longer side surface of the access device insert 5164a. As shown in FIG. 79, the access device insert 5164b has a generally oblong or oval shaped cross section. The access device insert 5164b is coupled with the fiber optic elements 5166b along a shorter side surface of the access device insert 5164b. Use of an illumination element with an expandable access device having an oblong shaped proximal section, in some cases, allows a doctor to perform procedures that would be difficult to perform using an endoscope. Increased visualization of the surgical location through the access device can simplify some procedures. For example, decompression of the contra-lateral side can be achieved more easily in some cases without the use of an endoscope.

Figure 80:
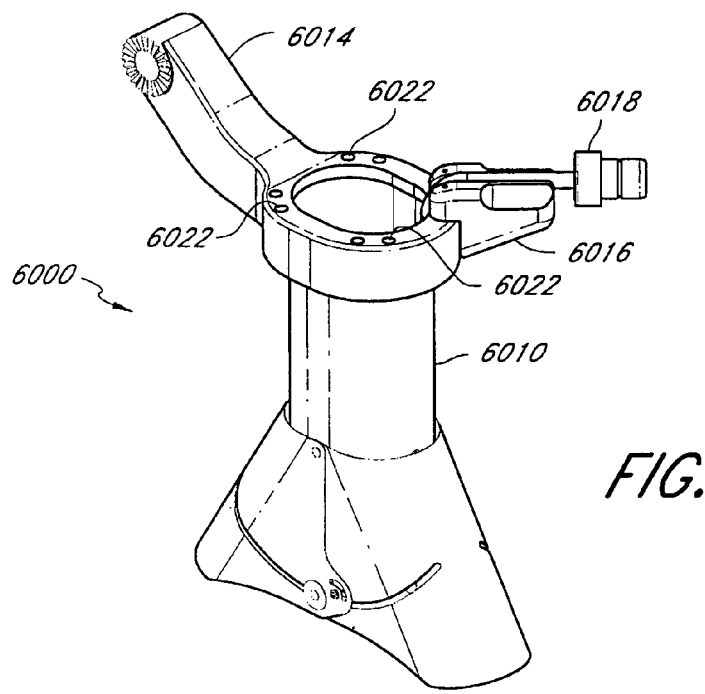
FIG. 80 is a perspective view of an access assembly.
Figure 81:
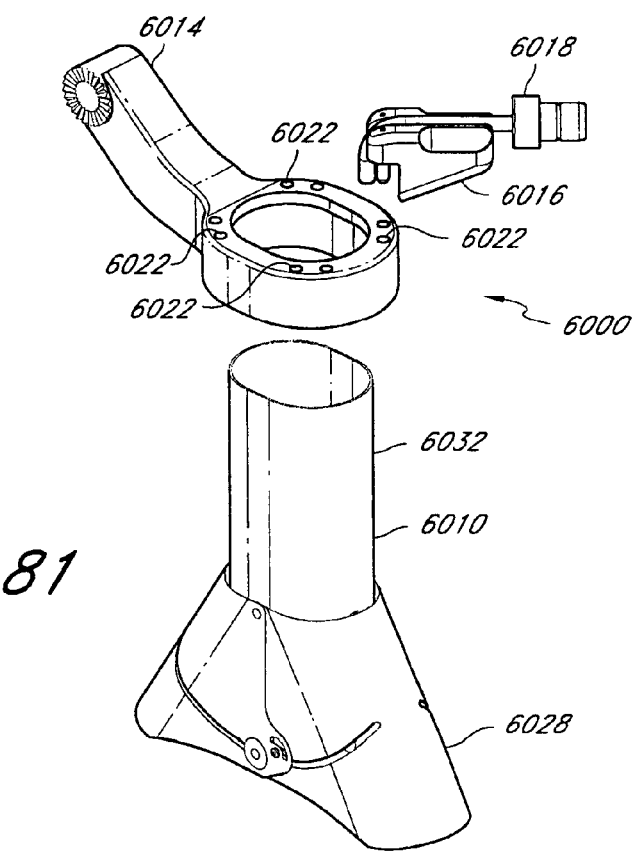
FIG. 81 is an exploded perspective view of the access assembly of FIG. 80.

FIGS. 80 and 81 show an access assembly 6000 that can be incorporated into a surgical system, such as the system 10. The access assembly 6000 includes an access device or retractor 6010 coupled with a mount fixture 6014. The mount fixture 6014 may be coupled with a support arm, such as those discussed above. The access device 6010 preferably is provided with an oblong transverse cross-section near the proximal end thereof, which can be coupled with the mount fixture 6014. More preferably, the access device 6010 can be provided with an oval transverse cross-section in some embodiments. The cross section can be generally elliptical in some embodiments. The oblong shaped cross-section of the access device 6010 is particularly beneficial for surgical procedures (such as two level pedicle screw fixation) that are performed at an elongated surgical field. Also coupled with the mount fixture 6014 is a guide fixture 6016. In one embodiment, the guide fixture 6016 is configured to be coupled with a viewing element 6018, such as any of those discussed herein, or any other suitable viewing element.

The mount fixture 6014 and the guide fixture 6016 advantageously are configured to introduce the viewing element 6018 into the access device 6010 at discrete locations. In the illustrated embodiment, the mount fixture 6014 and the guide fixture 6016 are configured to enable a viewing element to be positioned at four discrete locations that are located at opposite corners of the elongated mount fixture 6014. In the illustrated embodiment, a plurality of holes 6022 (e.g., two holes) is provided at each of four corners on the top surface of the mount fixture 6014. Each of the holes 6022 is configured to receive a pin that extends from the lower surface of the guide fixture 6016. The engagement of the pins in the holes 6022 is such that the guide fixture 6016 is securely coupled with the mount fixture 6014 so that the guide fixture 6016 will not be dislodged inadvertently during a procedure. However, the engagement of the pins in the holes 6022 also is such that a user of the access assembly 6000 can disengage the guide fixture 6016 and the viewing element 6018 and reposition it at any of the other discrete locations during a procedure. Although the coupling of the mount fixture 6014 and the guide fixture 6016 is illustrated as a two hole-two pin arrangement, other arrangements are possible and contemplated. For example, more or less than two holes and pins, couplers of other shapes (e.g., pins and holes of different shapes, tongues and slots, etc.), and clamp devices could be used in place of or in combination with the illustrated two hole-two pin arrangement.

Figure 82:
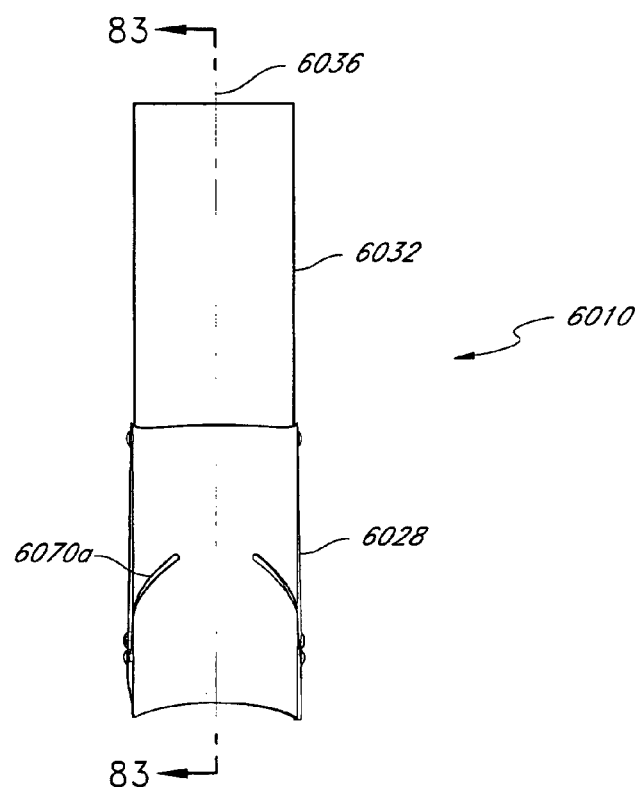
FIG. 82 is a side view of an access device of the access assembly of FIG. 80, the access device having a lock to maintain a state of expansion thereof.

FIG. 82 shows one embodiment of the access device 6010 that is similar to those hereinbefore described, except as set forth below. The access device 6010 has an elongate body with a distal portion 6028 and a proximal portion 6032. Each of the distal and proximal portions 6028, 6032 defines a portion of a passage that extends through the access device 6010. In some embodiments, the distal portion 6028 of the access device 6010 is shorter compared to the distal portion of some of the other access devices described herein. In particular, the distal portion 6028 is configured such that when the access device 6010 is applied to the patient, the distal portion 6028 is completely or substantially completely beneath the skin, as discussed below. This arrangement is advantageous in that the access device 6010 does not need to further dilate the incision at the skin.

Although the illustrated embodiment of the access device 6010 has two discrete portions that are coupled in a suitable manner, other access devices embodying features discussed herein can be configured without multiple, discrete portions. Both the proximal and distal portions preferably are made from a rigid, radiolucent material that is visible under fluoroscopy. The distal and proximal portions 6028, 6032 preferably both have sufficient strength or stiffness to retract tissue, though the strength or stiffness of the proximal and distal portions need not be the same. Examples of materials that may be used and other features that can be incorporated into the access device 6010 are discussed above and in the patents and applications incorporated by reference herein.

The proximal portion 6032 preferably is elongated and has a length along a longitudinal axis 6036 that is selected based upon the anatomy (e.g., the portion of the spine) being treated. The length of the proximal portion 6032, and other aspects of the access device 6010, also can be based in part on the individual patient's anatomy, e.g., on the amount of tissue between the skin and the surgical location, which varies across the patient population.

Figures 85, 85A:
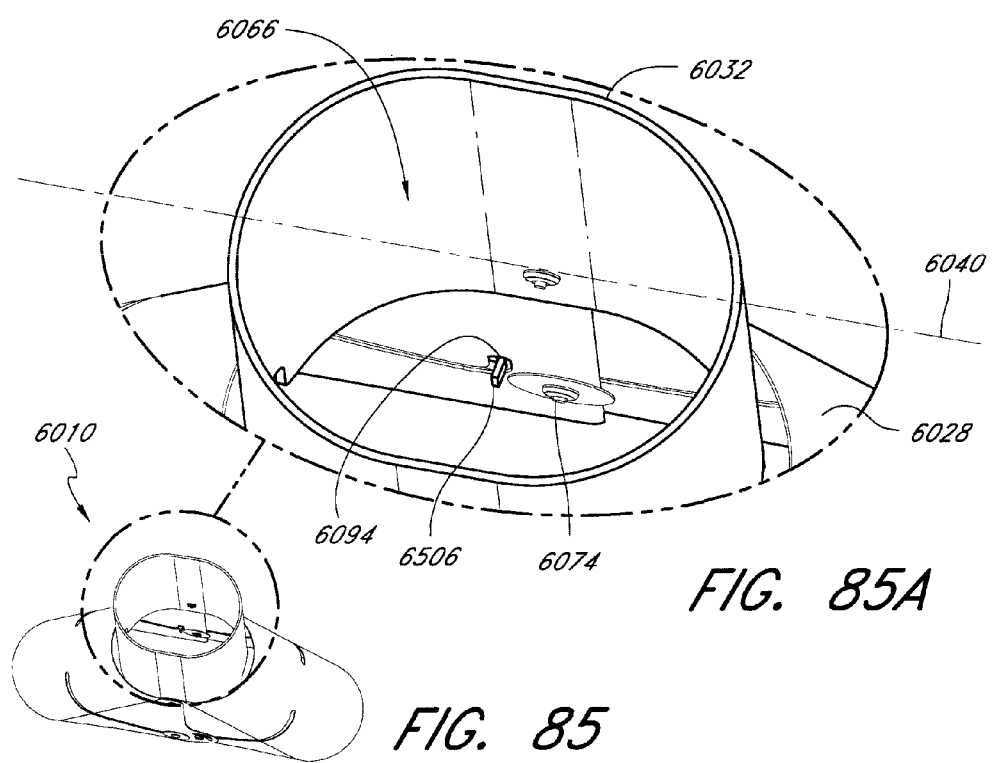
FIGS. 85 and 85A are top perspective and detailed views respectively of the access device of FIG. 82 with the lock in a locked position.
Figures 86, 86A:
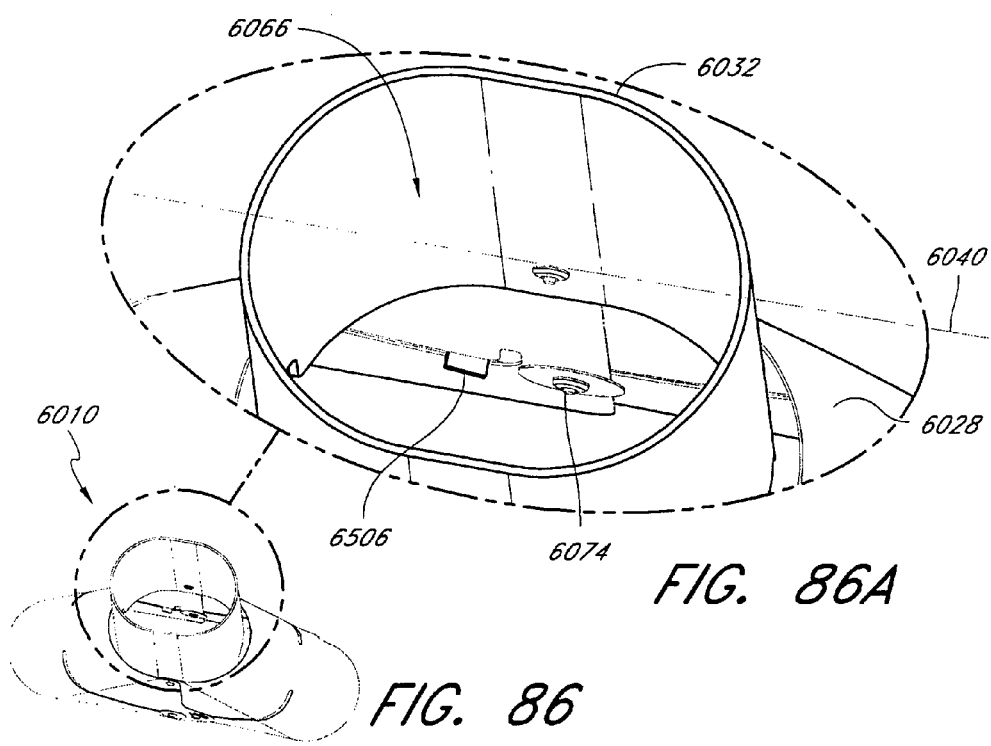
FIGS. 86 and 86A are top perspective and detailed views respectively of the access device of FIG. 82 with the lock in an unlocked position.

As discussed above, the configuration of at least a portion of the proximal portion 6032 is elongated in at least one direction in a plane perpendicular to the axis 6036. One advantageous arrangement of the proximal portion 6032 provides an oblong transverse cross-section. Another advantageous arrangement provides an oval transverse cross-section. The configuration of the proximal portion 6032 is illustrated in FIGS. 85-86A, which show that the transverse cross-section of the proximal portion 6032 is elongated along a line 6040. As will be discussed in more detail below, the line 6040 extends along the main axis of expansion of the access device 6010.

There are several advantages to configuring the proximal portion 6032 with an oblong transverse cross-section. Many bone and joint procedures, particularly spine procedures, are performed at elongated surgical fields. For example, multi-level procedures may be much more convenient for the surgeon and beneficial for the patient if access can be provided to at least a portion of three or more adjacent vertebrae. While symmetrical access could be provided to three or more adjacent vertebrae, much non-adjacent tissue (i.e., tissue not in the immediate vicinity of the structures being treated) would be disrupted, causing greater trauma to treat the patient than necessary. This additional trauma approaches that of open surgery as the length of the surgical field increases. In contrast, the use of an oblong transverse cross-section proximal portion 6032 and access device 6010 lessens, if not minimizes, the amount of non-adjacent tissue that is disrupted. Oblong access from a posterior or posterolateral approach is particularly advantageous in that it provides access to anatomy for a wide variety or procedures, e.g., those that affect the pedicles.

The distal portion 6028 also extends along the longitudinal axis 6036 and comprises a first overlapping portion 6050 and a second overlapping portion 6054. The first overlapping portion 6050 extends between a proximal end 6058 and a distal end 6062 of the distal portion 6028. The second overlapping portion 6054 extends between the proximal end 6058 and the distal end 6062 of the distal portion 6028. The overlapping portions 6050, 6054 overlap each other to create an enclosed space 6066 therebetween. In one embodiment, each of the overlapping portions 6050, 6054 extends along the axis 6036 when the overlapping portions are coupled with the proximal portion 6032 and is formed from a thin, rigid material (such as sheet metal) that is curled into a generally U-shaped structure.

The first and second overlapping portions 6050, 6054 are coupled in a manner that permits expansion of the distal portion 6028 at the distal end 6062. The advantages of being able to expand the distal portion are discussed above. The first and second overlapping portions 6050, 6054 also are configured to be selectively locked or unlocked in one or more states of expansion or contraction. Further advantages of the locking aspect of the first and second overlapping portions 6050, 6054 are discussed below.

In one embodiment, the distal portion 6028 has a slot and guide member arrangement that enables expansion of the distal portion 6028. Corresponding arcuate slots 6070a, 6070b are formed in the first overlapping portion 6050 and the second overlapping portion 6054, respectively. In one embodiment, a guide member, such as a sliding rivet 6074, extends through the corresponding slots 6070a, 6070b thereby coupling the slots. The slots 6070a, 6070b and the rivet 6074 enable the distal portion 6028 to be expanded by allowing the rivet 6074 to slide along the slots as the overlapping portions 6050, 6054 move away from or toward each other. In the illustrated embodiment, a second pair of slots and a corresponding guide member (e.g., a rivet) are provided on the opposite side of the access device 6010 from the slots 6070a, 6070b and the rivet 6074. Thus, two rivets 6074 are provided in corresponding pairs of slots adjacent each edge of the overlapping sections 6050, 6054. This arrangement enables generally linear expansion of the distal portion 6028 along and parallel to a vertical plane extending along the long dimension of the proximal portion 6032 and containing the line 6040. Another arrangement provides one or more slots on only one side of the access device 6010, which would provide a more multi-directional expansion (e.g., both cephalad-caudad and medial-lateral) near the distal end 6062 of the distal portion 6028.

The distal portion 6028 is configured to be actuatable from a non-expanded configuration to an expanded configuration. The non-expanded configuration is said to be "low-profile" in that the transverse cross-section of the distal portion 6028, particularly at the distal end 6062, is relatively small. The access device 6010, like the other access devices described herein, is configured to be inserted over a dilating structure, such as a dilator or an obturator. One suitable dilator is described below in connection with FIGS. 120-122. Providing a low-profile distal end 6062 in the non-expanded configuration enables a generally smaller dilating structure to be used, reducing the amount of trauma to the patient during insertion. In one embodiment the distal portion 6028 has an oblong cross-section similar to that of the proximal portion 6032 when the distal portion 6028 is in a low profile configuration. The transverse cross-section of the distal portion 6028 in the low profile configuration need not be constant from the distal end 6058 to the proximal end 6062 thereof. For example, in one embodiment the transverse cross-section of the distal portion 6028 transitions from generally circular near the distal end 6058 to generally oblong near the proximal end 6062 (e.g., generally matching the transverse cross-section of the proximal portion 6062 at the distal end thereof). The distal portion 6028 may also be arranged to transition from a circular cross-section configuration to a non-circular cross-section configuration.

The distal portion 6028 also is provided with a lock 6090 that enables a user to selectively lock the distal portion 6028 into one or more states of expansion. The lock 6090 can take many forms. In one embodiment, the lock 6090 includes a slot 6094 and an L-shaped flange 6098 that can be moved (e.g., rotated) in and out of the slot 6094.

In one embodiment, the slot 6094 extends generally perpendicularly from the slot 6070a and the slot 6094 has a first side 6094a and a second side 6094b. Each of the first and second sides 6094a, 6094b of the slot 6094 restrains relative movement of the overlapping portions 6050, 6054 to selectively limit expansion or un-expansion of the distal portion 6028 when the lock 6090 is engaged.

In one embodiment, the L-shaped flange 6098 includes an elongated planar portion 6502 and a lock tab 6506. The elongated portion 6502 preferably is relatively thin so that it may reside between the overlapping portions 6050, 6054. In one embodiment, the elongated portion 6502 is rotatably coupled (e.g., with a pin or a portion of a rivet, e.g., a half-rivet) with the overlapping portion 6054 near one edge thereof. The elongate portion 6502 is thereby enabled to swing about an arc. In one embodiment, the lock tab 6506 extends generally perpendicularly from the end of the elongated portion 6502 that is opposite the rotatably coupled end. The length of the lock tab 6506 is greater than the thickness of the first overlapping portion 6050. In one embodiment, the lock tab 6506 extends far enough beyond the first overlapping portion 6050 into the area defined within the access device 6010 to enable a user to engage and manipulate the lock tab 6506 in the enclosed space 6066. Where the access device 6010 is to be inserted over a dilating structure, the lock tab 6506 preferably is configured to not interfere with the dilating structure. For example, the lock tab 6506 can be made short enough so that the lock tab 6506 does not extend far enough into the enclosed space 6066 defined inside the access device 6010 to interfere with the dilating structure. Any suitable tool may be used to articulate the lock 6090, e.g., by engaging and manipulating the lock tab 6506. For example, a tool that is long enough to extend from a location proximal of the proximal end of the proximal portion 6032 to the location of the lock 6090 could be used. A number of conventional tools can be configured in this manner, including a cobb elevator, a penfield, and a nerve hook.

In one application, the access device 6010 is used to provide minimally invasive access to the spine for a spinal procedure, such as a one-level or a multi-level procedure. The patient is positioned prone on a radiolucent table and draped for posterior spinal surgery. The location of the spine anatomy to be treated is identified, e.g., via fluoroscopy. In one technique, the location of adjacent pedicles on one side of the mid-line of the spine are identified. Thereafter, an incision is made through the skin above the adjacent pedicles. In one technique, an incision of about 30-40 mm in length is made between two adjacent pedicles where a single level procedure (one involving two adjacent vertebrae) is to be performed. In another technique where a two-level procedure (one involving three vertebrae) is to be performed, an incision of 40-50 mm in length is made. As discussed above, in some embodiments, the access device 6010 is configured to be applied such that the distal portion 6028 is completely or substantially completely submerged beneath the skin. In one technique, an incision of about 30 mm is made in the skin so that an access device configured to be applied in this manner may be applied to the patient. In some embodiments of the access devices described herein, a proximal portion thereof is configured to be expandable. In some techniques for applying access devices with expandable proximal portions, a larger incision may be made to accommodate all or substantially all of the expansion of the proximal portion.

Thereafter a dilating structure, such as a series of dilators or an obturator, is inserted into the incision to enlarge the incision. It may be desirable to use round or oblong dilators. Preferably the last dilator has an outer profile that matches the un-expanded inner profile of the access device 6010. In one technique for a single level procedure, a 5 mm dilator is first inserted through the skin near the center of the skin incision and is docked on the lateral aspect of the superior facet. In a two-level procedure, a 5 mm dilator is first advanced through the skin near the center of the incision and is docked on the mamillo-accessory ridge of the middle pedicle. Placement of the 5 mm dilator may be verified by fluoroscopy. Subsequently, progressively larger dilators are inserted over each other. After a larger dilator is inserted, the next-smaller dilator is normally removed. One or more of the dilators, a cobb device, or even one of the surgeon's fingers may also be used to probe and to dissect soft tissue to ease expansion of the access device 6010, as discussed below. Placement of the final dilator may be verified by fluoroscopy. Other procedures employ similar dilating techniques by initially approaching other anatomical features on or near the spine.

Thereafter, the access device 6010 is advanced to the anatomy to be treated. As discussed above, a sleeve deployable by a string may be employed to maintain the access device 6010 in the low-profile configuration (e.g., in the un-expanded state) until the access device is in place. Various embodiments of the sleeve and string are discussed herein, e.g., in connection with FIGS. 123-124. In one technique, the assembly of the access device 6010, the sleeve, and the string is inserted into the incision and positioned so that the string faces the mid-line of the spine. Thereafter the string is withdrawn, releasing the sleeve from the access device 6010. In particular, in one technique, the string is pulled from near the proximal end of the access device 6010. This action causes the sleeve to be torn along a line extending proximally from the distal end of the sleeve. The sleeve may be partially or completely torn from distal to proximal, releasing at least the distal end of the access device 6010 for expansion. After the sleeve is released from the access device 6010, the access device 6010 is free to expand and to be expanded.

Figure 83:
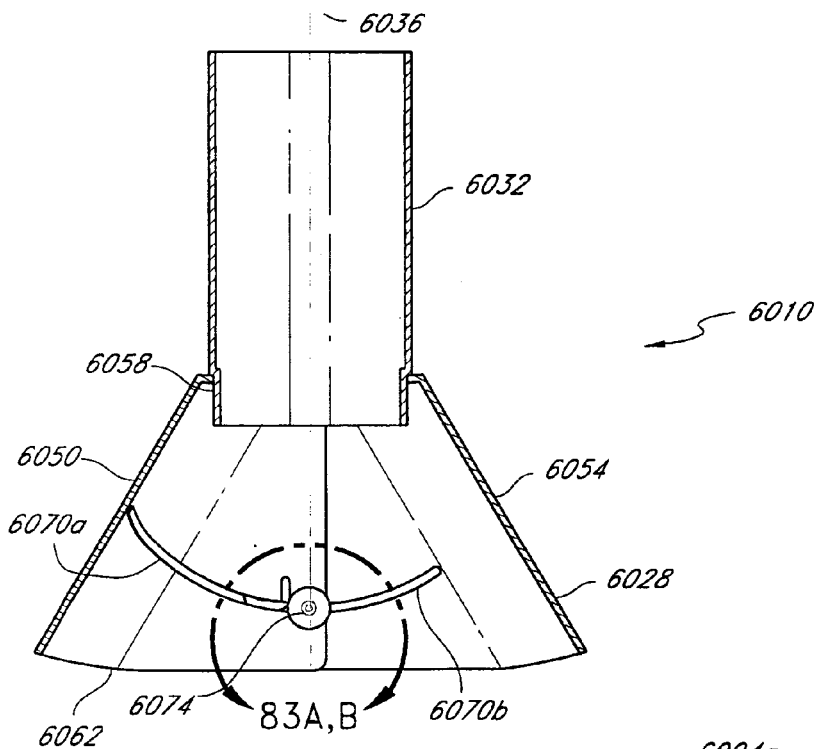
FIG. 83 is a cross-sectional view of the access device of FIG. 82 taken along section plane 83-83.
Figure 83A:
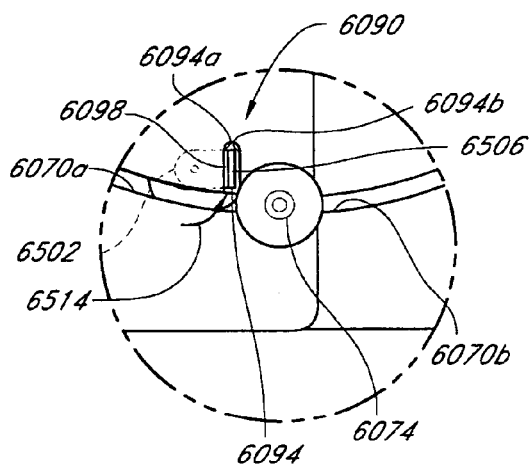
FIG. 83A is a detail view of one embodiment of a lock to maintain a state of expansion of an access device, the lock shown in the locked position.
Figure 83B:
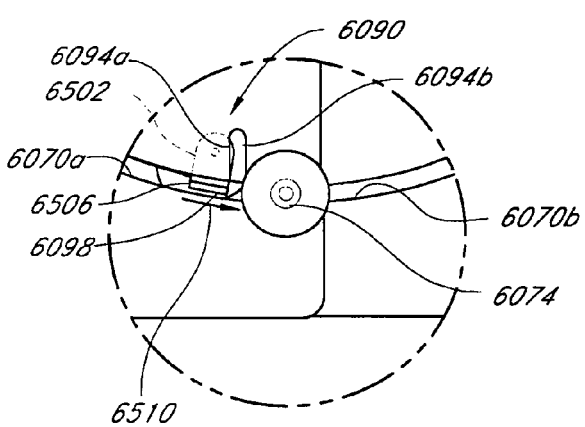
FIG. 83B is a detail of the lock of FIG. 83A, the lock shown in the unlocked position.

FIG. 83B shows that prior to and during expansion of the access device 6010, the L-shaped flange 6098 is positioned so that the lock tab 6506 is located in the arcuate slot 6070*a*. The lock tab 6506 has a thickness that is less than the proximal to distal width of the slot 6070*a* so that the lock tab 6506 can translate along the slot 6070*a* between positions corresponding to the un-expanded and expanded configurations of the access device 6010. The access device 6010 may resiliently expand with the lock tab 6095 in the slot 6070*a*. Further expansion of the access device 6010 may be achieved by inserting and articulating an expander tool, such as the expander tool 200 discussed above. The expansion and location of the access device 6010 may be confirmed by fluoroscopy.

After the access device 6010 has been fully expanded, the lock 6090 may be articulated to lock the access device 6010 in the expanded configuration. In particular, the lock tab 6098 may be positioned in the slot 6094. As discussed above, the lock tab 6098 is pivotable at the end opposite the lock tab 6506. In one procedure, the user grasps and rotates the lock tab 6506 from the expansion position in the slot 6070*a* to the locked position in the slot 6094. As discussed above, the lock 6090 may be manipulated in any convenient manner, e.g., by any suitable tool, as discussed above. FIG. 83B shows an arrow 6510 that indicates the rotation of the lock tab 6098 to the locked position. When in the locked position, the lock tab 6098 may engage one of the sides 6094*a*, 6094*b* of the slot 6094 to prevent either inadvertent further expansion or un-expansion of the access device 6010.

In one variation, another slot analogous to the slot 6094 is provided at the opposite end of the arcuate slot 6070*a* to enable the access device 6010 to be locked in the un-expanded configuration. This arrangement and variations thereof may substitute for the sleeve and string arrangement, discussed above.

After the access device 6010 is locked in position, various procedures may be performed on the spine (or other joint or bone segment). As discussed above, these procedures may be performed with much less trauma than that associated with open surgery. After the procedures are complete, the access device 6010 may be un-expanded by articulating the lock 6090 from the locked position to the unlocked position, e.g., by moving the lock tab 6098 from the slot 6094 to the slot 6070*a*, wherein it is free to translate. FIG. 83A shows an arrow 6514 that indicates the rotation of the lock tab 6098 to the unlocked position.

Figure 84:
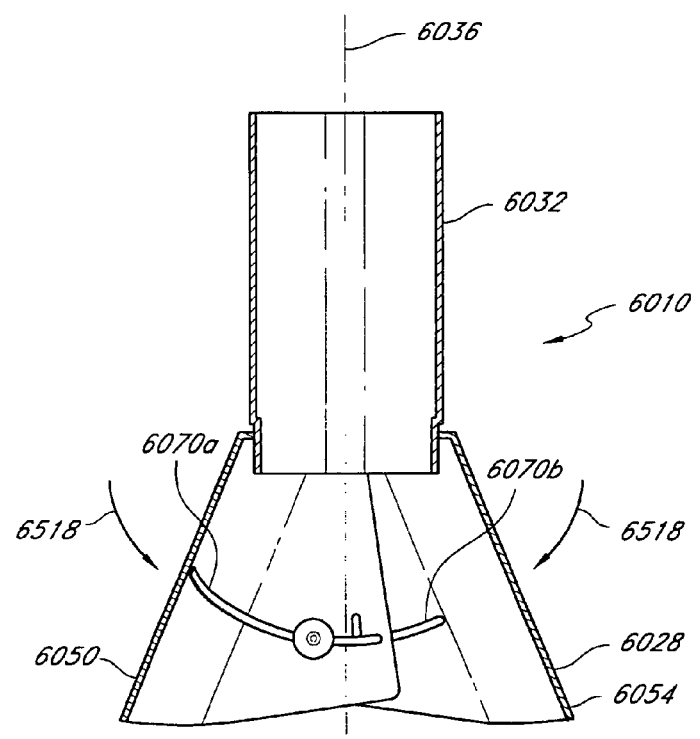
FIG. 84 is a cross-section view similar to that of FIG. 83 with the lock device in the unlocked position during the un-expansion of the access device.

FIG. 84 shows an arrow 6518 that indicates un-expansion of the access device 6010 after the procedure is complete.

Figure 87:
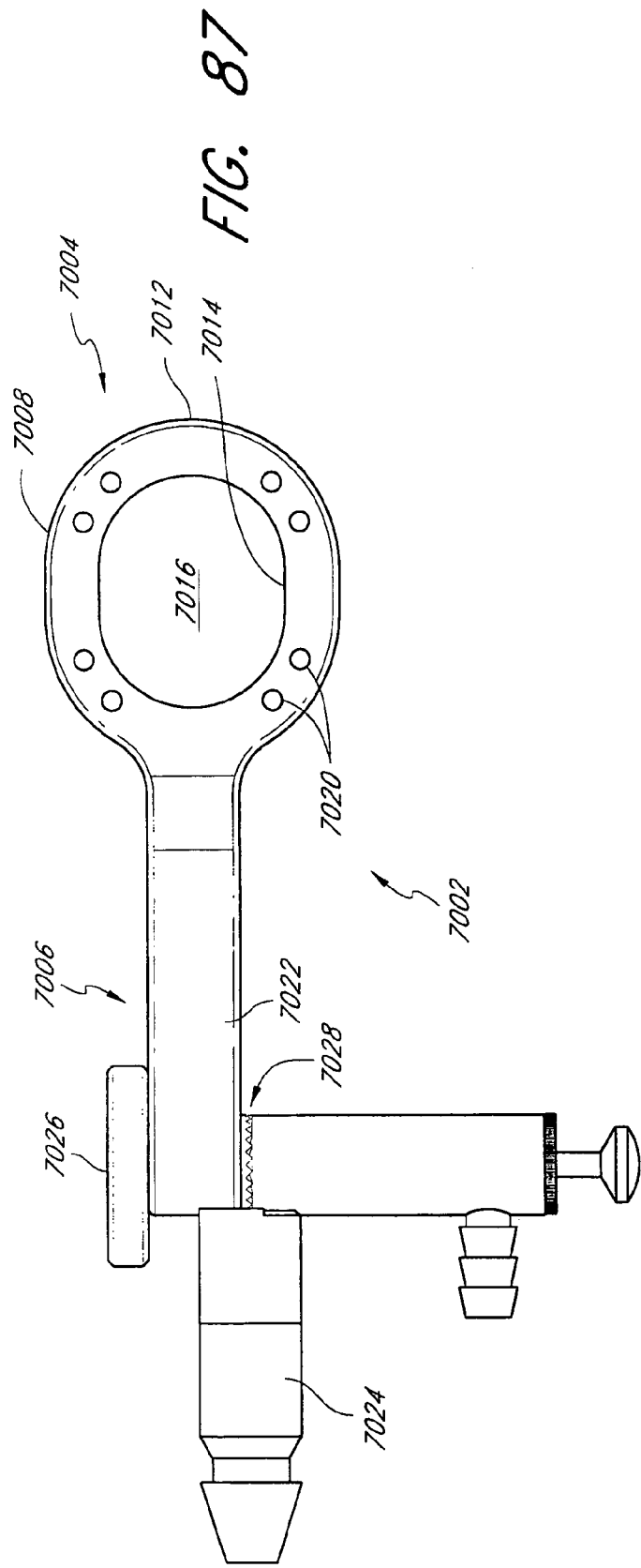
FIG. 87 is a top view of a viewing element mounting assembly having a light post mount or visualization mount, according to one embodiment.

FIGS. 87-150 illustrate and describe systems, devices, components, and methods according to some additional embodiments. Details shown or described in FIGS. 87-150 are merely representative of some preferred embodiments and are not intended to limit other embodiments. Some of the systems, devices, components, and methods shown are similar to those described above or in the documents incorporated by reference herein. Additional features and advantages of the illustrated embodiments will be apparent to those of ordinary skill in the art in view of the disclosure herein.

FIGS. 87-122 illustrate instrumentation, systems, devices, components, and methods according to some embodiments. FIGS. 87-122 illustrate portions of support arms, light post mounts, visualization mounts, light posts, visualization elements, indexing collar assemblies, and dilators, according to some embodiments. These devices and components can cooperate with access devices in access systems, such as those described and shown herein to facilitate various surgical procedures.

FIGS. 87-119 illustrate portions of a visualization assembly 7000. The visualization assembly 7000 preferably is configured to be coupled with a proximal portion of an access device. In the illustrated embodiment, the visualization assembly 7000 is configured to be coupled with an access device having a proximal portion with an oval shaped cross-sectional area. In other embodiments, the visualization assembly 7000 can be configured to be coupled with a proximal portion of an access device having any other oblong shaped or circular shaped (as suggested in FIG. 102) cross-sectional area. In one embodiment, the visualization assembly 7000 is configured to be coupled with an access device having a proximal portion that has a generally oval shaped opening that is about 24 mm wide and about 30 mm long. In another embodiment, the visualization assembly can be configured to be coupled with an access device having a proximal portion with a generally oval shaped opening that is about 24 mm wide and about 35 mm long.

Figure 88:
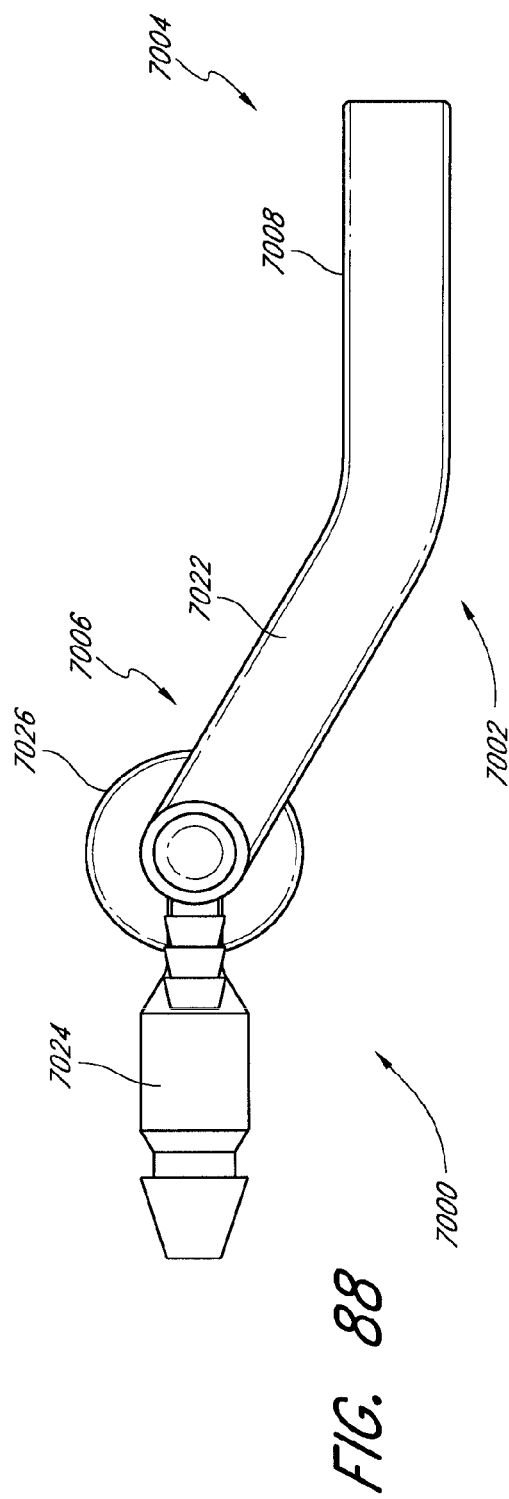
FIG. 88 is a side view of the viewing element mounting assembly of FIG. 87.

FIGS. 87 and 88 show a visualization assembly 7000 that is similar to the other visualization assemblies described herein, except as set forth below. With reference to FIGS. 87 and 88, the visualization assembly 7000 has a light post mount 7002. In other embodiments, other suitable visualization element mounts can be used. The light post mount 7002 has a distal portion 7004 and a proximal portion 7006. The distal portion 7004 has a generally oval shaped mounting portion 7008. In other embodiments, the distal portion 7004 can have any other oblong shaped or circular shaped mounting portion 7008. A light post assembly 7010 (see FIGS. 98-99) preferably can be supported on a mounting portion 7008 of the light post mount 7002. The mounting portion 7008 has an outside surface 7012 and an inside surface 7014. The inside surface 7014 preferably defines an oblong shaped opening 7016 to provide access to a passage of an access device. In the illustrated embodiment, the inside surface 7014 defines a generally oval shaped opening 7016.

FIGS. 89-94 show a viewing element support mount that is similar to the other viewing element support mounts described herein, except as set forth below. With reference to FIGS. 89-94, the light post mount 7002 has a ledge 7018 on the inside surface 7014 of the light post mount 7002. The ledge 7018 preferably is configured so that the light post mount 7002 can rest on a top surface, a top edge, or an end of a proximal portion of an access device. The inside surface 7014 of the light post mount 7002, below the ledge 7018, can extend over a proximal portion of an access device. The mounting portion 7008 preferably has openings 7020, such as, for example, holes or slots, defined in the wall of the mounting portion 7008 for supporting the light post assembly 7010 or other visualization tool. As shown in the illustrated embodiment, the mounting portion 7008 preferably is configured to receive the light post assembly 7010 at a plurality of locations or positions.

Figure 89:
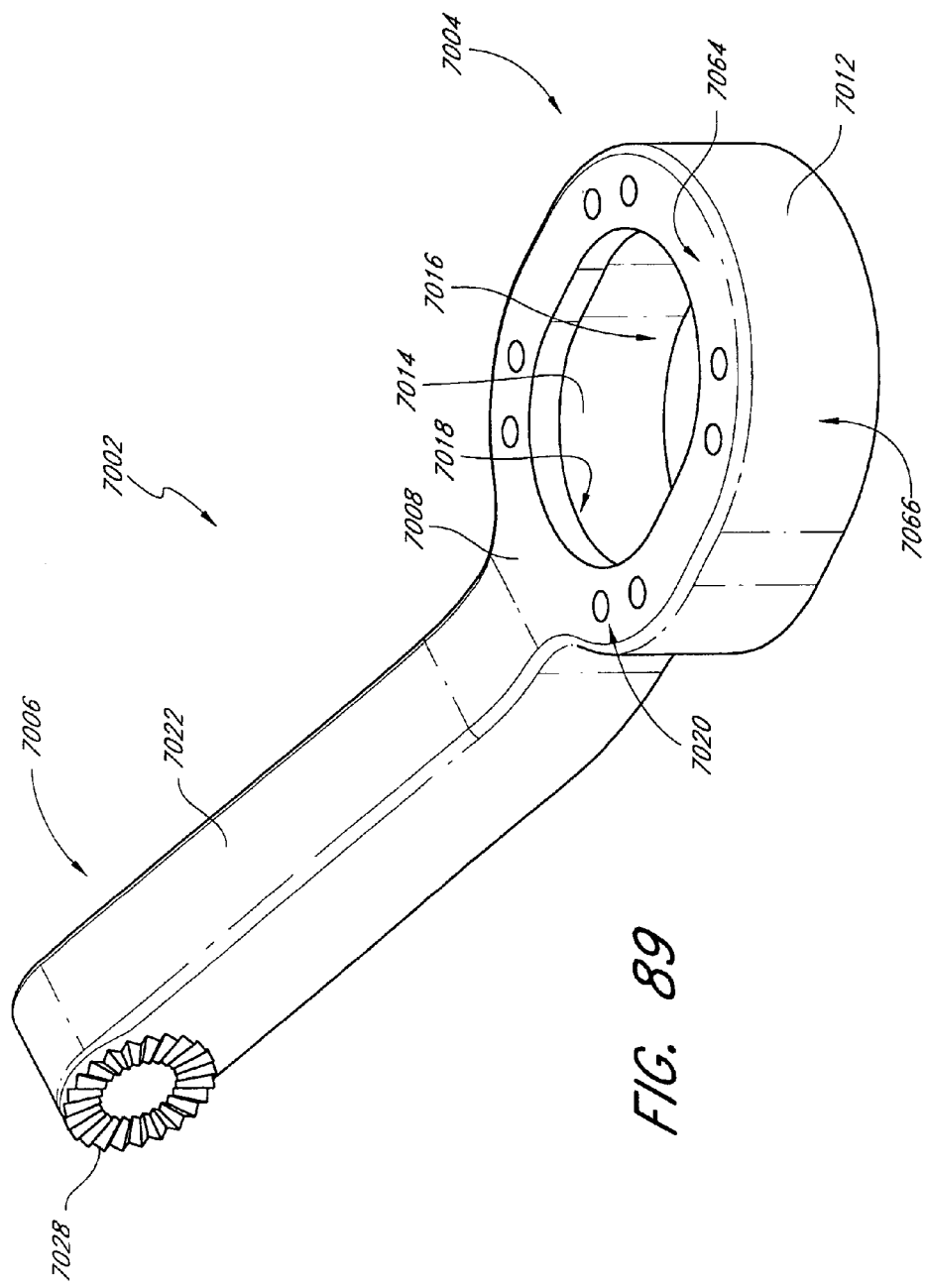
FIG. 89 is a perspective view of the light post mount or visualization mount of FIG. 87.

The light post mount 7002 has a support arm 7022 extending proximally from the mounting portion 7008. With reference to FIGS. 87 and 88, the support arm 7022 preferably is coupled with an arm extension assembly 7024 via an arm locking screw 7026. With reference to FIG. 89, the light post mount 7002 has a spline ring 7028 at a proximal portion 7006 of the support arm 7022. The spline ring 7028 preferably is configured for coupling the light post mount 7002 with the arm extension assembly 7024 via the arm locking screw 7026.

Figure 97:
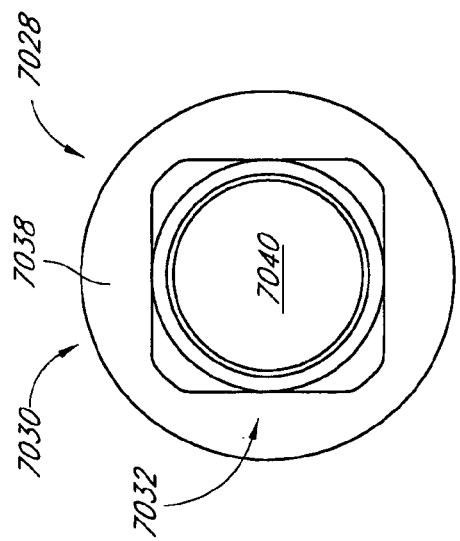
FIG. 97 is another end view of the spline ring of FIG. 95.
Figure 96:
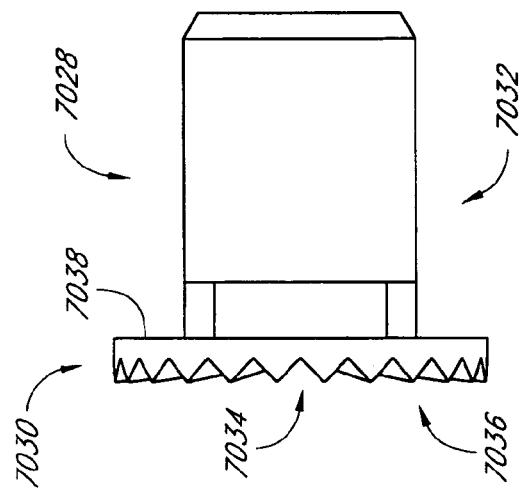
FIG. 96 is a side view of the spline ring of FIG. 95.
Figure 95:
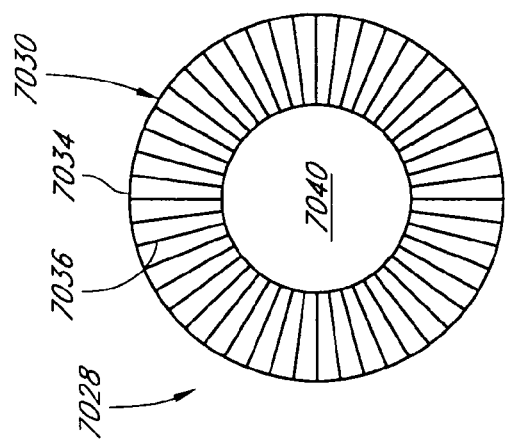
FIG. 95 is an end view showing a spline surface of a spline ring for the light post mount or visualization mount of FIG. 89.
Figure 100:
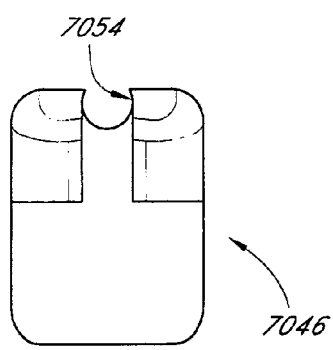
FIG. 100 is a front view of a light post mount block or visualization element mount block, according to one embodiment.
Figure 101:
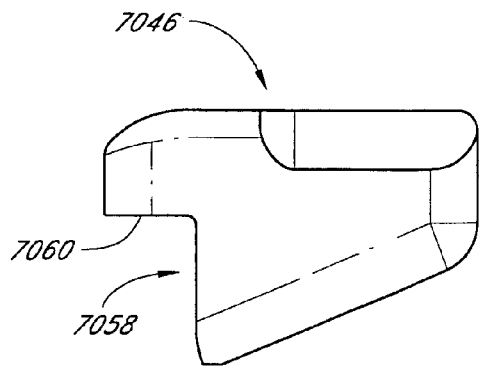
FIG. 101 is a side view of the light post mount block or visualization element mount block of FIG. 100.
Figure 102:
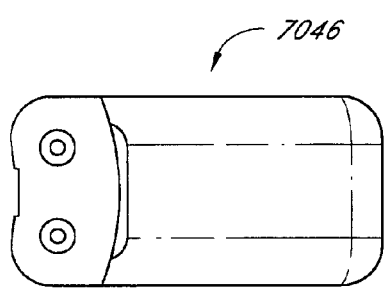
FIG. 102 is a top view of the light post mount block or visualization element mount block of FIG. 100.
Figure 103:
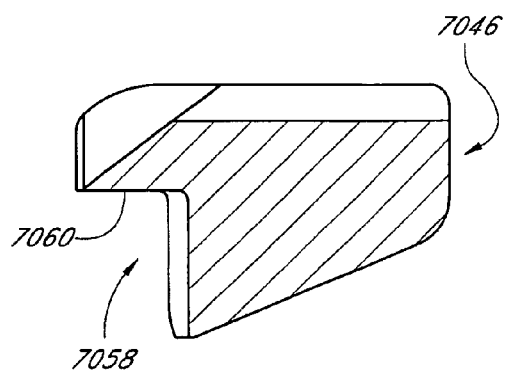
FIG. 103 is a side cross section view of the light post mount block or visualization element mount block of FIG. 100.
Figure 104:
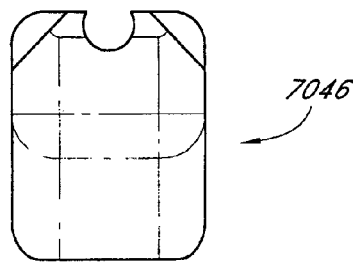
FIG. 104 is a back view of the light post mount block or visualization element mount block of FIG. 100.
Figure 105:
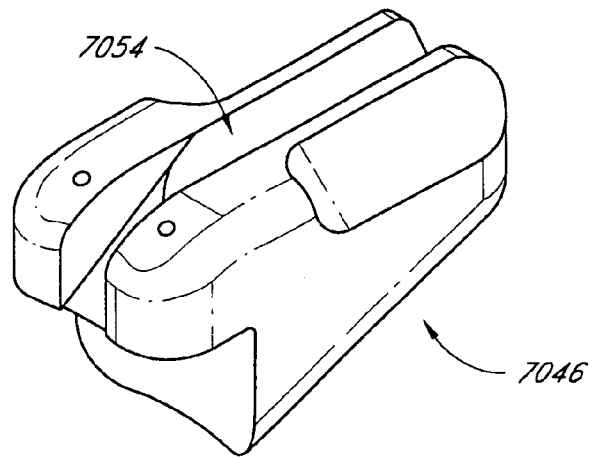
FIG. 105 is a top perspective view of the light post mount block or visualization element mount block of FIG. 100.
Figure 106:
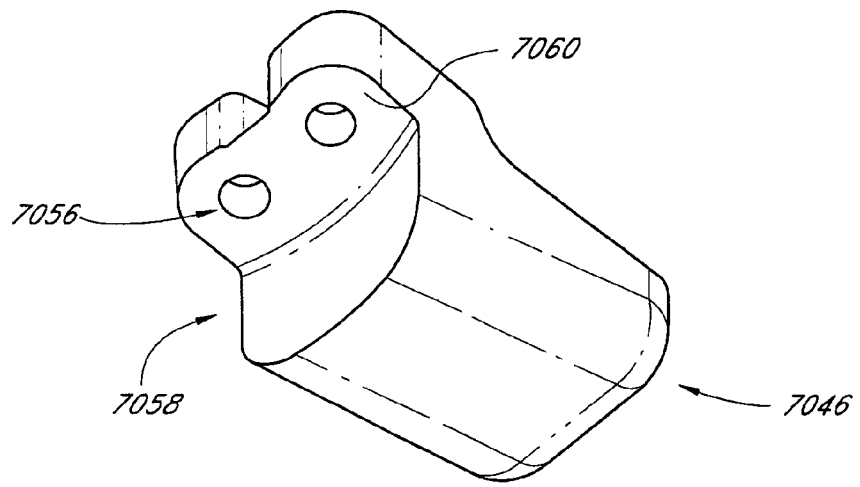
FIG. 106 is a bottom perspective view of the light post mount block or visualization element mount block of FIG. 100.

With reference to FIGS. 95-97, the spline ring 7028 has a spline portion 7030 and an anchor portion 7032. The spline portion 7030 preferably comprises a plurality of notches 7034 formed in a first surface 7036 of the spline portion 7030 to interface with the arm extension assembly 7024 via the arm locking screw 7026. The anchor portion 7032 of the spline ring 7028 extends from a second surface 7038 of the spline portion 7030 generally opposite the spline surface 7036. The anchor portion 7032 and spline portion 7030 define an opening 7040 extending through the spline ring 7028. The anchor portion 7032 can be inserted into an opening 7042 (see FIGS. 90 and 93) in the light post mount 7002 and preferably is secured therein using an epoxy.

FIGS. 98-99 show a viewing element that is similar to the other viewing elements described herein, except as set forth below. With reference to FIGS. 98-99, a light post assembly 7010 preferably comprises a light tube 7044, a light post mount block 7046, and one or more locator pins 7048. The light post assembly 7010 preferably is configured to be coupled with the light post support mount 7002. The light post assembly 7010 has a coupler 7050 for connecting the light post assembly 7010 to a light source (not shown). The light tube 7044 preferably is angled to direct light down into a channel or passage of an access device when the light post assembly 7010 is supported on the light post support mount 7002. The light tube 7044 in the illustrated embodiment is about 3 mm in diameter and about 15 mm long. A longer light tube 7044 may be used where it is desired to locate the end 7052 of the light tube 7044 farther distally in an access device.

Figure 107:
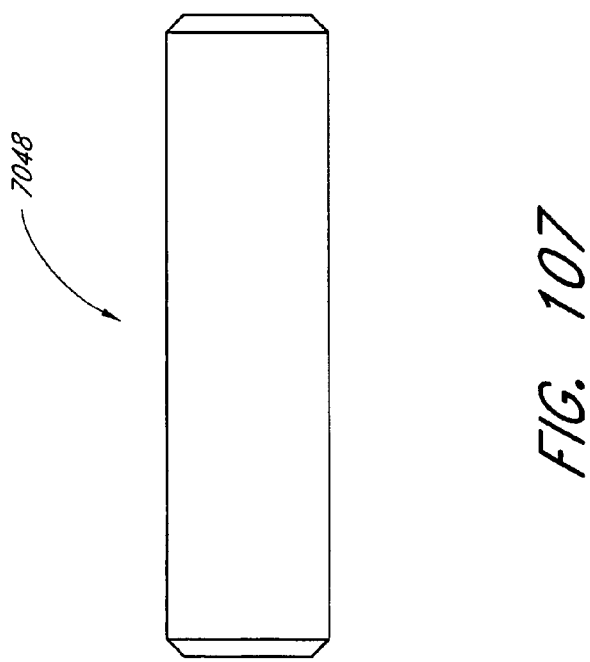
FIG. 107 illustrates a pin configured to be coupled with the light post mount block or visualization element mount block of FIG. 100.
Figure 110:
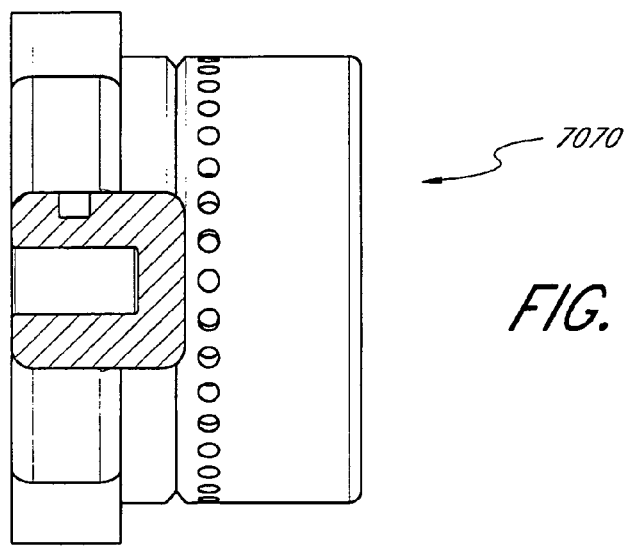
FIG. 110 is an end cross section view of the indexing collar of FIG. 108.
Figure 111:
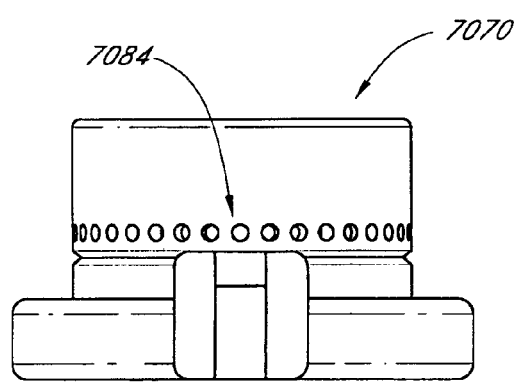
FIG. 111 is an end view of the indexing collar of FIG. 108.
Figure 112:
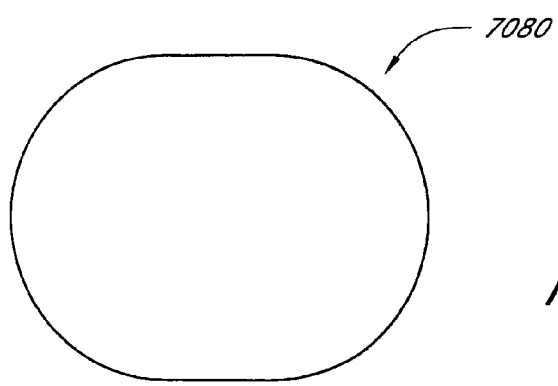
FIG. 112 is a schematic view of a passage of the indexing collar of FIG. 108.
Figure 113:
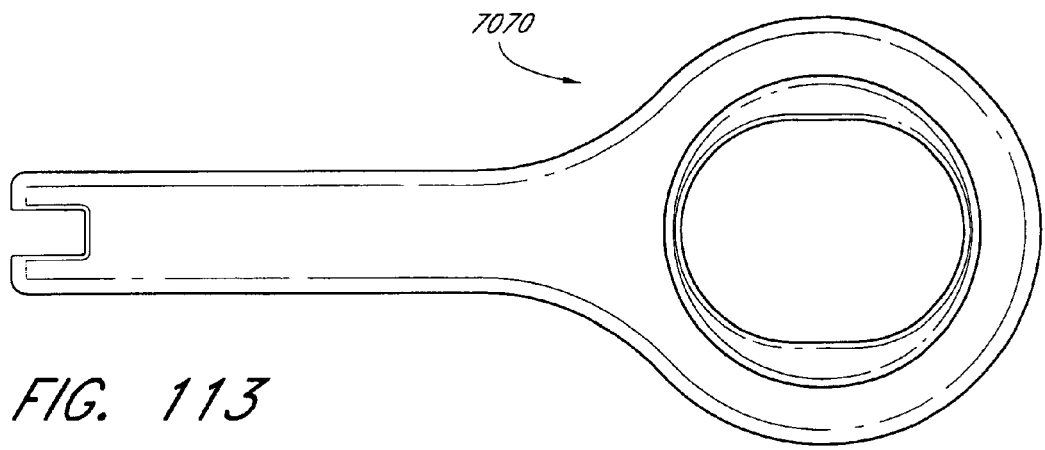
FIG. 113 is a top view of the indexing collar of FIG. 108.
Figure 114:
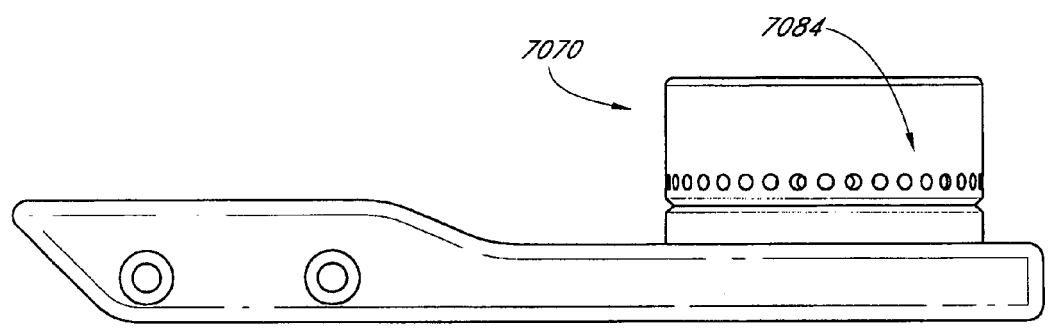
FIG. 114 is a side view of the indexing collar of FIG. 108.
Figure 115:
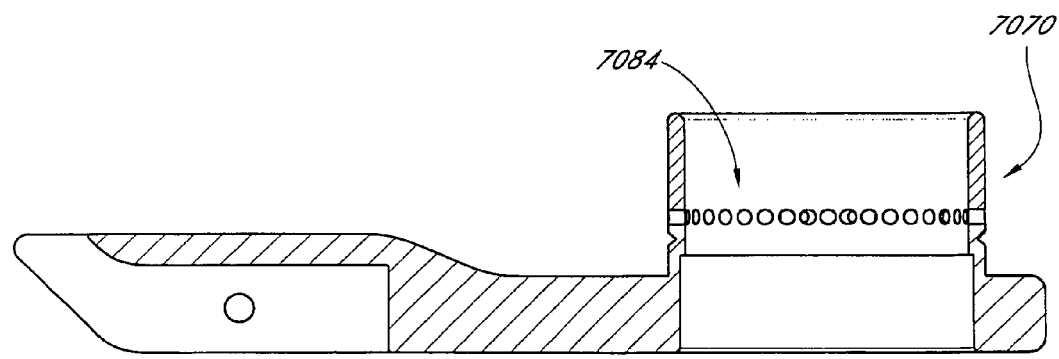
FIG. 115 is a side cross section view of the indexing collar of FIG. 108.
Figure 116:
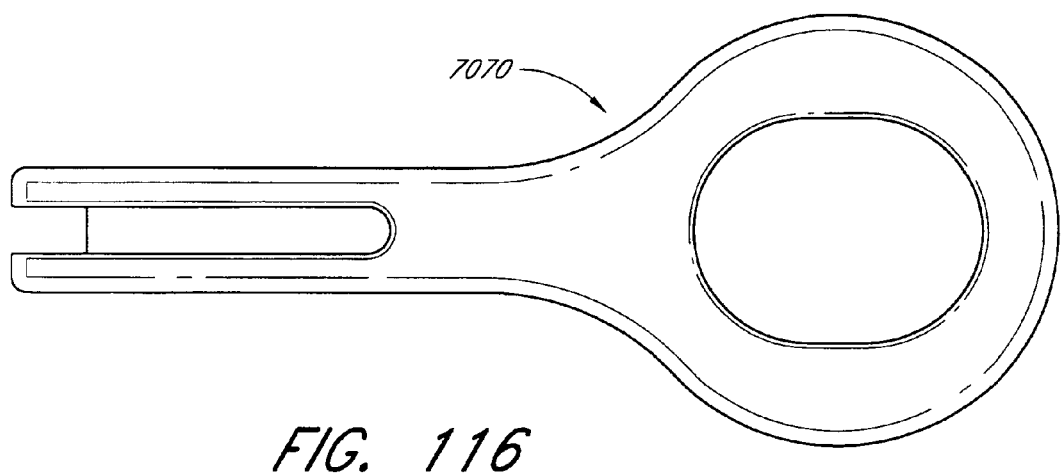
Figure 117:
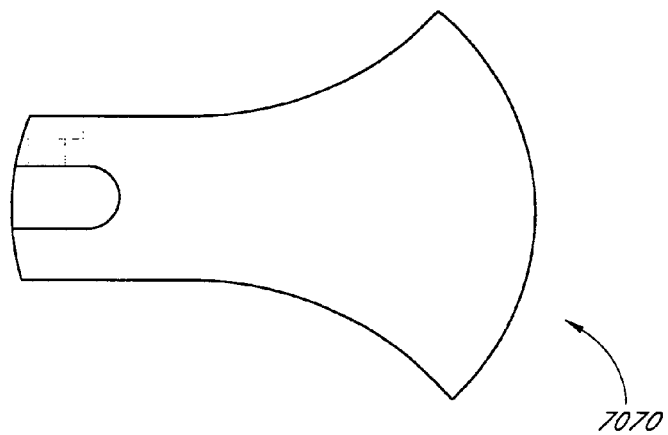
Figure 118:
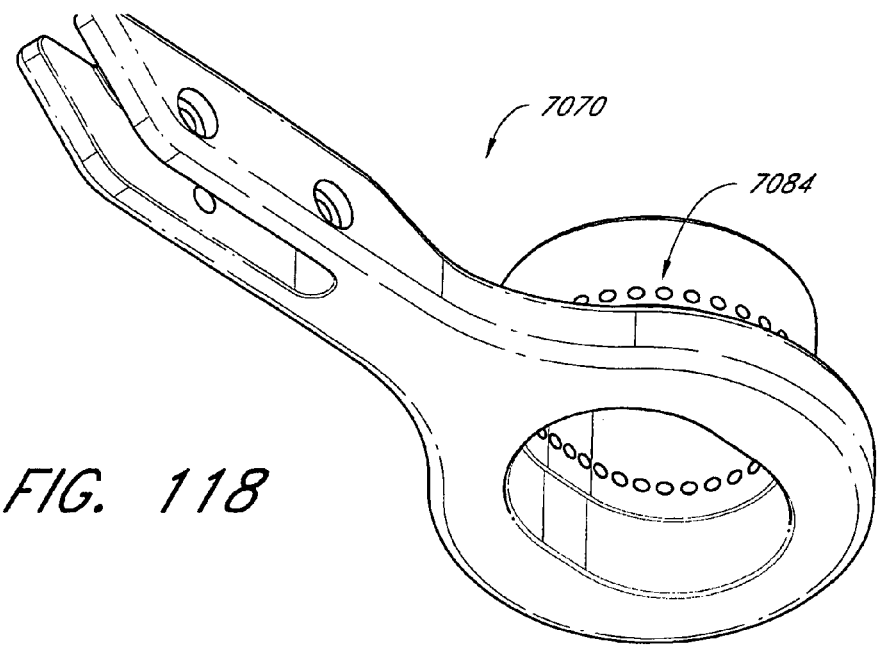

FIGS. 100-106 show a viewing element support block that is similar to the other viewing element support blocks described herein, except as set forth below. With reference to FIGS. 100-106, the light post mount block 7046 is configured to receive and support the light tube 7044, or other viewing element. In one embodiment, the light post mount block 7046 has an upper surface 7054 that is contoured for receiving the light tube 7044. The light post mount block 7046 can have one or more openings 7056 for receiving one or more locator pins 7048. The light post mount block 7046 has a notched portion 7058 including a first surface 7060 for contacting a top surface 7064 (see FIG. 89) of the light post mount 7002 and a second surface 7062 for contacting a side surface 7066 of the light post mount 7002. FIG. 107 shows one embodiment of a locator pin 7048. The locator pin 7048 is generally cylindrical, though other shapes may be used in some embodiments. The locator pin 7048 can be coupled with the light post mount block 7046 to retain the light post mount assembly 7010 in a desired location on the light post mount 7002.

FIGS. 108-109 show an indexing collar assembly that is similar to the other indexing collar assemblies described herein, except as set forth below. With reference to FIGS. 108-109, one embodiment of an indexing collar assembly 7068 comprises an indexing collar 7070, as shown in more detail in FIGS. 110-119. The indexing collar assembly 7068 also preferably comprises a support arm 7072 or clamp arm, an arm extension assembly 7074, and an arm locking screw 7076. In the illustrated embodiment, the indexing collar 7070 is configured to be coupled with an access device having a proximal portion with a generally oval shaped cross-sectional area. In other embodiments, the indexing collar 7070 can be configured to be coupled with an access device having any other oblong shaped cross-sectional area. In one embodiment, the indexing collar 7070 is configured to be coupled with an access device having a proximal portion that has a generally oval shaped opening that is about 24 mm wide and about 30 mm long. In another embodiment, the indexing collar 7070 is configured to be coupled with an access device having a proximal portion with a generally oval shaped opening that is about 24 mm wide and about 35 mm long.

Figure 119:
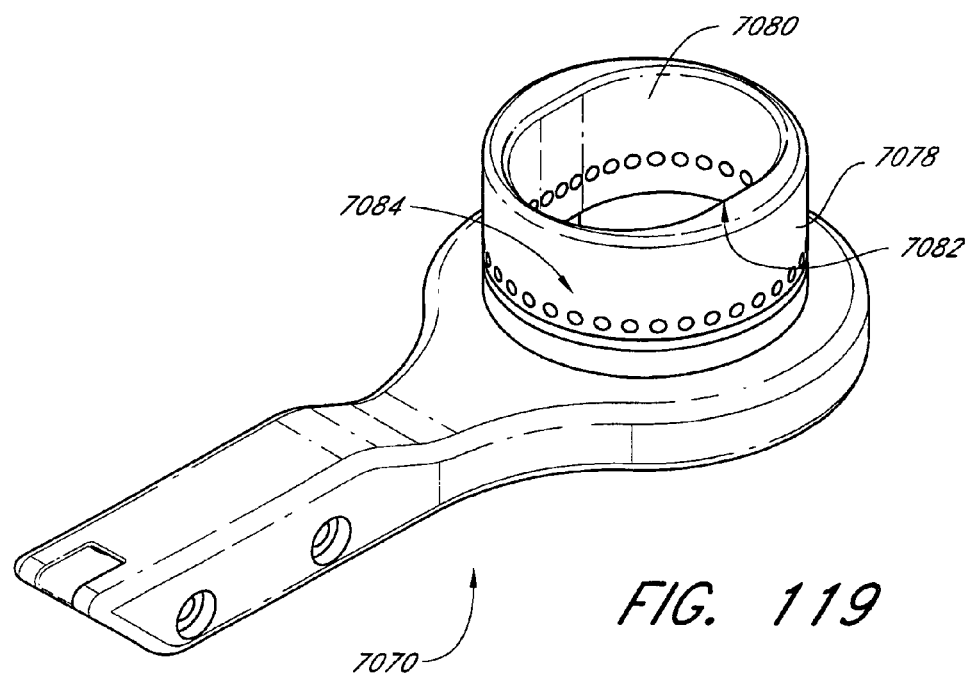

FIGS. 108-119 show an indexing collar that is similar to the other indexing collars described herein, except as set forth below. With reference to FIGS. 108-119, in one embodiment, the support arm 7072 is coupled with an indexing collar 7070, which can be configured to be received in a central opening of a base of an endoscope mount platform or other viewing element mount platform, such as shown in FIGS. 20-23. The indexing collar 7070 has an outer peripheral wall surface 7078, an inner wall surface 7080, and a wall thickness 7082 that is the distance between the wall surfaces. With reference to FIG. 119, the outer peripheral wall surface 7078 has a generally constant diameter. The inner wall surface 7080 preferably has a variable diameter resulting in a generally oval shaped cross-sectional area defined by the inner wall surface 7080. In other embodiments, the inner wall surface 7080 can define any other oblong shaped cross-sectional area. Accordingly, the wall thickness 7082 varies between the outer peripheral wall surface 7078 and the inner wall surface 7080.

In one embodiment, access devices of different shapes and dimensions can be supported by providing indexing collars to accommodate each access device size while using a single endoscope mount platform. The central opening of the endoscope mount platform can have a constant dimension, e.g., a diameter of about 1.28 inches (32.5 mm). An appropriate indexing collar is selected, e.g., one that is appropriately sized to support a selected access device. Thus, the outer wall and the outer diameter preferably are unchanged between different indexing collars, although the inner wall and the inner diameters of the oval shape can vary to accommodate differently sized access devices.

The indexing collar 7070 can be positioned at or rested on a proximal portion of an access device to allow angular movement of the endoscope mount platform, or other viewing element mount platform, with respect thereto about the longitudinal axis. In one embodiment, the outer wall of the indexing collar 7070 includes a plurality of hemispherical recesses, or through holes 7084, that can receive one or more ball plungers on the endoscope mount platform. This arrangement permits the endoscope mount platform, along with an endoscope, or other viewing element, to be fixed in a plurality of discrete angular positions relative the indexing collar 7070.

Figure 120:
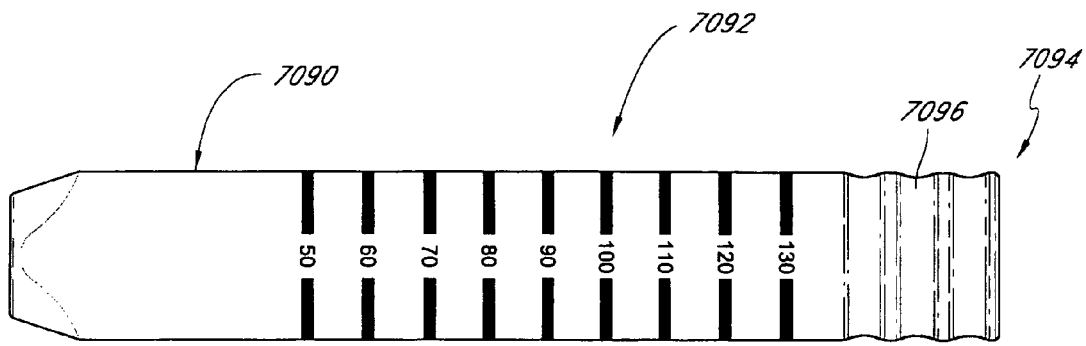
Figure 121:
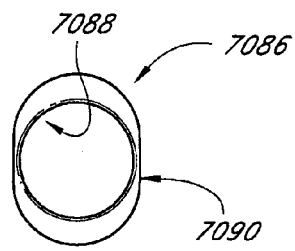
Figure 122:
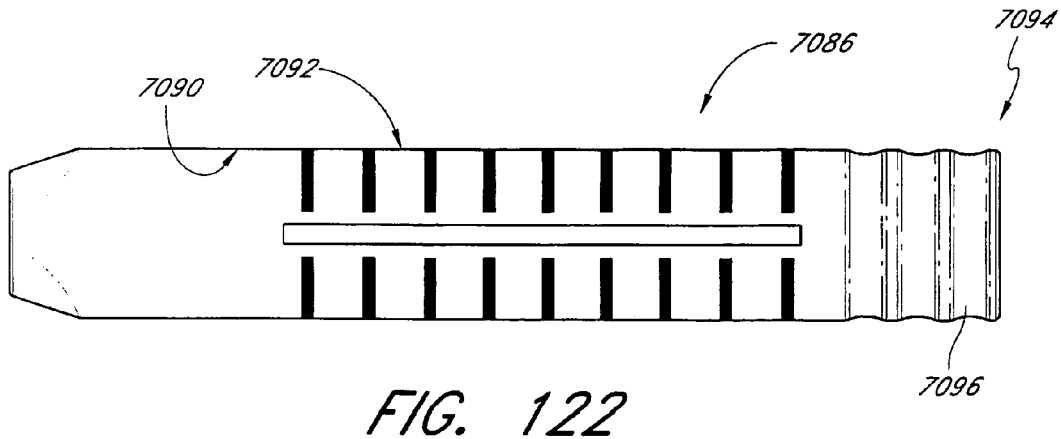

FIGS. 120-122 show a dilation element that is similar to the other dilation elements described herein, except as set forth below. FIGS. 120-122 illustrate one embodiment of a dilating structure or tool for use with an access device. As shown in the illustrated embodiment, a cannulated oval dilator 7086 can have an inner surface 7088 that has a generally circular cross section and an outer surface 7090 that has a generally oval shaped cross section. In other embodiments, the outer surface 7090 can have any other oblong shaped cross section. The outer surface 7090 preferably provides indications 7092 regarding instrument depth. In one embodiment, a proximal portion 7094 of the dilator 7086 comprises a gripping portion 7096 to facilitate handling and to aid in the insertion of the dilator 7086 into a patient. The gripping portion 7096 of the dilator 7086, in some embodiments, can have, for example, raised portions or a knurled surface. The dilator 7086 preferably has a tapered distal portion.

Figure 124:
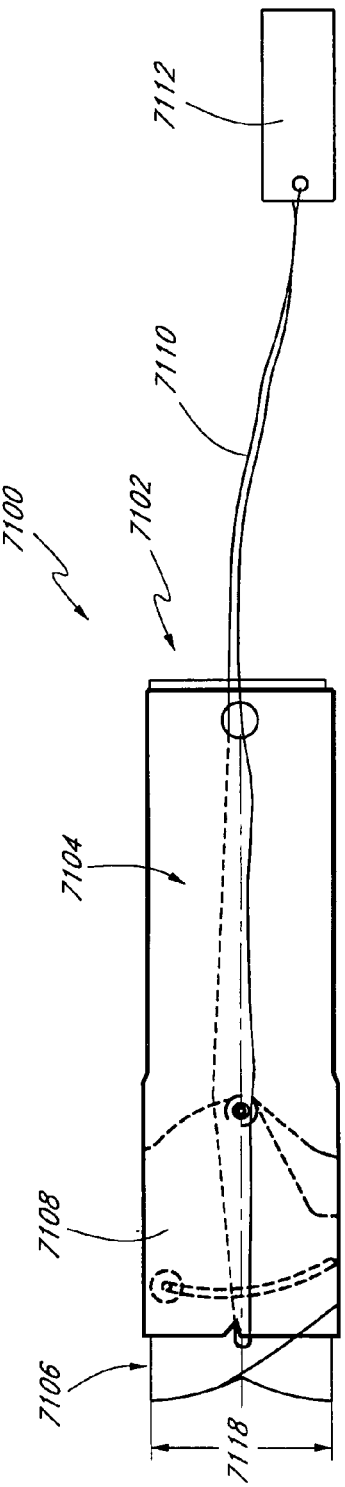

FIGS. 123-150 illustrate some embodiments of access devices, access assemblies, and portions of access devices. FIGS. 123-150 show access devices that are similar to the other access devices described herein, except as set forth below. With reference to FIGS. 123-124, one embodiment of an access device 7100 can be positioned in a low-profile configuration for insertion into a patient. As shown in FIGS. 123-124, the access device 7100 has a passage 7102 with a generally oval shaped cross section. In one embodiment, the cross section of a proximal portion 7104 of the passage 7102 preferably has a width of about 24 mm and a length of about 30 mm. The cross section of the passage 7102 at the distal portion 7106 of the access device 7100, in the low profile configuration, preferably has a width of about 24 mm and a length of about 30 mm. The access device 7100 can be held in a low profile position using a sleeve 7108 or a length of shrink tubing. A pull string 7110 and tab 7112 can be used to at least partially release the shrink tubing from the access device 7100.

FIGS. 125-126 show the access device 7100 in an expanded configuration. In the illustrated embodiment, the access device 7100 has a distal portion 7106 that expands to a cross section at or near the distal end having a width of about 24 mm and a length of about 50 mm. In other embodiments, the sizes and lengths associated with the access device 7100 can vary, as will be described further below. The length 7128 of the access device 7100 from the proximal end of the proximal portion 7104 to the distal end of the distal portion 7106 preferably is between about 2 inches (50.8 mm) and about 5 inches (127 mm). In some embodiments, the length 7128 of the access device 7100, e.g., about 60 mm, about 70 mm, about 80 mm, about 90 mm, about 100 mm, about 110, or more than any of the foregoing dimensions, preferably is selected based on the anatomy of the patient and/or the type of procedure to be performed.

With reference to FIGS. 125-129, the proximal portion 7106 of the access device 7100 includes a tube 7114. The distal portion 7106 of the access device 7100 has an expandable skirt portion 7116. The skirt portion 7116 preferably has a reduced profile configuration with an initial dimension 7118 and corresponding cross-sectional area. The skirt portion 7116 preferably is expandable to an enlarged configuration with a relatively larger dimension 7120 and corresponding cross-sectional area. In one embodiment, the skirt portion 7116 is coupled with the proximal portion 7104. A rivet 7122, pin, or similar connecting device can be used to couple the proximal and distal portions 7102, 7104. The rivet 7122 preferably permits movement of the skirt portion 7116 relative to the proximal portion 7104. The skirt portion 7116 is shown coupled with the proximal portion in FIG. 129.

In the illustrated embodiment, the skirt portion 7116 is manufactured from a resilient material, such as stainless steel. The skirt portion 7116 preferably is manufactured so that it normally assumes an expanded configuration. The skirt portion 7116 preferably is sufficiently rigid that it is capable of displacing the tissue surrounding the skirt portion 7116 as it expands. Depending upon the resistance exerted by surrounding tissue, the skirt portion 7116 preferably is sufficiently rigid to provide some resistance against the tissue to remain in the expanded configuration. In some embodiments, one feature of the skirt portion 7116 is the provision of a shallow concave profile 7124 defined along a distal edge of the skirt portion 7116, which allows for improved placement of the skirt portion 7116 with respect to body structures and surgical instruments. In some embodiments, one or more portions of the skirt portion 7116, e.g., along the distal edge, are formed to accommodate long implants or tools. For example, cut outs can be provided on opposite sides of the distal edge of the skirt portion 7116 to enable a fixation element to be at least partially extended out of the working space.

FIGS. 130-132 further illustrate the proximal portion 7104 of the access device 7100, according to one embodiment. The length 7126 of the proximal portion 7104 of the access device 7100 preferably is between about 1 inch (25.4 mm) and about 4 inches (101.6 mm) in one embodiment. The length 7104 of the proximal portion of the access device, e.g., about 27 mm, about 37 mm, about 47 mm, about 57 mm, about 67 mm, or about 77 mm, preferably is selected based on the anatomy of the patient and/or the type of procedure to be performed.

FIGS. 133-134 show distal skirt portions 7116 of the access device 7100 according to one embodiment. The size and shape of the skirt portion 7116 advantageously provides access to a surgical location when coupled with the proximal portion of the access device and placed in an expanded configuration. In other embodiments, skirt portions 7116 have different sizes and shapes. In some embodiments, the shape of the distal portion 7106 of the access device 7100 can provide an oval shaped access area when expanded. In other embodiments, the shape of the distal portion 7106 of the access device 7100 can provide any other oblong shaped access area when expanded. In some embodiments a locking mechanism 7130 is provided on the distal portion 7106 of the access device 7100 as will be described further below.

FIGS. 133-134 show right and left skirt portions 7148, 7150 in initial flattened configurations. FIG. 133 illustrates a right skirt portion 7148 for an access device 7100 with an oval shaped cross section having an expanded length 7120 of about 50 mm along the long axis. FIG. 134 illustrates a cooperating left skirt portion 7150 for the access device 7100. The skirt portions 7116 can be manufactured from sheets of stainless steel having a thickness of about 0.007 inches (0.178 mm). Other materials, such as nitinol or plastics having similar properties, may also be used. The skirt portions 7148, 7150 preferably each have a protruding portion 7132 along one of the sides for providing a locking feature, as will be described further below.

As discussed above, the skirt portions 7148, 7150 are coupled with the proximal portion 7104 with pivotal connections, such as rivets 7122. A first rivet hole 7134 and second rivet hole 7136 can be provided in each of the right and left skirt portions 7148, 7150 to receive the rivets 7122. In the illustrated embodiment, the right and left skirt portions 7148, 7150 each have first and second free ends 4138, 4140 that are secured by slidable connections, such as additional rivets 7142. In the illustrated embodiment, a first slot 7144 and a second slot 7146 are defined in the right skirt portion 7148 near the free ends 7138, 7140 respectively. In the illustrated embodiment, a first slot 7152 and a second slot 7154 are defined in the left skirt portion 7150 near the free ends 7138, 7140 respectively. With reference to FIGS. 133-134, in one embodiment, the first slots 7144, 7152 preferably are longer than the second slots 7146, 7154. The right and left skirt portions 7148, 7150 preferably are configured so that a rivet 7142 that is positioned within the longer slot 7144 in the right skirt portion 7148 is positioned in the shorter slot 7154 in the left skirt portion 7150. Similarly, a rivet 7142 that is positioned within the longer slot 7152 in the left skirt portion 7150 is positioned in the shorter slot 7146 in the right skirt portion 7148. The rivets 7142 are permitted to move freely within the slots 7144, 7154, 7152, 7146. This slot and rivet configuration allows the skirt portions 7148, 7150 to move between the reduced profile configuration of FIGS. 123-124 and the expanded configuration of FIGS. 125-129. The skirt portion 7116 preferably can expand to span up to three or more vertebrae, e.g., L4, L5, and S1. This arrangement enables multi-level procedures, such as multilevel fixation procedures alone or in combination with a variety of other procedures. One of the rivets 7142 coupling the left and right skirt portions 7148, 7150 together, along with a pair of washers 7156, is shown in FIG. 128.

In the illustrated embodiment, the access device 7100 has a locking mechanism 7130. The distal portion 7106 is provided with a lock that enables a user to selectively lock the distal portion 7106 into a state of expansion. In some embodiments, the user can lock the distal portion in a contracted configuration. In the illustrated embodiment, a first locking mechanism 7130 is provided on a first side of the access device 7100. A second locking mechanism preferably is provided on a second side of the access device 7100. The locking mechanism 7130 can take many forms. In one embodiment, the locking mechanism 7130 includes a first locking slot 7160, a second locking slot 7162, and a clip or locking element 7164 that can be moved (e.g., rotated, actuated, manipulated) to lock the access device 7100 in a desired configuration. In the illustrated embodiment, first and second locking slots 7160, 7168 are defined in the right skirt portion 7148 near the free ends 7138, 7140. In the illustrated embodiment, first and second locking slots 7166, 7162 are defined in the left skirt portion 7150 near the free ends 7138, 7140. With reference to FIGS. 133-134, the first locking slots 7160, 7166 preferably are longer than the second locking slots 7162, 7168. The longer slots 7160, 7166 preferably are curved or angled near an end of the slots. The shorter slots 7162, 7168 preferably are also curved. In one embodiment, each of the shorter slots 7162, 7168 generally forms an arc. The right skirt portion 7148 has an opening 7170 positioned near the shorter slot 7168. The left skirt portion 7150 has an opening 7172 positioned near the shorter slot 7162. The shorter curved slots 7162, 7168 preferably are formed on or near protruding portions 7132 of the skirts.

FIGS. 135-137 illustrate a locking clip or locking element 7164, according to one embodiment. With reference to FIGS. 135-137, a locking element 7164, e.g., a lock, a stop, a tab, a flange, a clip, or a hook, preferably is coupled with one or more of the left and right skirt portions 7148, 7150. In the illustrated embodiment, the locking element 7164 has a generally L-shaped configuration. The locking element 7164 preferably is movable, e.g., rotatable, articulable, manipulatable, or positionable, relative to one or more of the skirt portions 7148, 7150. As shown in FIGS. 135-137, the locking element has a base portion 7174, a tab portion 7176, and a disk portion 7178. The base portion 7174 preferably has a length of about 0.21 inches (5.33 mm) and a thickness of about 0.0155 inches (0.394 mm) in one embodiment. An opening 7180 is defined in the base portion 7174. The opening 7180 preferably is sized to receive a coupling member, such as, for example, a rivet 7182. In the illustrated embodiment, the opening 7180 preferably has a diameter of about 0.046 inches (1.17 mm). In some embodiments the opening 7180 can be located generally centrally on the base portion 7174. The disk portion 7178 preferably extends from a first surface 7184 of the base portion 7174. In the illustrated embodiment, the disk portion 7178 extends from the first surface 7184 a distance of about 0.0155 inches (0.394 mm) and has a diameter of about 0.04 inches (1.02 mm). The disk portion 7178 preferably is positioned near a first end of the base portion 7174. In some embodiments, the disk portion 7178 can be welded to the base portion 7174. In the illustrated embodiment, the tab portion 7176 is positioned generally normal to the base portion 7174 near a second end of the base portion 7174. The tab portion 7176 preferably extends about 0.055 inches (1.40 mm) from a second surface 7186 of the base portion 7174 and has a thickness of about 0.0155 inches (0.394 mm). In one embodiment, the locking element 7164 is made of stainless steel. In some embodiments, the locking element 7164 can be fabricated by machining or formed and welded.

With reference to FIGS. 125-127 and 133-134, in one embodiment, the locking mechanism 7130 comprises the right and left skirt portions 7148, 7150, the locking element 7164, one or more compression washers 7188 (See FIGS. 127 and 138) and a rivet 7182. The locking element 7164 preferably is coupled with the right skirt portion 7148 at the opening 7170 on or near the protruding portion 7132 of the skirt using the one or more compression washers 7188 and the rivet 7182. The locking element 7164 preferably is positioned between the right and left skirt members 7148, 7150 and oriented such that the first surface 7184 of the base portion 7174 of the locking element 7164 faces toward the right skirt portion 7148. The disk portion 7178 preferably is positioned to face toward the smaller arcuate slot 7168 on the protruding portion 7132 of the right skirt portion 7148. The locking element 7164 is sized and configured so that when the locking rivet 7182 is positioned in the opening 7180 of the locking element 7164 and also in the opening 7170 on the right skirt portion 7148, the disk portion 7178 of the locking element 7164 can be positioned so that it extends into the smaller arcuate slot 7168 on the right skirt portion 7148. In the illustrated embodiment, the disk portion 7178 is oriented such that the disk portion 7178 faces toward the outside of the access device 7100. The access device 7100 preferably is also configured so that when the sliding rivets 7142 coupling the right and left skirt portions 7148, 7150 are positioned within the appropriate slots, e.g., the rivet 7142 within slots 7144 and 7154, the tab end 7176 of the locking mechanism 7130 can extend toward, and be positioned within, the longer curved or angled slot 7166 on the left skirt portion 7150. In the illustrated embodiment, the tab portion 7176 extends toward the inside of the access device 7100. The locking element 7164 preferably is rotatably coupled with the right skirt portion 7148 at the opening 7170 with the one or more compression members 7188 and the rivet 7182, as shown in FIG. 127.

When the access device 7100 is in the closed position, or the low profile position, the locking element 7164 preferably is rotated so that the tab portion 7176 is positioned within the longer portion of the longer curved or angled slot 7166. In this configuration, the right and left skirt portions 7148, 7150 are free to slide past one another into the expanded configuration. When the access device 7100 is in the expanded configuration, the tab portion 7176 of the locking element 7164 can be rotated into the shorter curved or angled portion of the longer slot 7166. The locking element 7164 can be actuated, manipulated, or rotated using an instrument or in any other suitable manner to position the tab portion 7176 in the angled portion of the slot 7166. When the tab portion 7176 is engaged in the locked position, the sides of the curved or angled portion of the longer slot 7166 act to restrain the relative movement of the overlapping skirt portions 7148, 7150 to selectively limit expansion or un-expansion of the distal portion 7106 of the access device 7100. In some other embodiments, the relative sizes and configurations of the locking structures and mechanisms can vary.

In one application, the access device 7100 is used to provide minimally invasive access to the spine for a spinal procedure as described herein. The expansion and location of the access device 7100 may be confirmed by fluoroscopy. After the access device 7100 has been fully expanded, the lock can be articulated to lock or unlock the access device 7100.

FIGS. 139-150, illustrate another embodiment of an access device 7200. The structure and configuration of the access device shown in FIGS. 139-150 is similar to that described in connection with FIGS. 123-138, except as shown or noted below. Like reference numerals have been used to identify like features in the two embodiments, except that the reference numerals used with respect to FIGS. 139-150 will be in the "7200s" rather than the "7100s."

As shown in FIGS. 139-150, the access device 7200 has a passage 7202 with a generally oval shaped cross section. FIGS. 141-142 show the access device 7200 in an expanded configuration. In the illustrated embodiment, the access device 7200 has a distal portion 7206 that expands to a cross section having a width of about 24 mm and a length 7220 of about 80 mm. The sizes and lengths associated with the access device 7200 can vary. In some embodiments, a generally longer cross-sectional length provides increased access for performing some surgical procedures. FIGS. 149-150 show distal skirt portions 7216 of the access device 7200 according to one embodiment. The size and shape of the skirt portion 7216 advantageously provides increased access to a surgical location in an expanded configuration. In other embodiments, skirt portions 7216 have different sizes and shapes. In some embodiments, the shape of the distal portion 7206 of the access device 7200 can provide an oblong shaped access area when expanded. FIGS. 149-150, show right and left skirt portions 7248, 7250 in initial flattened configurations. In the illustrated embodiment, the skirt portions 7248, 7250 are configured to form an access device 7200 having an oval shaped cross section with an expanded length 7220 of about 80 mm along the long axis. In the illustrated embodiment, a locking mechanism 7230 generally similar to that described with respect to the embodiment shown in FIGS. 123-138 is provided.

IV. Additional Apparatuses Configured to be Coupled with Vertebrae

FIGS. 151-155 illustrate various embodiments of apparatuses that can be coupled with vertebrae in connection with a variety of surgical procedures, including those discussed herein.

FIGS. 151-153 illustrate an apparatus 8010 constructed according to one embodiment. The apparatus 8010 includes a surgically implantable longitudinal member or rod 8012 for maintaining bone portions, such as vertebrae of a spinal column, in a desired spatial relationship. The member 8012 is connected with vertebrae of the spinal column by fasteners 8016.

The rod 8012 is made of a suitable biocompatible material and has a length which is at least sufficient to enable the rod to span at least two vertebrae. The length of the rod 8012 in any particular installation will depend upon the condition to be corrected and the number of vertebrae to be held in a desired spatial relationship relative to each other by the rod.

The rod 8012 (FIGS. 151-153) is connected to a respective vertebra by the fastener 8016 made of a suitable biocompatible material. The fastener 8016 (FIGS. 151-152) has a longitudinal axis 8018 and a threaded end portion 8022 having a course thread convolution 8024 which engages the vertebra. A second end portion 8026 of the fastener 8016 is provided with a spherical surface 8028. A recess 8032 (FIG. 151) is provided on the end portion 8026 of the fastener 8016. The recess 8032 receives a tool, such as the endoscopic screwdriver apparatus 660 shown in FIGS. 28-29, that applies torque to the fastener 8016 to turn the thread convolution 8024 into the vertebra.

The fastener 8016 (FIGS. 151-153) extends into a housing 8040 that interconnects the rod 8012 and the fastener 8016. The housing 8040 has a first passage 8042 through which the rod 8012 extends. The housing 8040 has a second passage 8044 with a longitudinal axis 8046 that extends transverse to the passage 8042. The fastener 8016 extends through an opening 8050 in the housing 8040 and into the second passage 8044. The spherical surface 8028 (FIG. 153) of the fastener 8016 engages a concave part spherical surface 8052 of the housing 8040. Accordingly, the fastener 8016 is universally pivotable relative to the housing 8040 so that the longitudinal axis 8018 of the fastener 8016 is positionable in any one of a plurality of angular positions relative to the longitudinal axis 8046 of the passage 8044.

The passage 8044 (FIG. 153) is defined by a pair of first or upper axially extending part cylindrical surfaces 8054 having a first diameter. The housing 8040 has a second or lower cylindrical surface 8056 having a second diameter smaller than the first diameter. A tapered surface 8058 extends from the first cylindrical surfaces 8054 to the second cylindrical surface 8056.

The housing 8040 (FIG. 153) includes a pair of upper portions 8060. Each of the upper portions 8060 includes at least one thread 8062. The upper portions 8060 also include circumferentially extending grooves 8064. The grooves 8064 are defined by cylindrical surfaces 8066 extending generally parallel to the longitudinal axis 8046 of the housing 8040. The surfaces 8066 have diameters larger than the diameter of cylindrical surfaces 8054. Lower radially extending surfaces 8068 extend generally perpendicular to the cylindrical surfaces 8066. The radially extending surfaces 8068 extend radially outward from and generally perpendicular to the axially extending cylindrical surfaces 8054. The threads 8062 extend axially from upper surfaces 8071 of the housing 8040 to the grooves 8064. Accordingly, the threads 8062 terminate axially above the rod 8012 when the rod is connected to the housing 8040. The grooves 8064 permit the threads 8062 to be easily formed in the housing 8040.

The housing 8040 (FIGS. 151-153) includes two diametrically opposed openings 8072. The openings 8072 (FIG. 153) are defined by deformable radially inner portions or walls 8074. The walls 8074 are deformed radially inwardly after insertion of the fastener 8016. Dimples 8076 are formed in the walls 8074 to help retain the fastener in the housing 8040.

A spacer 8080 is housed in the second passage 8044 of the housing 8040. The spacer 8080 (FIG. 153) has a lower portion 8082 engageable with the fastener 8016. A concave part spherical surface 8084 of the lower portion 8082 engages the spherical surface 8028 of the fastener 8016.

An axially extending portion 8086 of the lower portion 8082 extends from the spherical surface 8084 and is spaced from the spherical surface 8028 of the fastener 8016. The axially extending portion 8086 includes an arcuate surface 8088 extending from the spherical surface 8084. An axially extending cylindrical surface 8090 extends axially downward, as viewed in FIG. 3, from the arcuate surface 8088. The arcuate surface 8088 and the cylindrical surface 8090 are spaced from the spherical surface 8028 of the fastener 8016. The axially extending portion 8086 helps position the spacer 8080 in the housing 8040.

The spacer 8080 (FIGS. 151-153) has an upper portion 8090 with an upper surface 8092 engageable with the rod 8012. The spacer 8080 has an axially extending opening 8094 that extends through the upper portion 8090 and the lower portion 8082. A tool, such as the endoscopic screwdriver apparatus 660, extends through the opening 8094 to engage the recess 8032 in the fastener 8016. The tool extends through the opening 8094 to apply torque to the fastener 8016 and connect the fastener to the vertebra.

The lower portion 8082 of the spacer 8080 (FIGS. 151 and 153) has a first radially outer cylindrical surface 8096 with an outer diameter slightly smaller than the diameter of the lower cylindrical surface 8056 of the housing 8040. The upper portion 8090 of the spacer 8080 includes a second radially outer cylindrical surface 8098 having a diameter smaller than the cylindrical surface 8096. A radially extending surface 8100 extends from the cylindrical surface 8096 to the cylindrical surface 8098.

A ring-shaped retaining or positioning member 8110 holds the spacer 8080 in the housing 8040. The retaining member 8110 has a radially inner cylindrical surface 8112 with a diameter slightly larger than the outside diameter of the radially outer cylindrical surface 8098 on the spacer 8080. The retaining portion 8110 has a radially outer cylindrical surface 8114 that engages the housing 8040. The outer cylindrical surface 8114 has a diameter which is slightly smaller than the diameter of first or upper cylindrical surfaces 8054 of the housing 8040 and slightly larger than the diameter of second or lower cylindrical surface 8056 of the housing. Accordingly, the retaining member 8110 is easily inserted into the housing 8040. The retaining member 8110 engages the tapered surface 8058 of the housing 8040. The retaining member 8110 is then press fit into engagement with the surface 8056 of the housing 8040.

A ring-shaped spring member 8120 engages the retaining member 8110 and the spacer 8080. The spring member 8120 engages the radially extending surface 8100 on the spacer 8080 to apply an axial force to the spacer to prevent relative movement between the fastener 8016 and the housing 8040 when the rod 8012 is disengaged from the spacer and the spacer engages the fastener. The spring member 8120 urges the spacer 8080 axially relative to the housing 8040 toward the fastener 8016. The spring member 8120 urges the part spherical surface 8052 of the housing 8040 against the spherical surface 8028 of the fastener 8016. The part spherical surface 8084 of the spacer 8080 frictionally engages the spherical surface 8028 of the fastener 8016 and the spherical surface 8028 of the fastener frictionally engages the part spherical surface 8052 of the housing 8040. The fastener 8016 and the housing 8040 are manually movable relative to each other by a surgeon when the rod 8012 is disengaged from the spacer 8080 and the spring member 8120 applies the axial force. The force applied by the spring member 8120 may be overcome by the surgeon to move the housing 8040 relative to the fastener 8016. Accordingly, the housing 8040 can be positioned relative to the fastener 8016 and held in position relative to the fastener by the spring member 8120 without the rod engaging the spacer 8080.

The spring member 8120 (FIGS. 151 and 154) has an annular shape with an outer diameter smaller than the diameter of the lower cylindrical surface 8056 of the housing 8040. The spring member 8120 has an inner diameter larger than the outer cylindrical surface 8098 of the spacer 8080. The spring member 8120 has an arched shape, as viewed in FIG. 5, when the spring member is disengaged from the spacer 8080 and the retaining member 8110. When the spring member 8120 is received between the spacer 8080 and the retaining member 8110, the spring member is compressed and applies an axial force to the spacer. The spring member 8120 is formed by bending a flat ring to form the arched shape. Diametrically opposite sides of the spring member 8120 are bent toward each other to form the arched shape.

The amount of axial force applied by the spring member 8120 to the spacer 8080 depends on the position of the retaining member 8110 relative to the housing 8040 and the spacer. The retaining member 8110 may be press-fit into the housing 8040 in any one of a plurality of axial positions relative to the housing. Accordingly, the amount of axial force applied by the spring member 8120 to the spacer 8080 may be adjusted to a desired force. The force applied by the spring member 8120 increases as the retaining member 8110 gets closer to the radially extending surface 8100 on the spacer 8080.

The retaining member 8110 is also connected to the housing 8040 by a pair of diametrically opposed circumferential welds 8122. The welds 8122 may be laser welds that fixedly connect the retaining member 8110 to the housing 8040. The laser welds 8122 may extend circumferentially around the retaining member any desired distance. It is contemplated that any desired number of welds 8122 may be used to connect the retaining member 8110 to the housing 8040.

A clamping mechanism or cap screw 8124 (FIGS. 152 and 153) threadably engages the threads 8062 on the housing 8040. The cap screw 8124 engages and applies a force to the rod 8012 to press the rod against the spacer 8080 and the spacer against the fastener 8016. The cap screw 8124 clamps the rod 8012, the spacer 8080, and the housing 8040 to the fastener 8016 to prevent relative movement between the fastener, the housing and the rod. The force applied by the cap screw 8124 cannot be overcome by the surgeon to move the housing 8040 relative to the fastener 8016.

The apparatus 8010 is assembled by inserting the fastener 8016 through the opening 8050 in the housing 8040 so that the spherical surface 8028 of the fastener engages the part spherical surface 8052 of the housing. The spacer 8080 is inserted into the housing 8040 and into engagement with the fastener 8016. The spring member 8120 is inserted into the second passage 8044 and into engagement with the spacer 8080. The retaining member 8110 is inserted into the second passage 8044 and into engagement with the spring member 8120. The retaining member 8110 is inserted into the passage to compress the spring member 8120 until the spring member applies the desired force to the spacer 8080. The retaining member 8110 is press fit into the housing 8040 to retain the fastener 8016, the spacer 8080, and the spring member 8120 in the housing 8040.

The walls 8074 of the housing 8040 are deformed radially inward to form the dimples 8076, as shown in FIG. 153. The dimples 8076 are axially spaced from the retaining member 8110. Accordingly, the dimples 8076 help retain the retaining member 8110, the spring member 8120, the spacer 8080, and the fastener 8016 in the housing 8040. The retaining member 8110 is then welded to the housing 8040 to further help retain the retaining member, the spring member 8120, the spacer 8080, and the fastener 8016 in the housing.

As discussed above, the apparatus 8010 is particularly well suited for minimally invasive procedures. In one such procedure, the apparatus 8010 is applied to the spine through an access device or a retractor, such as one similar to the access device 5000, any of the other access devices described herein, and any of the access devices described in documents incorporated by reference herein. A preliminary step in such a procedure is to deliver the access device, as discussed above. At least a portion of the access device optionally is expanded to increase access to a surgical location. In a one level fixation procedure, the access device provides access to two adjacent vertebrae, e.g., the pedicles of two adjacent vertebrae, as discussed above. Additional adjacent vertebrae may be exposed by an access device for procedures performed over longer surgical fields.

Thereafter, a tool, such as the endoscopic screwdriver apparatus 660, is inserted through the opening 8084 in the spacer 8080 and into the recess 8032 in the fastener 8016. The fastener 8016 preferably is advanced through the access device to the surgical locations. Torque is applied to the fastener 8016 to turn the thread convolution 8024 into the vertebra. Once the fastener 8016 is connected with the vertebra, the housing 8040 can be positioned relative to the fastener. The spring member 8120 maintains the position of the housing 8040 relative to the fastener 8016 while the rod 8012 is disengaged from the spacer 8080. By enabling the housing 8040 to be maintained in a selected position relative to the fastener 8016, the surgeon's hands are free to manipulate other tools or implants to complete the procedure. This feature simplifies and shortens the procedure, benefiting the patient and the surgeon.

Once the housing 8040 is positioned relative to the fastener 8016, the rod 8012 is placed into the passage 8042 and in engagement with the spacer 8080. Placing the rod 8012 in the passage 8042 may be facilitated by a suitable tool, such as the grasper apparatus 700, discussed above. Also, placing the rod 8012 may include additional optional steps related to a spondy reduction procedure. Spondy procedures and tools configured to perform them are described in PCT Application No. PCT/US03/27879, filed Sep. 5, 2003, which is hereby expressly incorporated by reference herein in its entirety. The cap screw 8124 is threaded into the housing 8040 and into engagement with the rod 8012. The endoscopic screwdriver apparatus 660 may be used to thread the cap screw 8124 into the housing 8040. The cap screw 8124 clamps the rod 8012, the spacer 8080, and the housing 8040 to the fastener 8016 to prevent movement of the fastener relative to the housing. Alternatively, the fastener 8016 may be connected to the vertebra prior to the spacer 8080, the spring member 8120, and the retaining member 8110 being inserted into the housing 8040.

If the apparatus 8010 is deployed in a minimally invasive procedure, delivery of the cap screw 8124 may be facilitated by the guide apparatus 800 or other similar tool. Prior to clamping the cap screw 8124, additional procedures that manipulate the position of the apparatus 8010 relative to another apparatus 8010 or the position of adjacent vertebrae may be performed. Such procedures include compression and distraction procedures. Useful tools for performing such procedures include the compressor-distractor instrument 900 and additional compressor-distractor instruments described in PCT Application No. PCT/US03/020003, filed Jun. 24, 2003, which is hereby expressly incorporated by reference herein in its entirety.

PCT Application No. US03/04361, filed Feb. 13, 2003, and U.S. patent application Ser. No. 10/926,840, filed Aug. 26, 2004 are incorporated herein entirely by reference.

From the above description, those skilled in the art will perceive improvements, changes and modifications. Such improvements, changes and modifications within the skill of the art are intended to be covered by the appended claims.

The various devices, methods and techniques described above provide a number of ways to carry out the invention. Of course, it is to be understood that not necessarily all objectives or advantages described may be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

Many of the systems, apparatuses, methods, and features described herein can be combined with many of the systems, apparatuses, methods and features disclosed in the following patents and patent applications. The entire disclosure of all of the following patents and patent applications is hereby incorporated by reference herein and made a part of this specification: U.S. Pat. Nos. 6,361,488 (issued Mar. 26, 2002), 6,530,880 (issued Mar. 11, 2003), 6,648,888 (issued Nov. 18, 2003), 6,652,553 (issued Nov. 25, 2003), 6,641,583 (issued Nov. 4, 2003), 6,554,832 (issued Apr. 29, 2003), 6,673,074 (issued Jan. 6, 2004), U.S. patent application Ser. No. 09/821,666 (filed Mar. 29, 2001, published Oct. 3, 2002 as Publication No. U.S. 2002/0143328A1), Ser. No. 09/824,411 (filed Apr. 2, 2001, published Oct. 3, 2002 as Publication No. U.S. 2002/0143330A1), Ser. No. 09/921,326 (filed Aug. 2, 2001, published Feb. 6, 2003 as Publication No. U.S. 2003/0028191A1), Ser. No. 09/940,402 (filed Aug. 27, 2001, published Feb. 27, 2003 as Publication No. US 2003/0040656A1), Ser. No. 10/075,668 (filed Feb. 13, 2002, published Aug. 14, 2003 as Publication No. U.S. 2003/0153911A1), Ser. No. 10/087,489 (filed Mar. 1, 2002, published Sep. 4, 2003 as Publication No. U.S. 2003/0167058A1), Ser. No. 10/178,875 (filed Jun. 24, 2002, published Dec. 25, 2003 as Publication No. U.S. 2003/0236529A1), Ser. No. 10/280,489 (filed Oct. 25, 2002, published Apr. 17, 2003 as Publication No. US 2003/0073998A1), Ser. No. 10/280,799 (filed Oct. 25, 2002), Ser. No. 10/361,887 (filed Feb. 10, 2003, published Aug. 14, 2003 as Publication No. US 2003/0153927A1), Ser. No. 10/658,736 (filed Sep. 9, 2003), Ser. No. 10/678,744 (filed Oct. 2, 2003), Ser. No. 10/693,815 (filed Oct. 24, 2003), Ser. No. 10/693,250 (filed Oct. 24, 2003), Ser. No. 10/693,663 (filed Oct. 24, 2003), Ser. No. 10/842,651 (filed May 10, 2004), Ser. No. 10/845,389 (filed May 13, 2004) U.S. Provisional Application Nos. 60/471,431 (filed May 16, 2003), 60/497,763 (filed Aug. 26, 2003), 60/497,822 (filed Aug. 26, 2003), 60/513,796 (filed Oct. 22, 2003), 60/513,013 (filed Oct. 23, 2003), 60/514,559 (filed Oct. 24, 2003), 60/545,587 (filed Feb. 18, 2004), 60/558,296 (filed Mar. 31, 2004), 60/579,643 (filed Jun. 15, 2004).

What is claimed is:

1. An apparatus comprising:
a longitudinal member connectable with a bone portion;
a fastener having a longitudinal axis and engageable with the bone portion to connect said longitudinal member to the bone portion;
a housing having a first passage configured to receive said longitudinal member, said housing having a second passage with a longitudinal axis extending transverse to said first passage, said fastener extending through an opening in said housing into said second passage and being movable relative to said housing, said longitudinal axis of said fastener being positionable in any one of a plurality of angular positions relative to said longitudinal axis of said second passage;
a spacer received in said second passage of said housing and engageable with said fastener and said longitudinal member;
a spring member engageable with said spacer to apply a force to prevent relative movement between said fastener and said housing when said longitudinal member is disengaged from said spacer and said spacer engages said fastener, said fastener and said housing being manually movable relative to each other against said force when said longitudinal member is disengaged from said spacer and said member applies said force, said spring member being an arched continuous ring with diametrically opposite sides bent toward each other when said spring member is disengaged from said housing and said spacer; and
a clamping mechanism that clamps said longitudinal member, said spacer and said housing to said fastener to prevent movement of said fastener relative to said housing.

2. An apparatus as defined in claim 1 further including a retaining member engaging said spring member to retain said spring member, said spacer, and said fastener in said housing.

3. An apparatus as defined in claim 2 wherein said retaining member is fixedly connected to said housing.

4. An apparatus as defined in claim 3 wherein said retaining member is welded to said housing.

5. An apparatus as defined in claim 3 wherein said retaining member is press-fit into said housing.

6. An apparatus as defined in claim 5 wherein said retaining member is welded to said housing.

7. An apparatus as defined in claim 6 wherein said housing includes a deformable portion, said deformable portion being deformable into a position to help retain said retaining member in said housing.

8. An apparatus as defined in claim 2 wherein said housing includes a deformable portion, said deformable portion being deformable into a position to help retain said retaining member in said housing.

9. An apparatus as defined in claim 8 wherein said deformable portion is spaced from said retaining member when said deformable portion is in said position to help retain said retaining member in said housing.

10. An apparatus as defined in claim 1 wherein said fastener is universally pivotable relative to said housing.

11. An apparatus as defined in claim 10 wherein said fastener includes a spherical surface engageable with a part spherical surface of said housing.

12. An apparatus as defined in claim 11 wherein said spherical surface of said fastener is engageable with said spacer.

13. An apparatus as defined in claim 1 wherein said spacer has an opening through which a tool extends to engage said fastener when said longitudinal member is disengaged from said spacer.

14. An apparatus as defined in claim 1 wherein said clamping mechanism includes a threaded member threadably engageable with a thread on said housing.

15. An apparatus as defined in claim 14 wherein said threaded member engages said longitudinal member to clamp said longitudinal member against said spacer.

16. An apparatus as defined in claim 14 wherein said housing includes a radially extending surface extending radially outwardly from an axially extending surface defining said second passage, said radially extending surface defining a circumferentially extending groove, said thread on said housing extending axially from an upper surface of said housing to said groove.

17. An apparatus as defined in claim 1 wherein said housing includes a tapered surface engageable with said retaining member, said tapered surface extending from a first cylindrical surface of said housing having a diameter larger than a radially outer diameter of said retaining member to a second cylindrical surface of said housing having a diameter smaller than said radially outer diameter of said retaining member.

18. An apparatus as defined in claim 1 wherein said spacer includes an axially extending portion extending from a surface engaging said fastener, said axially extending portion being spaced from said fastener.

19. An apparatus comprising:
a longitudinal member connectable with a bone portion;
a fastener engageable with the bone portion, the fastener having a head, a shaft, and a longitudinal axis and connecting said longitudinal member to the bone portion;
a housing having a first passage through which said longitudinal member extends, said housing having a second passage with a longitudinal axis extending transverse to said first passage, said fastener extending through an opening in said housing into said second passage and being movable relative to said housing, said longitudinal axis of said fastener being positionable in any one of a plurality of angular positions relative to said longitudinal axis of said second passage;
a spacer received in said second passage of said housing and engageable with said fastener head and said longitudinal member, said spacer having a bottom surface engageable with the fastener head, the bottom surface including an axially extending portion spaced from said fastener such that a portion of the bottom surface is engageable with the fastener head and a portion of the bottom surface is spaced from the fastener head;
a retaining member that retains said spacer and said fastener in said housing, said retaining member being fixedly connected with one or more welds to said housing; and
a clamping mechanism that clamps said longitudinal member, said spacer, and said housing to said fastener to prevent movement of said fastener relative to said housing.

20. An apparatus as defined in claim 19 further including a spring member applying a force to said spacer to maintain said spacer in frictional engagement with said fastener to prevent relative movement between said fastener and said housing when said longitudinal member is disengaged from said spacer and said spacer engages said fastener, said fastener and said housing being manually movable relative to each other in opposition to said frictional engagement when said longitudinal member is disengaged from said spacer.

21. An apparatus as defined in claim 20 wherein said spring member is an axially compressible member.

22. An apparatus as defined in claim 21 wherein said spring member is arched when said spring member is disengaged from said spacer.

23. An apparatus as defined in claim 19 wherein said fastener is universally pivotable relative to said housing.

24. An apparatus as defined in claim 23 wherein said fastener includes a spherical surface engageable with a part spherical surface of said housing.

25. An apparatus as defined in claim 24 wherein said spherical surface of said fastener is engageable with said spacer.

26. An apparatus as defined in claim 19 wherein said spacer has an opening through which a tool extends to engage said fastener when said longitudinal member is disengaged from said spacer.

27. An apparatus as defined in claim 19 wherein said clamping mechanism includes a threaded member threadably engageable with a thread on said housing.

28. An apparatus as defined in claim 27 wherein said threaded member engages said longitudinal member to clamp said longitudinal member against said spacer.

29. An apparatus as defined in claim 27 wherein said housing includes a radially extending surface extending radially outwardly from an axially extending surface defining said second passage, said radially extending surface defining a circumferentially extending groove, said thread on said housing extending axially from an upper surface of said housing to said groove.

* * * * *